United States Patent
Ozbolat et al.

(10) Patent No.: US 11,903,612 B2
(45) Date of Patent: Feb. 20, 2024

(54) BIOPRINTER AND METHODS OF USING SAME

(71) Applicant: UNIVERSITY OF IOWA RESEARCH FOUNDATION, Iowa City, IA (US)

(72) Inventors: Ibrahim T. Ozbolat, North Liberty, IA (US); Howard Chen, Iowa City, IA (US); Yin Yu, Iowa City, IA (US); Yahui Zhang, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 676 days.

(21) Appl. No.: 15/034,004

(22) PCT Filed: Nov. 4, 2014

(86) PCT No.: PCT/US2014/063915
§ 371 (c)(1),
(2) Date: May 3, 2016

(87) PCT Pub. No.: WO2015/066705
PCT Pub. Date: May 7, 2015

(65) Prior Publication Data
US 2016/0288414 A1 Oct. 6, 2016

Related U.S. Application Data

(60) Provisional application No. 62/052,701, filed on Sep. 19, 2014, provisional application No. 61/899,565, (Continued)

(51) Int. Cl.
*B29C 64/209* (2017.01)
*B29C 64/227* (2017.01)
(Continued)

(52) U.S. Cl.
CPC ........ *A61B 17/3468* (2013.01); *B29C 64/118* (2017.08); *B29C 64/209* (2017.08);
(Continued)

(58) Field of Classification Search
CPC ..... B29C 64/20; B29C 64/227; B29C 64/232; B29C 64/236; B29C 64/241;
(Continued)

(56) References Cited

U.S. PATENT DOCUMENTS

2004/0237822 A1 12/2004 Boland et al.
2004/0253365 A1* 12/2004 Warren ............... A61B 5/0066
427/2.1
(Continued)

OTHER PUBLICATIONS

Beyer, Simon T, "A Microfluidics based 3D Bioprinter with on-the-fly Multi-material Switching Capability," Oct. 31, 2013, International Conference on Miniaturized Systems for Chemistry and Life Sciences, p. 176-178 (Year: 2013).*
(Continued)

*Primary Examiner* — Philip Y Louie
*Assistant Examiner* — Sonny V Nguyen
(74) *Attorney, Agent, or Firm* — Ballard Spahr LLP

(57) ABSTRACT

A bioprinter and methods of using the bioprinter. The bioprinter permits selective three-dimensional movement of multiple nozzle assemblies during operation of the bioprinter. The bioprinter can be used to produce scaffold-free tissue constructs having a plurality of cellular elements interspersed among a semi-permeable vascular network. The bioprinter can also be used to print a tissue construct directly onto a tissue defect of a subject. The bioprinter can be provided as part of a bioprinting system that includes a scanner for imaging the tissue defect.

12 Claims, 75 Drawing Sheets

Related U.S. Application Data filed on Nov. 4, 2013, provisional application No. 61/899,584, filed on Nov. 4, 2013.

(51) Int. Cl.

| | | |
|---|---|---|
| *A61B 17/34* | (2006.01) | |
| *B33Y 80/00* | (2015.01) | |
| *B33Y 10/00* | (2015.01) | |
| *B33Y 30/00* | (2015.01) | |
| *C12M 3/00* | (2006.01) | |
| *C12M 1/26* | (2006.01) | |
| *B41J 3/407* | (2006.01) | |
| *B41J 3/54* | (2006.01) | |
| *C09D 11/38* | (2014.01) | |
| *C09D 11/30* | (2014.01) | |
| *B29C 64/40* | (2017.01) | |
| *B29C 64/118* | (2017.01) | |
| *C09D 11/04* | (2006.01) | |
| *C09D 11/102* | (2014.01) | |
| *B33Y 50/02* | (2015.01) | |
| *B29K 105/00* | (2006.01) | |

(52) U.S. Cl.
CPC ............ *B29C 64/227* (2017.08); *B29C 64/40* (2017.08); *B33Y 10/00* (2014.12); *B33Y 30/00* (2014.12); *B33Y 80/00* (2014.12); *B41J 3/407* (2013.01); *B41J 3/543* (2013.01); *C09D 11/04* (2013.01); *C09D 11/102* (2013.01); *C09D 11/30* (2013.01); *C09D 11/38* (2013.01); *C12M 21/08* (2013.01); *C12M 33/00* (2013.01); *B29K 2105/0061* (2013.01); *B33Y 50/02* (2014.12)

(58) Field of Classification Search
CPC ... B29C 64/205; B29C 64/209; B29C 64/295; B29C 64/106; B33Y 10/00; B33Y 30/00; B33Y 80/00

See application file for complete search history.

(56) References Cited

U.S. PATENT DOCUMENTS

| | | |
|---|---|---|
| 2006/0156978 A1 | 7/2006 | Lipson et al. |
| 2007/0140050 A1* | 6/2007 | Humphrey ............ B01F 7/1665 366/262 |
| 2009/0020919 A1* | 1/2009 | Marsac ................. B29C 64/118 425/130 |
| 2009/0208466 A1 | 8/2009 | Yoo et al. |
| 2009/0263849 A1 | 10/2009 | Sun et al. |
| 2011/0064784 A1* | 3/2011 | Mullens ................. B82Y 30/00 424/443 |
| 2011/0136162 A1* | 6/2011 | Sun ................... B01L 3/502761 435/29 |
| 2011/0172611 A1 | 7/2011 | Yoo et al. |
| 2012/0089238 A1* | 4/2012 | Kang ..................... A61L 27/225 623/23.72 |
| 2013/0017564 A1 | 1/2013 | Guillemot et al. |
| 2014/0012225 A1* | 1/2014 | Yoo ...................... A61B 5/6835 604/503 |
| 2014/0035975 A1* | 2/2014 | Essien ................... B29C 64/112 347/6 |
| 2015/0037445 A1* | 2/2015 | Murphy ................ B29C 64/386 425/131.1 |
| 2016/0001461 A1* | 1/2016 | Gardiner ............... B29C 64/106 264/219 |
| 2016/0136895 A1* | 5/2016 | Beyer .................... B29C 64/209 264/241 |
| 2017/0369827 A1* | 12/2017 | Langenfeld ............ C12M 33/00 |
| 2019/0160203 A1* | 5/2019 | Gatenholm ......... A61L 27/3687 |

OTHER PUBLICATIONS

Morimoto, Yuya, "Three-dimensional cell culture based on microfluidic techniques to mimic living tissues," Nov. 20, 2012, Biomaterial Science, vol. 1, p. 257-264 (Year: 2012).*

Cornock, Rhys, "Development of a Coaxial Melt Extrusion Printing Process for Specialised Composite Bioscaffold Fabrication", Jul. 12, 2013, IEEE/ASME International Conference on Advanced Intelligent Mechatronics, p. 973-978 (Year: 2013).*

Perez, Roman A., "Utilizing Core-Shell Fibrous Collagen-Alginate Hydrogel Cell Delivery System for Bone Tissue Engineering", Electronically Published Sep. 21, 2013, Pubmed. (Year: 2013).*

Morimoto, Yuya, "Three-dimensional cell culture based on microfluidic techniques to mimic living tissues", Biomaterial Science, 1, pp. 257-264. (Year: 2013).*

Kaelin, Brooke; University of Iowa Team Creates Multi-Arm Bioprinter, 3-D Printer World, Aug. 5, 2013; retrieved from the internet: <URL: http://www.95printerworld.com/article/university-iowa-team-creates-multi-arm-bioprinter>.

\* cited by examiner

BIOPRINTER AND METHODS OF USING SAME

CROSS-REFERENCE TO RELATED APPLICATIONS

The present application is a U.S. National Phase Application of International Application No. PCT/US2014/063915, filed Nov. 4, 2014, which claims the benefit of the filing dates of U.S. Provisional Application No. 61/899,584, filed on Nov. 4, 2013, U.S. Provisional Application No. 61/899,565, filed Nov. 4, 2013, and U.S. Provisional Application No. 62/052,701, filed Sep. 19, 2014, each of which is incorporated by reference herein in its entirety.

STATEMENT REGARDING FEDERALLY SPONSORED RESEARCH

This invention was made with U.S. government support under grant number UL1RR024979 from the National Institutes of Health (NIH) and the Institute for Clinical and Translational Sciences (ICTS), under career award #1349716 from the National Science Foundation (NSF) Civil, Mechanical, Manufacturing Innovation (CMMI) Division, and a grant from the Diabetes in Action Research and Education Foundation. The U.S. government may have certain rights in this invention.

FIELD

This invention relates to a bioprinter for forming tissue constructs and printing such tissue constructs into defects within a subject. The invention also relates to methods of using the bioprinter to form tissue constructs and to print such tissue constructs into defects within a subject.

BACKGROUND

Tissue engineering holds promise for alleviating organ shortages while minimizing side effects and maximizing a patient's quality of life. The majority of strategies currently used in tissue engineering employ a scaffold, which is used to organize cells in a three-dimensional (3D) structure to direct the growth and formation of the desired tissue. Additive manufacturing (AM) processes, which build parts layer by layer through the addition of material, are frequently used in scaffold fabrication because of their ability to create parts with highly reproducible architecture and compositional variation. Despite the various developments in scaffold-based tissue engineering, existing scaffold fabrication systems do not permit precise placement of multiple cell types in high cell densities inside a 3D porous architecture. Existing multi-material bioprinting systems are only capable of (1) depositing one material at a time and/or (2) concurrently depositing multiple materials at a fixed spacing and with a fixed deposition velocity. Furthermore, existing scaffold fabrication systems do not allow successful tissue generation due to low cell density, decreased cell interaction, prolonged degradation times, and associated toxicity issues.

Bone defects in the craniomaxillofacial skeleton due to congenital defects or acquired injuries affect hundreds of thousands of people every year in the United States. Such defects are functionally debilitating, socially incapacitating, and medically and economically burdensome. These defects need to be treated for protection of the brain and for aesthetic and functional restoration of the calvaria of the bones. In general, patients with critical calvarial defects require countless procedures and are often left with poor aesthetic and functional results. Existing approaches for treating calvarial defects include autogenous bone grafts, allogeneic banked bone, demineralized matrix pastes, ceramic and polymeric scaffolds, and bone substitutes such as calcium ceramics. However, due to deficiencies in these existing approaches, successful healing of critically sized defects remains a significant challenge.

Thus, there is a need in the pertinent art for a bioprinter that is capable of simultaneously dispensing multiple biomaterials using at least two arms that selectively and independently move during deposition of the biomaterials. There is a further need in the pertinent art for a bioprinter that permits precise placement of multiple cell types in high-density porous tissue constructs, including, for example, perfusable vascularized tissue constructs, multi-cellular tissue constructs, and multi-material tissue constructs. There is still a further need in the pertinent art for vascularized scaffold-free tissue constructs. There is still a further need in the pertinent art for compositions, systems, and methods of treating tissue defects, including bone defects such as calvarial defects.

SUMMARY

Described herein, in one aspect, is a bioprinter having a processor, a support assembly, and at least two printer heads. The processor is configured to determine a desired tool path, optionally based upon at least one input from a user or other device. Each printer head is operatively coupled to the processor. Each printer head has an arm assembly with a proximal portion and a distal portion. The proximal portion of the arm of each printer head can be operatively coupled to the support assembly such that the arm assembly is selectively moveable relative to at least a first axis. Each printer head also has a nozzle assembly operatively coupled to the distal portion of the arm assembly of the printer head. The nozzle assembly of each printer head is configured to receive and dispense at least one biomaterial as the arm assembly of the printer head is moved relative to at least the first axis. The processor is configured to selectively adjust the positioning of the arm assembly of each printer head relative to at least the first axis in accordance with the desired tool path.

Optionally, the distal portion of the arm assembly can be selectively rotatable relative to the proximal portion of the arm assembly. The nozzle assembly can be configured to receive and dispense at least one biomaterial as the arm assembly is selectively moved relative to the first axis and the distal portion of the arm assembly is selectively rotated relative to the proximal portion of the arm assembly.

Optionally, the nozzle assembly of at least one printer head of the bioprinter can have a longitudinal axis, an outer nozzle, and an inner nozzle. The outer nozzle can have a proximal end, a distal end, an outer surface, and an inner surface. The inner surface of the outer nozzle can define a central bore and an inner diameter of the outer nozzle. The outer surface of the outer nozzle can define an inlet positioned in communication with the central bore, and the inner surface of the distal end of the outer nozzle can define an outlet in communication with the central bore. The inner nozzle can have a proximal end, a distal end, an outer surface, and an inner surface. The outer surface can define an outer diameter of the inner nozzle. The inner surface can define a central bore. The inner surface of the proximal end can define an inlet, and the inner surface of the distal end can define an outlet. The inner nozzle can be at least partially received within the central bore of the outer nozzle such that the outer nozzle and the inner nozzle have a common longitudinal axis that is in substantial alignment with the longitudinal axis of the nozzle assembly. The outer diameter of the inner nozzle can be less than the diameter of the outlet of the outer nozzle to thereby define a receiving space between the outer surface of the first nozzle and the inner surface of the outer nozzle. The inlet of the outer nozzle can be configured to receive at least one biomaterial and deliver the at least one biomaterial to the receiving space. The outlet of the outer nozzle can be configured to dispense the at least one biomaterial from within the receiving space. The inlet of the inner nozzle can be configured to receive at least one biomaterial and deliver the at least one biomaterial to the central bore of the inner nozzle, and the outlet of the inner nozzle can be configured to dispense the at least one biomaterial from within the central bore of the inner nozzle.

Optionally, the nozzle assembly of at least one printer head of the bioprinter can have means for maintaining the at least one biomaterial within the nozzle assembly at a desired temperature until the at least one biomaterial is dispensed from the nozzle assembly.

The bioprinter can optionally be provided as part of a bioprinting system for treating a tissue defect of a subject. The bioprinting system can have a scanner that is configured to scan the tissue defect and to generate an output indicative of the location of the tissue defect. The processor of the bioprinter can be configured to receive the output from the scanner, and the processor can be further configured to selectively adjust the positioning of the arm assembly of each printer head to permit printing of the at least one biomaterial directly into the tissue defect.

Methods of using the disclosed bioprinters are also described. For example, the disclosed bioprinters can be used to produce a tissue construct, such as, for example and without limitation, a vascular network or a bio-ink composition. In exemplary applications, the disclosed bioprinters can be used to print a tissue construct directly onto a tissue defect.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

Figure 6:
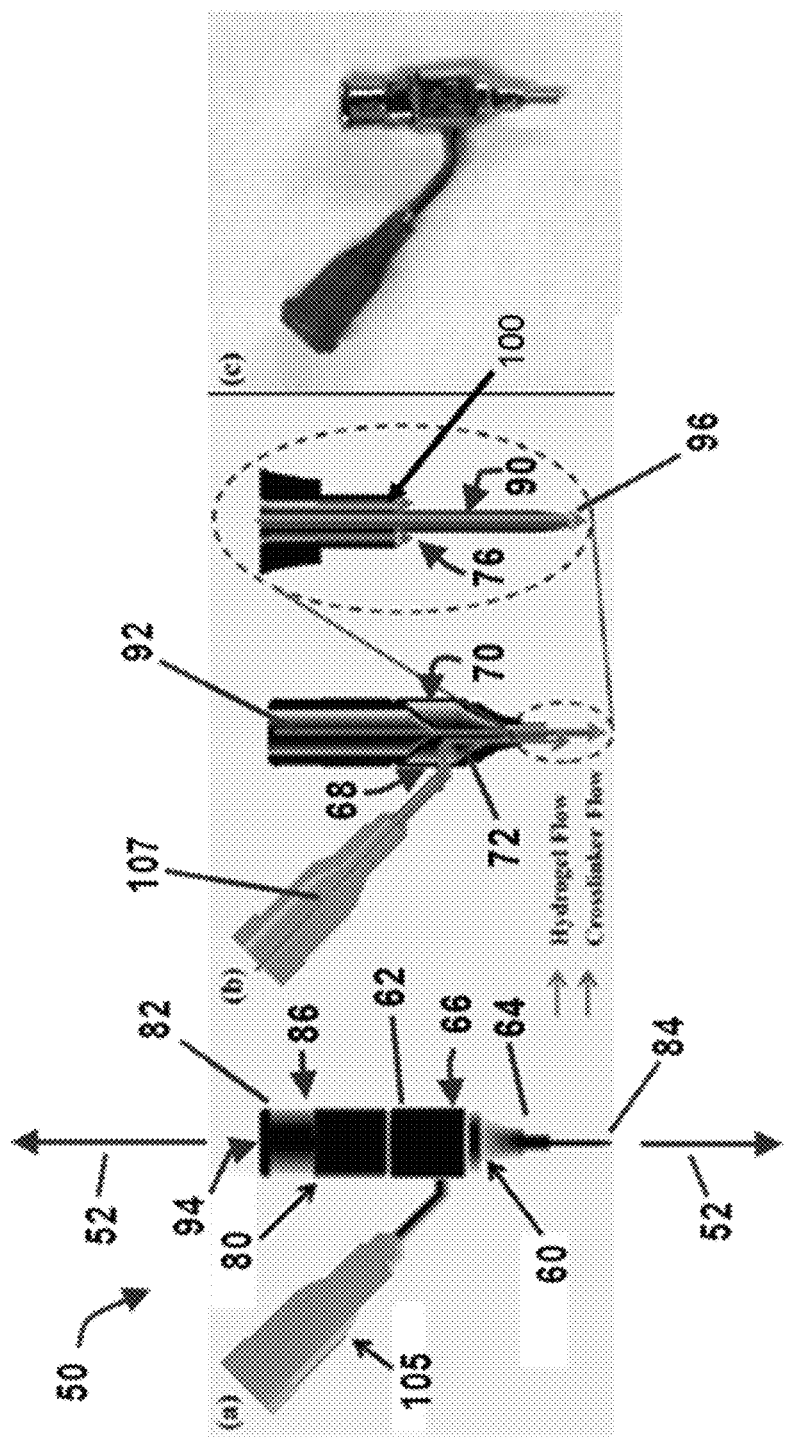

FIG. 6A depicts a three-dimensional model of an exemplary co-axial nozzle assembly as disclosed herein. FIG. 6B depicts a cross-sectional view of hydrogel and crosslinker flow within the nozzle assembly of FIG. 6A. FIG. 6C is an image of an exemplary co-axial nozzle assembly as disclosed herein.

Figure 7:
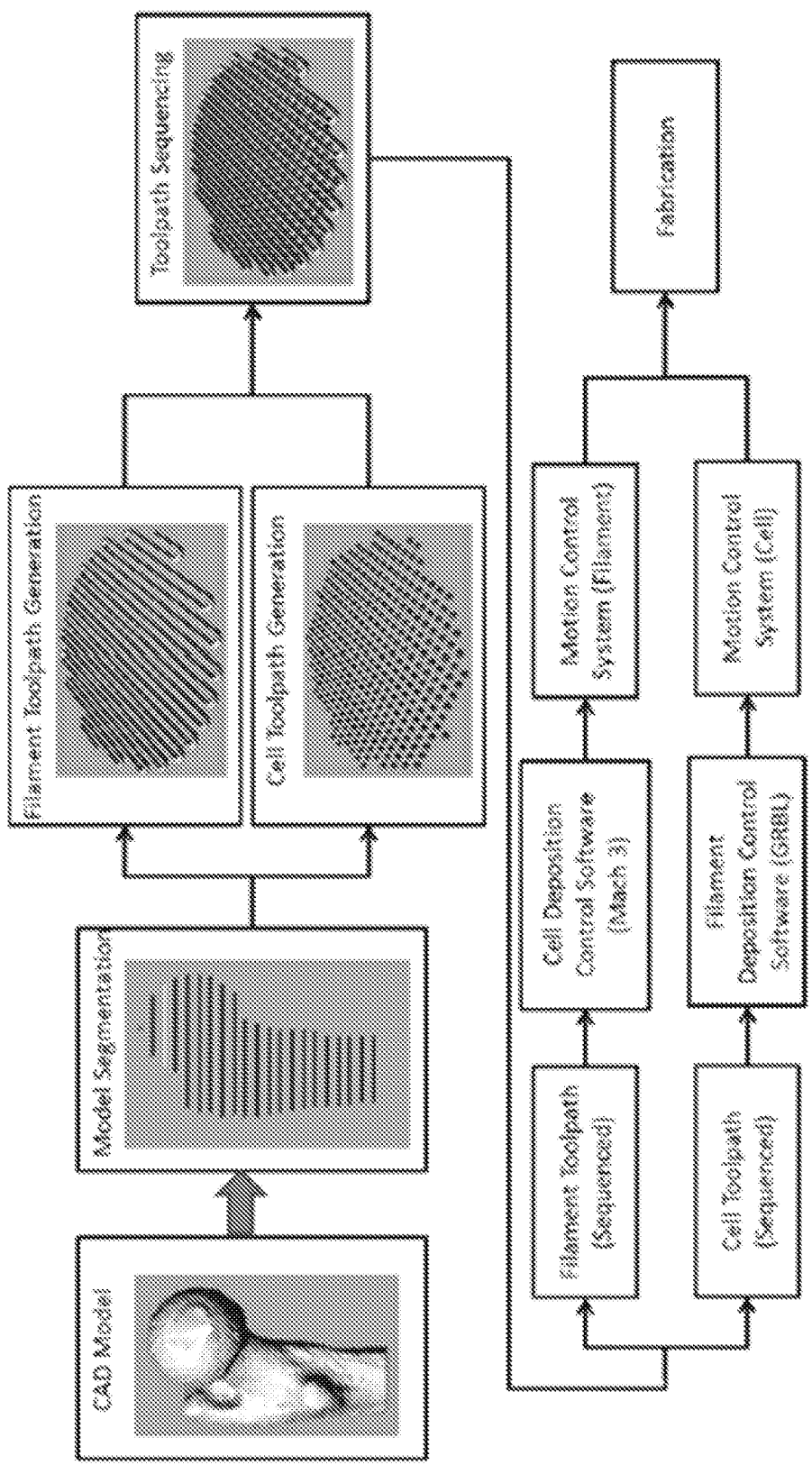

FIG. 7 is a schematic diagram depicting the operation of an exemplary bioprinter as disclosed herein.

Figure 8:
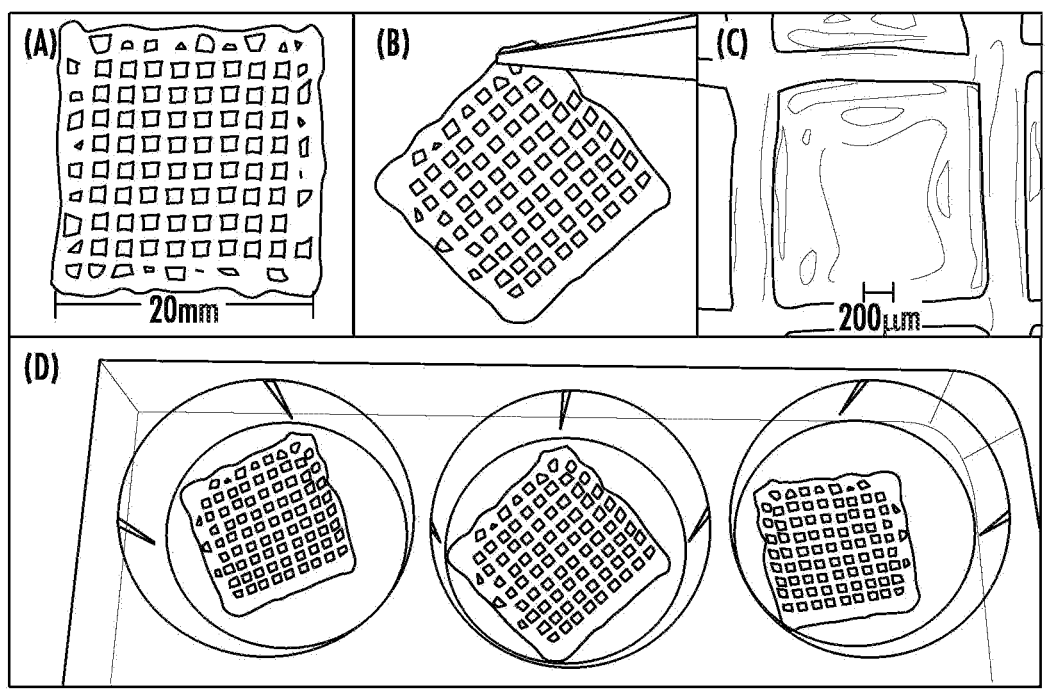

FIG. 8A is a top view of an exemplary 20 mm×20 mm, 20-layer alginate tissue construct produced using a bioprinter as disclosed herein. FIG. 8B is a side view of the alginate tissue construct of FIG. 8A, with the tissue construct positioned in a vertical position. FIG. 8C is a microscopic top view of the alginate tissue construct of FIG. 8A. FIG. 8D is an image of a two-week in-vitro culture of tissue constructs showing structural integrity.

Figure 9:
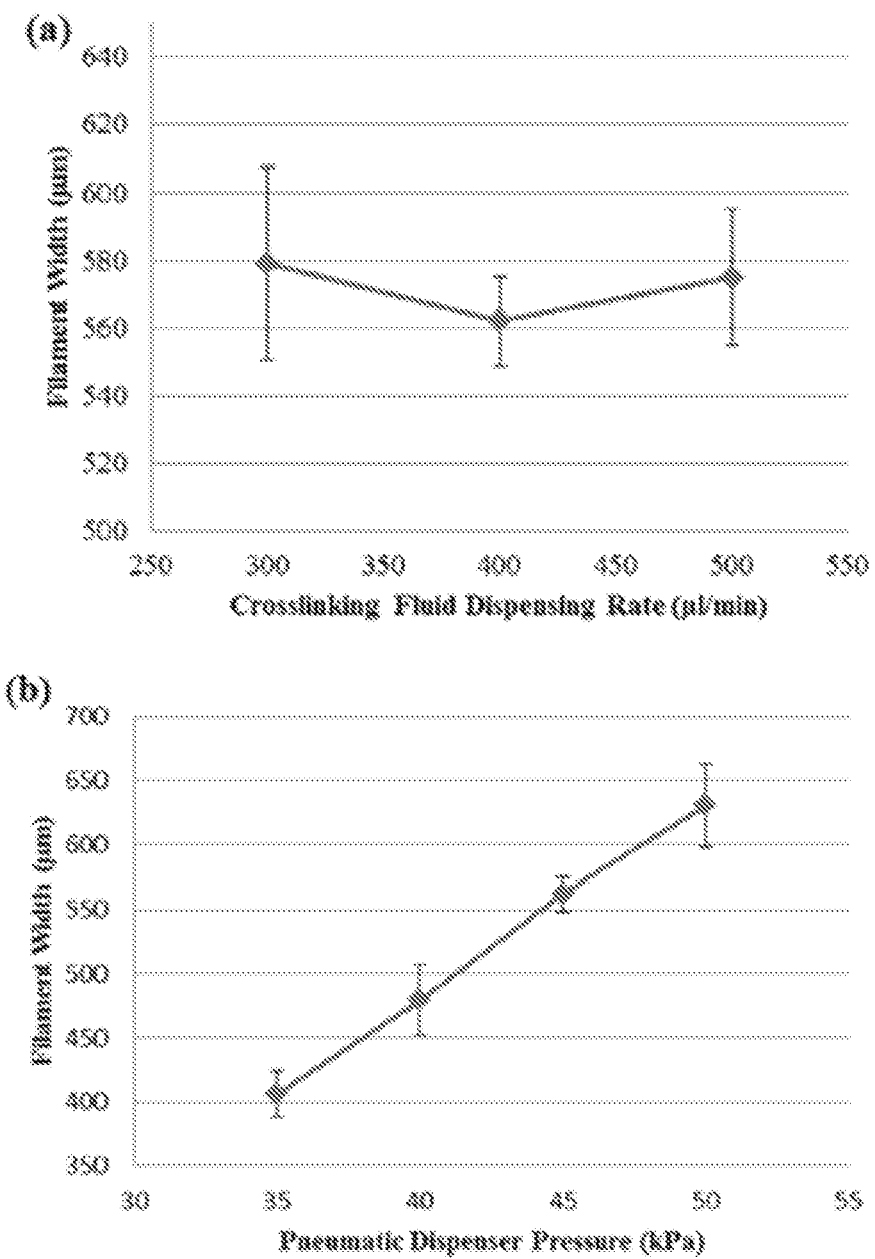

FIG. 9A is a graph depicting the measured width of filaments produced at various crosslinking fluid dispensing rates at a 45 kPa hydrogel dispensing pressure. FIG. 9B is a graph depicting the filament width measured at various crosslinking fluid dispensing rates at a dispensing rate of 400 µl/min.

Figure 10:
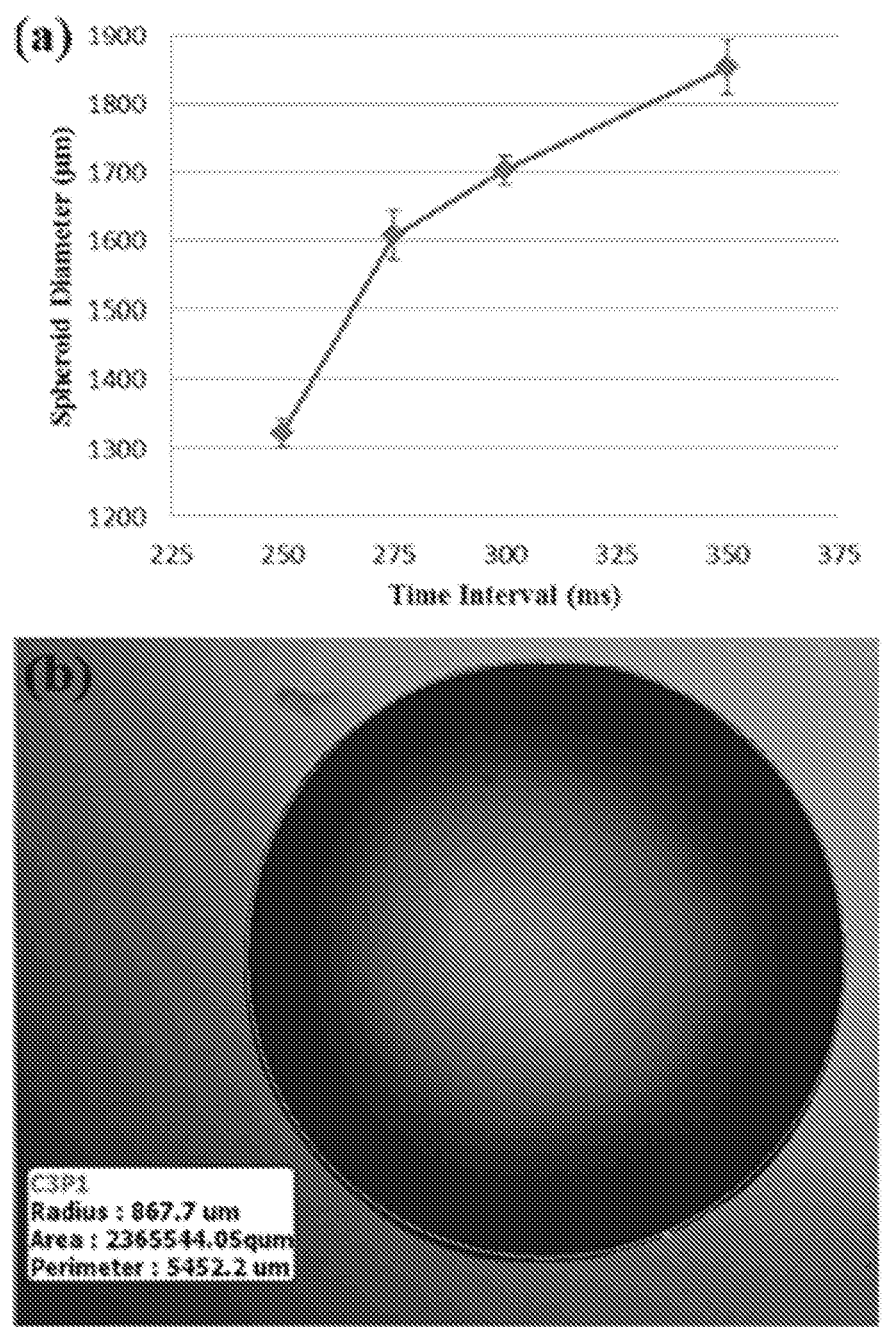

FIG. 10A depicts cell spheroid diameter measured at various time intervals. FIG. 10B depicts a sample measurement of spheroid diameter.

FIG. 11A depicts alginate sphere deposition on a multi-layer tissue construct halfway through the deposition process. FIG. 11B depicts alginate sphere deposition on a multi-layer tissue construct toward the end of the deposition process. FIG. 11C depicts the formation of an alginate sphere on a nozzle tip as disclosed herein. FIG. 11D depicts the deposition of an alginate sphere between filaments of a vascular network as disclosed herein. FIG. 11E depicts a 20 mm×20 mm sample tissue construct containing alginate spheres between the filaments, as disclosed herein. FIG. 11F depicts the spheroids and filaments under light microscopy.

Figure 12:
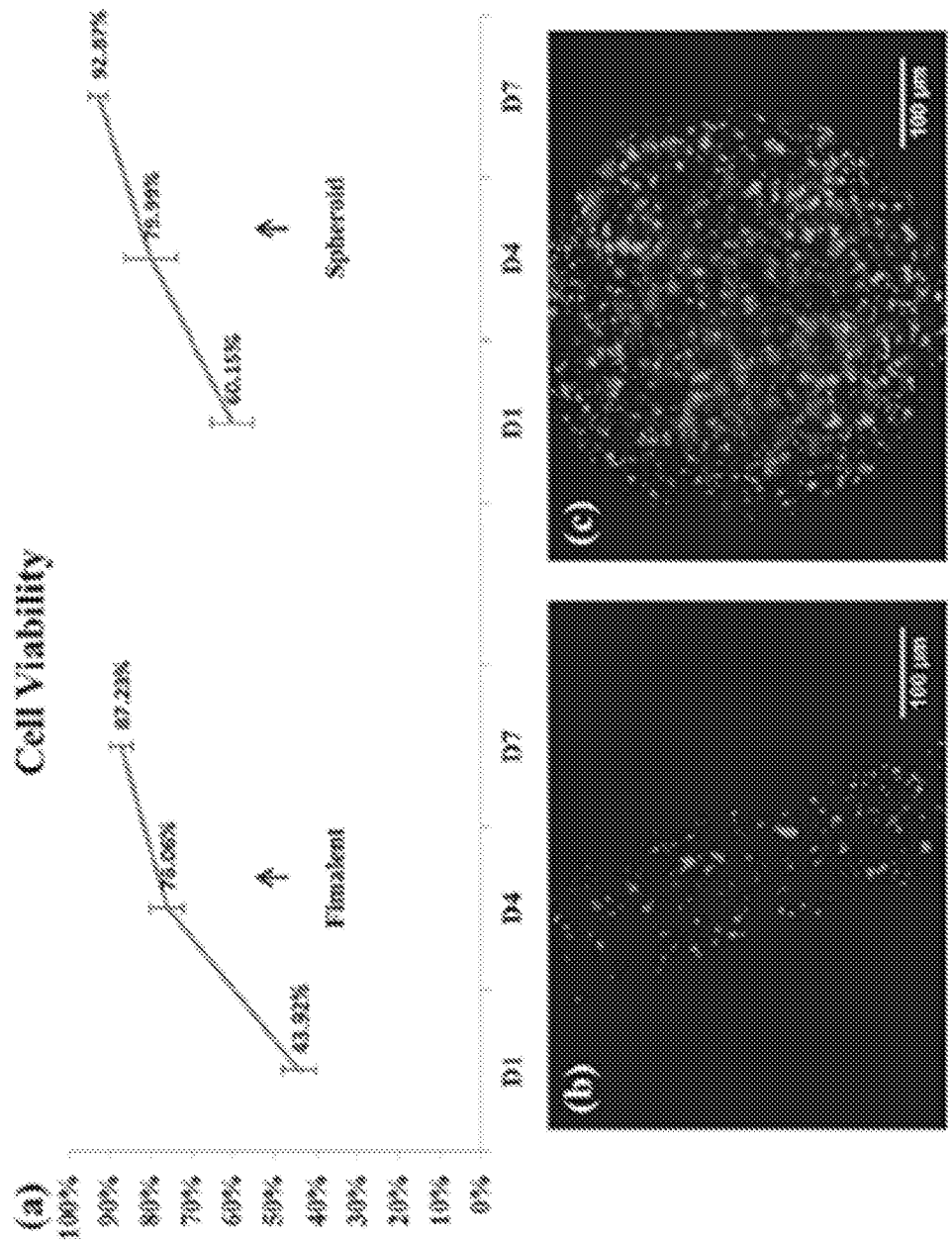

FIGS. 12A-12C depict cell viability over a 7-day culture period for filaments of a vascular network and spheroids as disclosed herein. FIG. 12A shows that relatively low cell viability was obtained one day after printing, whereas the viability rate increased during in vitro culturing, and fewer dead cells were observed after 7 days of culturing. FIG. 12B depicts a fluorescence image of the filaments of the vascular network. FIG. 12C depicts a fluorescence image of the spheroids.

Figure 13:
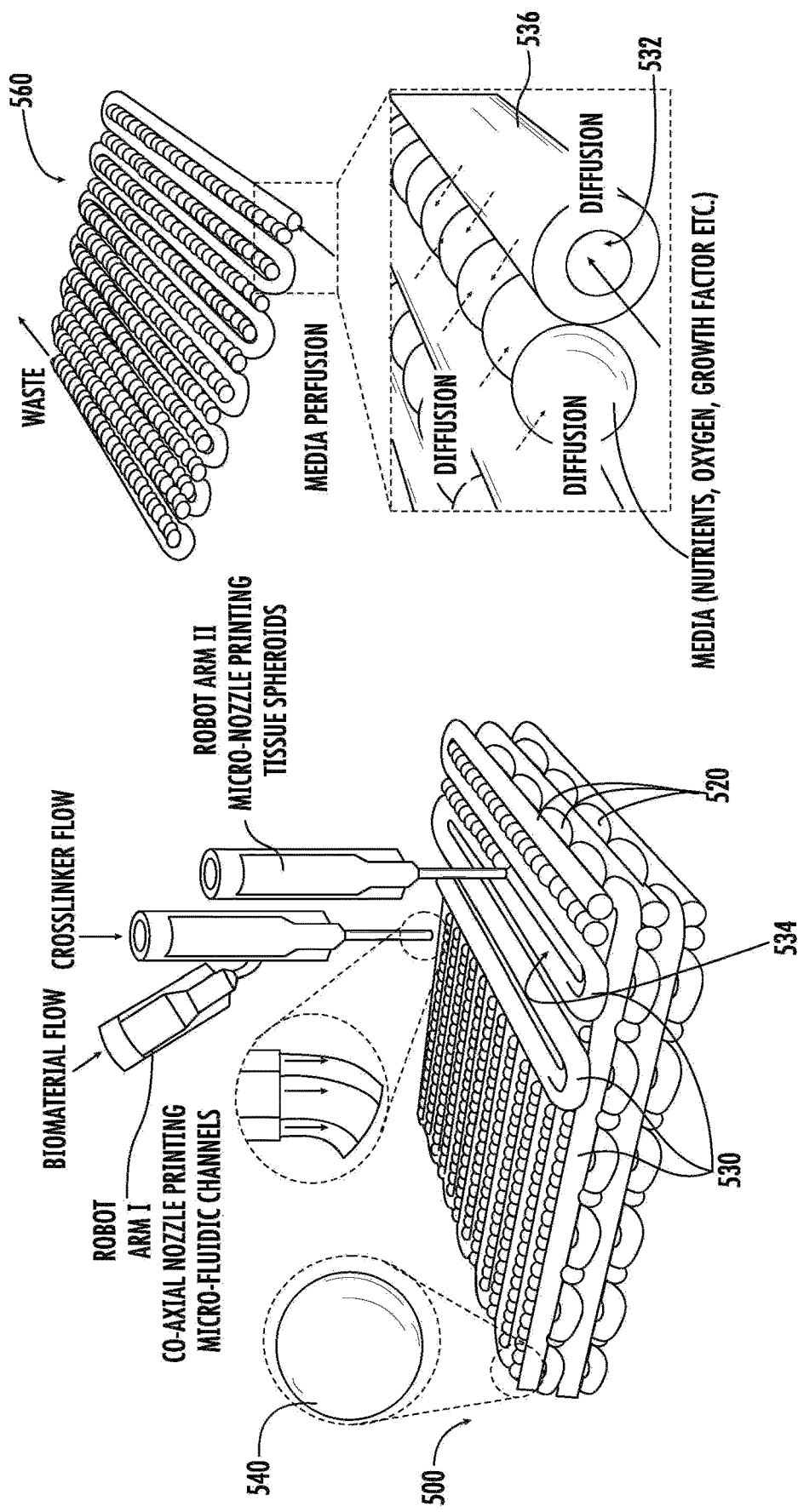

FIG. 13 schematically depicts an exemplary tissue construct produced by a bioprinter as disclosed herein. As shown, a vascular network was printed in tandem with tissue spheroids layer by layer, and the printed tissue construct can be connected to a bioreactor for media perfusion.

FIGS. 14A-14C depict an exemplary cellular vascular network printed by a bioprinter as disclosed herein. FIG. 14A depicts the perfusion of oxygenized cell type media. FIG. 14B depicts media flow with intentionally generated air bubbles. FIG. 14C depicts a laser confocal image of the mid-plane showing a single-lumen channel with live/dead staining where CPCs are labeled with calcein AM and ethidium homodimer.

Figure 15A:
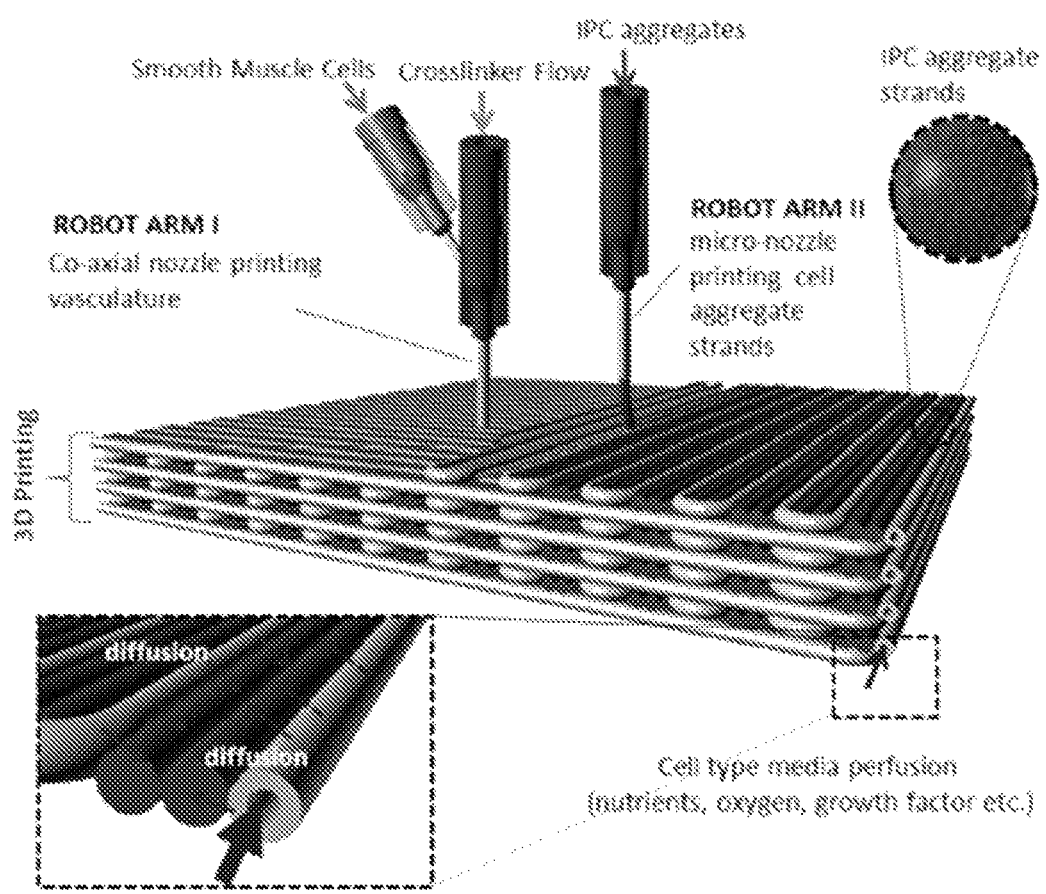
Figure 15B:

FIG. 15A depicts an exemplary hybrid bioprinting concept in which a tissue construct having cylindrical strands of cell aggregates interspersed with tubular micro-fluidic channels. FIG. 15B shows a mature version of the tissue construct produced as shown in FIG. 15A.

Figure 16:
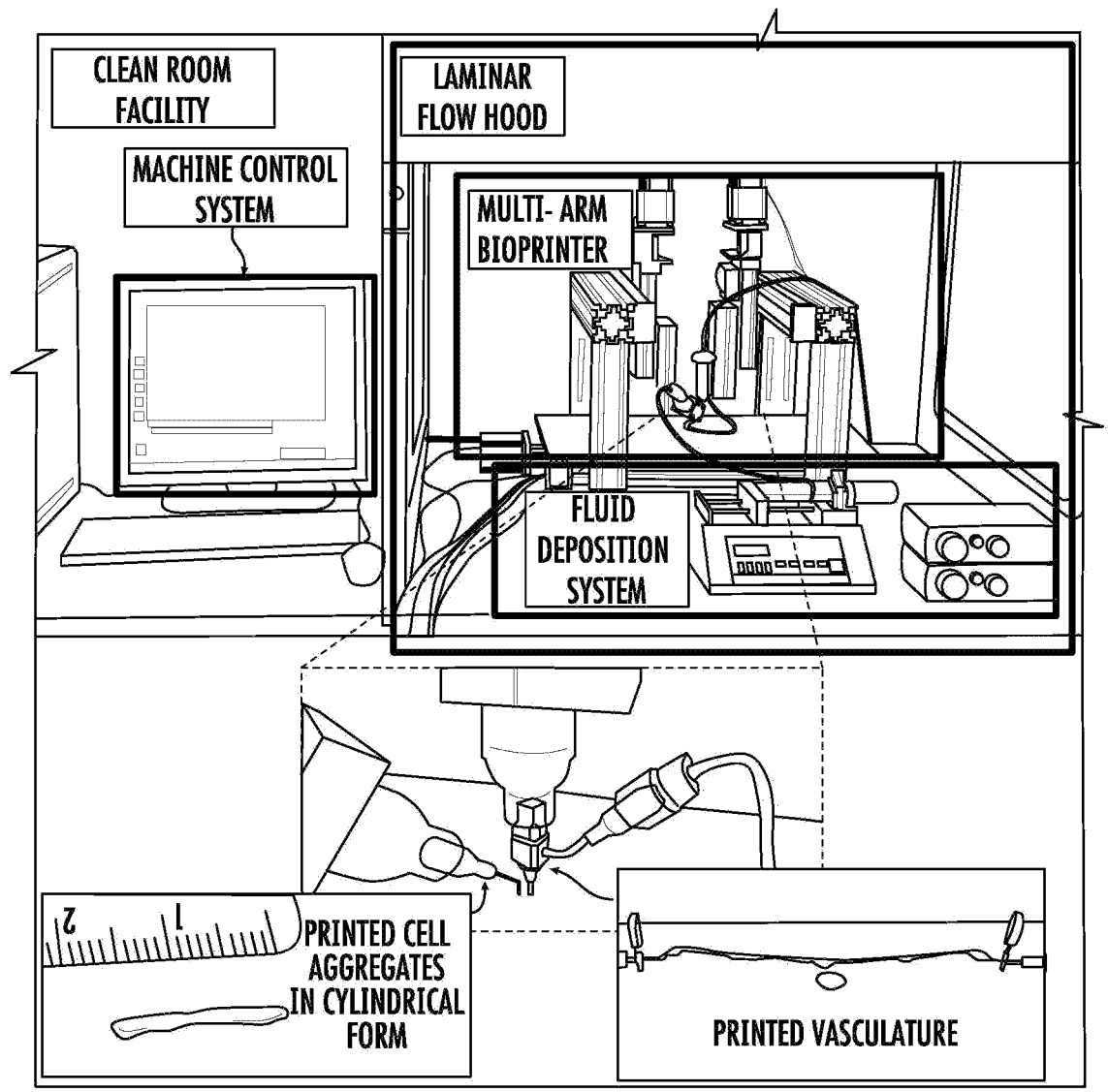

FIG. 16 depicts an exemplary bioprinter system as disclosed herein.

Figure 17A:
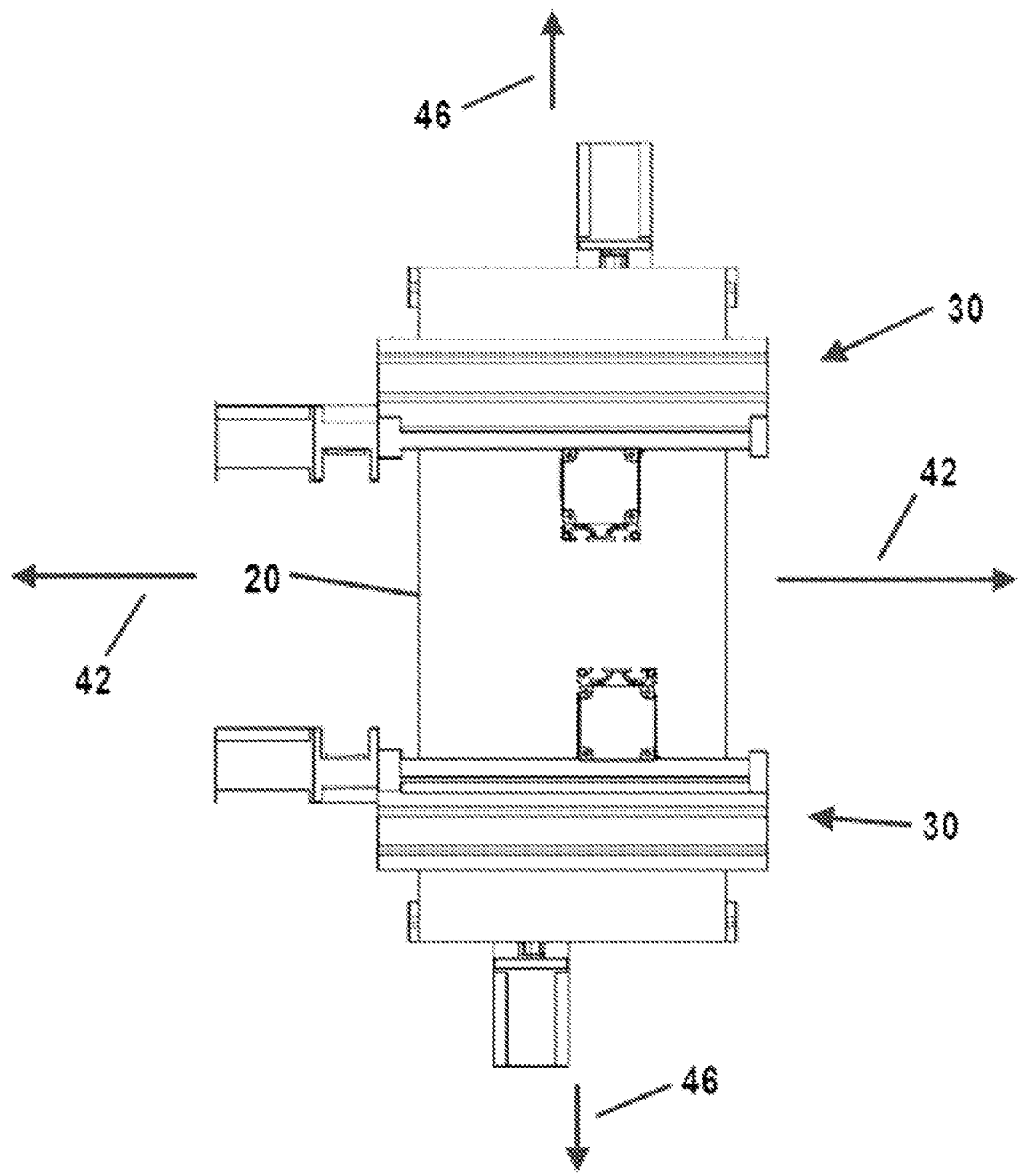
Figure 17B:
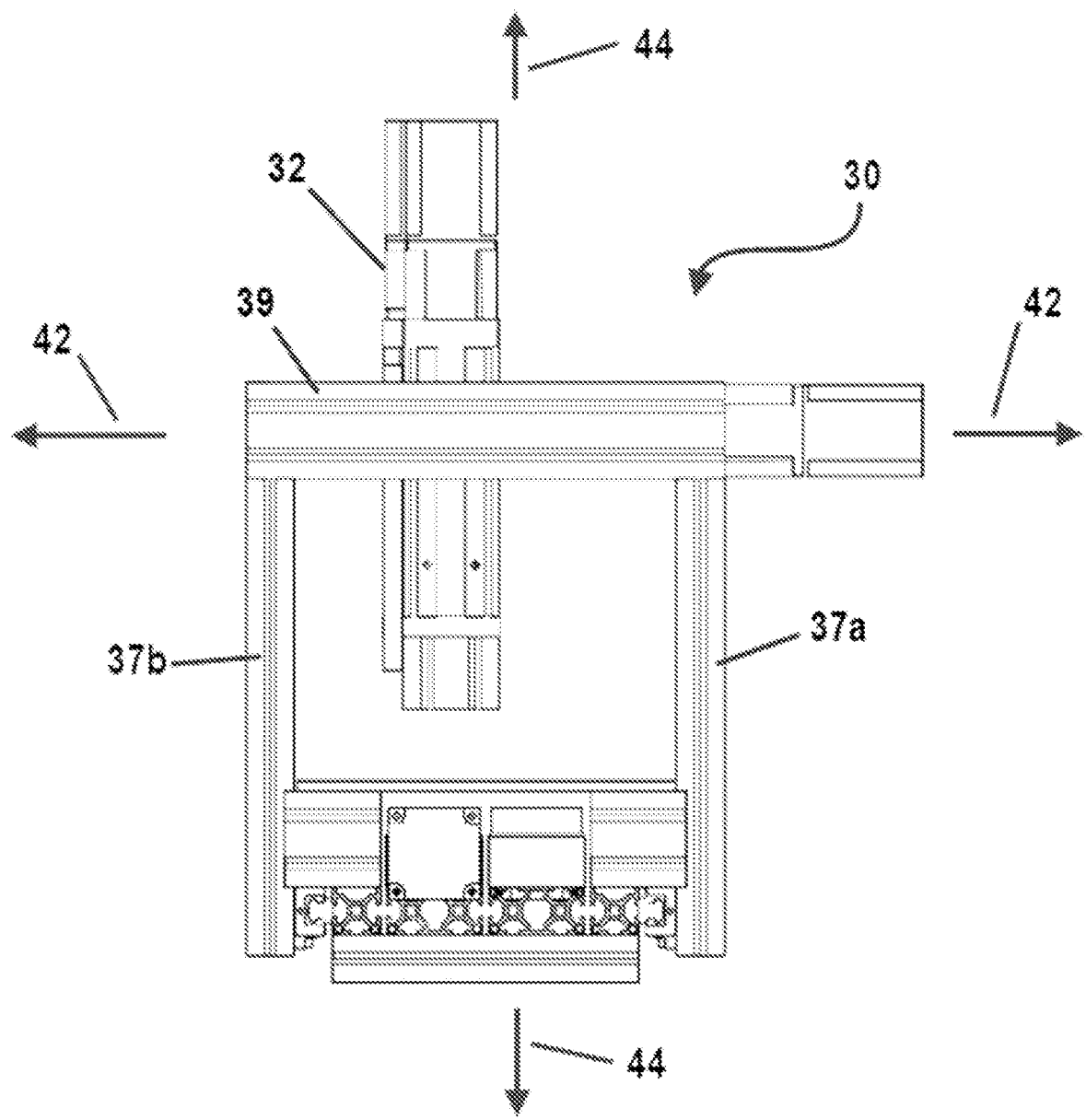

FIGS. 17A-17B are various perspective views of an exemplary bioprinter as disclosed herein. FIG. 17A is a top perspective view of an exemplary bioprinter as disclosed herein. FIG. 17B is a rear perspective view of an exemplary bioprinter as disclosed herein.

Figure 18:
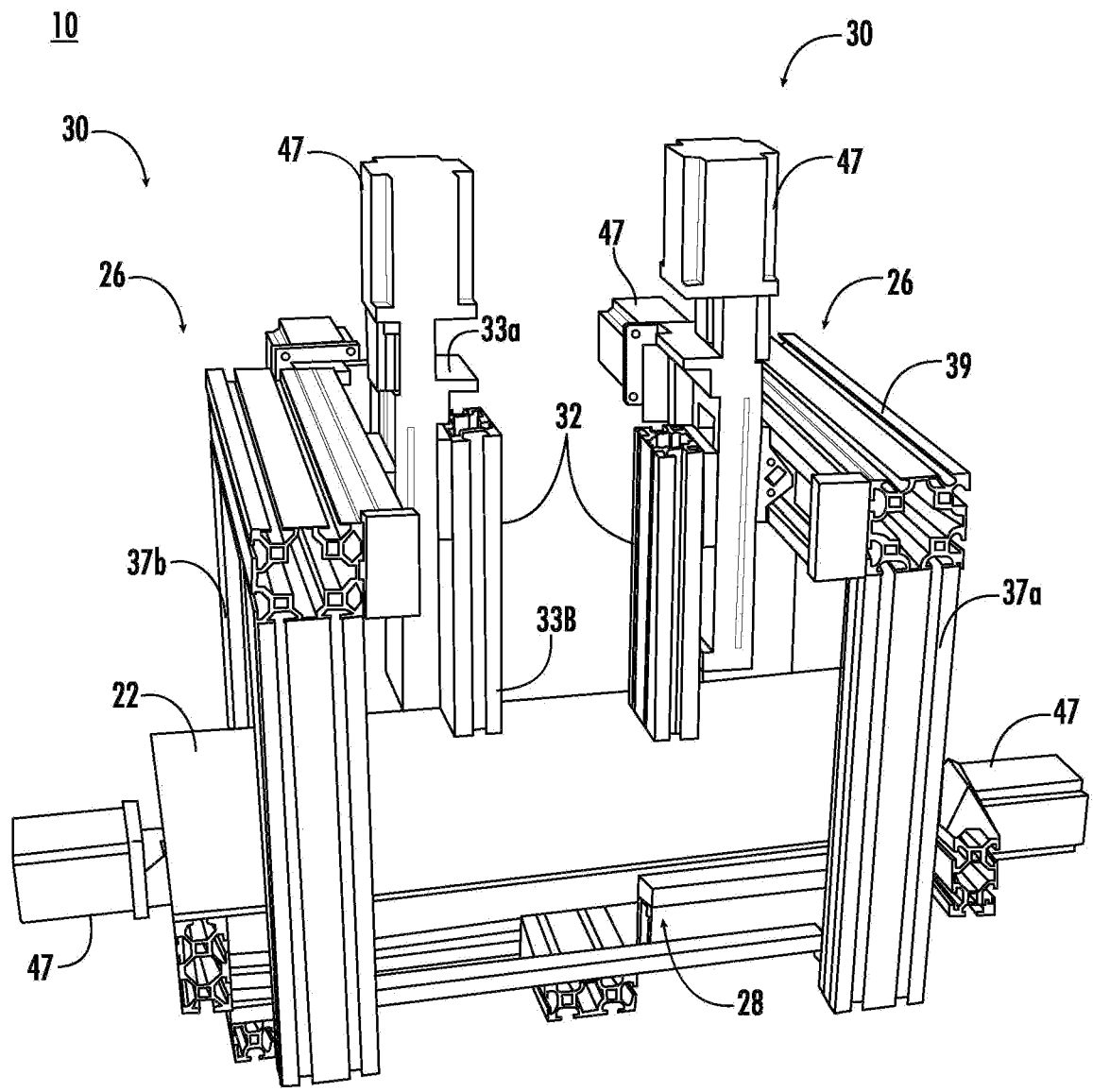

FIG. 18 is a side perspective view of an exemplary bioprinter as disclosed herein.

Figure 19:
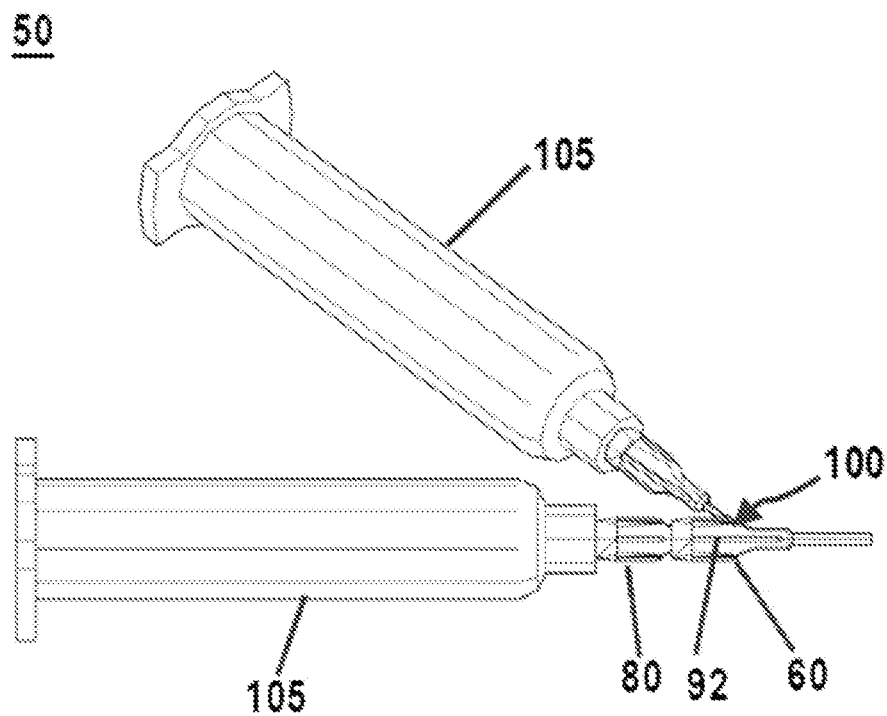

FIG. 19 is a perspective view of an exemplary co-axial nozzle assembly as disclosed herein.

Figure 20:
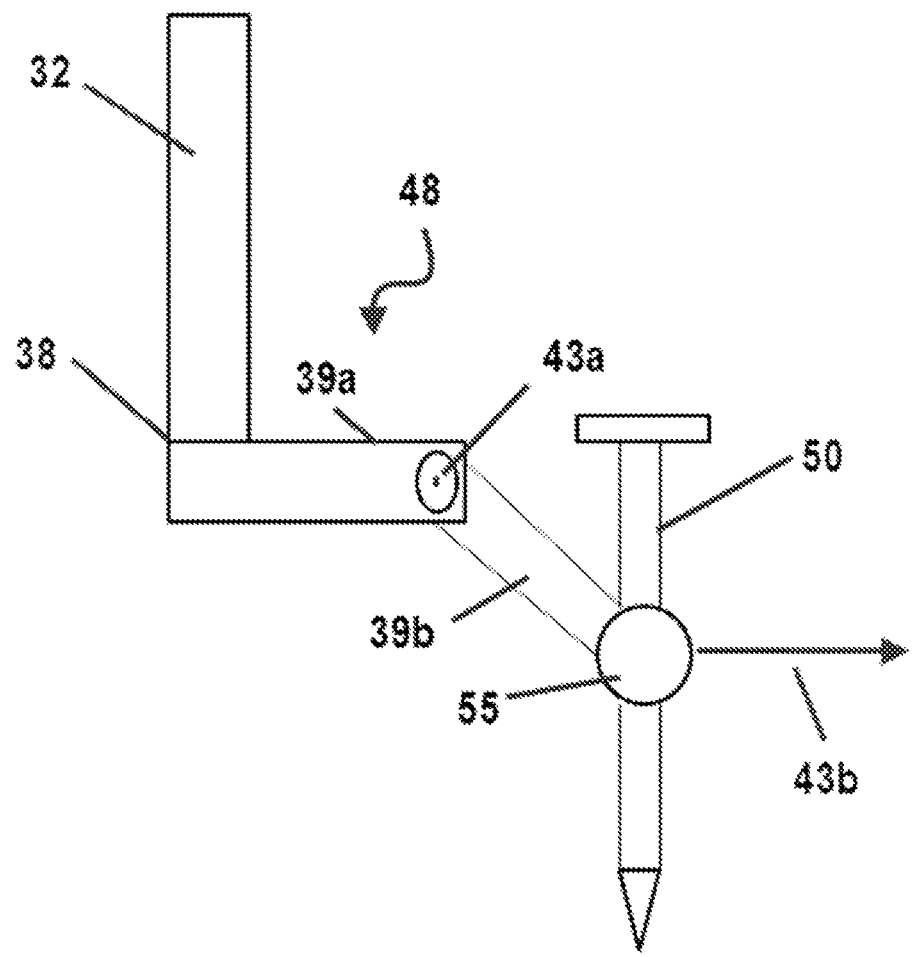

FIG. 20 is an isolated side perspective view of an exemplary nozzle support portion of a printer head assembly as disclosed herein. As shown, the nozzle support portion can be configured to securely receive and support at least a portion of the nozzle assembly. The nozzle support portion can be operatively coupled to the distal portion of the arm assembly such that, when the nozzle assembly is engaged by the nozzle support portion, the nozzle assembly can be selectively rotated relative to one or more rotational axes.

Figure 21:
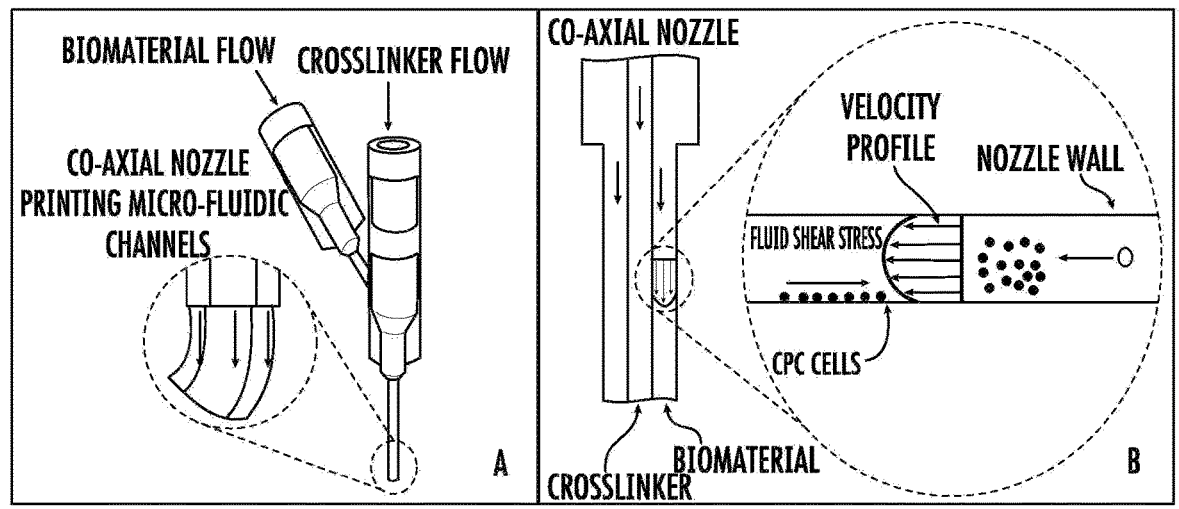

FIGS. 21A-21B depict an exemplary coaxial nozzle assembly and associated mechanical forces. FIG. 21A depicts an exemplary coaxial nozzle design for tubular channel manufacturing. FIG. 21B depicts the shear stress generated by the exemplary coaxial nozzle system.

Figure 22:
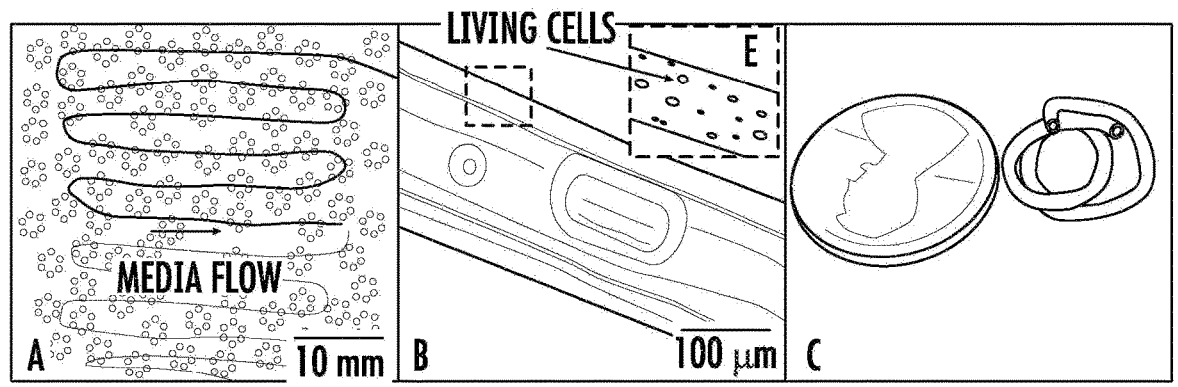

FIGS. 22A-22C depict exemplary bioprinted cell-laden tubular constructs. FIG. 22A depicts tubular channels that were printed into a zigzag orientation with perfused cell-type media. FIG. 22B depicts bubble inclusion in a tubular center demonstrating its hollow feature and microscopy images showing cell encapsulation in the wall of cellular channels with relatively uniform distribution of cells. FIG. 22C depicts a 1-week cultured cell-laden tubular channel showing promising mechanical and structural integrity.

Figure 23:
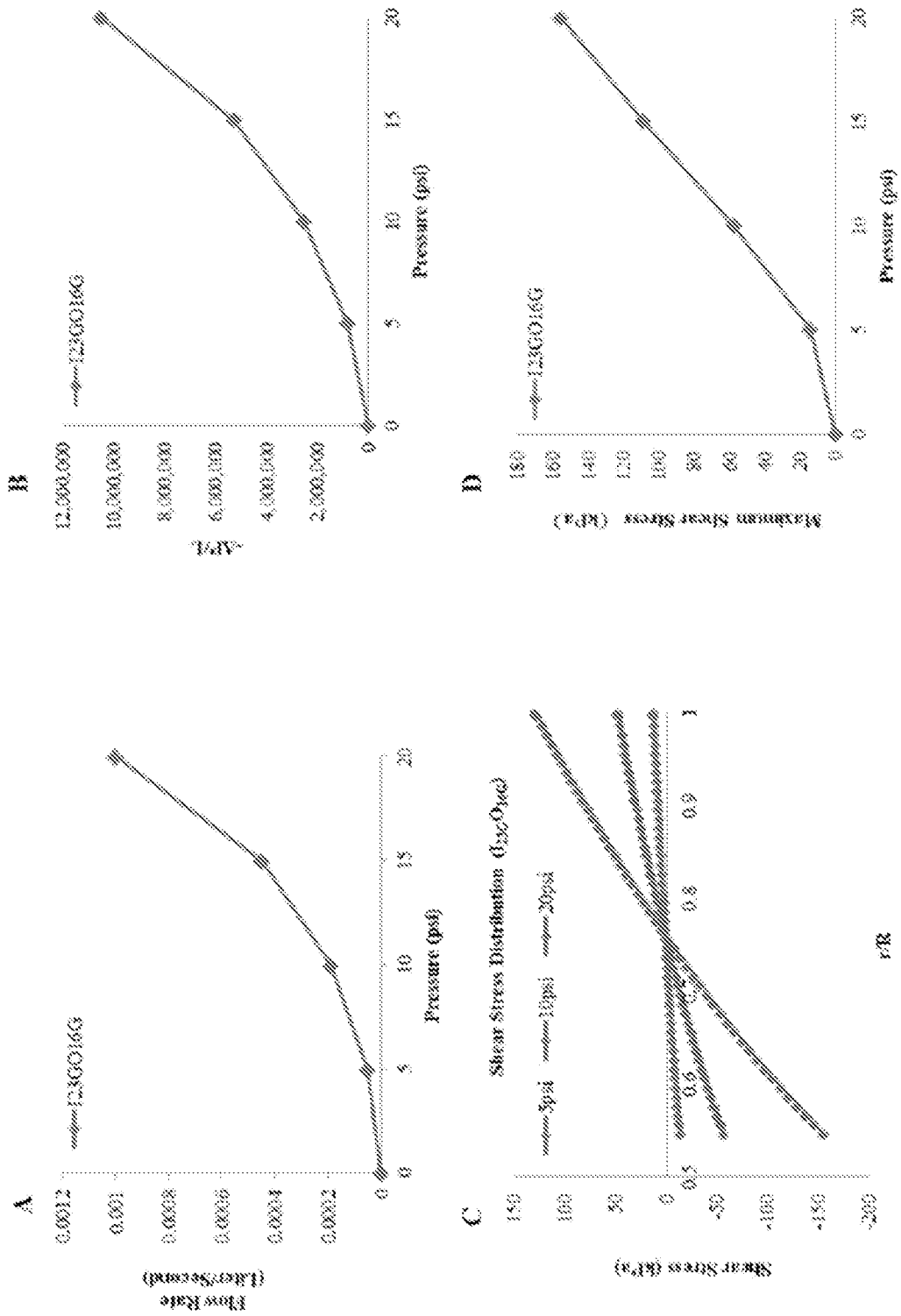

FIGS. 23A-23D depict exemplary dispensing rheology for a co-axial nozzle assembly having a 23 gauge inner nozzle and a 16 gauge outer nozzle ($I_{23G}O_{16G}$) as disclosed herein. FIG. 23A graphically depicts the effect of alginate pressure rate on volume flow rate of 4% alginate solution. FIG. 23B depicts the effect of pressure rate on $-\Delta P/L$. FIG. 23C depicts the shear stress distribution in coaxial nozzles. FIG. 23D depicts the maximum shear stress with varying alginate dispensing pressure.

Figure 24:
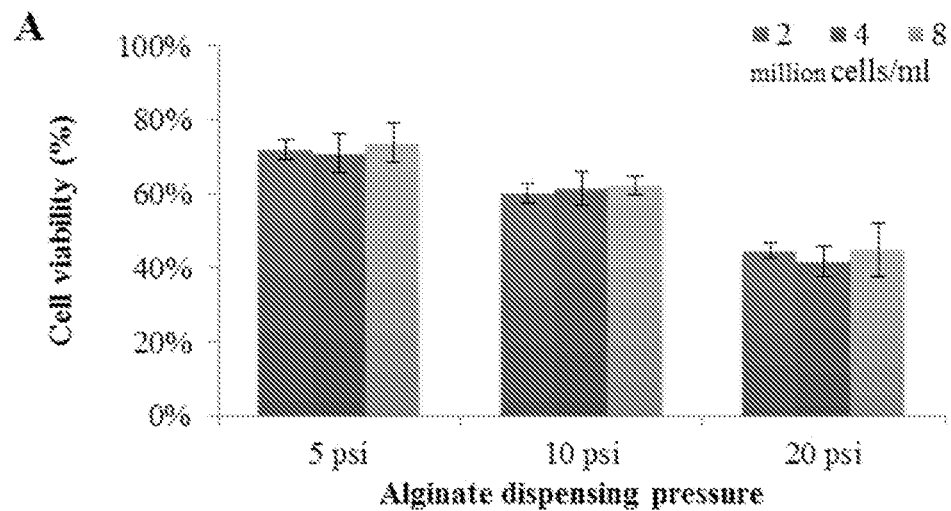
Figure 24:
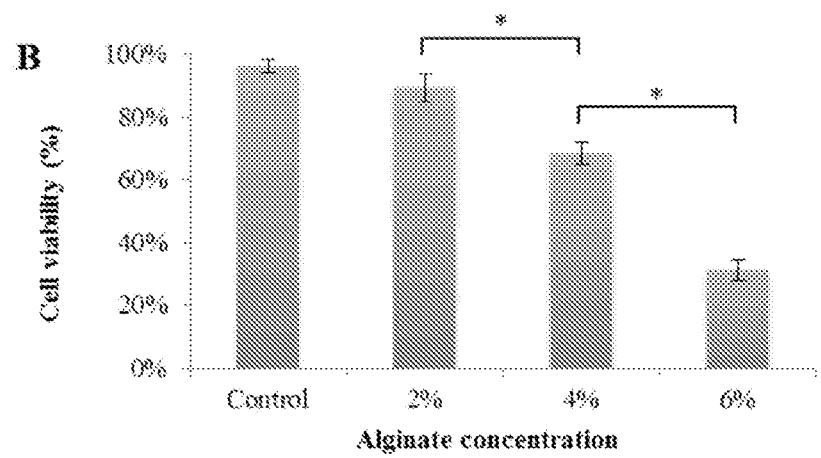

FIGS. 24A-24B depict quantitative cell viability for various cell densities and alginate concentrations. Specifically, FIG. 24A depicts the effect of cell density on cell viability at different alginate dispensing pressures, while FIG. 24B depicts the effect of sodium alginate concentration on cell viability at 5 psi with cell density of $2\times10^6$ cells/ml (data are mean±SD; $p<0.05$).

FIGS. 25A-25B depict laser confocal imaging for live/dead staining of the printed structure at 5 psi with $I_{23G}O_{16G}$ nozzle: CPCs labeled with calcein AM and ethidium homodimer after cell encapsulation and imaged with confocal laser scanning microscope. FIG. 25A shows that quantifiable dead cells were present, while most of cells were viable. FIG. 25B is a close-up image showing live and dead cells with fluorescence.

Figure 26:
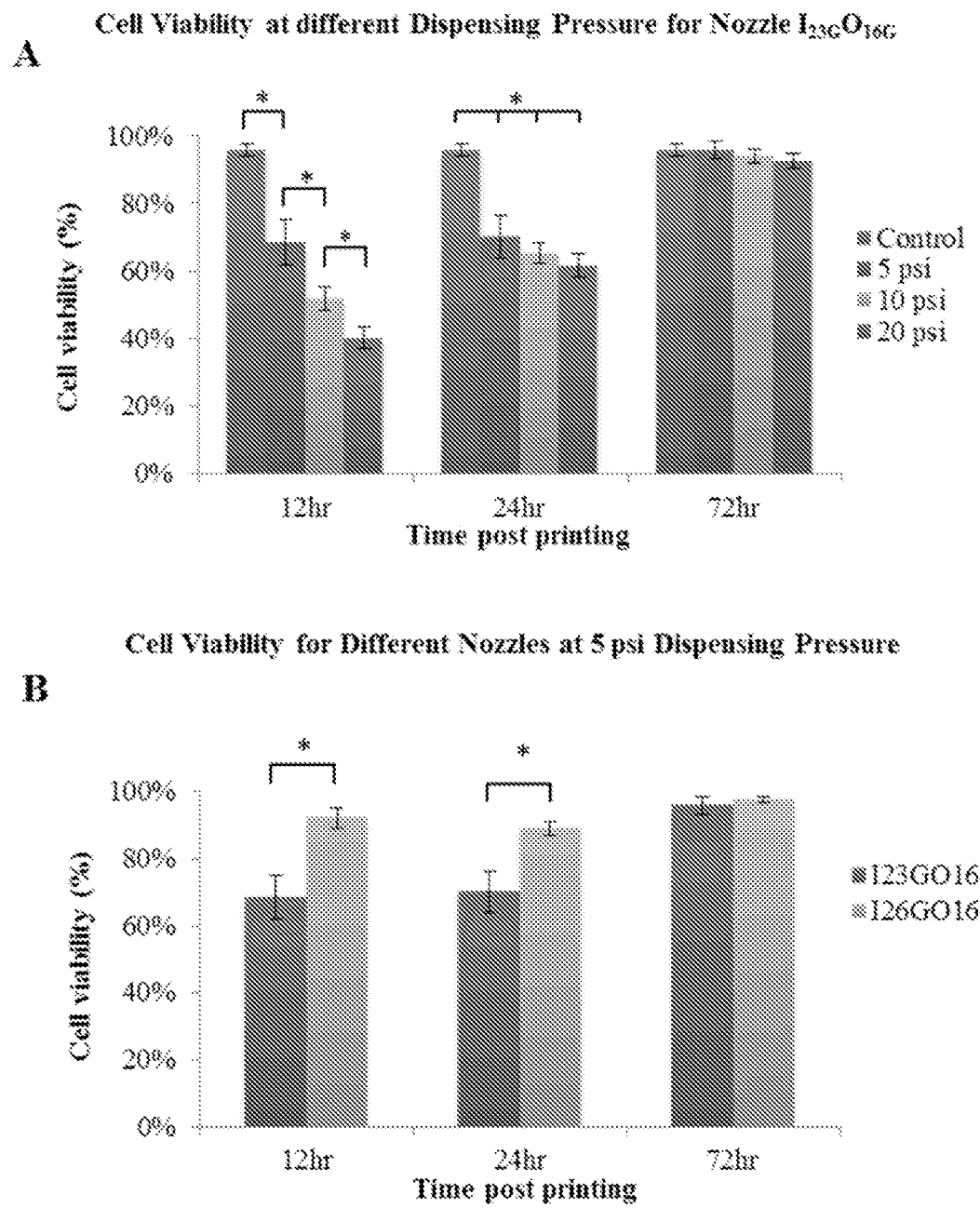

FIGS. 26A-26B demonstrate the effect of bioprinting parameters on cell viability for 72 hr post-bioprinting. FIG. 26A graphically depicts the effect of alginate dispensing pressure (psi) on cell viability. FIG. 26B graphically depicts the cell viability for different-sized coaxial nozzle assemblies (data are mean±SD; $p<0.05$).

Figure 27:
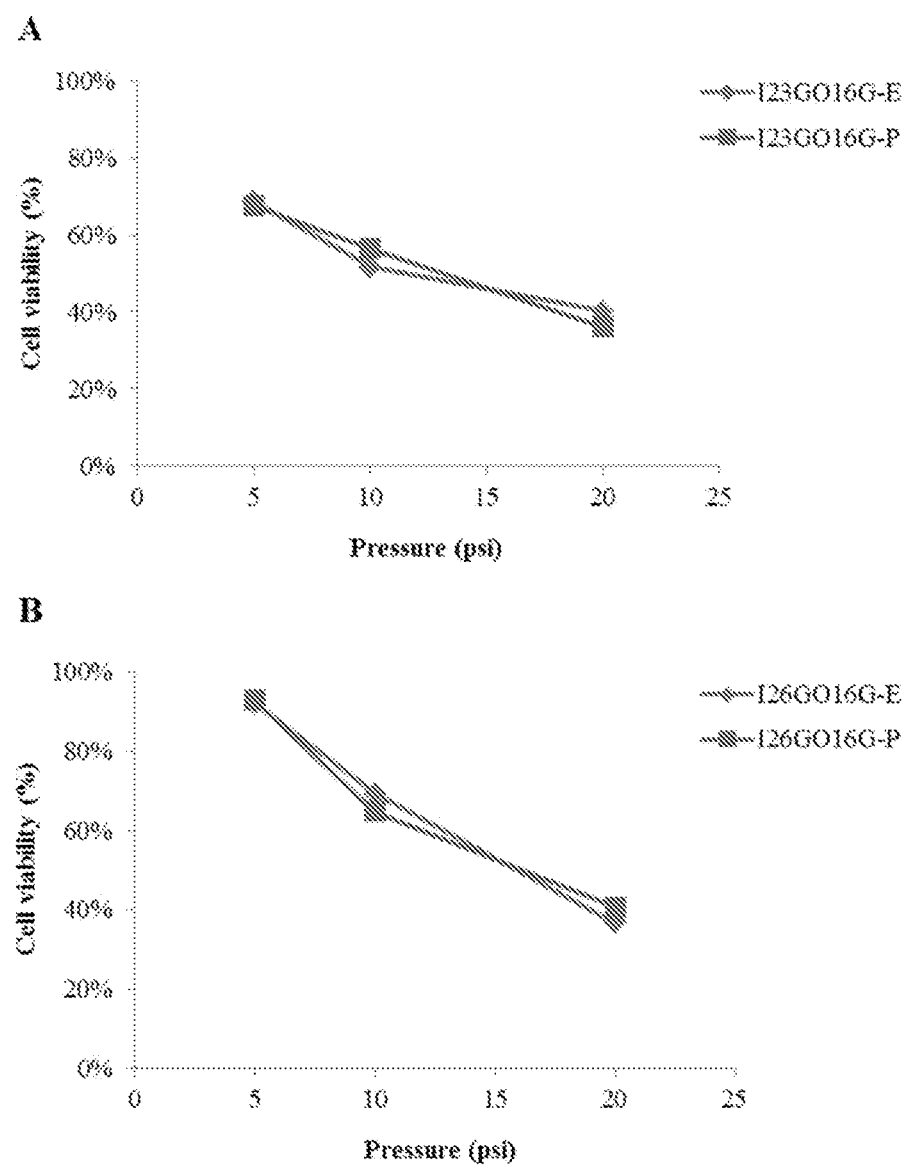

FIG. 27A depicts the experimental and predicted cell viability (E: experimental; P: predicted) for a co-axial nozzle having a 23 gauge inner nozzle and a 16 gauge outer nozzle ($I_{23G}O_{16G}$). FIG. 27B depicts the experimental and predicted cell viability (E: experimental; P: predicted) for a co-axial nozzle having a 26 gauge inner nozzle and a 16 gauge outer nozzle ($I_{26G}O_{16G}$).

Figure 28:
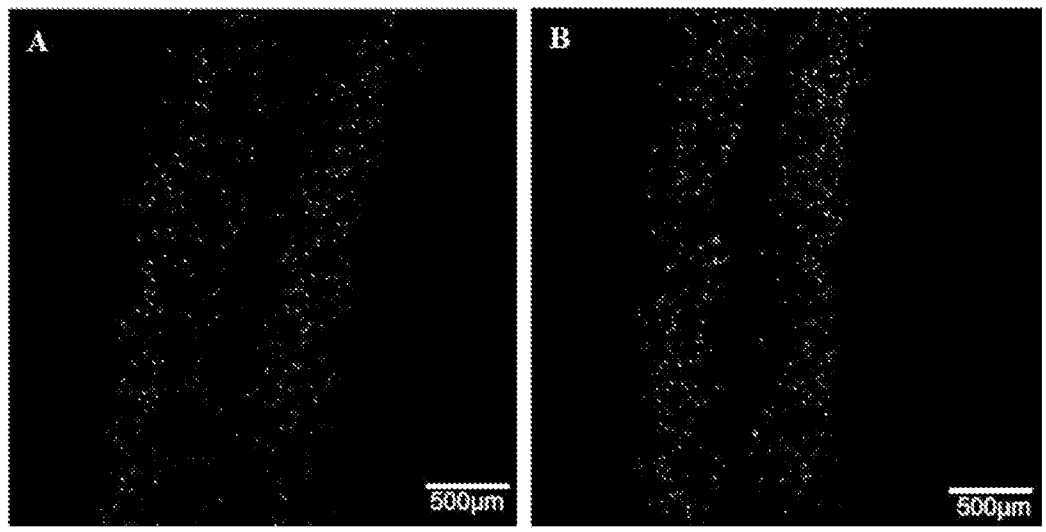

FIGS. 28A-28B depict laser confocal imaging for live/dead staining of a tissue sample at different time points. FIG. 28A shows the sample at 12 h post-printing, with massive cell death observed all over the printed structure. FIG. 28B shows the sample after 72 h incubation, with a few dead cells scattered among an increasing number of live cells.

Figure 29:
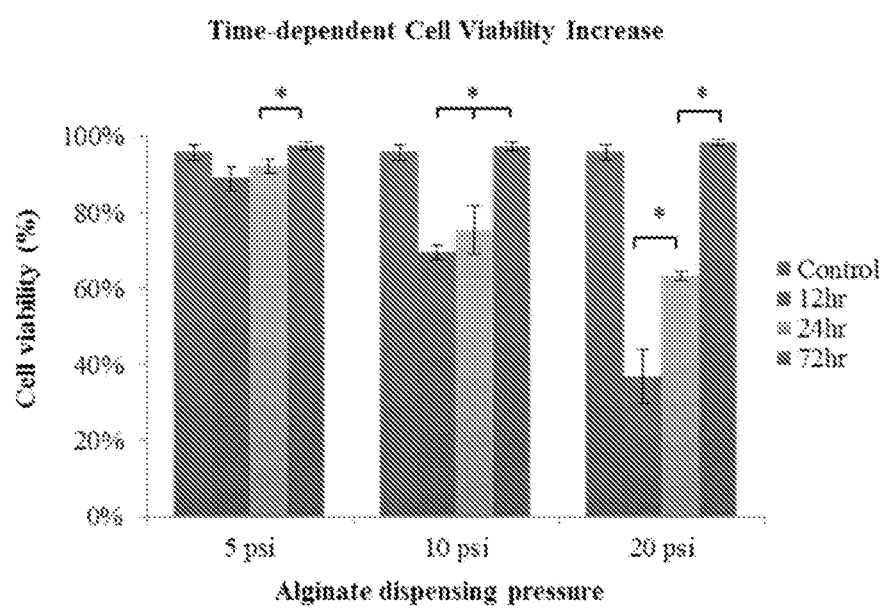

FIG. 29 depicts the cell recovery in the printed structure using a co-axial nozzle assembly ($I_{26G}O_{16G}$) during post-printing incubation for a 72 h period. Increased cell viability is observed from 12 h post bioprinting to 72 h incubation at different alginate dispensing pressures (data are mean±SD; $p<0.05$).

Figure 30:
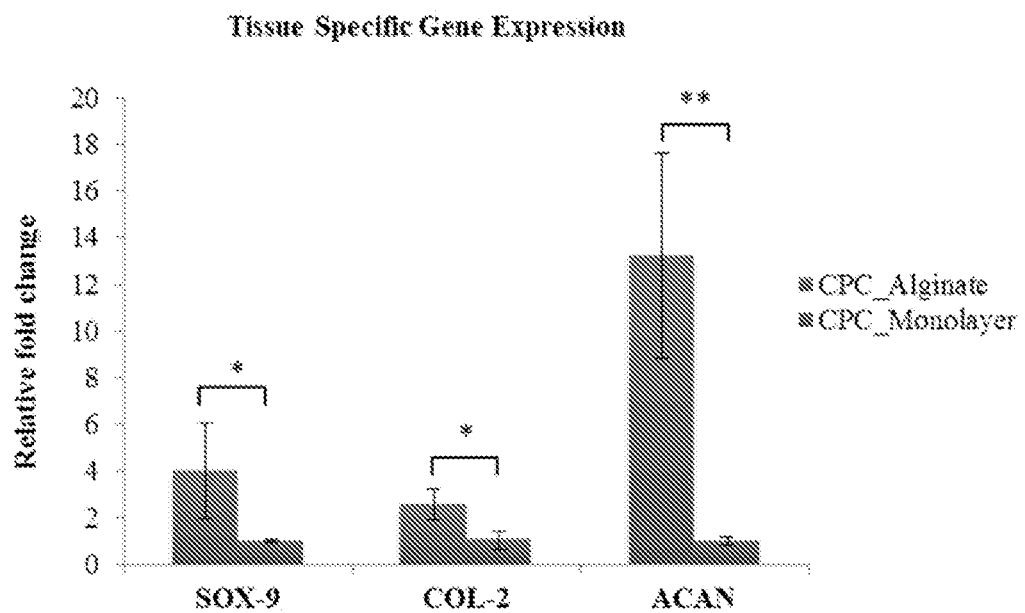

FIG. 30 depicts tissue specific gene expression results. Real-time PCR revealed significantly higher expression of cartilage-specific markers; PRG-4, Sox-9, and COL-2 all showed over a two-fold up-regulation in alginate tubular channel encapsulated CPCs compared with CPCs in the monolayer culture after bioprinting. ACAN showed over a twelve-fold higher expression level (data are mean±SD; (*: $p<0.05$; **:$p<0.01$)).

Figure 31:
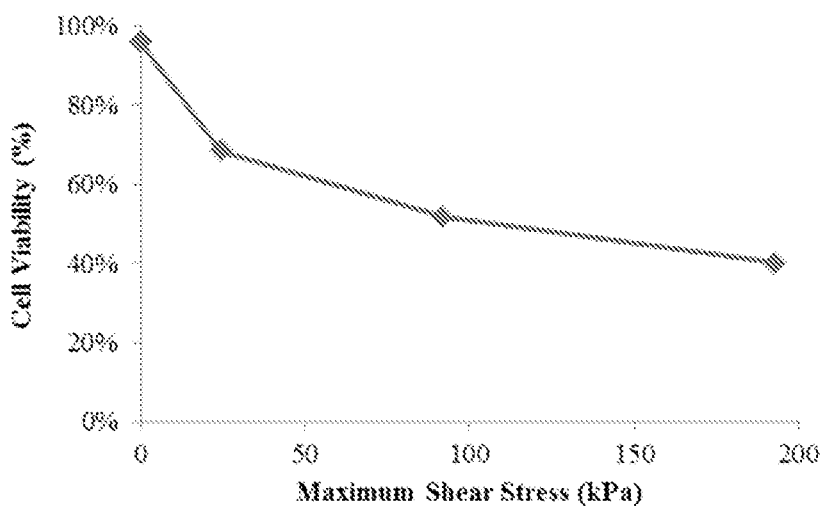

FIG. 31 graphically depicts cell viability under various maximum shear stress levels.

Figure 32:
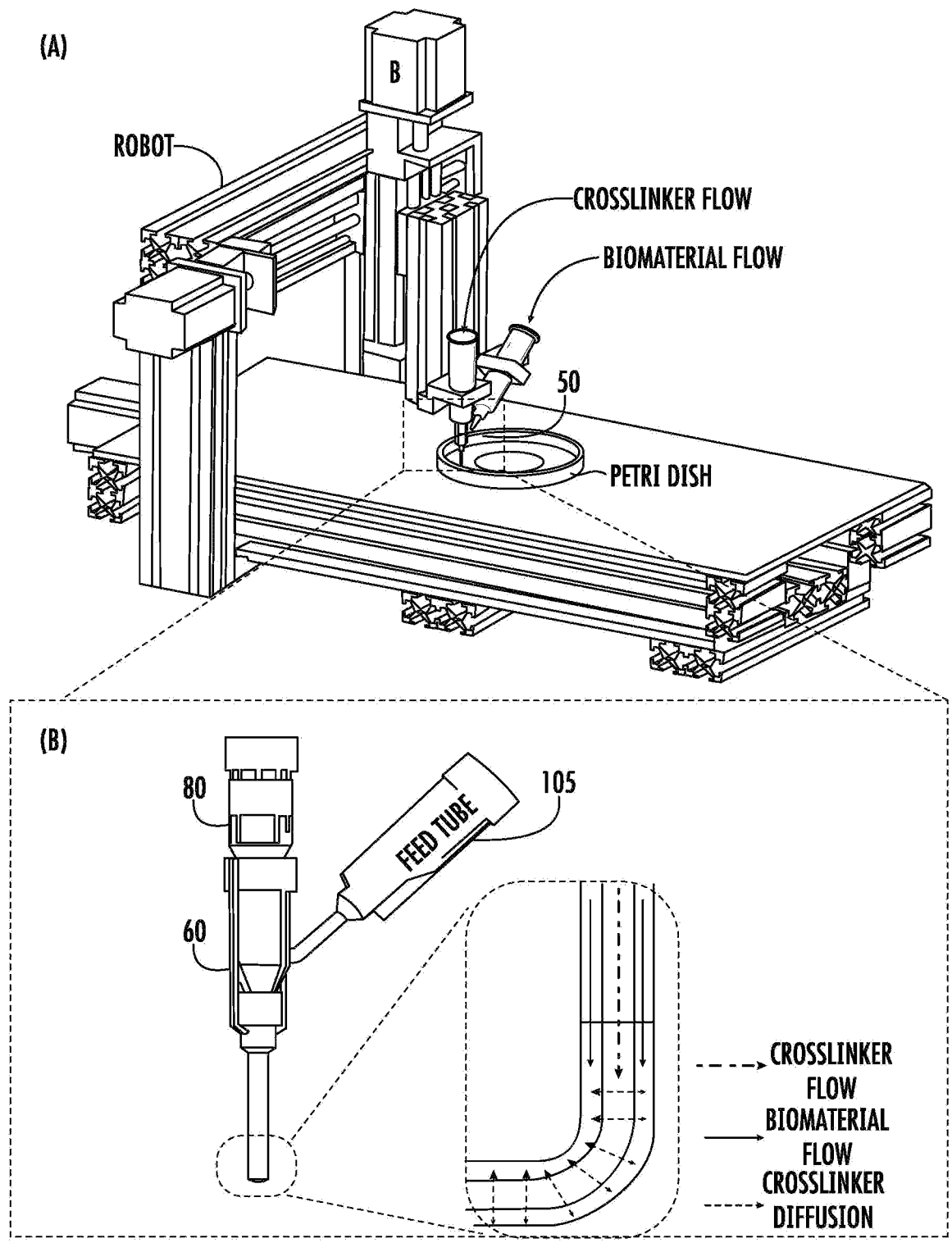

FIG. 32A is a representative image of an exemplary experimental setup showing one of the arms of a multi-arm bioprinter as disclosed herein. FIG. 32B depicts an exemplary coaxial nozzle assembly with fluid flow paths for hydrogel and crosslinker solutions. As shown, the co-axial nozzle assembly comprised an inner tube, a feed tube, and an outer tube.

Figure 33:
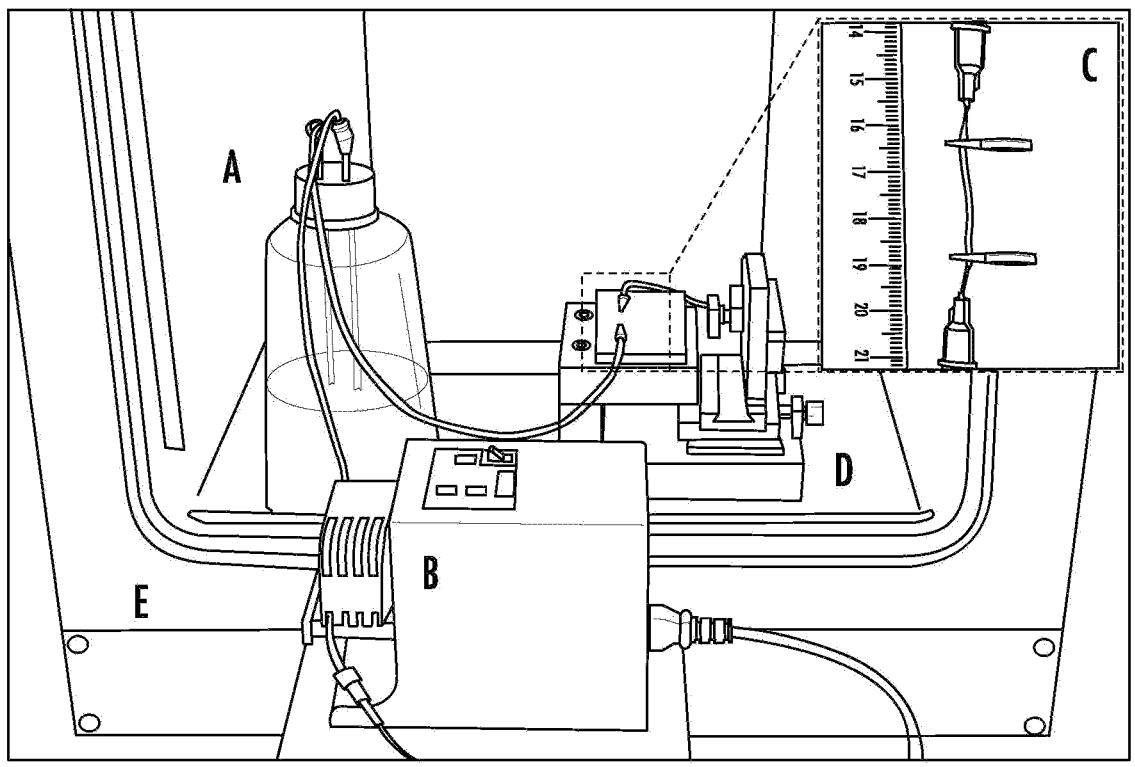

FIG. 33 depicts an exemplary media perfusion system in an incubator, comprising: (a) culture media reservoir with capacity of 1 L, (b) digital pump, (c) media perfused cellular vascular network; (d) three-axis motion stages, and (e) cell and tissue culture incubator.

Figure 34:
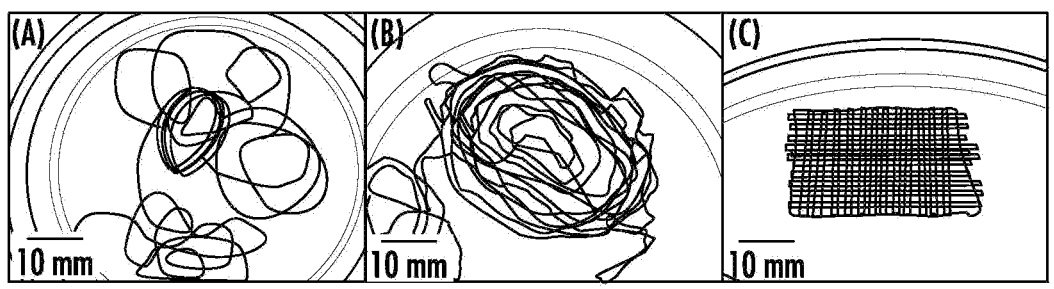

FIGS. 34A-34B depicts an exemplary printed vascular network. As shown in FIG. 34A, an alginate vascular network can have acceptable mechanical strength and structural integrity. As shown in FIG. 34B, a chitosan vascular network can be fragile and easy to rupture. FIG. 34C shows a printed 8-layer alginate vascular network with well-defined morphology.

Figure 35:
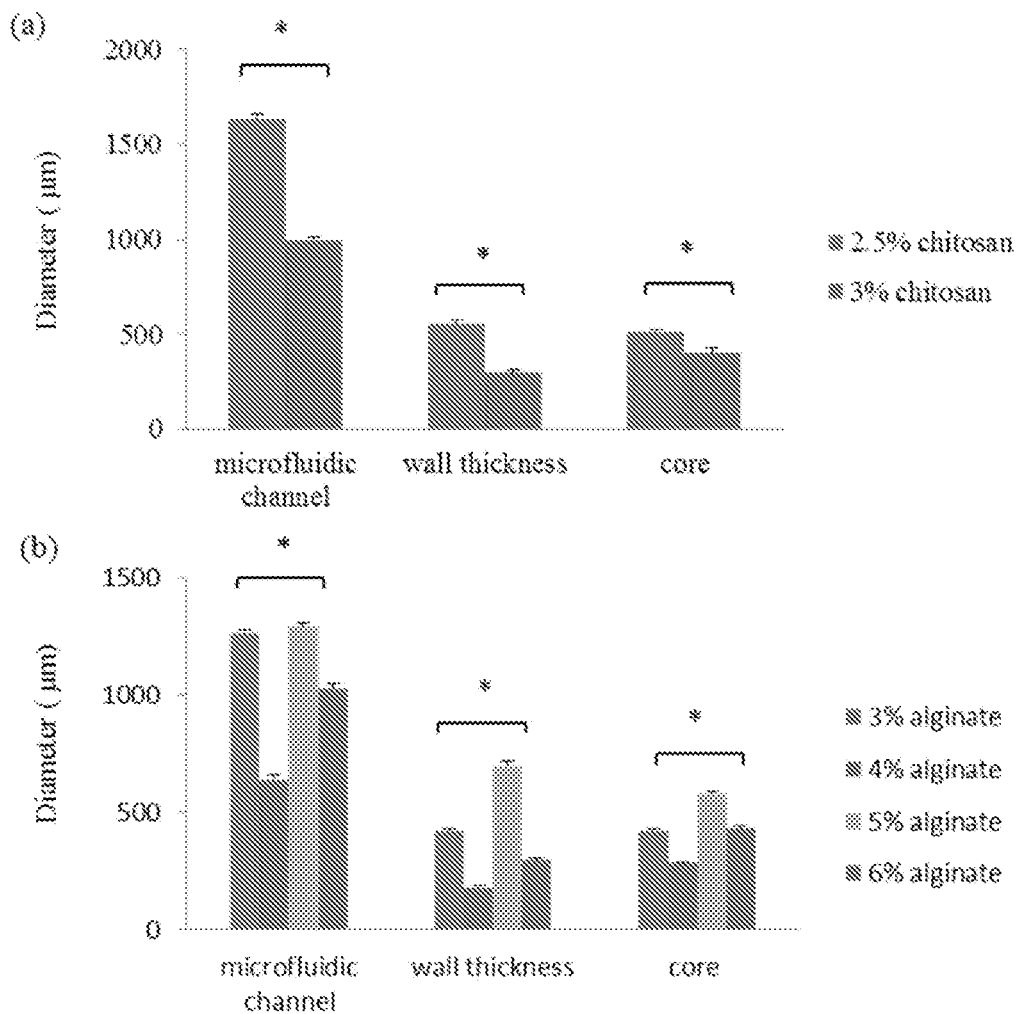

FIGS. 35A-35B depict a geometric comparison of printed vascular networks per variation in hydrogel concentrations. FIG. 35A shows the geometric comparison at various chitosan concentrations, while FIG. 35B shows the geometric comparison at various alginate concentrations. (Single asterisk (*) indicates significant differences between groups ($p<0.05$)).

Figure 36:
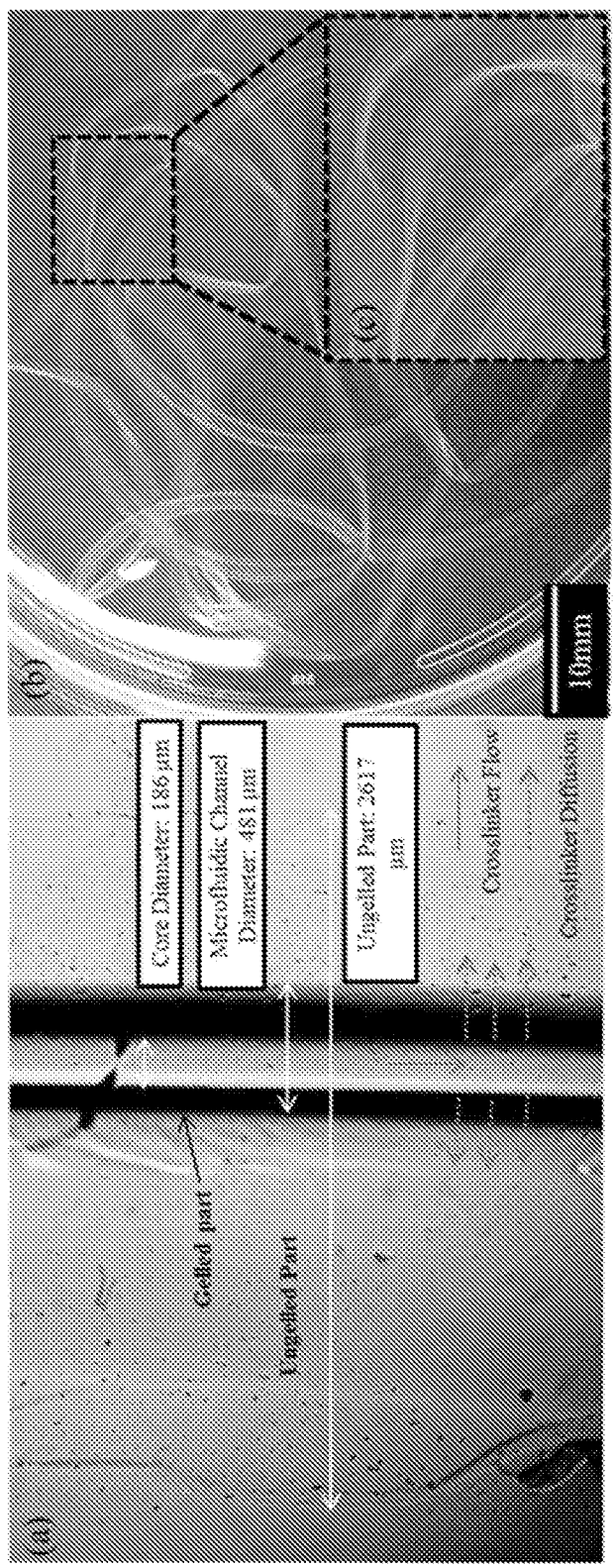

FIG. 36A is a cross-sectional image of partially cross-linked alginate. FIGS. 36B-36C are images of the structure of the alginate.

FIGS. 37A-37D depict the effect of flow rheology on the geometry of an exemplary vascular network. FIG. 37A depicts the effect of varying alginate dispensing rate, FIG.

37B depicts the effect of varying CaCl$_2$ dispensing rate, FIG. 37C depicts the effect of varying chitosan dispensing rate, and FIG. 37D depicts the effect of varying sodium hydroxide dispensing rate (Single asterisk (*) indicates significant differences between groups ($p<0.05$)).

Figure 38:
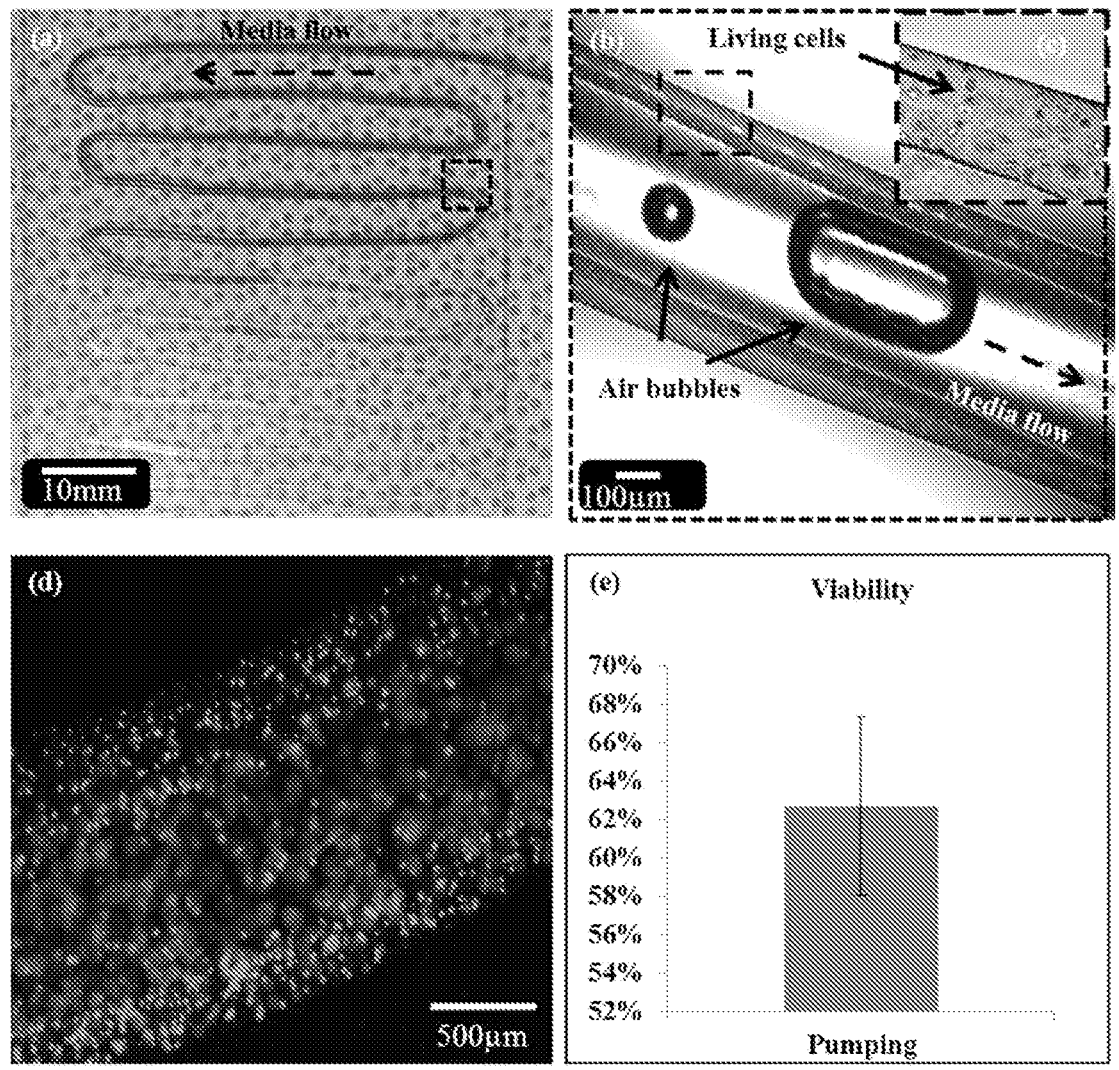

FIGS. 38A-38E depict an exemplary media perfusion and cell viability analysis. FIG. 38A depicts perfusion of exemplary cell culture media through a zigzag patterned channel showing no blockage or disturbance. FIG. 38B depicts intentionally generating air bubbles illustrating media flow through a hollow feature of exemplary printed channels. FIG. 38C depicts cells that were uniformly distributed throughout a channel wall. FIG. 38D depicts quantifiable cell death that was observed along a vascular network, with most of the cells remaining viable. FIG. 38E depicts cell viability of around 62.7±0.05% after 12 hours of media perfusion.

Figure 39:
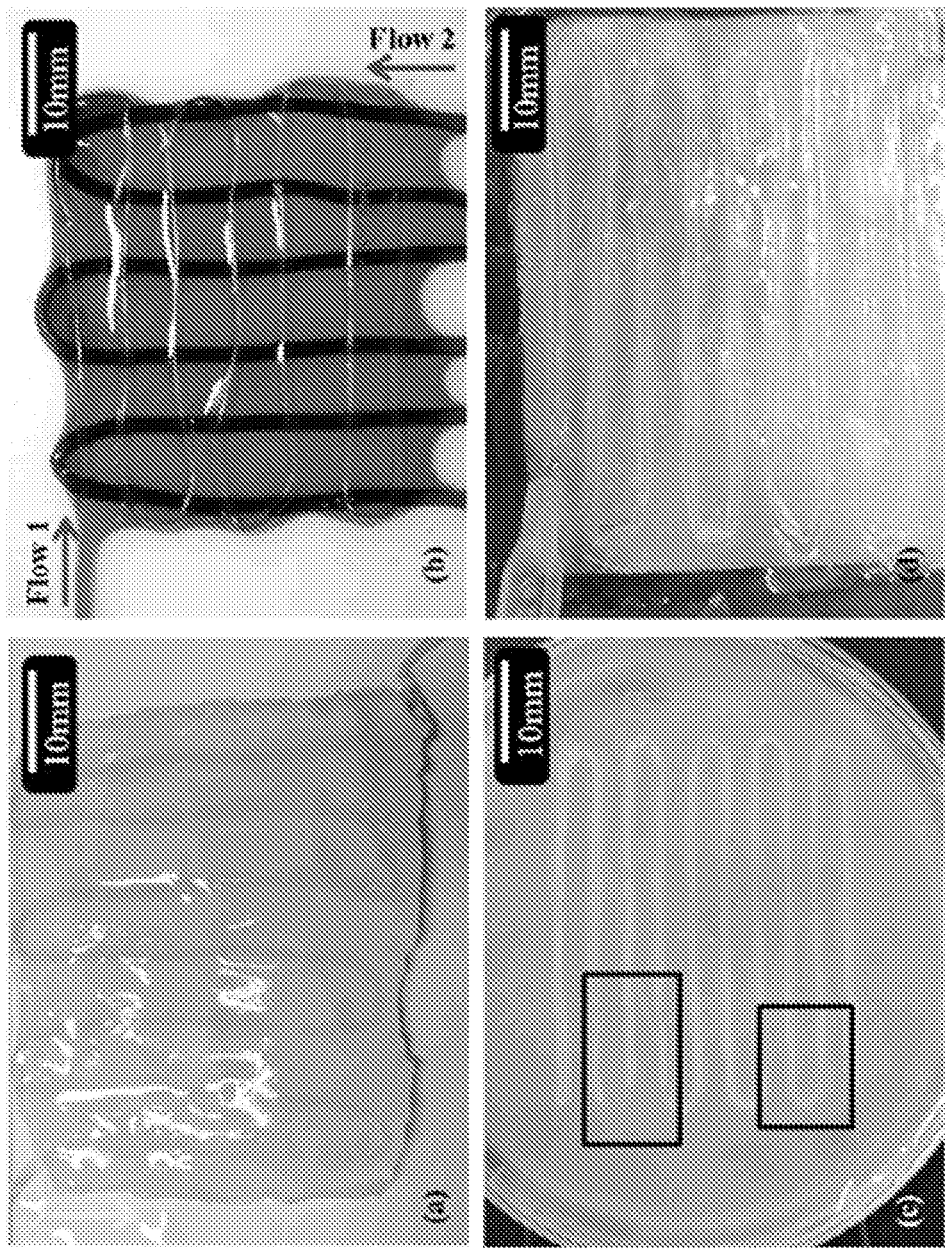

FIGS. 39A-D depict embedding a vascular network in bulk hydrogels. As shown in FIG. 39A, the alginate vascular network embedded in bulk alginate can display well-defined structure, and can transport media smoothly without any swirling formation (arrows indicate media flow direction). FIG. 39B depicts two layers of alginate channels with multi-directional media perfusion (flow). As shown in FIG. 39C, an exemplary alginate vascular network embedded in bulk chitosan displayed a well-defined pattern but ruptures were observed at respective locations along channels (circled sections). As shown in FIG. 39D, a chitosan vascular network failed to transport media smoothly due to disrupted channels.

Figure 40:
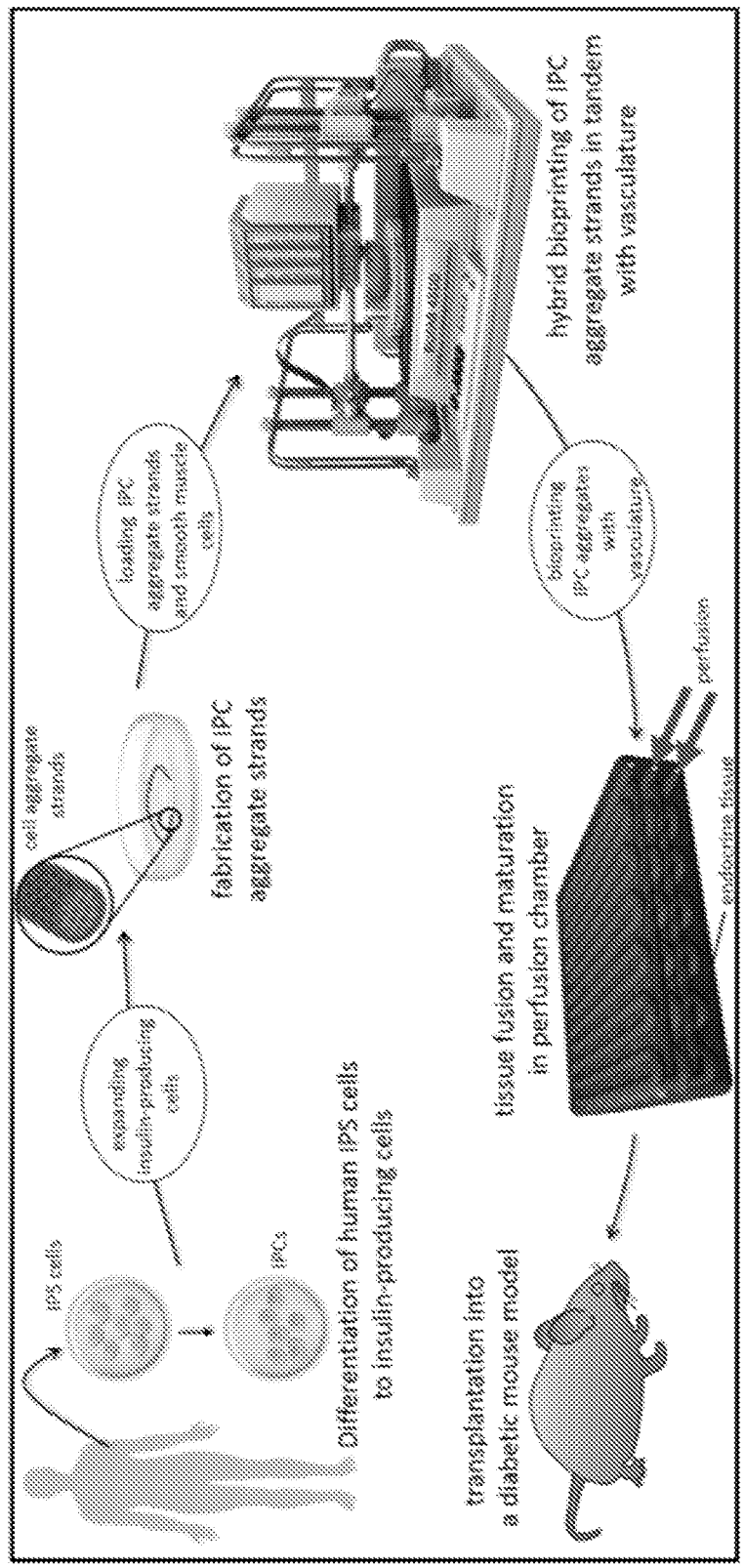

FIG. 40 is a schematic diagram depicting an exemplary process for producing an insulin-producing tissue construct, as disclosed herein.

FIG. 41A depicts Human IPCs derived from iPS cells forming spheres in culture at 16, 20, 23, and 25 days, as disclosed herein. FIG. 41B graphically depicts the secretion of insulin by Human iPS cell-derived IPCs.

Figure 42:
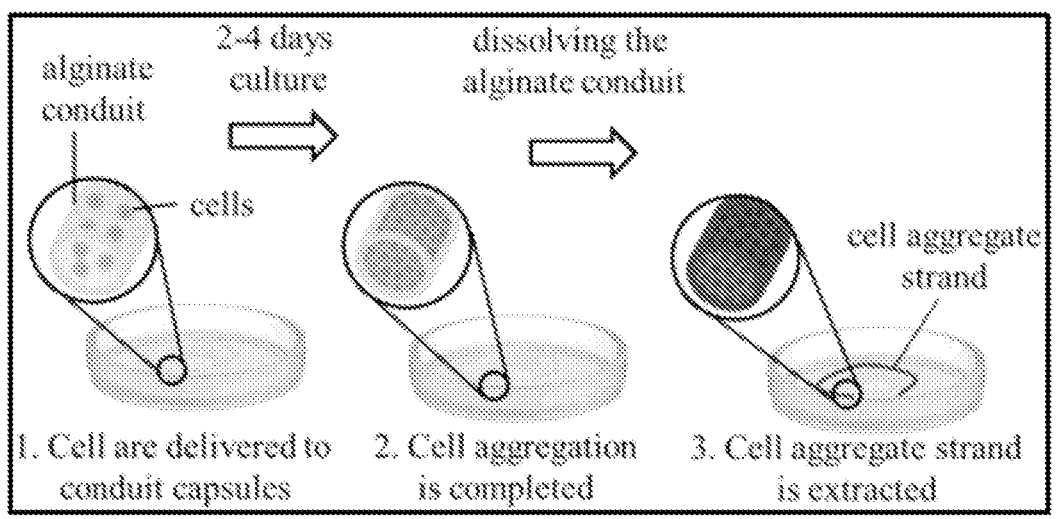

FIG. 42 is a schematic diagram depicting an exemplary scaffold-free cell aggregate strand fabrication method.

Figure 43:
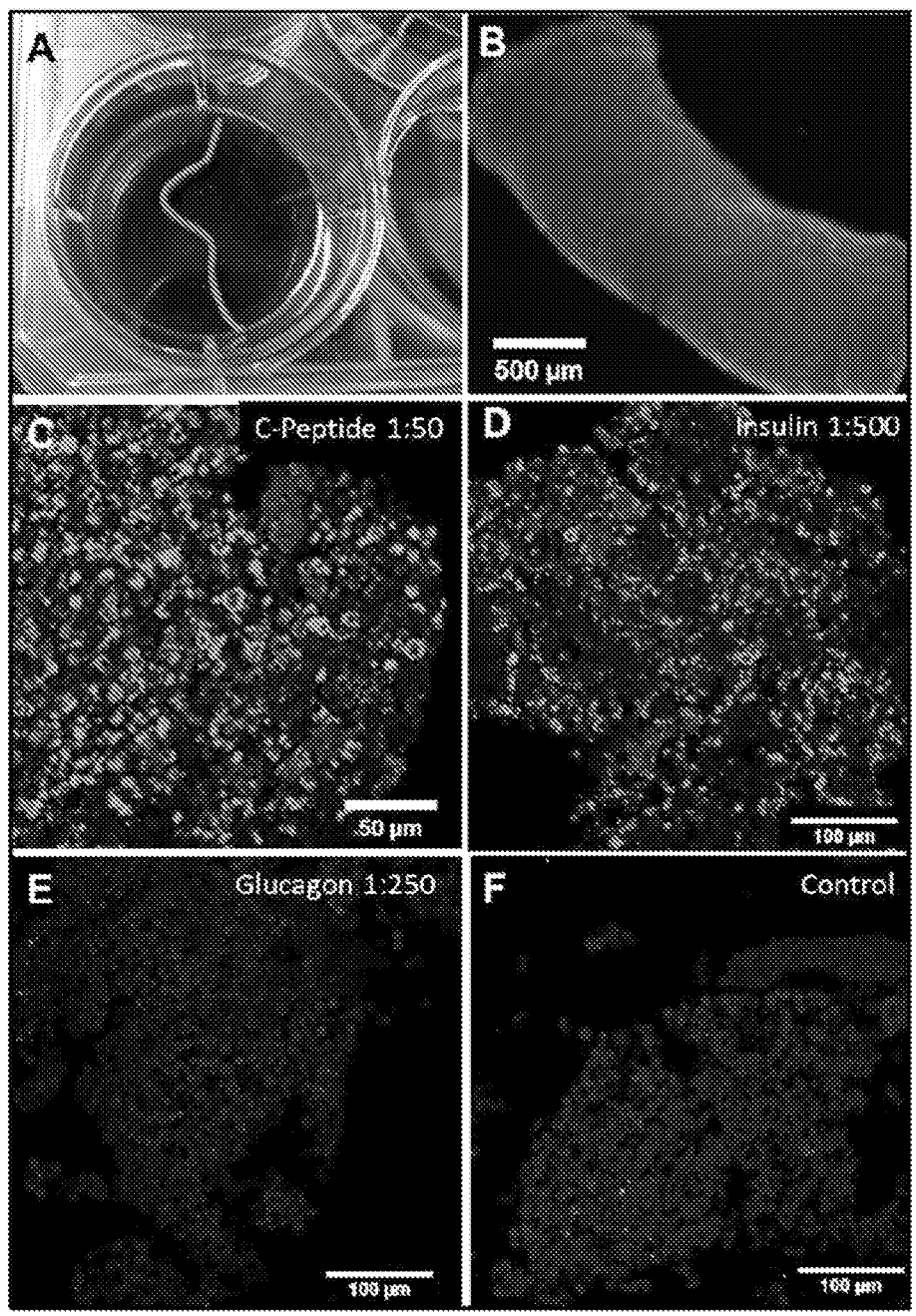

FIG. 43A depicts exemplary fabricated TC3 cell aggregate cylinders. FIG. 43B depicts viability staining showing very strong cell viability. FIGS. 43C-43F depict immunohistochemistry staining showing (C) strongly positive C-peptide expression, (D) strongly positive insulin expression, (E) glucagon remained negative, and (F) control (DAPI). Note: DAPI was stained with blue in all results.

Figure 44:
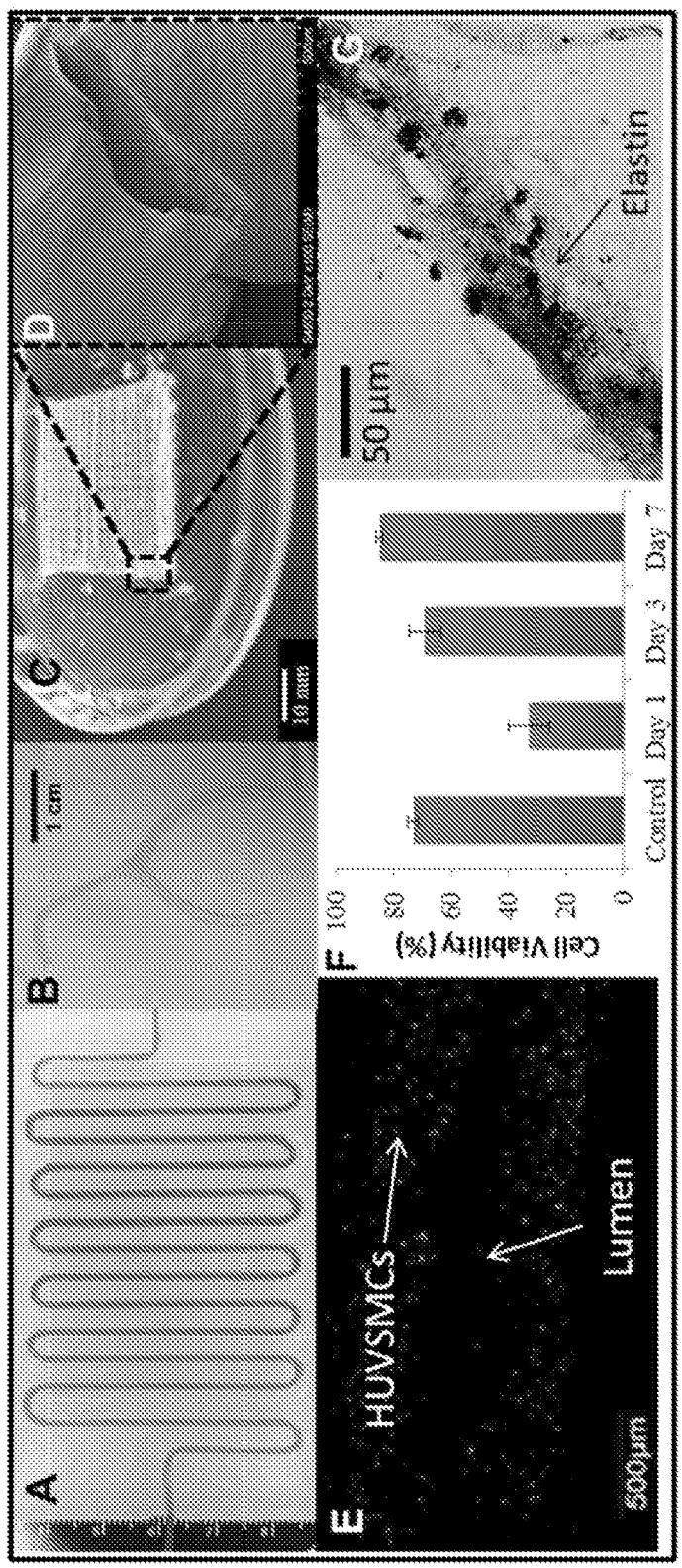

FIG. 44A depicts perfusion through an exemplary 103 cm long vasculature. FIG. 44B depicts exemplary printed branched vasculature. FIGS. 44C and 44D depict an S-layer printed vascular network with SEM picture showing the lumen. FIG. 44E provides a confocal image showing viability staining HUCSMCs. FIG. 44F depicts a cell viability study showing increased cell viability in one week significantly greater than the control group (free suspended cells in alginate) and elastin deposition.

Figure 45:
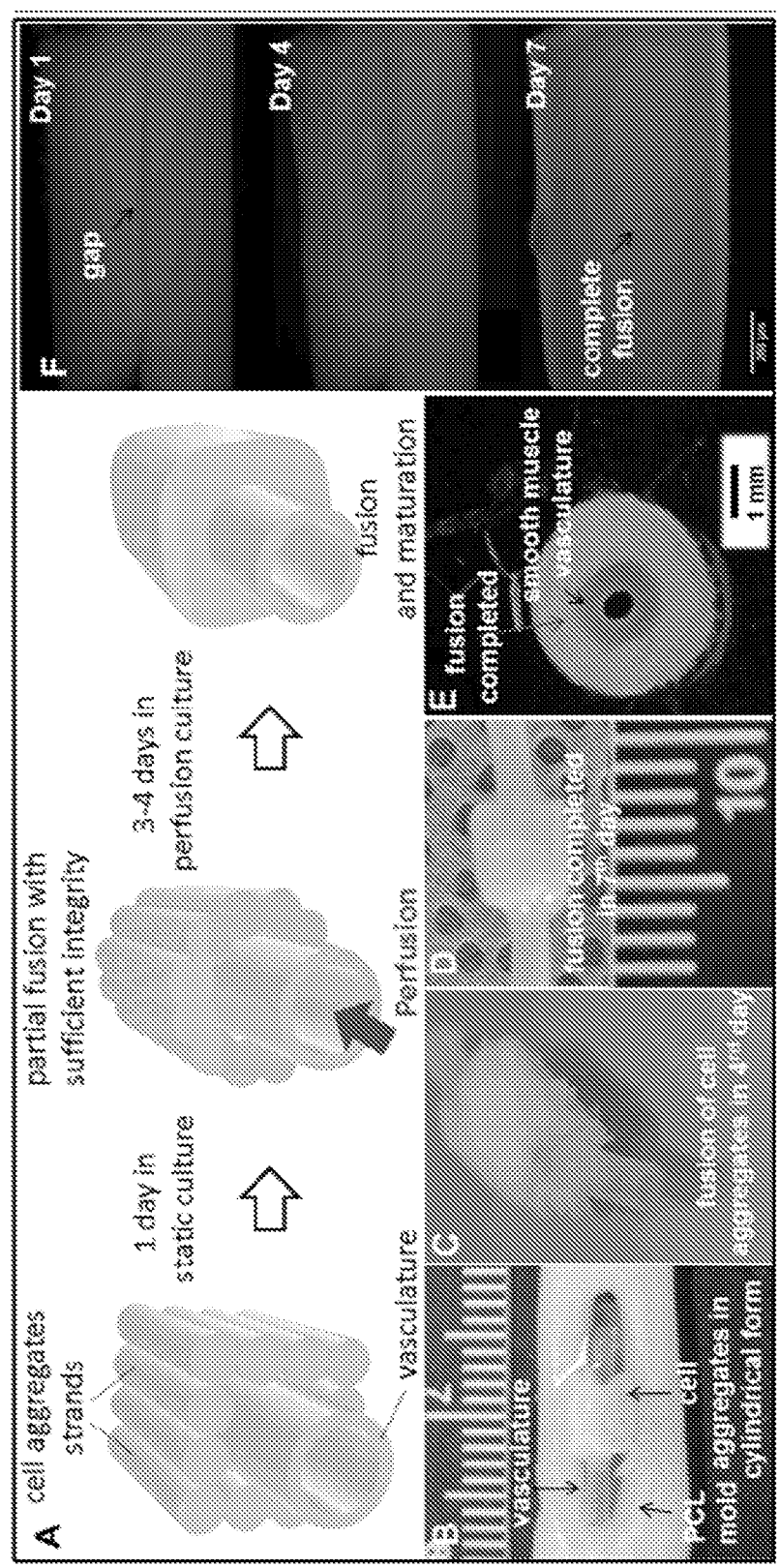

FIGS. 45A and 45B depict an exemplary tissue assembly around a vasculature for scale-up tissue fabrication. First cell aggregate strands were stacked around a vasculature for perfusion purposes. The tissue construct was kept 1 day in static culture for tissue fusion, partially providing sufficient structural integrity for perfusion. Tissue fusion and maturation were completed in 6-7 days in perfusion culture. In experiments, fibroblast cell aggregate strands were stacked around a vasculature in a mold for a few days. FIG. 45C depicts the tissue construct in Day 4 and FIGS. 45D and 45E depict the tissue construct at Day 7. Cell aggregate strands completely fused and enclosed the vasculature and attached to it. FIG. 45F shows fluorescence images showing fusion of the cell aggregate strands.

Figure 46:
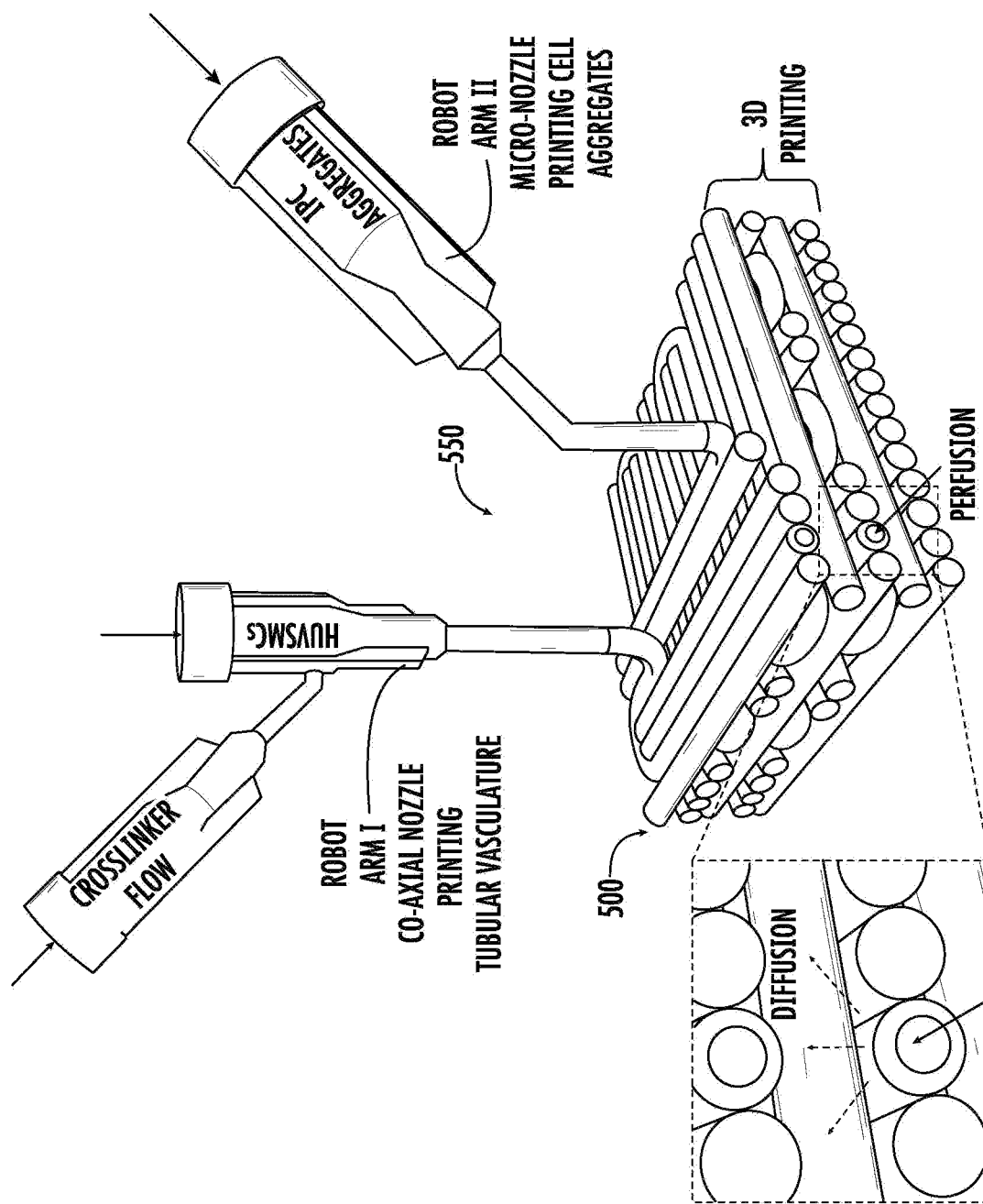

FIG. 46 schematically depicts an exemplary scale-up hybrid pancreatic organ printing process, where IPC aggregates are printed in tandem with the vasculature network.

Figure 47:
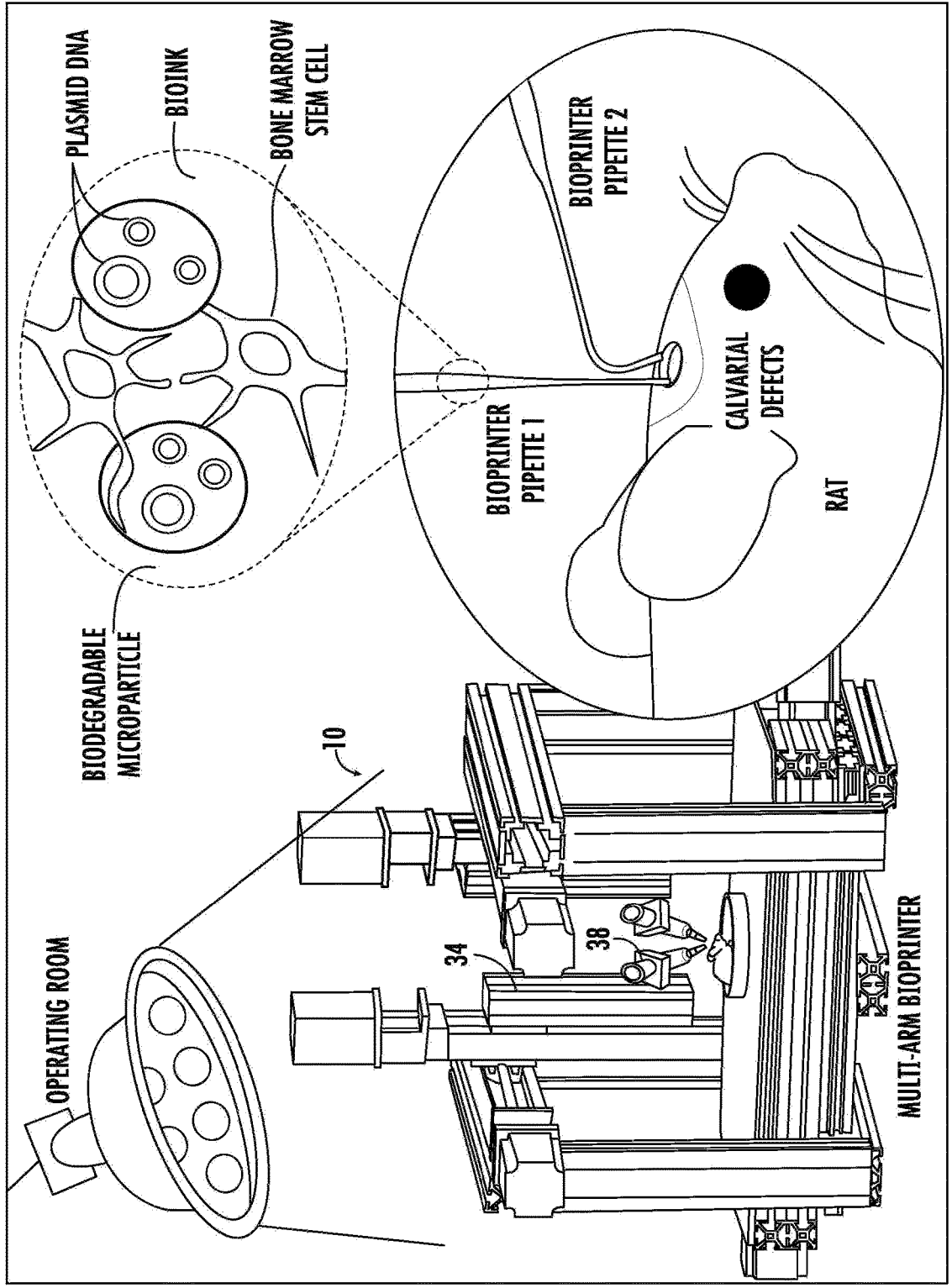

FIG. 47 is a schematic diagram depicting an exemplary in situ multi-arm bioprinting process as disclosed herein, wherein the robotic-assisted arms of a bioprinter are activated to print bone tissue within a defect of an animal subject.

Figure 48A:
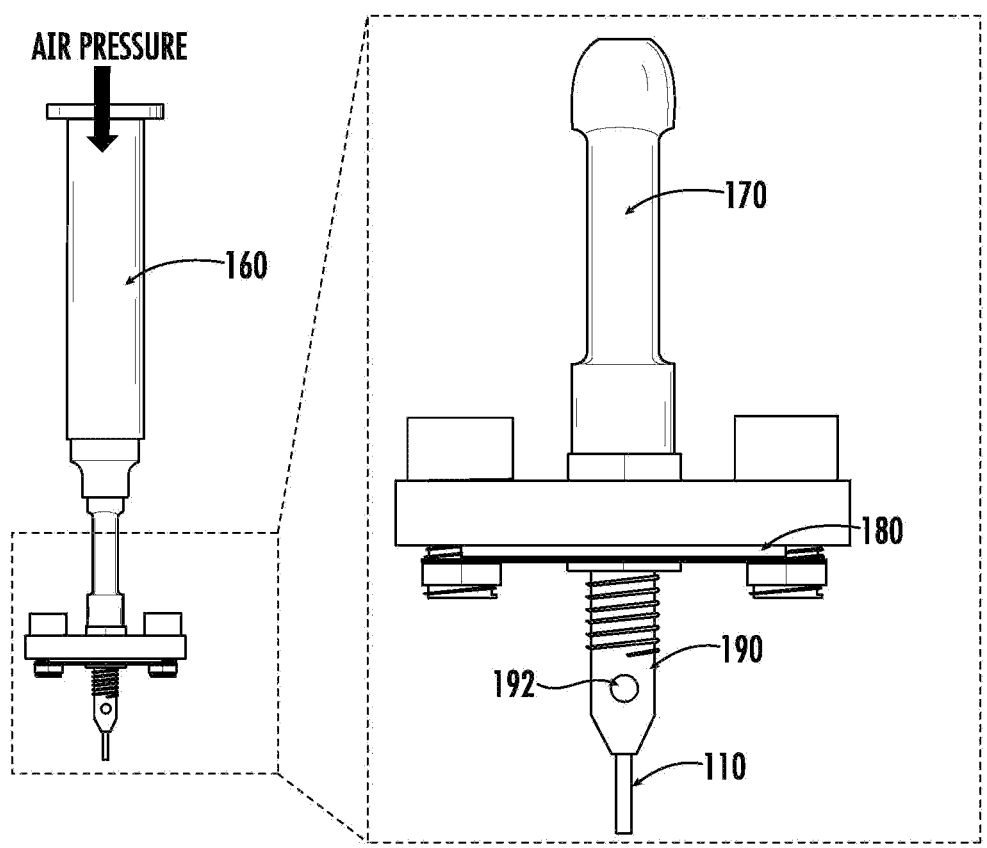
Figure 48B:
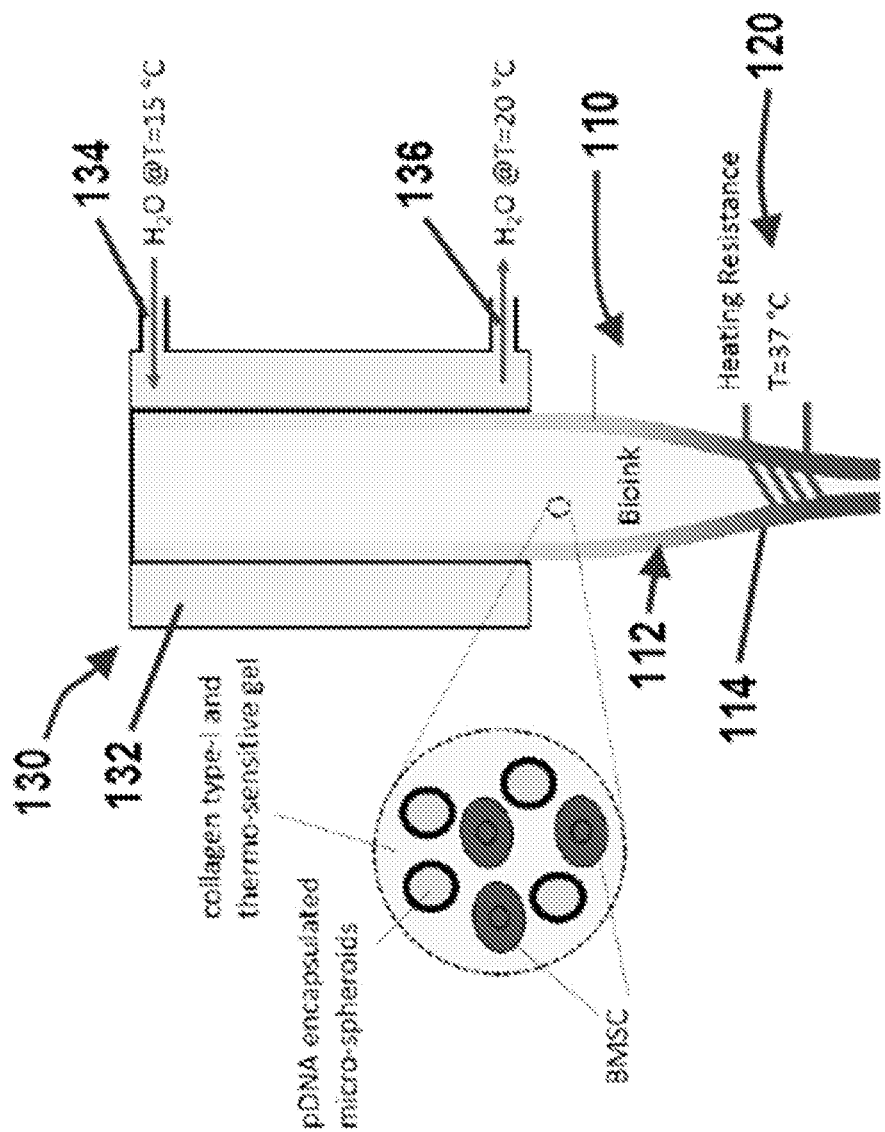

FIGS. 48A-48B are schematic diagrams depicting exemplary nozzles as disclosed herein. As shown, the nozzle can have a heating and cooling system for printing a bio-ink composition as disclosed herein.

Figure 49:
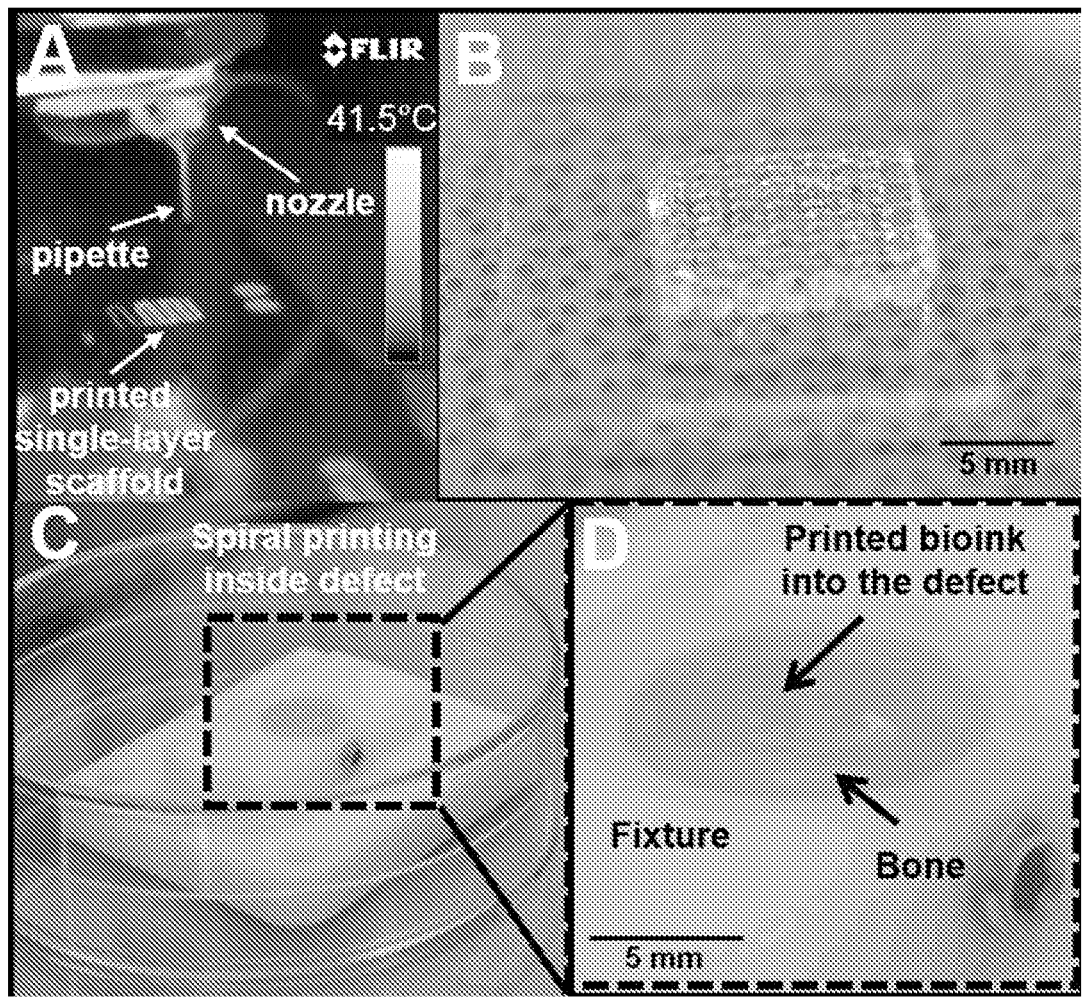

FIG. 49A depicts a thermographic image of the bioprinting process, where the bioink is extruded near 37° C. FIG. 49B depicts a 20-layer printed tissue construct in vitro, where 92±1.7% BMCS viability is achieved shortly after bioprinting. FIGS. 49C-49D depict the direct printing of a bio-ink composition onto a 5 mm diameter bone defect with 2 mm depth.

Figure 50:
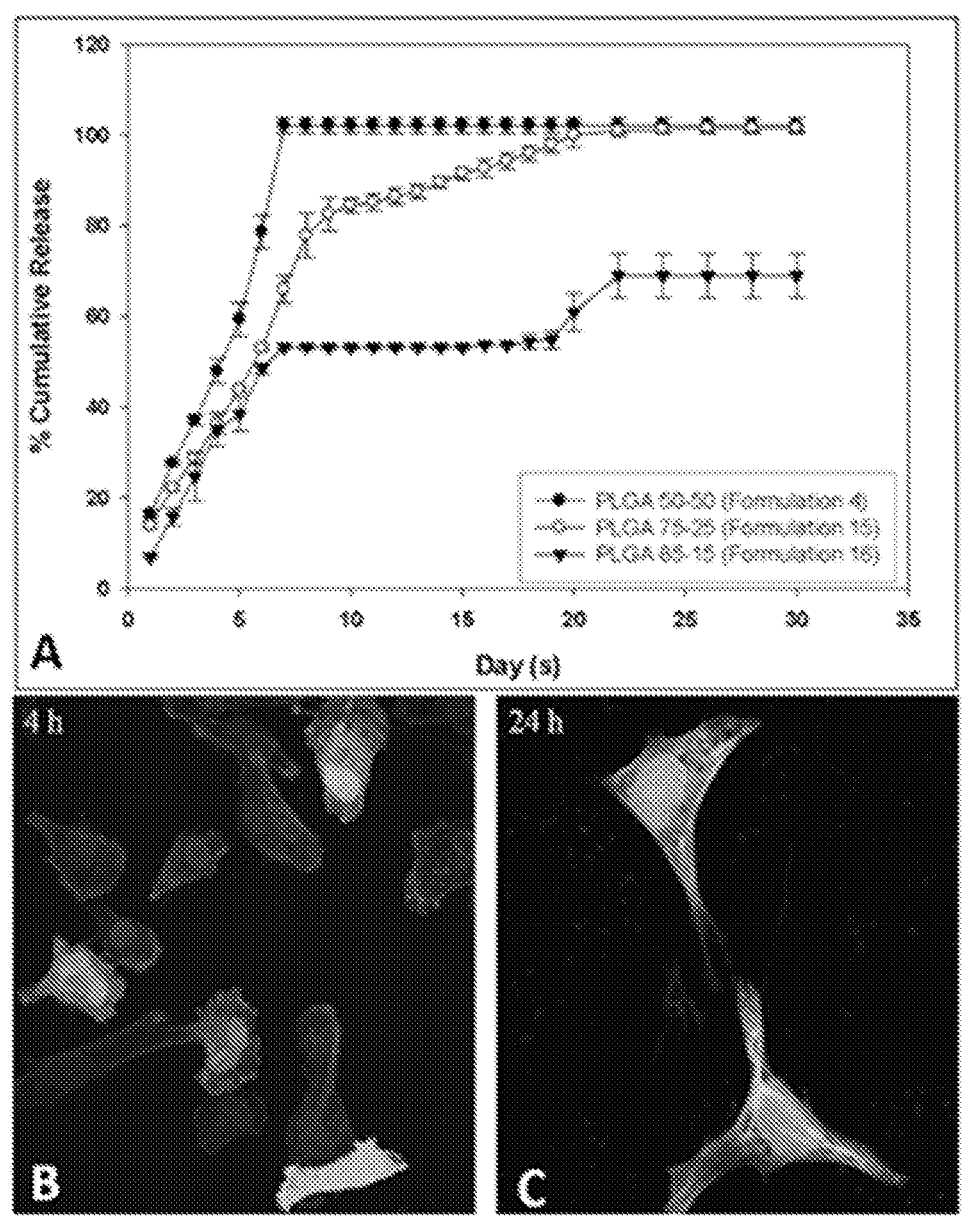

FIG. 50A is a graph depicting the controlled release of pDNA-PEI complexes from PLGA particles with different molecular weights using PLGA 50-50, PLGA 75-25 and PLGA 85-15. FIG. 50B provides an immunostaining image showing successful transfection of BMSCs using PEI-pDNA complexes at 4 hours. FIG. 50C provides an immunostaining image showing successful transfection of BMSCs using PEI-pDNA complexes at 24 hours.

Figure 51:
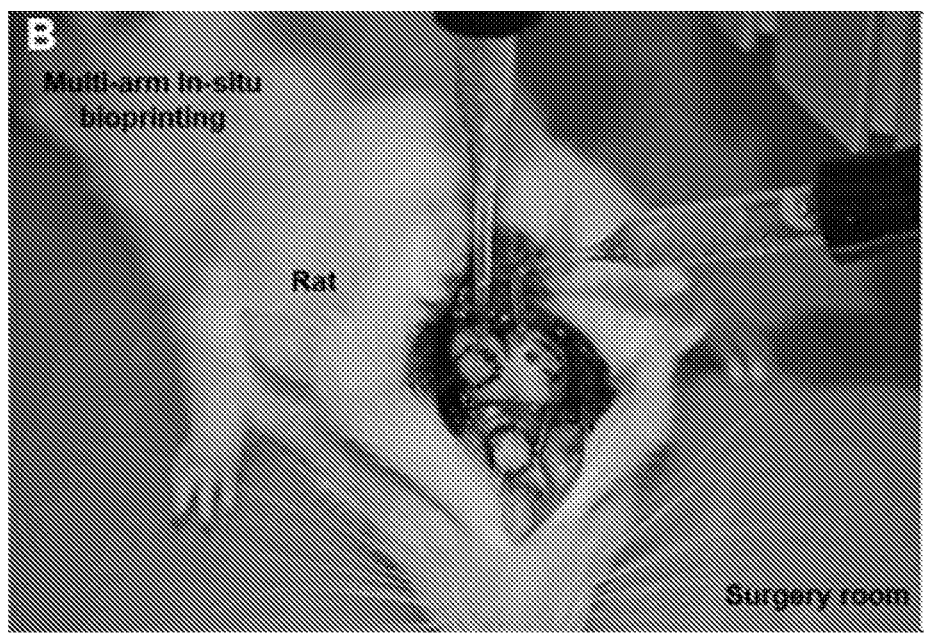

FIG. 51 depicts an exemplary surgical procedure of printing a bio-ink composition into a tissue defect of a rat.

Figure 52:
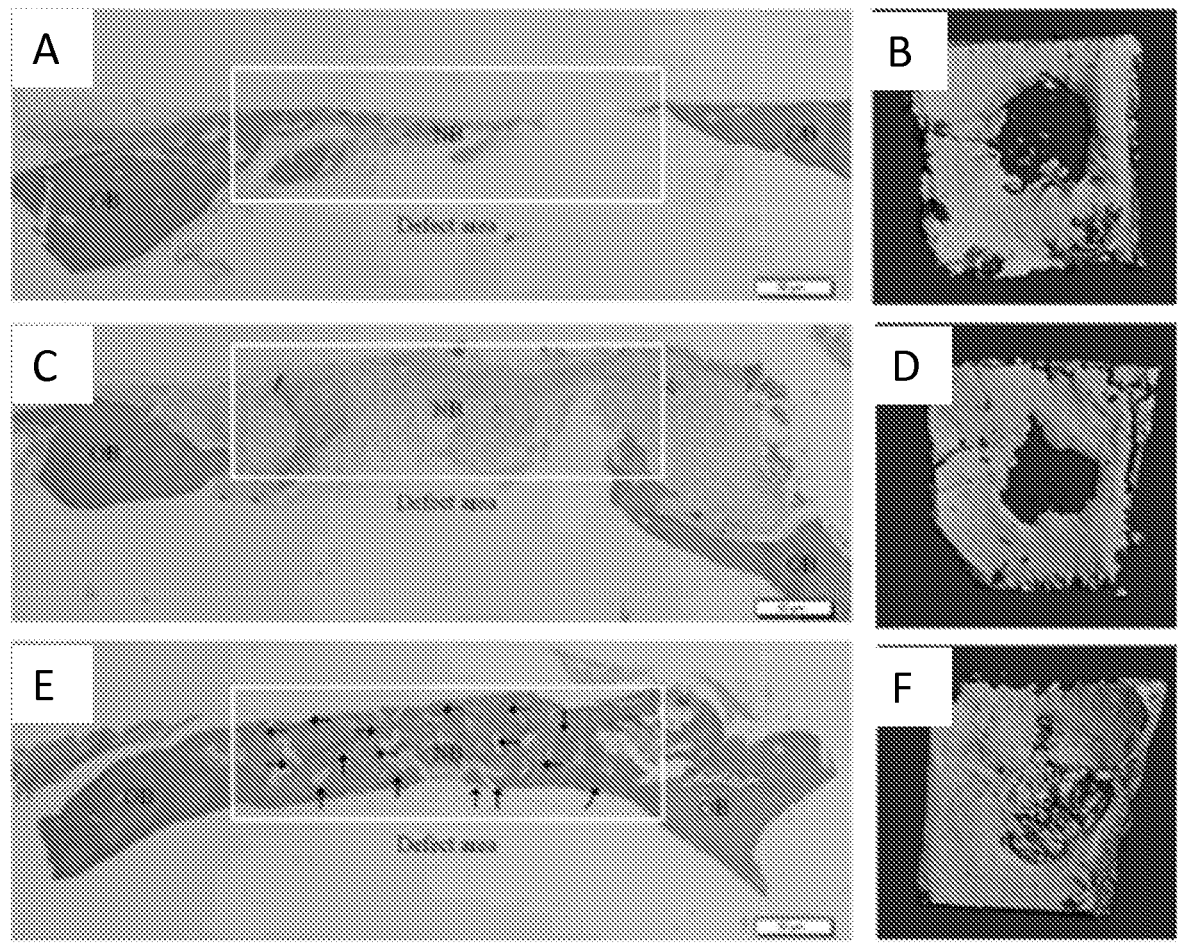

FIGS. 52A, 52C, and 52E depict representative histology sections demonstrating the extent of new bone formation in the defects at 4 weeks due to various treatments. FIG. 52A depicts empty defects, FIG. 52C depicts empty collagen scaffolds, and FIG. 52E depicts complex loaded collagen scaffolds (pDNA and BMSCs). FIGS. 52B, 52D, and 52F depict representative μCT scans showing the level of regenerated bone tissue after 4 weeks. FIG. 52B depicts empty defects, FIG. 52D depicts empty collagen scaffolds, and FIG. 52F depicts complex loaded collagen scaffolds (pDNA and BMSCs).

FIG. 53A depicts a printed vasculature in perfusion chamber under pulsatile flow. FIG. 53B depicts a printed vasculature in zigzag shape longer than 80 cm in length demonstrating perfusion in a custom-made perfusion chamber. FIG. 53C depicts a histology image showing collagen and smooth muscle deposition by human umbilical smooth muscle cells in 6 weeks.

Figure 54:
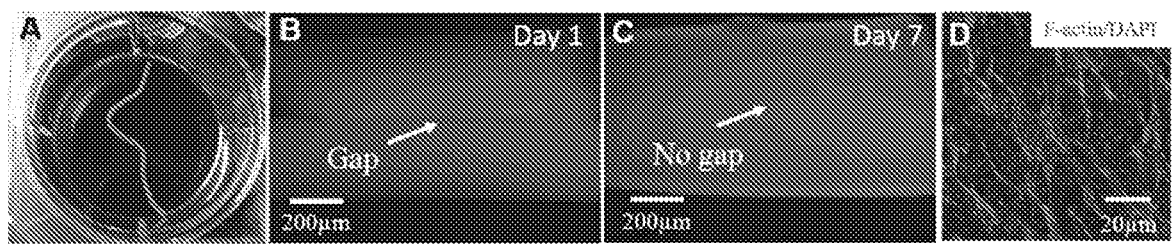

FIG. 54A depicts fabricated tissue strands, which are mechanically coherent and possess high cell viability. FIGS. 54B-54C depict fusion of tissue strands under fluorescence microscope, where the gap between tissue strands closes in 7 days. FIG. 54D is an immunostaining image demonstrating F-actin expression (note: DAPI stained cell nucleus).

Figure 55:
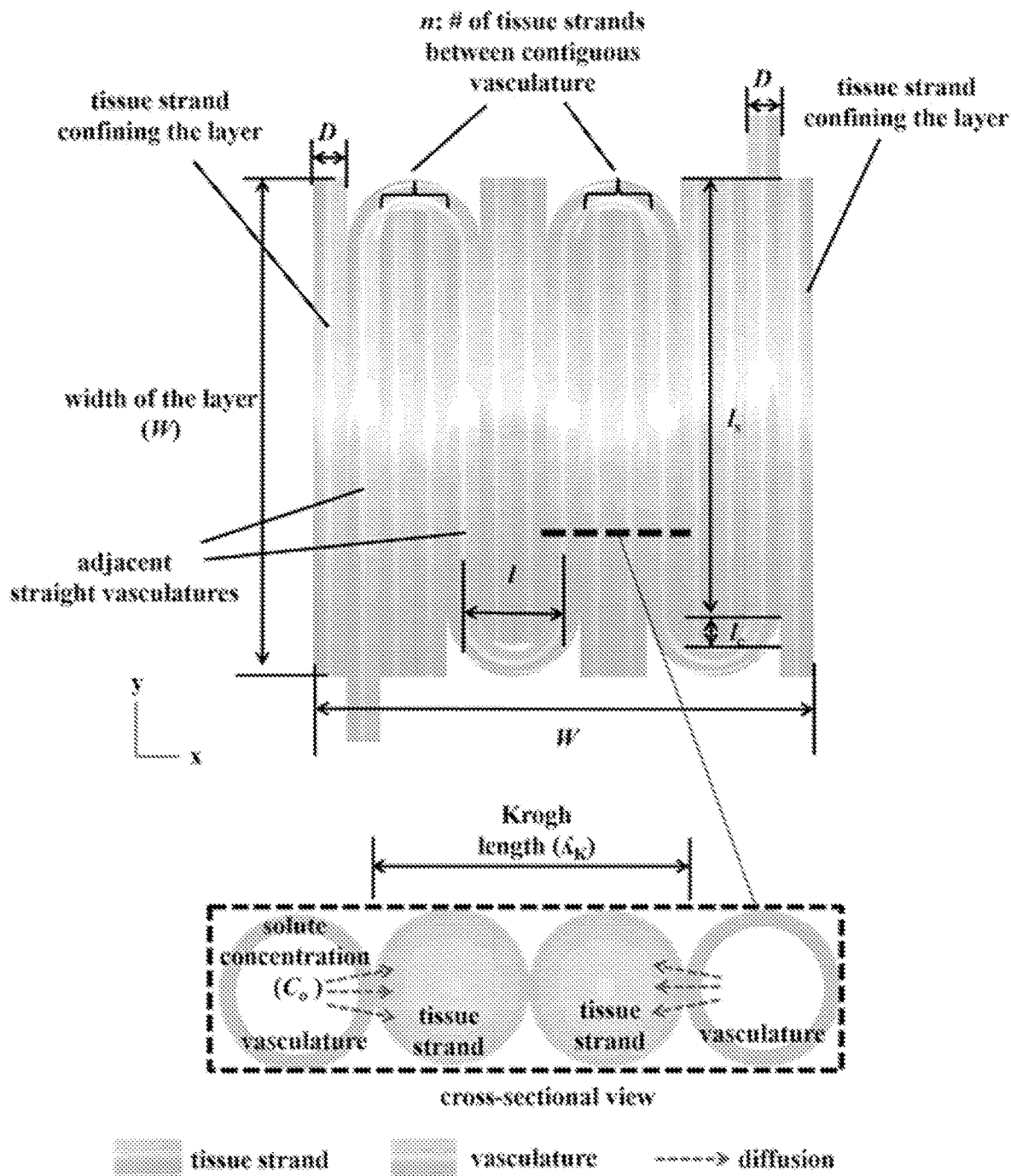

FIG. 55 depicts a representative model of an exemplary single layer hybrid tissue construct produced by the disclosed bioprinting methods.

Figure 56:
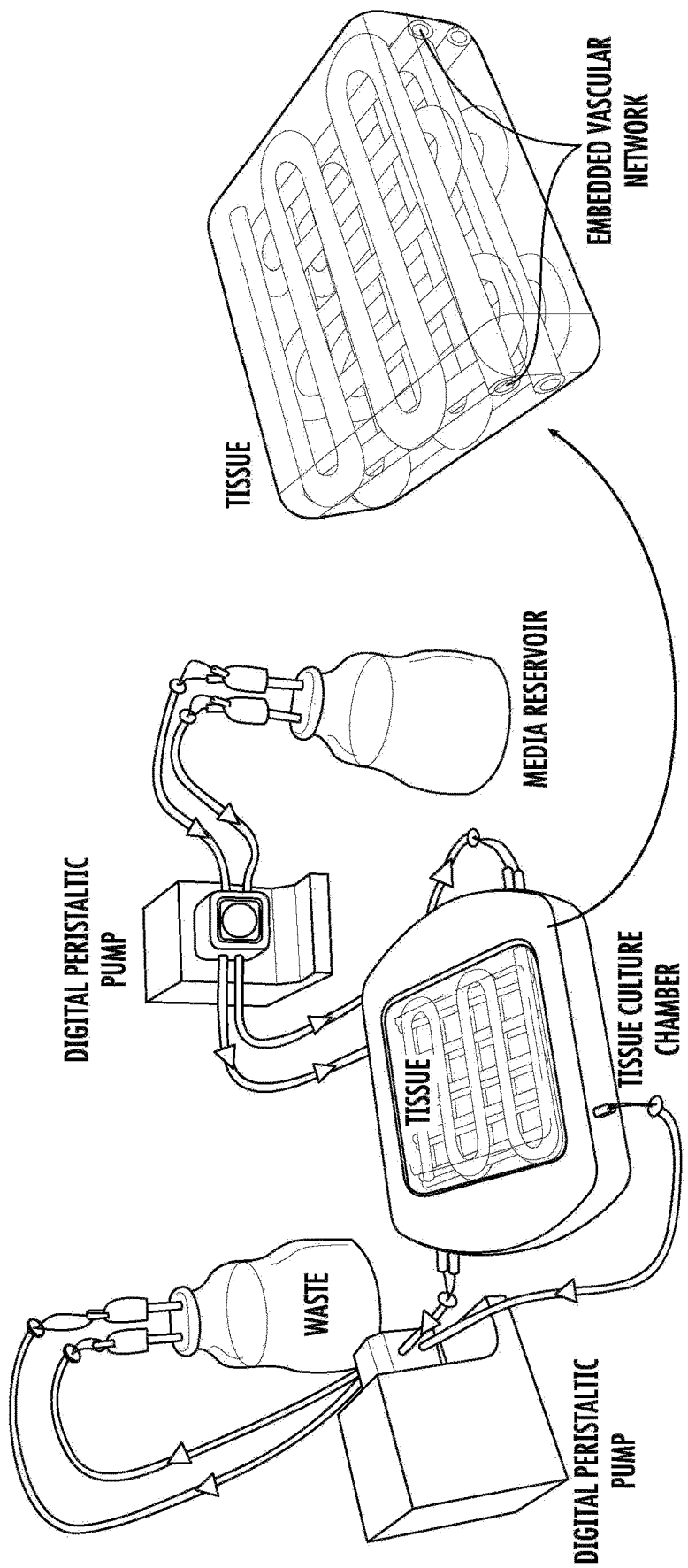

FIG. 56 depicts a perfusion system for fusion and maturation of tissues enclosing an exemplary vasculature network. Arrowheads show fresh media and waste. The whole system can be easily enclosed within an incubator.

Figure 57:
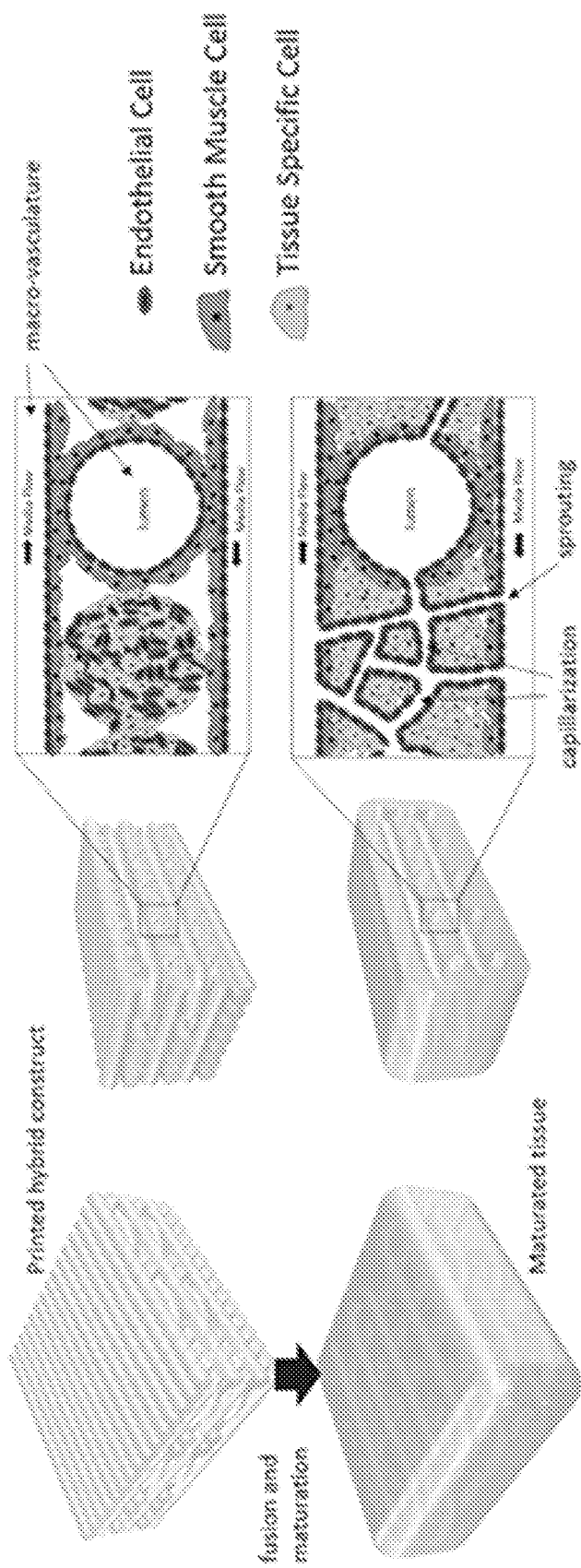

FIG. 57 depicts capillarization within maturated tissues: cut-away views demonstrate a close-up view of macro-vasculatures and co-cultured tissue strands, where endothelial cells self-organize and create capillarization under hemodynamically equivalent media flow with required growth factors.

Figure 58:
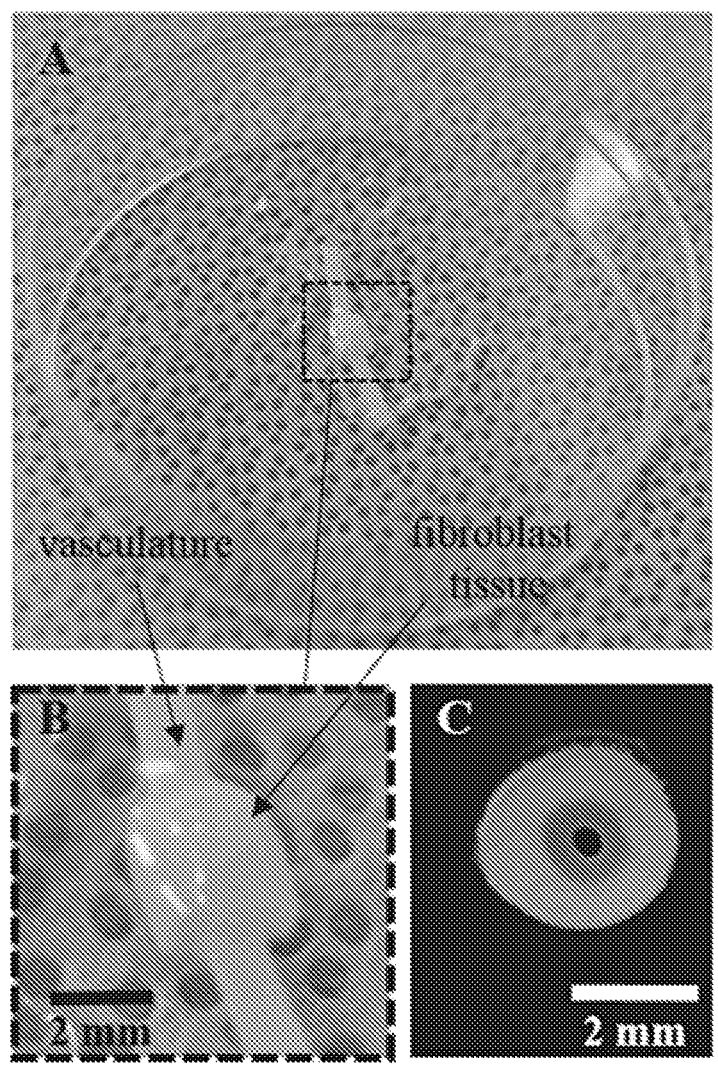

FIG. 58A depicts self-assembly of fibroblast tissue strands around a vasculature supporting pulsatile perfusion. FIG. 58B is a close-up view of the fibroblast strands around the vasculature. FIG. 58C is a cross-sectional view of the fibroblast strands around the vasculature.

Figure 59:
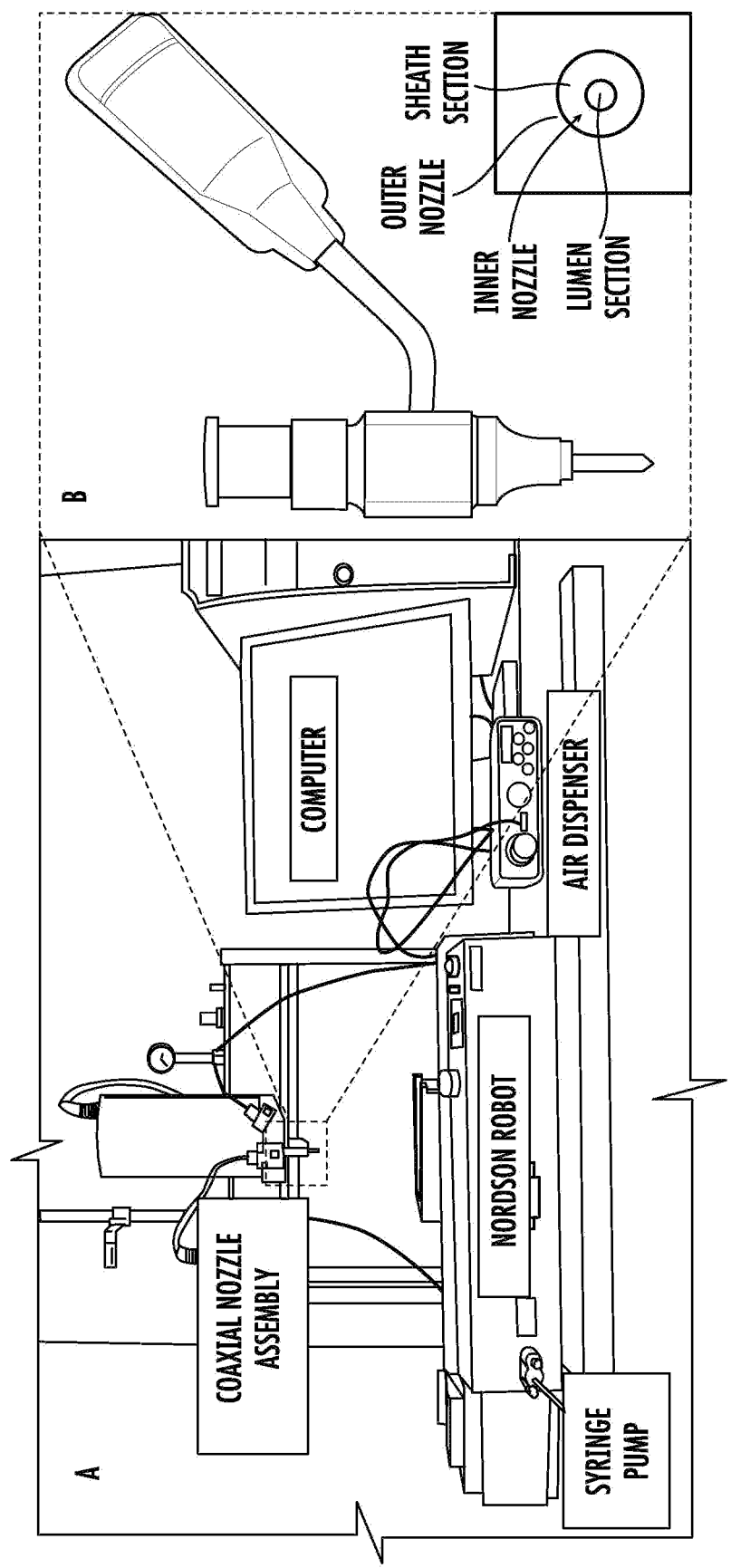

FIG. 59A depicts an exemplary fabrications system as disclosed herein. FIG. 59B depicts an exemplary coaxial nozzle assembly as disclosed herein.

Figure 60:
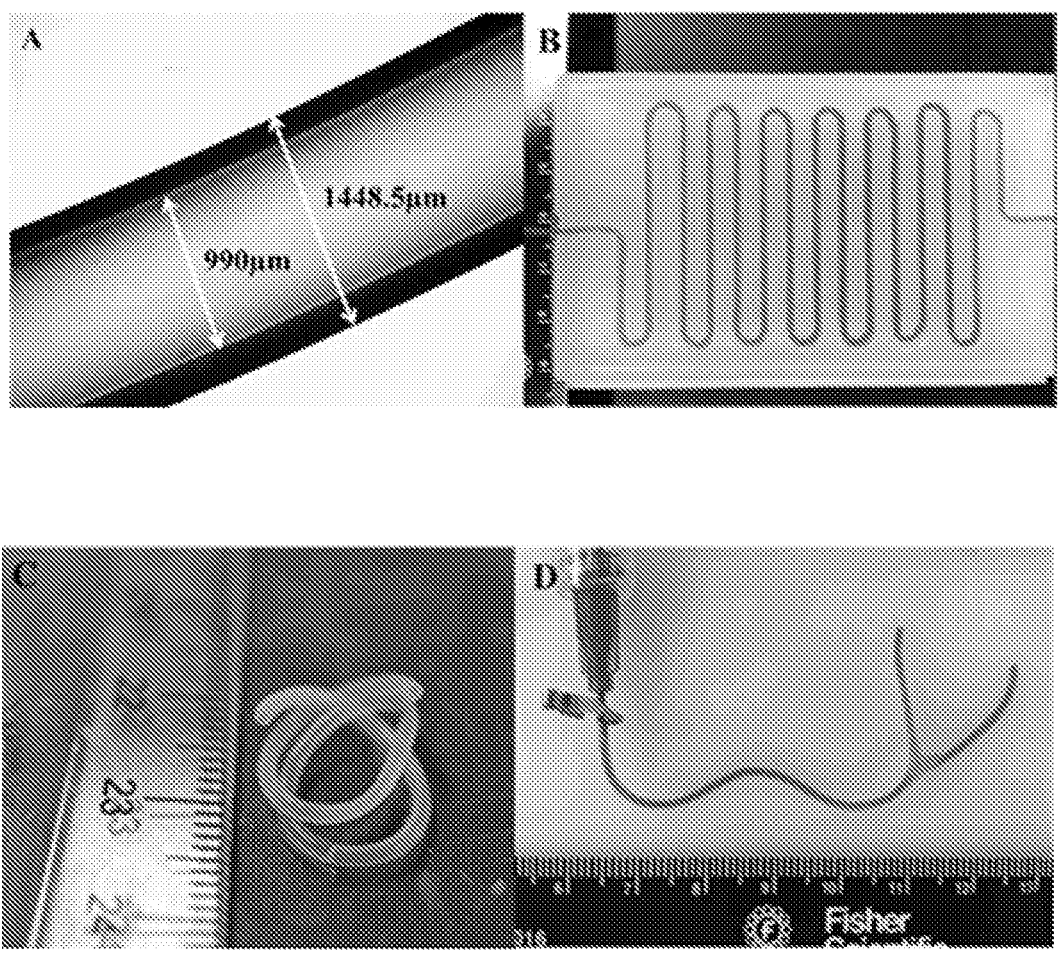

FIGS. 60A-60D depict exemplary vasculature conduits as disclosed herein. FIG. 60A provides a light microscope image of the conduits. FIG. 60B shows a long vasculature conduit printed in a zigzag pattern with perfused cell culture media. FIG. 60C depicts a two-week-cultured vasculature conduit. FIG. 60D depicts a branched vasculature.

Figure 61:
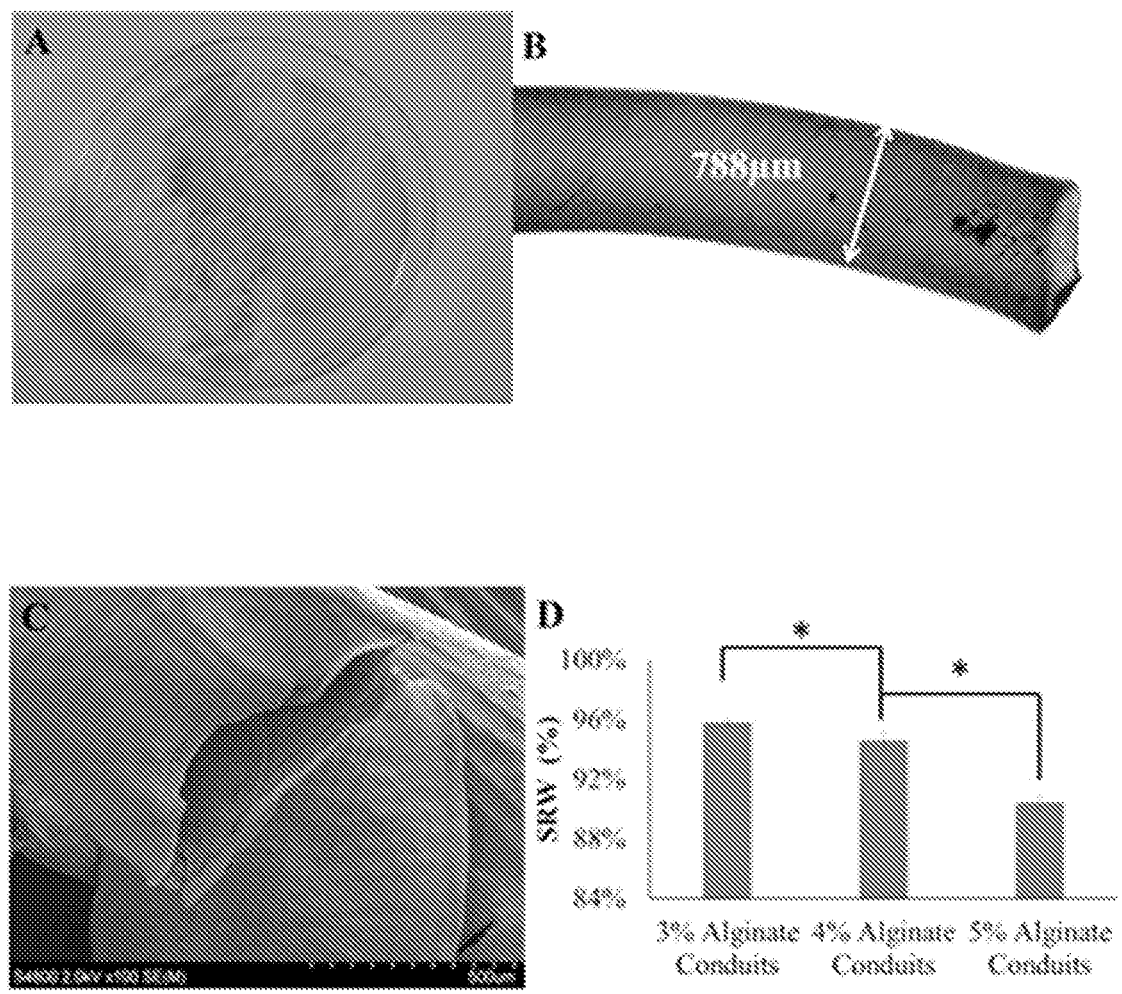

FIGS. 61A-61D depict alginate conduits in dehydration experiments as disclosed herein. FIG. 61A provides a macroscopic image of a dehydrated 5% alginate group. FIG. 61B shows a dehydrated 5% alginate conduit under light microscope. FIG. 61C shows a SEM micrograph of a dehydrated 5% conduit, which still demonstrated a tabular shape. FIG. 61D is a graph depicting shrinkage rate by weight (SRW) of different alginate concentrations (the single asterisk (*) indicates significant difference between groups (p<0.05)).

Figure 62:
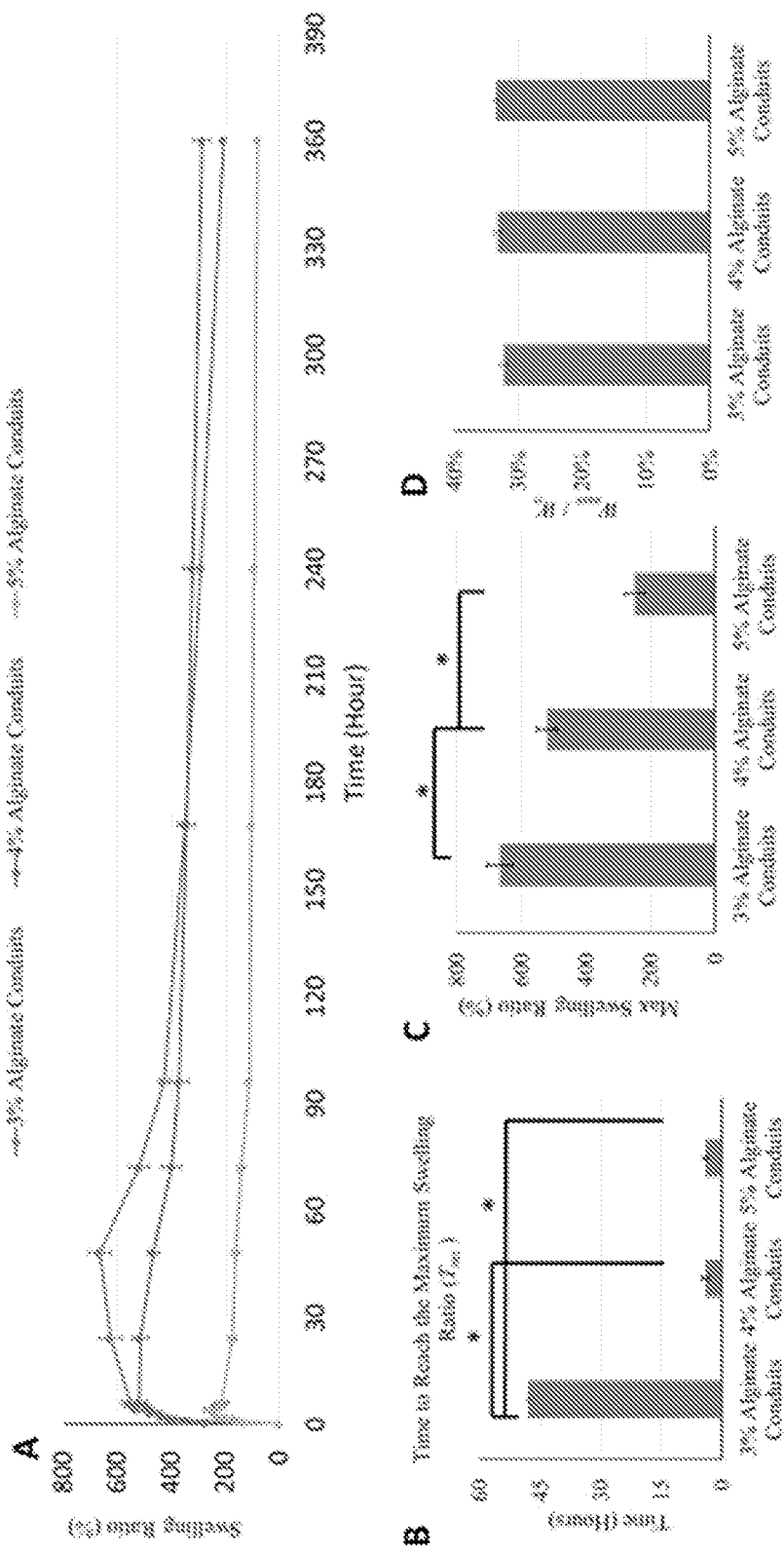

FIGS. 62A-62D are graphs depicting the results of swelling experiments with different alginate concentrations as disclosed herein. FIG. 62A provides a swelling ratio curve. FIG. 62B provides the time to reach the maximum swelling ratio ($T_{ms}$). FIG. 62C provides the maximum swelling ratio. FIG. 62D provides the liquid reabsorption capability (the single asterisk (*) indicates significant difference between groups (p<0.05)).

Figure 63:
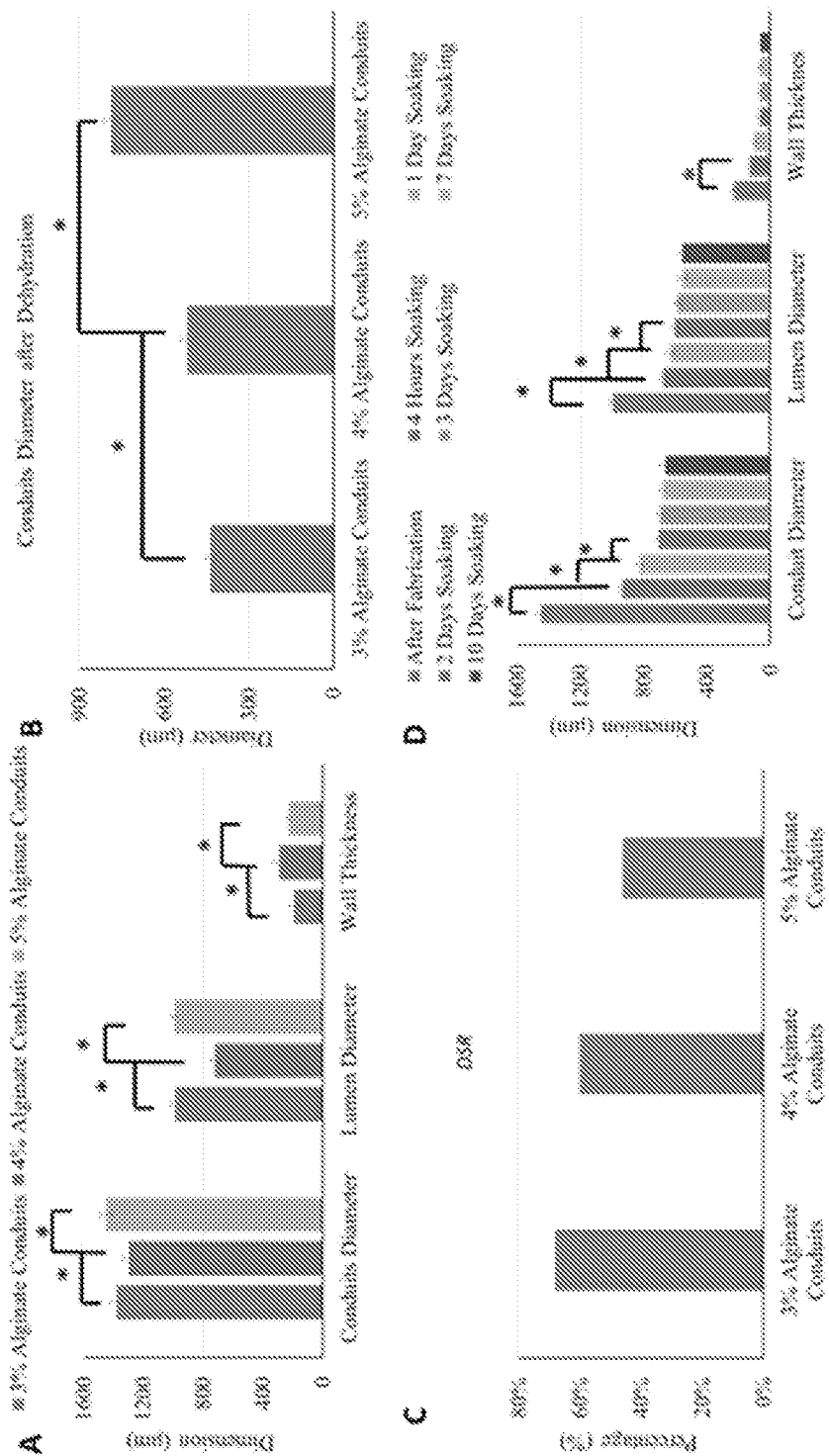

FIGS. 63A-63D are graphs depicting the dimensional characterization of alginate conduits during the dehydration process. FIG. 63A provides the dimensional variations in conduit groups. FIG. 63B provides the conduit diameter after dehydration. FIG. 63C provides the diameter shrinkage rate (DSR) of conduit groups. FIG. 63D provides the dimensional changes of 5% alginate conduits over time (the single asterisk (*) indicates significant difference between groups (p<0.05)).

Figure 64:
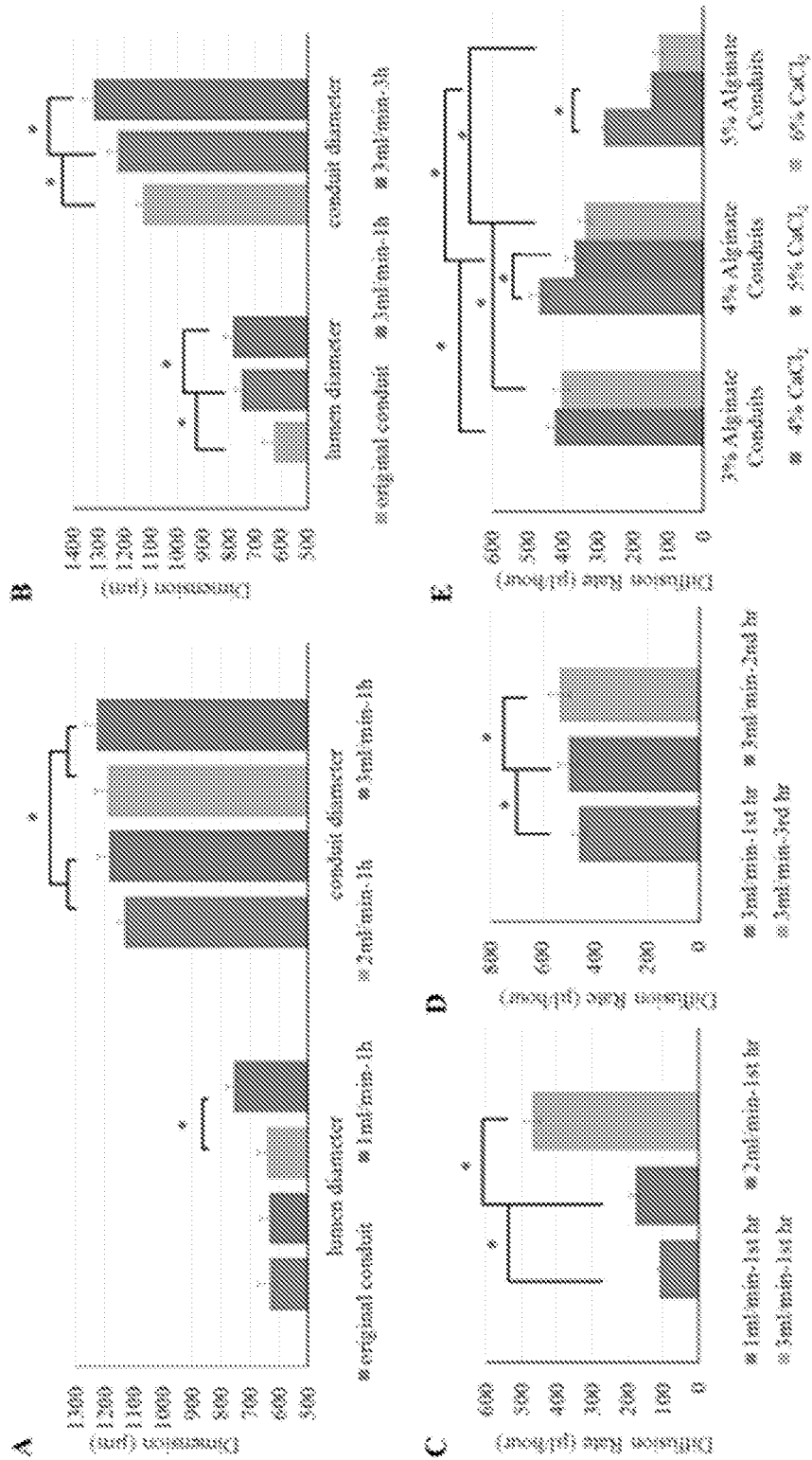

FIGS. 64A-64E are graphs depicting the results of perfusion and permeability studies on alginate conduits. FIG. 64A provides the influence of the perfusion rate on the 4% alginate conduit dimensions. FIG. 64B provides the influence of the perfusion time on the 4% alginate conduit dimensions. FIG. 64C provides the influence of the perfusion rate on the 4% alginate conduit diffusion rate. FIG. 64D provides the influence of the perfusion time on 4% alginate conduit diffusion rate. FIG. 64E provides the influence of the material concentration, biomaterial and crosslinker on the diffusion rate (the single asterisk (*) indicates significant differences between groups (p<0.05)).

Figure 65:
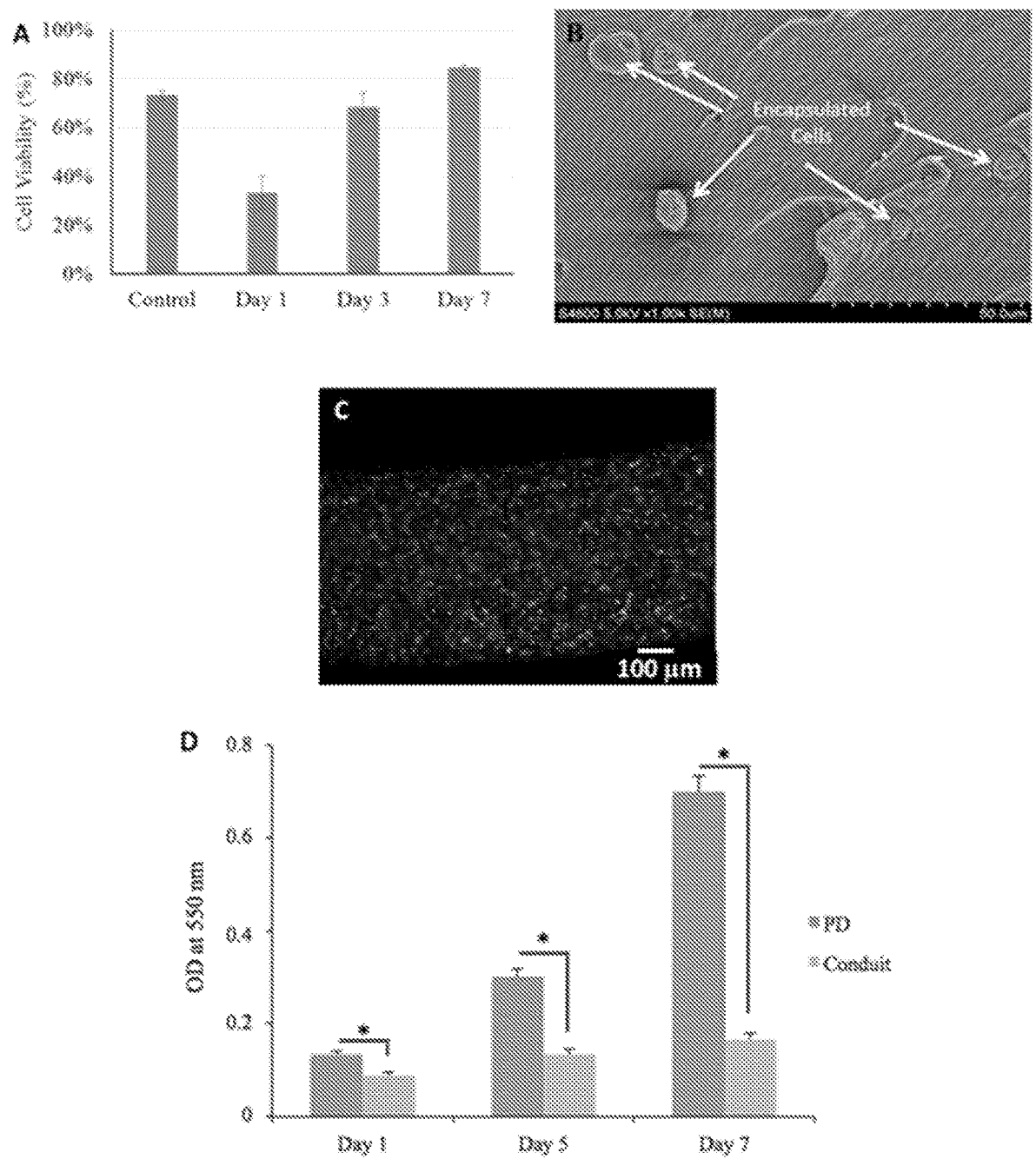

FIGS. 65A-65D depict the results of cell viability testing. FIG. 65A is a graph depicting the cell viability percentage over a one-week time period. FIG. 65B provides a SEM micrograph showing encapsulated cells. FIG. 65C provides a fluorescence image of a three-day-cultured conduit showing increasing cell viability. FIG. 65D is a graph depicting cell proliferation assessed by MTT assay (asterisk (*) indicates significant difference between groups (p<0.05).

Figure 66:
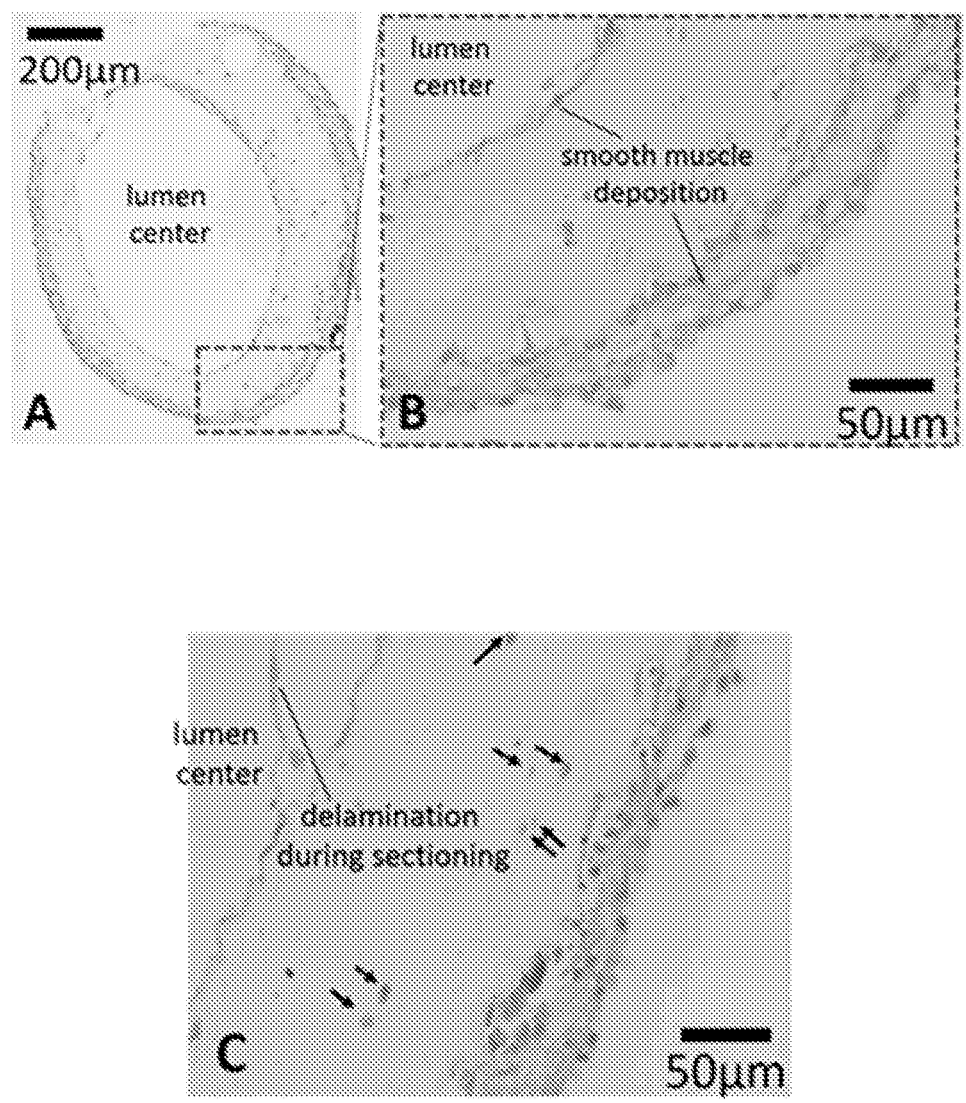

FIGS. 66A-66C depict the histology test for six-week-cultured conduits. FIG. 66A depicts reasonable collagen deposition observed on long-term cultured vasculatures. FIGS. 66B-66C show that thick cell sheets were formed on the conduit walls, where arrowheads show intact cells.

Figure 67:
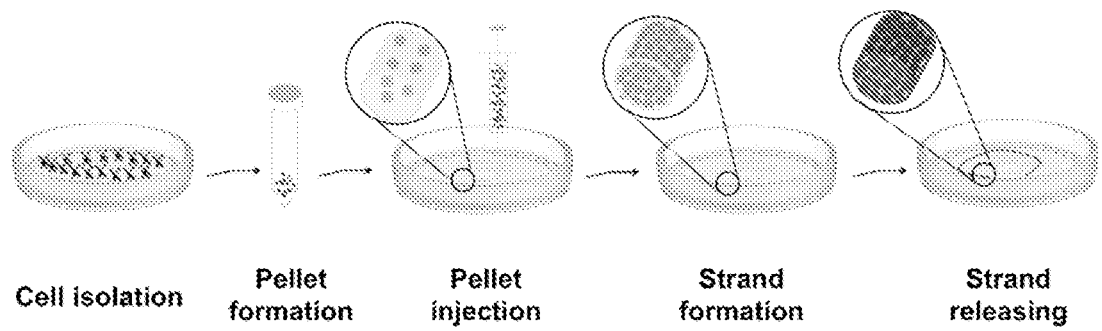

FIG. 67 is a schematic diagram depicting the procedure for tissue strand fabrication process.

Figure 68:
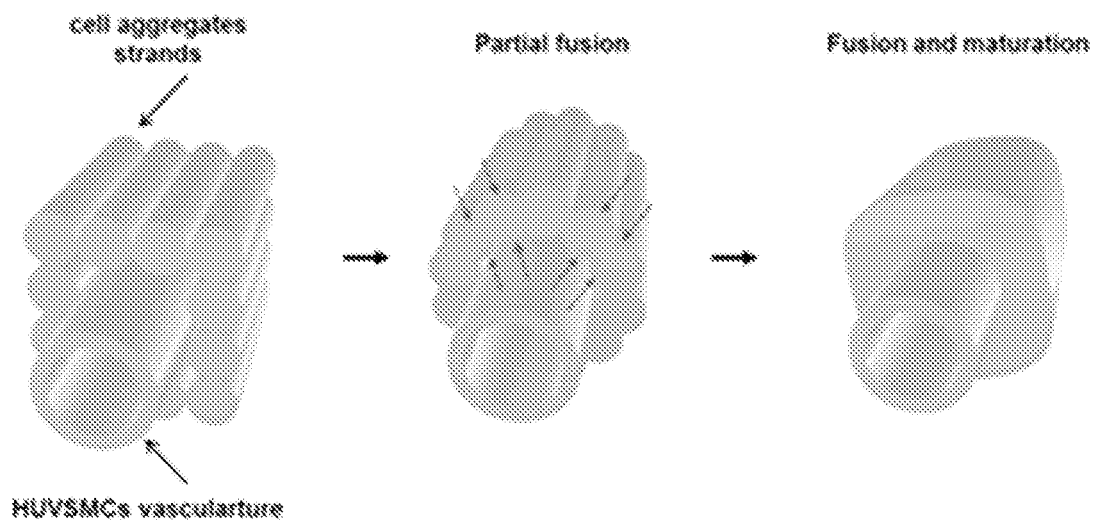

FIG. 68 is a schematic representation of hybrid tissue fabrication using cell aggregate strands and a vascular network as disclosed herein.

FIGS. 69A-69D show printed tabular conduits. FIG. 69A provides an image of a tabular conduit with luminal center and uniform wall thickness (scale bar: 200 µm). FIG. 69B is a graph depicting the dimension of tubular conduit and its lumen. FIG. 69C provides an image of a cellular conduit. FIG. 69D provides an image of a long-term cultured vascular conduit (scale bar: 2 mm).

FIGS. 70A-70F depict tissue strand fabrication and characterization. FIG. 70A provides an image of the cell pellet encapsulated into a tubular conduit. FIG. 70B provides an image of a tissue strand released from the tubular conduit. FIG. 70C provides an image of the cell pellet encapsulated into a tubular conduit. FIG. 70D provides an image of cells encapsulated with high density. FIG. 70E provides an image of a tissue strand released from the tubular conduit. FIG. 70F provides an image of viable cells labeled with green fluorescence. FIG. 70G is a graph depicting the dimension of tissue strands at different time points. FIG. 70H is a graph depicting the viability of tissue strands over time. FIG. 70I is a graph depicting the cell proliferation of tissue strands over time. (Scale bars for FIG. 70A and FIG. 70B: 1 mm; for FIGS. 70C-70F: 200 µm.)

Figure 71:
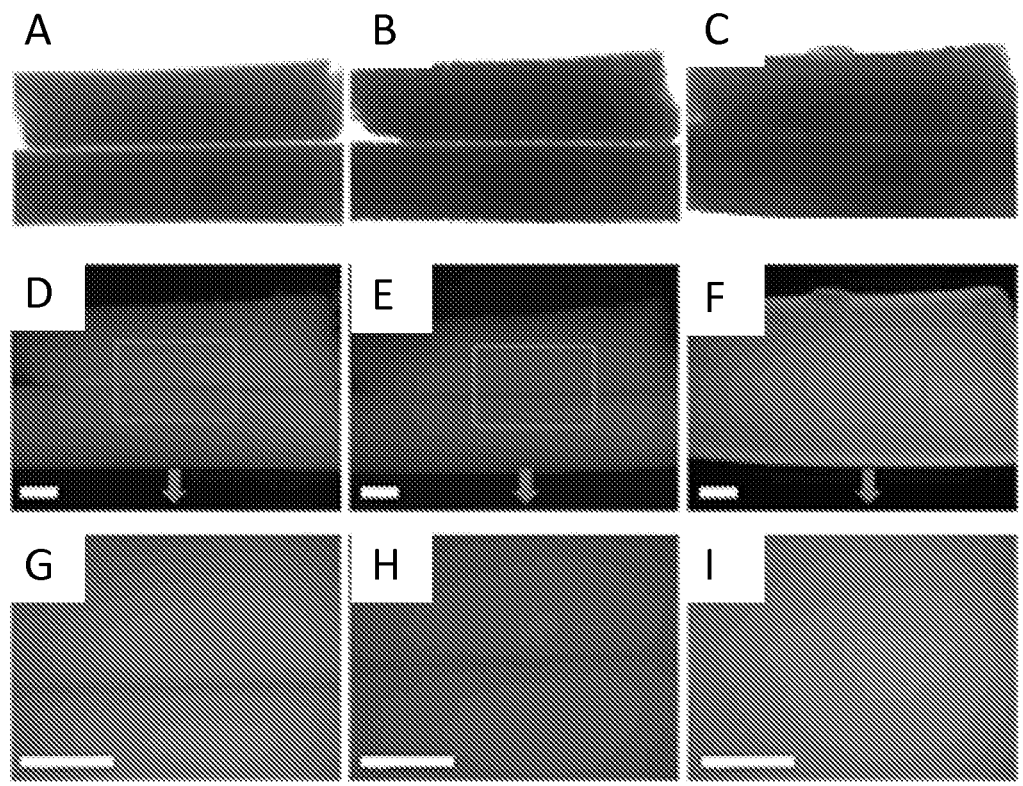

FIGS. 71A-I depict the self-assembly of tissue strands as disclosed herein. (Scale bar: 200 µm). FIGS. 71A, 71D, and 71G show a first sequence of self-assembly. FIGS. 71B, 71E, and 71H show a second sequence of self-assembly. FIGS. 71C, 71F, and 71I show a third sequence of self-assembly.

Figure 72:
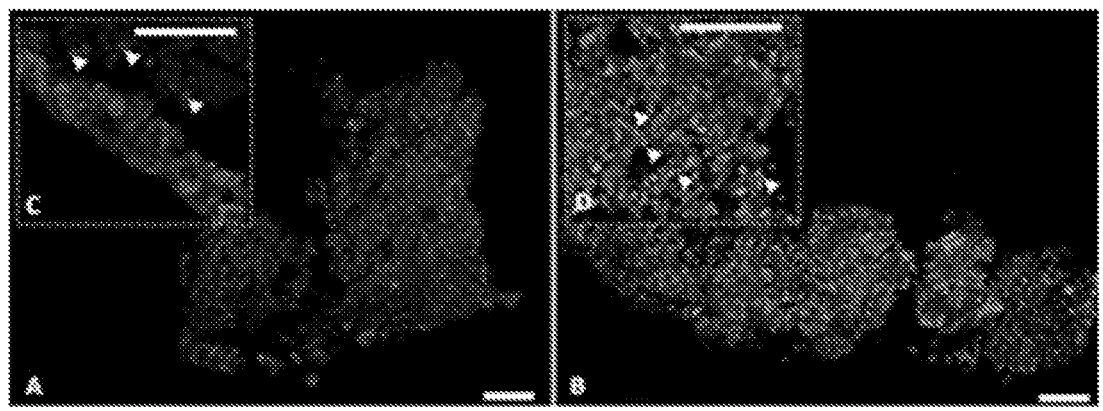

FIG. 72 provides an image of immunofluorescence staining of bTC3 cell markers: (A, C) C-peptide staining; (B, D) insulin staining (scale bar: 200 µm.)

Figure 73:
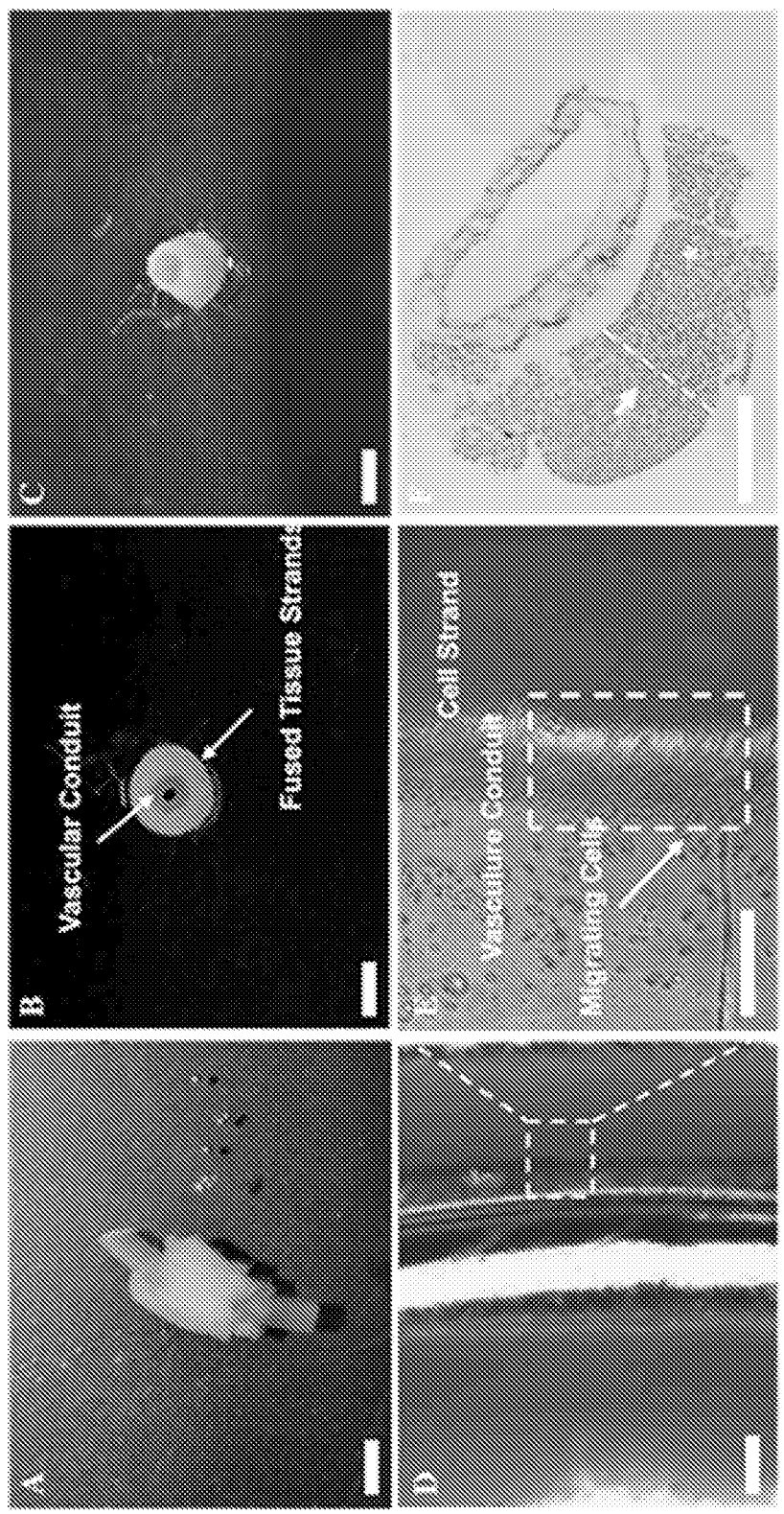

FIGS. 73A-73F depict hybrid macro-vascularized fabrication. FIGS. 73A-73C are schematic representations of the hybrid tissue fabrication process. Specifically, FIGS. 73A-73C depict the fusion of tissue strands with vasculature and maturation of hybrid tissue. FIGS. 73D and 73E provides images of the integration of tissue strands with vasculature through cell migration. FIG. 73F provides histological evidence of fusion.

Figure 74:
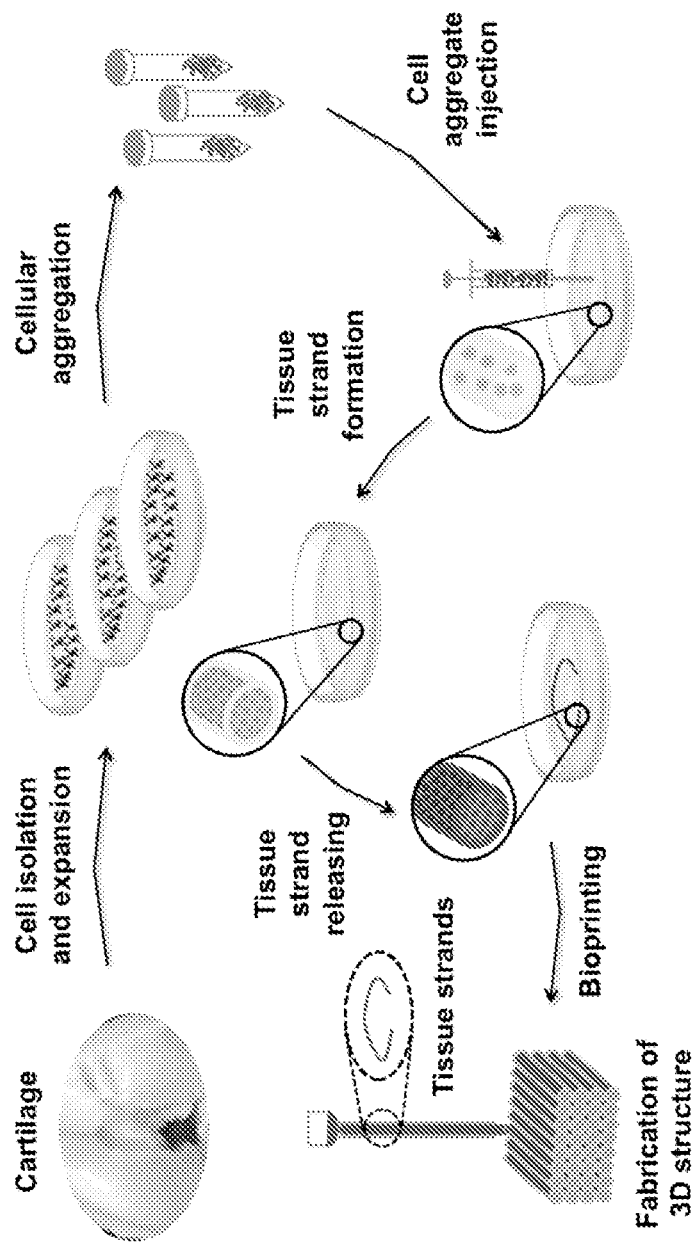

FIG. 74 is a detailed schematic diagram depicting an exemplary process for fabricating tissue strands as disclosed herein.

Figure 75:
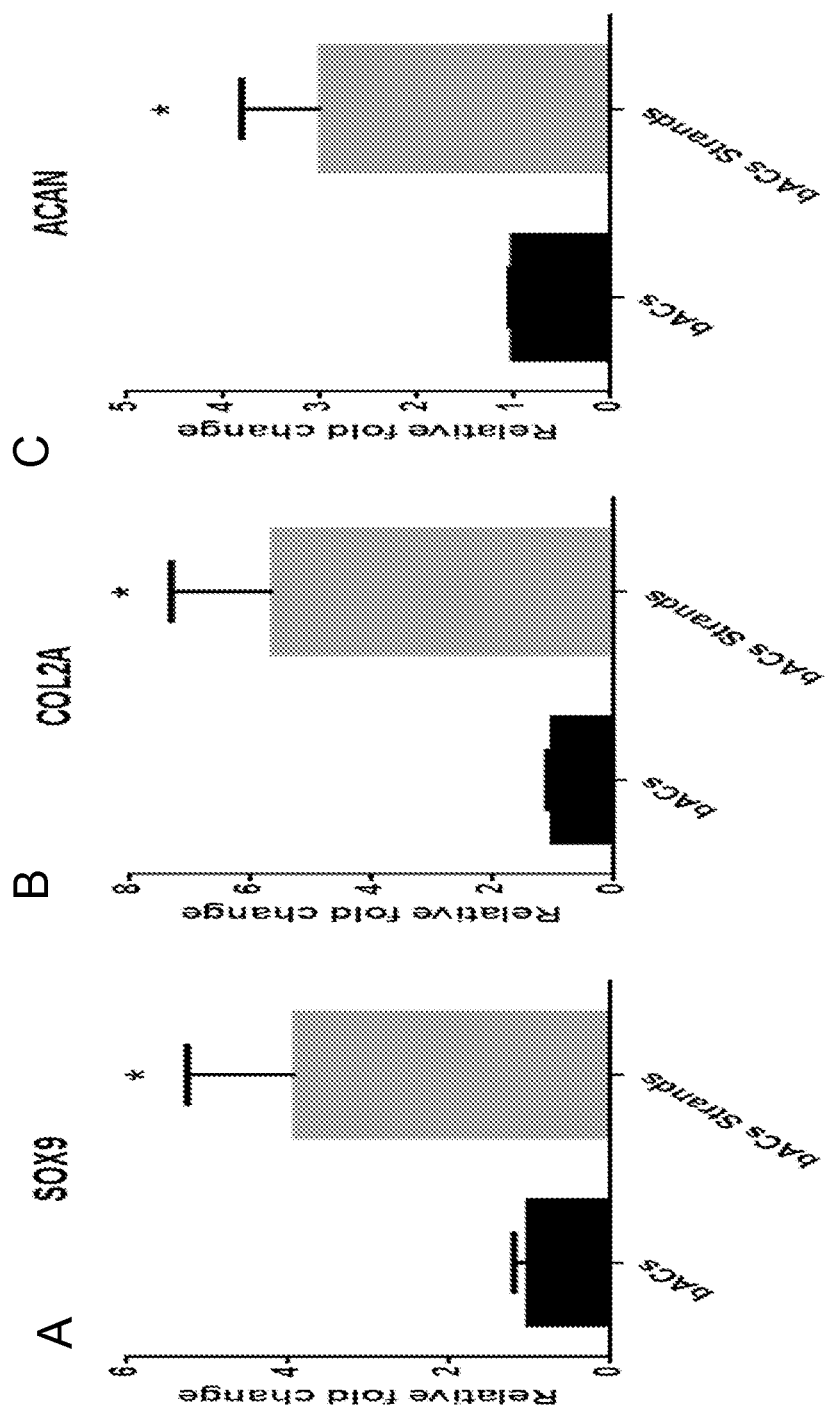

FIGS. 75A-75C depict real-time gene expression analysis. As shown in FIG. 75A, SOX-9 showed a nearly 4-fold change (p=0.0069) in tissue strands compared to a control group (cultured bovine articular chondrocytes (bACs)). As shown in FIG. 75B, COL2A gene showed a nearly 6-fold increase (p=0.0089) in tissue strands compared to the control group. As shown in FIG. 75C, Aggrecan gene (ACAN) showed nearly a 3-fold change (p=0.014) in tissue strands compare to the control group.

Figure 76:
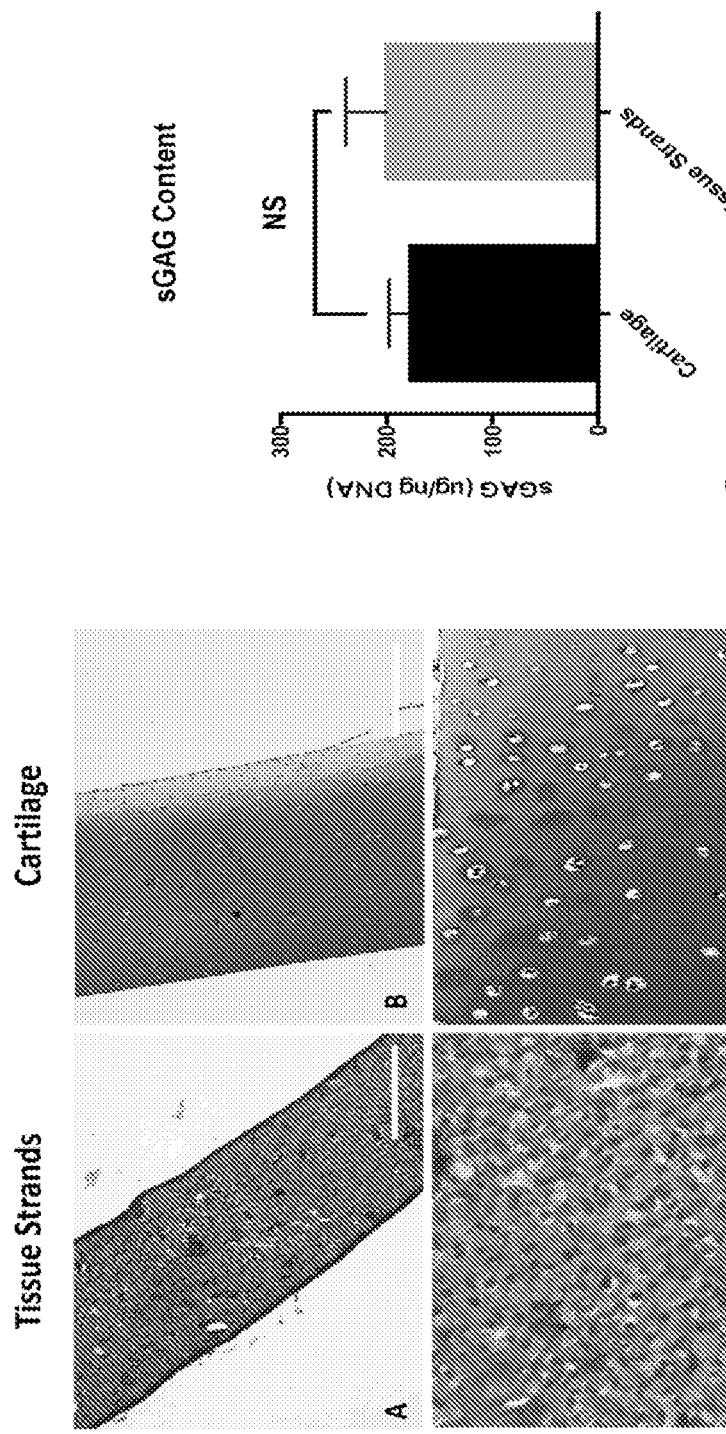

FIG. 76A depicts a tissue strand showing strong positive staining for safranin-O. FIG. 76B depicts the staining of native cartilage. FIGS. 76C-76D are high resolution close-up images of FIGS. 76A-76B, respectively. FIG. 76E depicts the results of a DMMB assay, in which sGAG content from tissue strands were 200.9±21.69 µg/ng DNA, while native cartilage had sGAG content of 178.1±11.45 µg/ng DNA (p<0.05).

Figure 77:
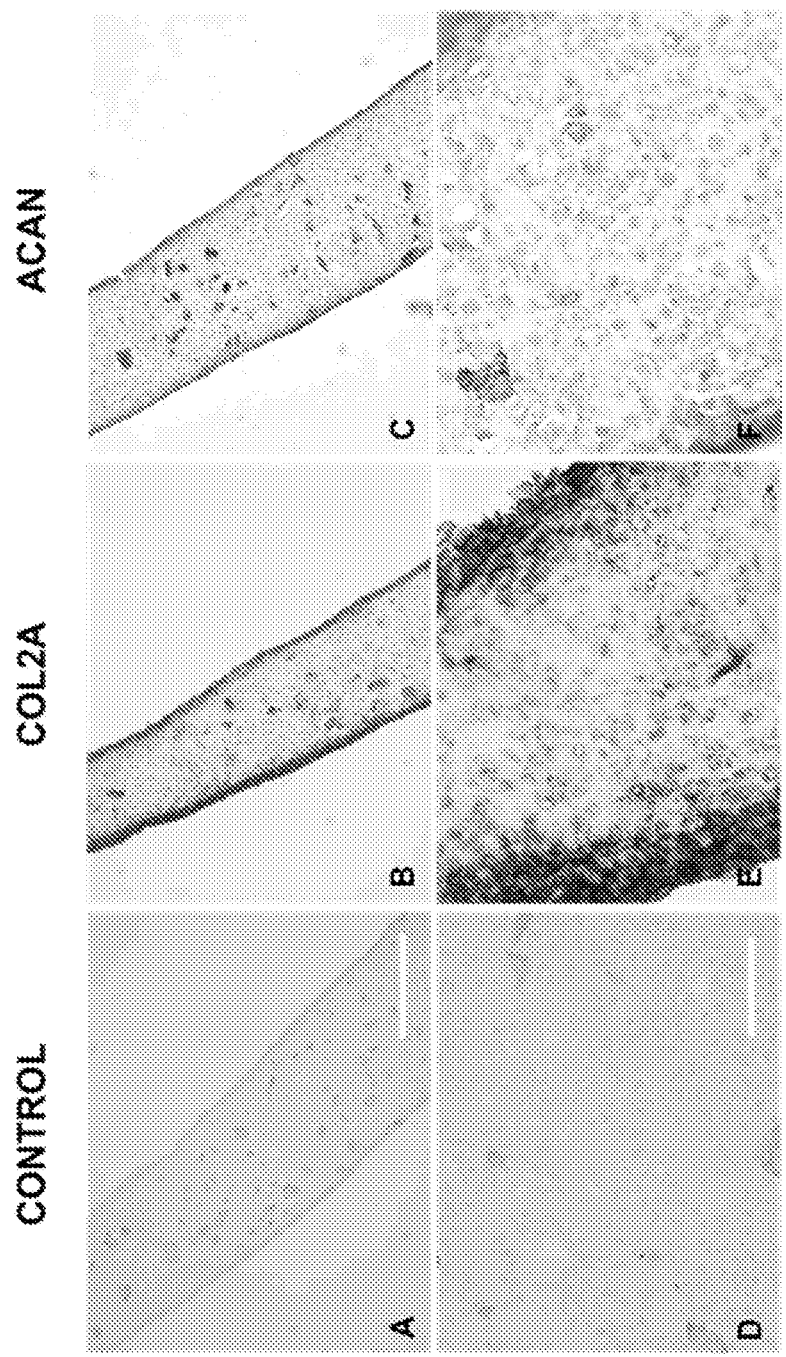

FIGS. 77A-77F depict the results of an immunostaining study. FIG. 77A shows expression of isotype IgG antibody control. FIG. 77B shows expression of type II collagen. FIG. 77C shows expression of aggrecan. FIGS. 77D-77F are higher resolution close-up images of FIGS. 77A-77C, respectively.

Figure 78A:
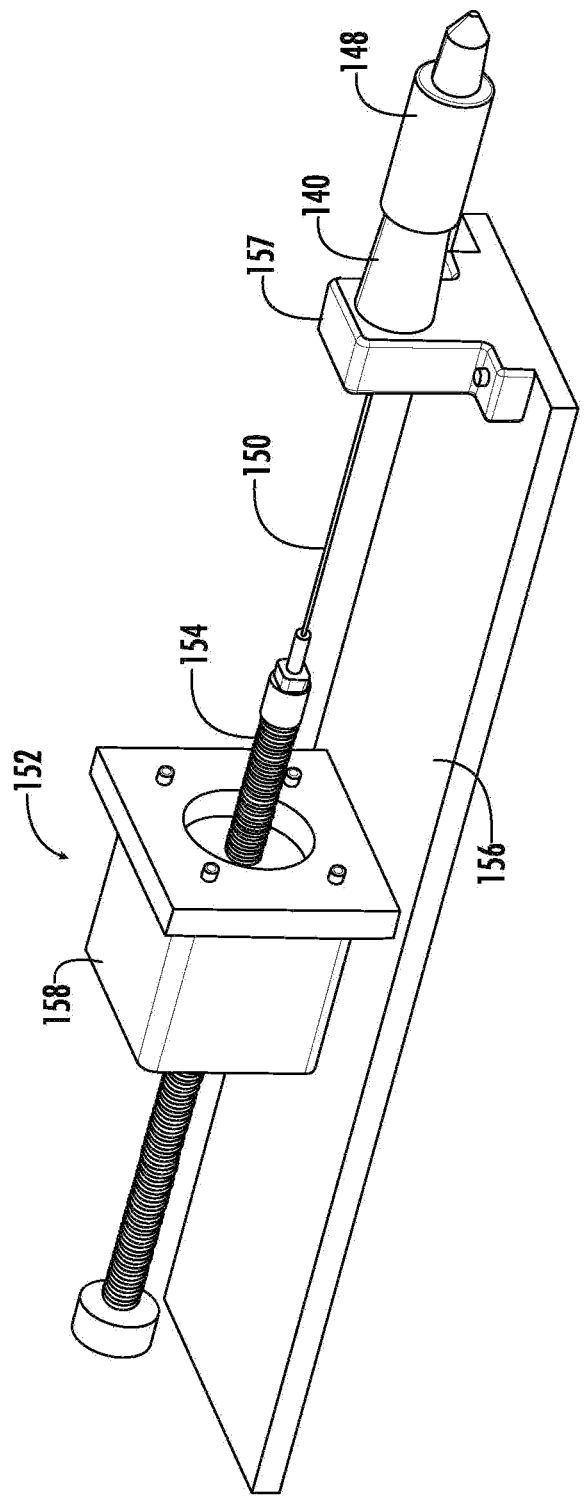
Figure 78B:
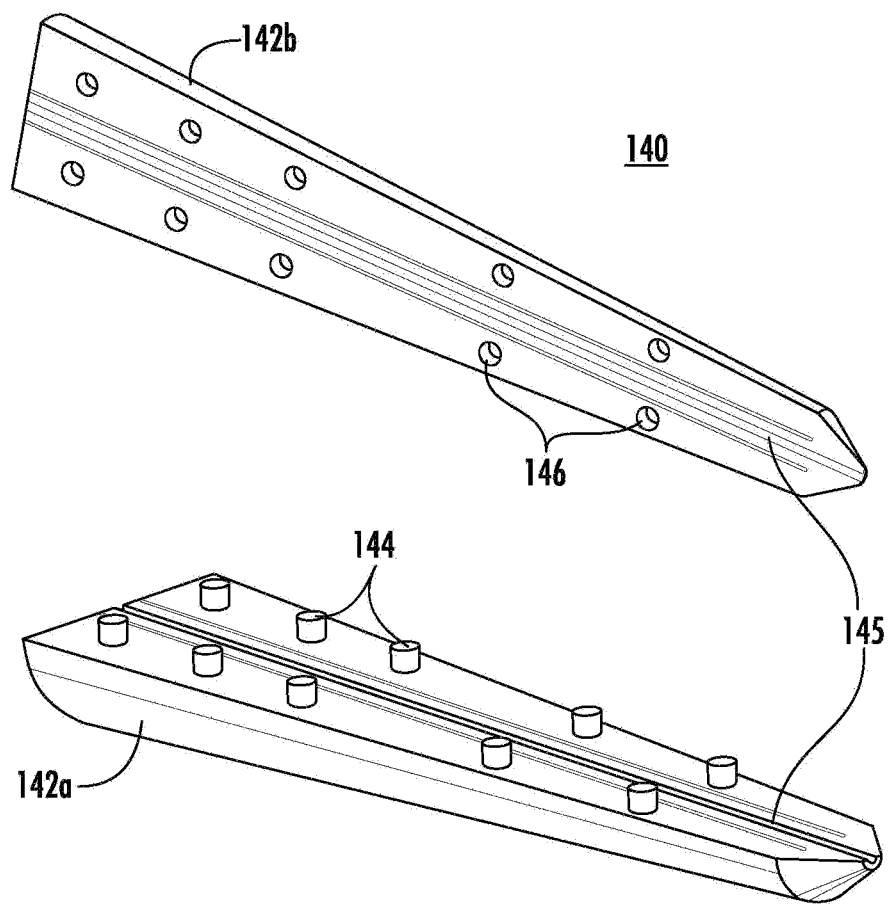

FIGS. 78A-78B depict an exemplary nozzle assembly that can be selectively assembled and disassembled as disclosed herein. FIG. 78A is a perspective view of the nozzle assembly in an operative position. FIG. 78B is an exploded view of the nozzle assembly, showing the two shell portions of the nozzle assembly.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an arm assembly" can include two or more such arm assemblies unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

As used herein, the term "actuator" refers to any conventional device that is configured to effect axial movement of an object relative to a translation axis. For example, it is contemplated that an actuator can comprise a linear actuator, such as, for example and without limitation, a pneumatic actuator, a hydraulic actuator, a motorized linear actuator, or a manually-powered linear actuator. It is understood that an actuator can comprise a motor component that is configured to generate movement of the actuator.

Throughout this application, including in the References list, various publications are referenced. The disclosures of these publications in their entireties are hereby incorporated by reference into this application in order to more fully describe the state of the art to which this invention pertains.

Bioprinter and Bioprinting Systems

Described herein with reference to FIGS. 1A-7, 13, and 15A-21, 32-33, 46-48B, 51A, and 78A-78B is a bioprinter 10 for producing a desired three-dimensional (3D) construct, such as, for example and without limitation, a desired 3D tissue construct 500. In exemplary aspects, the bioprinter 10 can have a support assembly 20 and at least one printer head 30. Optionally, it is contemplated that the at least one printer head 30 can comprise at least two printer heads. It is further contemplated that any required number of printer heads can be used for a particular application.

In one aspect, and with reference to FIGS. 17A-18, the support assembly 20 can comprise a base portion and at least one frame assembly 26. In this aspect, the base portion can comprise a platform 22 configured to support a 3D construct, such as, for example and without limitation, a 3D tissue construct 500, printed by the bioprinter 10. It is contemplated that the platform 22 can have a longitudinal axis (corresponding to a first translation axis 46 of the bioprinter). Optionally, it is further contemplated that the base portion can be configured to remain substantially stationary during printing of the 3D construct. In exemplary aspects, the base portion can comprise a table that defines the platform 22.

In additional aspects, each frame assembly 26 of the support assembly 20 can be operatively coupled to opposed first and second sides of the base portion, with the frame assembly defining a central opening 33 that is shaped to receive at least a portion of the platform 22. It is contemplated that each frame assembly 26 can be operatively coupled to the first and second sides of the base portion such that the frame assembly is configured for selective movement relative to the first translation axis 46. In exemplary aspects, it is contemplated that the first and second sides can define respective receiving channels 39 configured to receive a complementary portion of the frame assembly 26. In other exemplary aspects, each frame assembly 26 of the support assembly 20 can comprise a first frame element 37a operatively coupled to the first side of the base portion and extending vertically from the platform 22 (relative to a second translation axis 44), a second frame element 37b operatively coupled to the second side of the base portion and extending vertically from the platform (relative to the second translation axis), and a connecting element 39 coupled to and positioned between the first and second frame elements (extending relative to a third translation axis 42). Thus, in these aspects, the second translation axis 44 can substantially correspond to a vertical axis (moving toward and away from the base portion), and the third translation axis 42 can optionally be substantially perpendicular to both the first translation axis 46 and the second translation axis 44 (substantially transverse to the longitudinal axis of the platform 22). In these aspects, it is contemplated that the first and second frame elements 37a, 37b of each frame assembly 26 can define complementary engagement portions configured for receipt within the receiving channels 28 defined by the first and second sides of the base portion, thereby permitting selective movement of each frame assembly 26 relative to the first translation axis 46. It is contemplated that each frame assembly 26 can be operatively coupled to an actuator 47 configured to effect movement of the frame assembly relative to the first translation axis 46.

In another aspect, each printer head 30 of the bioprinter 10 can have an arm assembly 32 with a proximal and a distal portion 38. In exemplary aspects, the proximal portion 34 of the arm assembly 32 of each printer head 30 can be operatively coupled to the support assembly 20 such that the arm assembly is selectively moveable relative to at least one axis (e.g., at least one of translational axes 42, 44, 46). For example, it is contemplated that the arm assembly 32 can be selectively moveable relative to at least the second translation axis 44 during operation of the bioprinter 10. It is contemplated that the arm assembly 32 can be selectively moveable relative to at least the third translation axis 42 during operation of the bioprinter 10. It is further contemplated that the arm assembly 32 can be selectively moveable relative to at least the first translation axis 46 during operation of the bioprinter 10. Optionally, it is contemplated that the proximal portion 34 of the arm assembly 32 of each printer head 30 can be operatively coupled to the support assembly 20 such that the arm assembly is selectively moveable relative to at least two axes. For example, in exemplary aspects, it is contemplated that the arm assembly 32 can be selectively moveable relative to at least the second translation axis 44 and the third translation axis 42 during operation of the bioprinter 10.

In exemplary aspects, each arm assembly 32 can comprise first and second arm elements 33a, 33b. In these aspects, it is contemplated that the first and second arm elements 33a, 33b can have respective longitudinal axes oriented substantially parallel to the second translation axis 44. It is further contemplated that the first arm element 33a can define the proximal portion 34 of the arm assembly 32 and be operatively coupled to the connecting element 39 such that the first arm element is configured for selective movement relative to the third translation axis 42 during operation of the bioprinter 10. It is still further contemplated that the second arm element 33b can define the distal portion 38 of the arm assembly 32 and be operatively coupled to the first arm element 33a such that the second arm element is configured for selective movement relative to the second translation axis 44 during operation of the bioprinter 10. It is further contemplated that each arm assembly 32 can comprise at least one actuator 47 configured to effect movement of the arm assembly relative to the at least one axis. In exemplary aspects, the at least one actuator 47 can comprise a first actuator configured to effect movement of the first arm element 33a and a second actuator configured to effect movement of the second arm element 33b.

In additional aspects, and with reference to FIGS. 1-6, 13, 15A, 16, 19, 32, and 47, each printer head 30 can have a nozzle assembly 50 coupled to the distal portion 38 of the arm assembly 32 of the printer head. In these aspects, the nozzle assembly 50 of each printer head 30 can be configured to receive and dispense at least one biomaterial as the arm assembly 32 of the printer head is moved relative to at least one of the first, second, and third translation axes 42, 44, 46.

In exemplary aspects, and with reference to FIGS. 6A-6B, the nozzle assembly 50 of the at least one printer head 30 can have a longitudinal axis 52 and comprise an outer nozzle 60 and an inner nozzle 80. In these aspects, the outer nozzle 60 can have a proximal end 62, a distal end 64, an outer surface 66, and an inner surface 70. It is contemplated that the inner surface 70 can define a central bore 72 and an inner diameter 74 of the outer nozzle 60. It is further contemplated that the outer surface 66 can define an inlet 68 positioned in communication with the central bore 72. It is still further contemplated that the inner surface 70 of the distal end 64 of the outer nozzle 60 can define an outlet 76 in communication with the central bore 72. In additional aspects, the inner nozzle 80 can have a proximal end 82, a distal end 84, an outer surface 86, and an inner surface 90. In these aspects, the outer surface 86 can define an outer diameter of the inner nozzle 80. It is contemplated that the inner surface 90 can define a central bore 92. It is further contemplated that the inner surface 90 of the proximal end 82 of the inner nozzle 80 can define an inlet 94. It is still further contemplated that the inner surface 90 of the distal end 84 of the inner nozzle 80 can define an outlet 96. In use, the inner nozzle 80 can be at least partially received within the central bore 72 of the outer nozzle 60 such that the outer nozzle and the inner nozzle have a common longitudinal axis that is in substantial alignment with the longitudinal axis 52 of the nozzle assembly 50. The outer diameter of the inner nozzle 80 can be less than the diameter of the outlet 76 of the outer nozzle 60 to thereby define a receiving space 100 between the outer surface 86 of the inner nozzle 80 and the inner surface 70 of the outer nozzle 60. In exemplary aspects, it is contemplated that the inner nozzle 80 can have a gauge size ranging from about 20 to about 28. It is further contemplated that the gauge size of the inner nozzle 80 can range from about 22 to about 26. In other exemplary aspects, it is contemplated that the outer nozzle 60 can have a gauge size ranging from about 14 to about 18. It is further contemplated that the gauge size of the outer nozzle 60 can be about 16. In another aspect, the inlet 68 of the outer nozzle 60 can be configured to receive at least one biomaterial and deliver the at least one biomaterial to the receiving space 100. In this aspect, the outlet 76 of the outer nozzle 60 can be configured to dispense the at least one biomaterial from within the receiving space 100. In a further aspect, the inlet 94 of the inner nozzle 80 can be configured to receive at least one biomaterial and deliver the at least one biomaterial to the central bore 92 of the inner nozzle. In this aspect, the outlet 96 of the inner nozzle 80 can be configured to dispense the at least one biomaterial from within the central bore 92 of the inner nozzle 80. In use, it is contemplated that the inner and outer nozzles 60, 80 can be configured to concurrently dispense at least one biomaterial, with the biomaterial dispensed by the outer nozzle 60 circumferentially surrounding the biomaterial dispensed by the inner nozzle 80.

In exemplary aspects, and with reference to FIG. 47, the distal portion 38 of the arm assembly 32 of at least one printer head 30 can be selectively rotatable relative to the proximal portion 34 of the arm assembly. In these aspects, the nozzle assembly 50 of the at least one printer head 30 can be configured to receive and dispense the at least one biomaterial as the arm assembly 32 is selectively moved relative to at least the first axis and the distal portion 38 of the arm assembly is selectively rotated relative to the proximal portion 34 of the arm assembly. In exemplary aspects, the distal portion of the second arm element 33b can be configured for selective rotation relative to at least first and second rotational axes 43a, 43b. Thus, it is contemplated that the bioprinting system can operate with five degrees of freedom by providing selective axial movement relative to the first, second, and third translational axes 42, 44, 46 and by providing rotational movement relative to the first and second rotational axes 43a, 43b. In exemplary aspects, and with reference to FIG. 3C, the distal portion 38 of the arm assembly 32 can comprise a nozzle support portion 48 that projects outwardly from the distal portion of the arm assembly and is configured to securely engage the nozzle assembly 50. In these aspects, it is contemplated that the nozzle support portion 48 can be configured for rotation relative to other portions of the distal portion 38 and to the proximal portion 38 of the arm assembly 32. In further exemplary aspects, it is contemplated that the nozzle support portion 48 can comprise a first arm 49a and a second arm 49b. In these aspects, the first arm 49a can be secured to the distal portion 38 of the arm assembly 32, and the second arm 49b can be pivotally connected to the first arm such that the second arm is configured for selective rotation relative to the first rotational axis 43a. Optionally, it is contemplated that the first rotational axis 43a can be in substantial alignment with the third translational axis 42. In another aspect, an opposed end of the second arm 49b can define a pivot joint 55 that is configured to securely engage and support a nozzle assembly 50. In this aspect, the pivot joint 55 can be further configured for pivotal movement relative to the remainder of the second arm 49b. It is contemplated that the pivot joint 55 can be configured for selective rotation relative to the second rotational axis 43b. Thus, when the pivot joint 55 securely engages and supports the nozzle assembly 50, rotation of the second arm 49b can effect a corresponding rotation of the nozzle assembly. Optionally, the second rotational axis 43b can be in substantial axial alignment with the first translational axis 46.

Figure 1A:
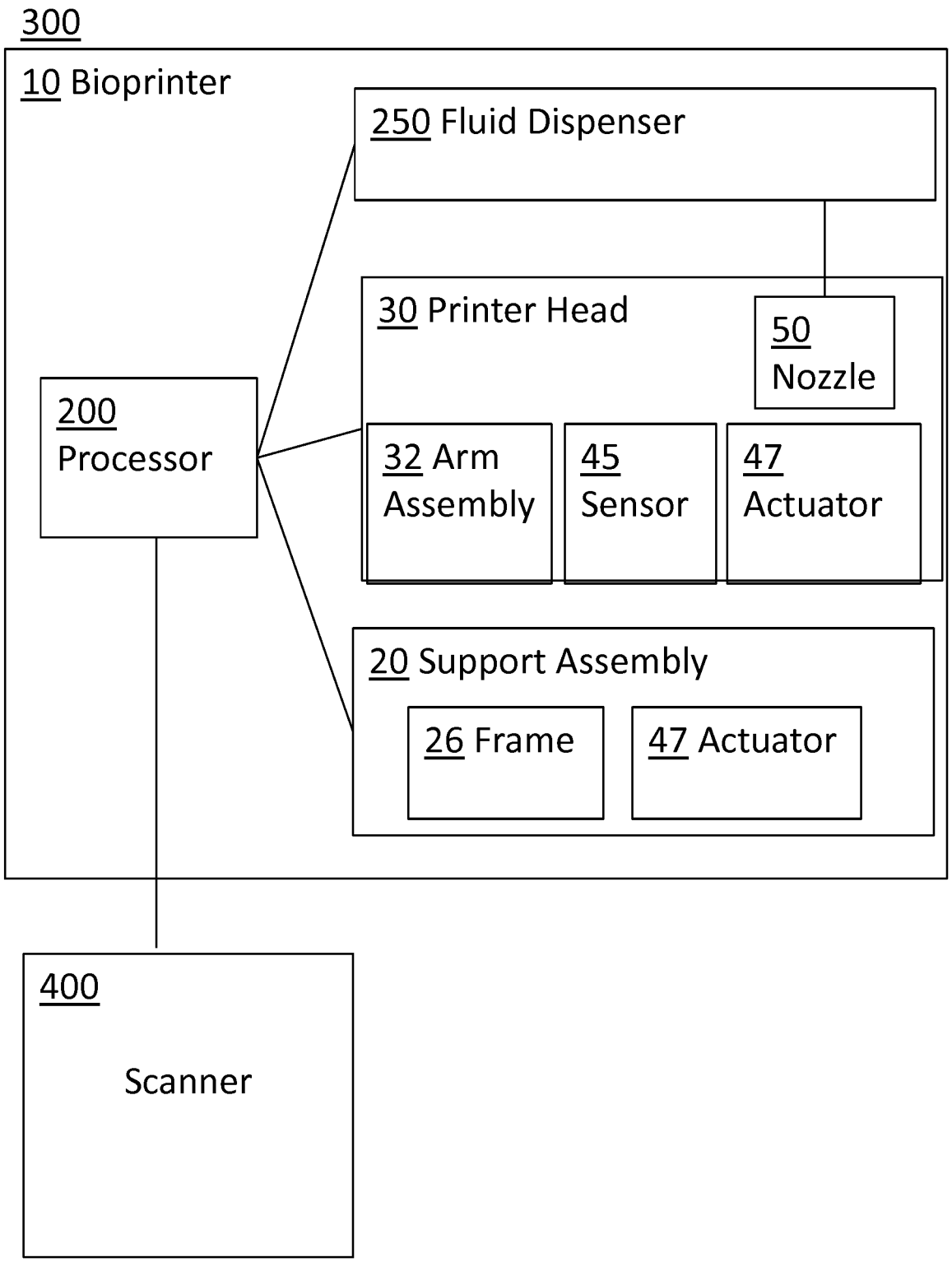
FIG. 1A is a schematic diagram depicting an exemplary bioprinting system as disclosed herein.

In exemplary aspects, and with reference to FIG. 1A, the bioprinter 10 can comprise a processor 200 as is conventionally known in the art. In these aspects, the processor 200 can optionally be a component of a computer or other device having a memory that is in electrical communication with the processor. In additional aspects, and as further disclosed herein, the memory can store control modules (such as, for example and without limitation, fluid deposition control modules, machine control modules, and the like) and other programming elements configured to effect desired operation of the bioprinter 10. In exemplary aspects, the processor can be configured to determine a desired tool path. In these aspects, the desired tool path can correspond to a desired path of movement of one or more of the print heads 30. Optionally, the desired tool path can be determined based upon at least one input received through one or more of a user interface, the memory, and other elements of the bioprinter positioned in communication with the processor. It is contemplated that the desired tool path can correspond to movement of one or more of the print heads 30 as required to produce a patterned tissue construct as disclosed herein. In exemplary aspects, the desired tool path can comprise at least one of a shape of the tissue construct, a sequence in which biomaterials are delivered by the respective print heads, the rate at which biomaterials are delivered by the print heads, the direction and degree of movement of the arm assembly, the direction and degree of rotation of the arm assembly, and the rate of movement of the arm assembly. In further exemplary aspects, the desired tool path can comprise distinct operational parameters for each respective print head 30. It is further contemplated that the processor 200 can be operatively coupled to the actuators 47 (e.g., operatively coupled to a motor of each actuator) of the bioprinter 10 to effect desired movement of the various elements of the bioprinter as further disclosed herein. In exemplary aspects, the processor 200 can be configured to selectively adjust the positioning of the arm assembly 32 of each printer head 30 relative to at least one axis (e.g., at least one translational axis 42, 44, 46) as disclosed herein. In further exemplary aspects, the processor 200 can be configured to selectively adjust the rotational position of the nozzle assembly 50 relative to at least one rotational axis (e.g., rotational axes 43a, 43b) as further disclosed herein.

Figure 1B:
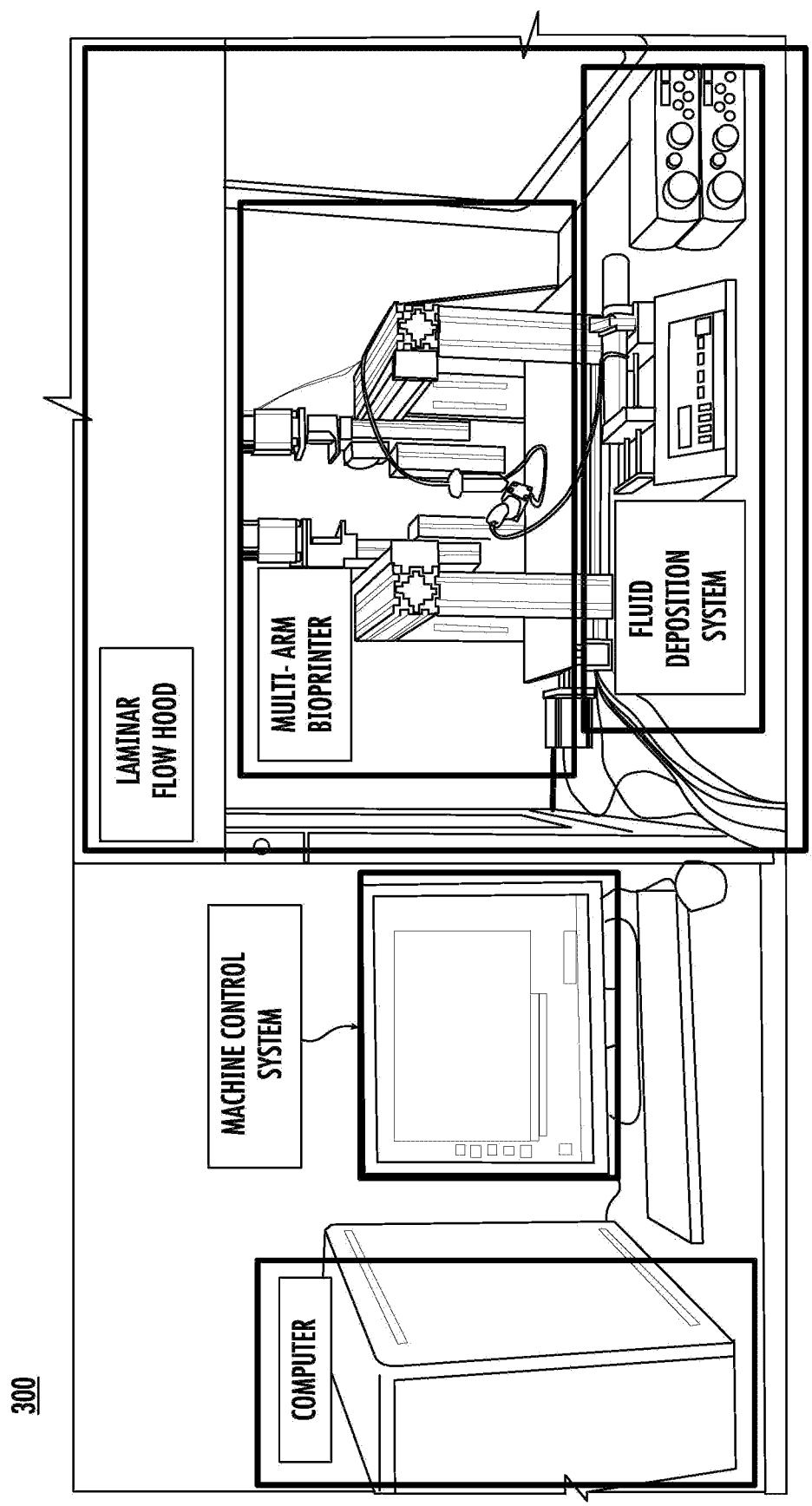
FIG. 1B displays an exemplary bioprinter setup comprising a computer, a machine control system, a fluid deposition system, and a bioprinter as disclosed herein.

With reference to FIGS. 1A-1B, in exemplary aspects, the bioprinter 10 can comprise a fluid dispenser or fluid deposition system 250 that is positioned in operative electrical communication with the processor 200. In these aspects, it is contemplated that the fluid dispenser 250 can comprise a container configured to receive at least one biomaterial or other fluid as disclosed herein. It is further contemplated that the fluid dispenser 250 can comprise means for delivering the at least one biomaterial or fluid within the container to a corresponding nozzle assembly 50 of the bioprinter 10. In exemplary aspects, the means for delivering the at least one biomaterial can be positioned in operative electrical communication with the processor 200. In these aspects, the processor 200 can be configured to selectively activate the means for delivering the at least one biomaterial to provide the at least one biomaterial to the nozzle assembly 50 in a desired manner. Optionally, it is contemplated that the processor 200 can be configured to selectively control the volume of biomaterial provided to the nozzle assembly 50 as well as the rate at which the biomaterial is provided to the nozzle assembly. In one aspect, the means for delivering the at least one biomaterial can comprise a fluid pump as is known in the art. In another aspect, the means for delivering the at least one biomaterial can comprise a mechanical fluid dispenser as is known in the art. In a further aspect, the means for delivering the at least one biomaterial can comprise a pneumatic fluid dispenser as is known in the art. In additional exemplary aspects, the container of the fluid dispenser 250 can comprise at least one syringe, and the means for delivering the at least one biomaterial can comprise one or more actuators that are operatively coupled to the syringes to effect dispensing of the biomaterial contained within the syringes. In further exemplary aspects, it is contemplated that the means for delivering the at least one biomaterial can comprise tubing that places the fluid dispenser 250 in fluid communication with the nozzle assembly 50.

In further exemplary aspects, it is contemplated that the bioprinter 10 can comprise at least one sensor 45 operatively positioned relative to the printer heads 30 of the bioprinter 10 (and in operative communication with the processor 200) to ensure appropriate spacing between the nozzle assemblies 50 during operation of the bioprinter. In these aspects, it is contemplated that the at least one sensor 45 can comprise at least one proximity sensor (e.g., limit switch) or position sensor as is known in the art. It is contemplated that the at least one sensor 45 can be configured to detect the position of the nozzle assembly 50 of a first printer head 30 relative to the nozzle assembly of a second printer head. In exemplary aspects, the at least one sensor 45 can be configured to transmit an output signal to the processor 200, with the output signal being indicative of the relative positions of the nozzle assemblies 50 of the first and second printer heads 30. In these aspects, it is contemplated that the processor 200 can be configured to determine whether the positions of the nozzle assemblies 50 are in accordance with a desired tool path as further disclosed herein. It is further contemplated that the processor 200 can be configured to automatically adjust the positioning of at least one of the nozzle assemblies 50 to avoid a collision between the nozzle assemblies or to prevent at least one of the nozzle assemblies from deviating from a desired tool path.

In operation, it is contemplated that each frame assembly 26 and arm assembly 32 can be configured to permit selective three-dimensional movement of each nozzle assembly 50 without requiring movement of the platform 22. It is contemplated that the concurrent printing by multiple nozzle assemblies permitted by the disclosed bioprinter 10 can reduce the fabrication time of tissue constructs, which is crucial for the development of scale-up technologies. It is further contemplated that the concurrent printing capabilities of the bioprinter 10 can enable substantially continuous deposition, which can yield more consistent results than conventional methods since material deposition during starts and stops is not as uniform as it is during other portions of the deposition process. It is further contemplated that continuous deposition can also alleviate nozzle clogging, which generally occurs when the material is in static conditions.

In various exemplary aspects, the nozzle assembly 50 of each printer head 30 can optionally comprise means for maintaining the at least one biomaterial within the nozzle assembly at a desired temperature until the at least one biomaterial is dispensed from the nozzle assembly. In additional exemplary aspects, and with reference to FIG. 48B, the nozzle assembly 50 of each printer head 30 can have a pipette portion 110 that receives the at least one biomaterial. In these aspects, the pipette portion 110 can have an outer surface 112 and a tip portion 114.

In additional aspects, and with reference to FIGS. 48A-48B, the means for maintaining the at least one biomaterial within the nozzle assembly at a desired temperature can comprise a heating system 120. In these aspects, the heating system 120 can optionally comprise a circumferential heating chamber that circumferentially surrounds the outer surface of the tip portion of the pipette portion, with the heating chamber defining at least one inlet and at least one outlet for permitting axial flow of a selected heating material. In exemplary aspects, as shown in FIG. 48B, the nozzle assembly 50 can comprise a barrel 160 configured to receive at least one biomaterial (for example, at least one biomaterial provided by fluid dispenser 250). In these aspects, the barrel 160 can be configured for operative coupling to the pipette portion 110 of the nozzle assembly 50 such that the pipette portion 110 can receive the at least one biomaterial from the barrel. In exemplary aspects, the fluid dispenser 250 can be configured to apply pressurized air to the barrel 160 to force the biomaterial into the pipette portion 110. In one optional aspect, the nozzle assembly 50 can further comprise a pipette holder 170 configured to receive at least a portion of the pipette portion 110 and support the pipette portion in communication with the barrel 160. In exemplary aspects, the heating system 120 can comprise a heating band 180 as is known in the art. In these aspects, the heating band can be positioned in contact with a metallic nozzle head 190 that surrounds at least a portion of the pipette portion 110. It is contemplated that the heating band can have one or more internal resistors that are electrically connected to a current source such that, upon activation of the current source, heat is generated within the heating band and then transferred to the metallic nozzle head 190. Optionally, an outer surface of the metallic nozzle head 190 can define a thermal coupling opening 192 that is configured to receive a thermometer or other temperature measurement device to thereby permit monitoring of the temperature of the at least one biomaterial. When the at least one biomaterial comprises a bio-ink composition as disclosed herein, it is contemplated that the heating system can be configured to raise the temperature of the bio-ink composition as the bio-ink composition exits the nozzle such that the thermosensitive polymer within the bio-ink composition effects solidification of the bio-ink composition.

Optionally, the means for maintaining the at least one biomaterial within the nozzle at a desired temperature can further comprise a cooling system 130. In one aspect, the cooling system 130 can comprise a circumferential chamber 132 configured to surround a portion of the outer surface 112 of the pipette portion 110. In this aspect, it is contemplated that the circumferential chamber 132 can have at least one fluid inlet 134 and at least one fluid outlet 136 axially spaced from the at least one fluid inlet. It is contemplated that the at least one fluid inlet 134 and the at least one fluid outlet 136 can be configured to permit axial flow of at least one coolant material within the circumferential chamber 132 to thereby cool the pipette portion 110. It is contemplated that the presence of a cooling system and a heating system can provide precise control of the temperature of the biomaterial within the nozzle.

In exemplary aspects, it is contemplated that the bioprinter 10 can be provided as part of a bioprinting system 300. Optionally, in these aspects, and as further disclosed herein, the bioprinting system 300 can be used to produce tissue constructs. Optionally, in other aspects, and as further disclosed herein, the bioprinting system 300 can be used to treat a tissue defect of a subject. In exemplary aspects, the bioprinting system 300 can comprise a scanner 400. In these aspects, the scanner 400 can be configured to scan the tissue defect and to generate an output indicative of the location of the tissue defect. In exemplary aspects, the scanner can be a laser scanner as is known in the art. However, it is contemplated that any suitable scanner or imaging system can be used.

As shown in FIG. 1A, it is contemplated that the processor 200 can be operatively coupled to the scanner 400 and configured to receive the output from the scanner. It is further contemplated that the processor 200 of the bioprinter 10 can be configured to determine the desired tool path and to selectively adjust the positioning of the arm assembly 32 of each printer head 30 to permit printing of the biomaterial directly into the tissue defect.

Optionally, in one aspect, and with reference to FIGS. 78A-78B, it is contemplated that the nozzle assembly 50 of at least one printer head 30 of the bioprinter 10 can be configured for selective assembly and disassembly. In this aspect, it is contemplated that the nozzle assembly can be a multi-piece nozzle assembly 140 comprising at least first and second shell portions 142*a*, 142*b*. It is further contemplated that the first and second shell portions 142*a*, 142*b* can be configured for complementary engagement with each other to define the nozzle assembly 140. For example, in exemplary aspects, the first shell portion 142*a* can define a plurality of projections 144 positioned on opposing sides of a central channel, and the second shell portion 142*b* can define a plurality of cavities 146 positioned on opposing sides of a central channel. In these aspects, the cavities 146 of the second shell portion 142*b* can be configured to receive corresponding projections 144 of the first shell portion 142*a*. Upon engagement between the first and second shell portions 142*a*, 142*b*, it is contemplated that the first and second shell portions can cooperate to define a central bore 145 of the nozzle assembly 140. In another aspect, the nozzle assembly 140 can comprise a sleeve element 148 that is configured to slidingly engage outer surfaces of the first and second shell portions 142*a*, 142*b* to secure the nozzle assembly 140 in an operative position as shown in FIG. 78A. Prior to engagement between the first and second shell portions 142*a*, 142*b*, it is contemplated that the central channel of one of the shell portions can receive at least one biomaterial such that, upon engagement between the shell portions, the at least one biomaterial can be positioned within the central bore 145. In exemplary aspects, the at least one biomaterial can be a tissue strand. Following delivery of a first tissue strand, the first and second shell portions 142*a*, 142*b* can be disengaged to permit insertion of a second tissue strand (or other biomaterial) within at least one of the shell portions. After the shell portions are engaged again, the second tissue strand can be delivered in a desired manner, and this process can be repeated as necessary. It is contemplated that tissue strands can be difficult to deliver through conventional nozzle, and it is further contemplated that the multi-piece nozzle assembly 140 can overcome these shortcomings of conventional nozzles.

In exemplary aspects, as shown in FIG. 78A, the print head 30 can comprise a base element 156. A motor housing 158 and a nozzle support 157 can project from the base element 156. The motor housing 158 can be configured to receive a motor 152, such as, for example and without limitation, a stepper motor as is known in the art. The nozzle support 157 can define an opening configured to receive at least a portion of the nozzle assembly 140 when the nozzle assembly is secured in an operative position. In additional aspects, the print head 30 can further comprise a barrel 150 configured for receipt within the central bore 145 of the nozzle assembly. The barrel 150 can be configured to receive at least one biomaterial as described herein. In exemplary aspects, the barrel 150 can be operatively coupled to the motor 152 by a connector 154. In these aspects, it is contemplated that the motor 152 can be positioned in operative electrical communication with the processor 200 such that the processor can control delivery of the tissue strands within the nozzle assembly 140.

In exemplary applications, the bioprinter can be used to concurrently print a structure and deposit cell spheroids and/or tubular cell constructs between filaments of the structure. It is contemplated that this can increase the cell density of cell-laden hybrid structures compared to traditional scaffolding approaches where cells are seeded following fabrication and subsequent processes. It is further contemplated that printing encapsulated cells in spheroids and/or printing tubular cellular materials can greatly reduce shear-stress-induced cell damage compared to printing cells directly loaded within biomaterial media and can also allow inclusion of multiple cell types in a spatially organized way by integrating another printer unit. It is still further contemplated that the tissue constructs disclosed herein can be configured to support cell spheroids and/or tubular cellular materials in three dimensions. It is still further contemplated that the use of two nozzle assemblies mounted on independent arms can allow for the filament structure to be deposited continuously, thereby minimizing filament variations due to the starting and stopping of the dispensing unit.

Tissue Constructs

Described herein with reference to FIGS. 1-78B are various tissue constructs (and tissue construct components) and systems and methods of producing such constructs (and components of such constructs). In exemplary aspects, the disclosed tissue constructs can be produced using the bioprinters, bioprinting systems, and methods disclosed herein.

Described herein, in one aspect, and with reference to FIGS. 13, 15A-15B, 45-47, 55, 57, 68, and 74 is a tissue construct 500 having at least one layer 520. In this aspect, it is contemplated that the tissue construct 500 can optionally comprise a plurality of layers 520 in a stacked configuration. It is further contemplated that the number of layers 520 of the tissue construct 500 can range from about 2 to about 40 layers.

In one aspect, each layer 520 of the tissue construct 500 can comprise a vascular network 530. Optionally, the vascular network 530 can comprise at least one vascular conduit, such as, for example and without limitation, at least one tubular filament or at least one microfluidic channel. It is contemplated that each vascular conduit of the at least one vascular conduit can define a central channel 532. In exemplary aspects, the vascular network can comprise sodium alginate, such as, for example and without limitation, a sodium alginate as hydrogel. Optionally, in these aspects, the vascular network can further comprise a cross-linker, such as, for example and without limitation, a cross-linker comprising calcium chloride. For example, when the vascular network is produced using a co-axial nozzle assembly as disclosed herein, it is contemplated that the cross-linker can be applied by the inner nozzle, while alginate (or another biomaterial) can be applied by the outer nozzle. However, it is contemplated that any suitable biomaterial can be used. In further exemplary aspects, the tissue construct 500 can comprise a single vascular conduit.

Optionally, it is further contemplated that the vascular network 530 can be positioned in a selected pattern such that the outer wall portions 536 of the vascular network define void space 534 within the layer 520 of the tissue construct 500. In exemplary aspects, as shown in FIGS. 13A-13B and 15, the vascular network 530 can be provided (e.g., printed) in a substantially serpentine pattern 560. In these aspects, it is contemplated that the at least one vascular conduit of the layer 520 of the tissue construct 500 can comprise a single vascular conduit positioned in the serpentine pattern 560. In other exemplary aspects, as shown in FIG. 46, the selected pattern can be a grid-like pattern 550. Optionally, in some aspects, when the tissue construct 500 comprises a plurality of stacked layers 520, it is contemplated that the pattern of the vascular network can be selectively varied among the various layers of the tissue construct. For example, as shown in FIGS. 13A-13B, it is contemplated that the tissue construct 500 can have at least one layer with a selected pattern oriented with respect to a first axis of the tissue construct and at least one layer with a selected pattern oriented with respect to a second axis substantially perpendicular to the first axis. In exemplary aspects, the overall structure of the selected pattern can be substantially uniform among the layers of the tissue construct, but the orientation of each respective layer can be varied relative to adjacent layers.

Optionally, in another aspect, each layer 520 of the tissue construct 500 can comprise a plurality of cellular elements 540 positioned within the void space 534 of the layer. In this aspect, the plurality of cellular elements 540 can optionally comprise a plurality of substantially cylindrical cellular elements. Alternatively, the plurality of cellular elements 540 can optionally comprise a plurality of cellular spheroids as disclosed herein. It is further contemplated that the plurality of cellular elements 540 can optionally comprise at least one substantially cylindrical cellular element and a plurality of cellular spheroids as disclosed herein. In exemplary aspects, it is contemplated that the cellular elements 540 disclosed herein can comprise cells and their associated extracellular matrix (ECM). In these aspects, it is contemplated that the cellular elements 540 can comprise any desired cell, including for example and without limitation, muscle cells, cartilage cells, bone cells, skin cells, fibroblasts, tissue-specific cells, endothelial cells, and the like. In exemplary aspects, the cellular elements 540 can comprise smooth muscle cells, such as, for example and without limitation, human umbilical vein smooth muscle cells (HUVSMCs). In further exemplary aspects, it is contemplated that the cellular elements 540 can comprise insulin-producing cells, such as, for example and without limitation, insulinoma bTC3 cells. In exemplary aspects, when a co-axial nozzle assembly as disclosed herein is used to produce a vascular conduit, it is contemplated that the vascular conduit can optionally comprise cellular components such as those described above.

In use, it is contemplated that the vascular network of each level of the tissue construct can be configured to permit perfusion of cell growth media within the layer of the tissue construct. It is further contemplated that the vascular network of each layer of the tissue construct can be configured to permit diffusion of cell growth media from the at least one center channel of the vascular network through the walls of the vascular network to surrounding cellular elements of the tissue construct. In exemplary aspects, it is contemplated that at least one vascular conduit as disclosed herein can define the vascular network and function as a perfusion matrix.

In exemplary aspects, and with reference to FIG. 56, the tissue constructs 500 disclosed herein can be perfused with cell growth media (or other media) using a media perfusion system. Optionally, in these aspects, the media perfusion system can comprise a receptacle configured to receive the tissue construct 500. The receptacle can define at least one inlet and at least one outlet. The vascular network can be positioned within the receptacle such that the outlet of the receptacle is positioned in alignment with an inlet opening of the vascular network of the tissue construct that is in communication with the center channel of the vascular network and the inlet of the receptacle is positioned in alignment with an outlet opening of the vascular network that is in communication with the center channel of the vascular network. Tubing can fluidly connect a media reservoir to the inlet of the receptacle and the inlet opening of the vascular network of the tissue construct 500, thereby permitting delivery of cell growth media to the center channel of the vascular network. Similarly, tubing can fluidly connect a waste collection canister to the outlet of the receptacle and the outlet opening of the vascular network of the tissue construct 500, thereby permitting collection of media and other fluids after circulation of the media through the vascular network. Optionally, it is contemplated that fluid pumping mechanisms can be employed to promote flow of cell growth media from the media reservoir to the tissue construct 500 and to promote flow of waste from the tissue construct to the waste collection canister. For example, as shown in FIG. 56, a first peristaltic pump can be positioned in operative communication with the tubing connecting the media reservoir to the tissue construct, and a second peristaltic pump can be positioned in operative communication with the tubing connecting the tissue construct and the waste collection canister. In exemplary aspects, it is contemplated that the cell growth media within the media reservoir can comprise one or more growth factors, such as, for example and without limitation, Fibroblast Growth Factor (FGF), Epidermal Growth Factor (EGF), and the like. In exemplary aspects, it is contemplated that the use of the receptacle as disclosed herein to permit perfusion of cell growth media can permit encapsulation of the tissue construct in a desired biomaterial as further disclosed herein.

It is contemplated that the precise positioning of cellular elements within the void space of each layer of the tissue construct can result in an increase in the cell density of the tissue construct compared to traditional scaffolding approaches where cells are seeded following fabrication and subsequent processes. It is further contemplated that the printing of encapsulated cells in spheroids and/or cylindrical encapsulated cell constructs can greatly reduce shear-stress-induced cell damage compared to printing cells directly loaded within biomaterial media and can also allow inclusion of multiple cell types in a spatially organized way (for example, by integrating another printer unit). In addition, it is contemplated that the selected pattern of the vascular network of each layer can be configured to mechanically support the plurality of cellular elements of each layer in three dimensions.

It is further contemplated that the disclosed systems and methods can permit scaffold-free fabrication of vascularized organs through integrating organ printing with stem cell technology to develop engineered functional artificial organs, such as, for example and without limitation, pancreases. The disclosed layer-by-layer assembly method can enable assembling of stem-cell-derived cells (such as, for example and without limitation, Insulin-producing Cells (iPCs)) through bioadditive manufacturing. It is contemplated that the tubular filaments and/or microfluidic channels disclosed herein can serve as a vascular network integrated within scaffold-free cell aggregates, thereby making cell viability feasible in 3D and permitting production of functional engineered artificial organs. It is contemplated that the vascular network can provide structural integrity and permit media transport throughout the cellular assembly. It is further contemplated that the scaffold-free bioprinting systems and methods disclosed herein can be used for scale-up organ fabrication, for 3D printing of other organs as well as production of tissue replacement parts. It is still further contemplated that the tissue constructs and systems and methods disclosed herein can provide a renewable source of potentially curative cells, such as, for example and without limitation, IPCs.

In exemplary aspects, the tissue constructs and systems disclosed herein can be used to provide a more efficient method of insulin secretion using scaffold-free cell aggregates in large strands, with micro-scale IPC aggregates, which are considered as bioprintable mini-tissues (bio-ink), can produce significantly high amounts of insulin, fuse to each other quickly, and assemble into larger tissues. It is contemplated that the cell aggregates can be configured to quickly fuse together upon contacting each other. It is contemplated that large-scale tissues can be easily obtained by this fusion process. It is further contemplated that the use of miniature tissues can significantly reduce the time needed for tissue maturation, since each cell aggregate strand contains a large number of cells that can be printed at once and does not include biomaterials (i.e., polymers) that overcome the issues associated with biomaterials such as long degradation times and toxicity. Moreover, it is contemplated that cell viability can be enhanced due to the large cell-seeding density and reduced mechanical stress experienced compared with direct cell manipulation. It is further contemplated that the integration of vasculature into the tissue constructs as disclosed herein can permit scale-up fabrication of a variety of organs, including those that require significant oxygenation in their natural environment.

It is contemplated that the tissue constructs, systems, and methods disclosed herein can provide new avenues for organ printing and ultimately help bridge the gap of organ shortage and transplantation needs, thereby saving human lives in the future. In exemplary aspects, as further disclosed herein, it is contemplated that human pluripotent stem-cell-driven IPC aggregates can be assembled and printed in 3D with a vascular network for the establishment of 3D glucose-sensitive artificial pancreatic organs for transplantation. It is further contemplated that this approach can serve as an alternative treatment for T1D management. It is still further contemplated that similar approaches can be applied to other organs.

Printed cell aggregate constructs are also described herein. Additionally, methods of producing the tissue constructs, vascular network, and cell aggregate constructs disclosed herein are also described.

In-Situ Bioprinting Methods

Described herein, in one aspect, is a method of treating a tissue defect of a selected tissue of a subject by printing a tissue construct directly onto the tissue defect. Optionally, the tissue construct can be a bio-ink composition. The bio-ink composition can include collagen, a thermosensitive polymer, deoxyribonucleic acid (DNA), and stem cells. The stem cells can be configured to differentiate into the selected tissue. The thermosensitive polymer can be configured to effect solidification of the bio-ink composition when the bio-ink composition contacts the selected tissue. In exemplary aspects, the tissue defect can be a bone defect, such as, for example, a calvarial defect.

In another aspect, described herein is a bio-ink composition for delivery into a defect of a selected tissue of a subject. The bio-ink composition can include collagen, a thermosensitive polymer, DNA, and stem cells. The stem cells can be configured to differentiate into the selected tissue. The thermosensitive polymer can be configured to effect solidification of the bio-ink composition when the bio-ink composition contacts the selected tissue. The thermosensitive polymer of the bio-ink composition can be a thermosensitive gel. The DNA of the bio-ink composition can be plasmid DNA (pDNA). The DNA of the bio-ink composition can include encapsulated micro-spheroids. The stem cells of the bio-ink composition can include bone marrow stem cells (BMSCs).

General Problems in the Art

Bony defects in the craniomaxillofacial skeleton are devastating and affect millions of people each year due to congenital defects or acquired injuries. For instance, about 7%, or 227,500, of the children born each year in the U.S. are affected by birth defects in the craniomaxillofacial skeleton. Humans up to 2 years of age have the capability of spontaneous reossification and healing of critical calvarial defects. Similar capabilities can be observed in juvenile animal models such as rats, where critical defects in juvenile mice have been healed almost completely. Critical calvarial defects in humans or animals over 2 years old, on the other hand, cannot heal without treatment.

Several approaches and materials for treating calvarial defects exist. For example, autogenous bone grafts, allogeneic banked bone, demineralized matrix pastes, ceramic and polymeric scaffolds, and bone substitutes such as calcium ceramics have been used. Despite some success, each of these approaches has significant limitations that render them inadequate for reconstructing critical defects. For example, and without limitation, these prior art approaches have been associated with donor-site morbidity, an obligatory graft resorption phase, inadequate autogenous resources, disease transmission, graft-versus-host disease, immunosuppression, foreign body infection, and structural failures.

Due to limited availability of bone grafts (which are considered the gold standard of treatment), scaffolding-based regenerative medicine approach stands as an alternative approach for bone tissue formation. Scaffolds from traditional approaches such as molding, freeze drying, solvent casting and particulate leaching, electrospinning, and foam-gel can be used as temporary porous constructs for seeding cells and delivering the cells to the defect site. More recently, three-dimensional (3D) printing has been used to produce hard polymeric scaffolds (hydroxyapatite, beta-tricalcium phosphate, calcium sulfate, calcium phosphates) reinforced with ceramic particles due to their osteocompatibility, which has been shown to allow osteogenesis, osteoinduction and osteoconduction. However, there are major limitations with these scaffolds. In particular, long term degradation profiles do not allow for successful new bone generation, and cell ceding density on these scaffolds is highly limited and does not allow complete healing of the defect.

Thus, despite the great progress in bone tissue engineering after numerous attempts in exploring strategies for an ideal solution, there remains a pressing need for reliable, effective and expeditious bone regeneration strategies for calvarial defects.

Introduction to Disclosed In-Situ Bioprinting Technology

The in situ bioprinting systems and methods disclosed herein can address the shortcomings of existing systems and methods for treating bone defects and other tissue defects. FIG. 47 illustrates a schematic diagram of an exemplary in situ multi-arm bioprinting process, as further disclosed herein. As depicted, an extrusion-based deposition technique is used by both arms of a bioprinter to print multiple tissue analogues (e.g., bone tissue analogues) in tandem directly into tissue defects (e.g., calvarial defects).

It is contemplated that the in situ bioprinting compositions, systems, and methods disclosed herein can be used in clinical settings for humans, thereby providing new investigative avenues that have a high clinical translational potential. More particular, it is contemplated that the disclosed in situ bioprinting compositions, systems, and methods can open up new avenues for research in in situ tissue printing. It is further contemplated that the disclosed in situ bioprinting compositions, systems, and methods can be applied to any organ or tissue type. Further, it is contemplated that the disclosed in situ bioprinting compositions, systems, and methods can provide mechanisms for bioprinting-mediated gene therapy, which can provide enhanced bone tissue regeneration.

It is further contemplated that the disclosed in situ bioprinting compositions, systems, and methods can significantly reduce the demand for bone graft transplantation to ultimately bridge the gap of bone graft shortage and transplantation needs, thereby saving human lives. It is contemplated that the in situ bioprinting compositions, systems, and methods disclosed herein can help establish an alternative solution to the treatment of skull defects, thereby opening a great avenue for clinical studies with robotic bioprinting of human parts directly on humans in clinical settings.

Bio-Ink Compositions

Disclosed herein with reference to FIGS. 47-49D are bio-ink compositions for delivery into a defect of a selected tissue of a subject. In exemplary aspects, the defect can be a calvarial defect, and the selected tissue can be bone (for example, the calvaria) of the subject. However, it is contemplated that the selected tissue can be any tissue and that the defect can be any conventional tissue defect.

In various aspects, the bio-ink composition can comprise a collagen and a thermosensitive polymer. In additional aspects, the bio-ink composition can further comprise stem cells. In these aspects, the stem cells can be configured to differentiate into the selected tissue. Optionally, in some aspects, the bio-ink composition can still further comprise DNA. In additional aspects, the thermosensitive polymer can be configured to effect solidification of the bio-ink composition when the bio-ink composition contacts the selected tissue. In these aspects, it is contemplated that the bio-ink composition can initially be maintained within a first temperature range (for example, within a conventional room temperature range) at which the bio-ink composition has fluidic flow characteristics. It is further contemplated that, upon delivery of the bio-ink composition into contact with the selected tissue of the subject, the bio-ink composition can be exposed to a temperature within a second temperature range (for example, at a temperature greater than about 37° C.) at which the thermosensitive polymer is configured to solidify the bio-ink composition. In one aspect, the thermosensitive polymer of the bio-ink composition can comprise a thermosensitive gel. Optionally, in one aspect, the thermosensitive polymer can comprise Pluronic® F-127 reagent (Sigma-Aldrich).

In one aspect, the collagen of the bio-ink composition can comprise collagen type-I. In an additional aspect, the DNA of the bio-ink composition can optionally comprise plasmid DNA. In another aspect, the DNA of the bio-ink composition can optionally comprise pDNA encapsulated microparticles, such as, for example, pDNA encapsulated microspheroids. In this aspect, the microparticles can be formed by adding polyethylenimine (PEI) solution drop wise to a pDNA solution and then mixing the PEI solution and pDNA solution. It is contemplated that the ratio between PEI and pDNA can be selectively varied. In a further aspect, the stem cells of the bio-ink composition can optionally comprise bone marrow stem cells. However, in other aspects, the stem cells of the bio-ink composition can optionally comprise mesenchymal stem cells, such as, for example and without limitation, adipose-derived mesenchymal stem cells.

In some exemplary aspects, the bio-ink composition can comprise a collagen, a thermosensitive polymer, and stem cells. In other exemplary aspects, the bio-ink composition can comprise a collagen, a thermosensitive polymer, stem cells, and DNA.

In various exemplary aspects, the bio-ink composition can comprise a solution. In one aspect, the collagen (for example, collagen type-I) can be provided at a selected concentration ranging from about 1 mg/mL of the solution to about 5 mg/mL of the solution. In this aspect, it is contemplated that the selected concentration of collagen can optionally range from about 1 mg/mL of the solution to about 4 mg/mL of the solution. Thus, it is contemplated that the selected concentration of the collagen can be about 2 mg/mL of solution, about 3 mg/mL of solution, or about 4 mg/mL of solution. In another aspect, it is contemplated that the thermosensitive polymer (for example, Pluronic® F127) of the solution can be provided at a selected concentration ranging from about 10% (w/w) to about 40% (w/w) of the solution. In this aspect, it is contemplated that the selected concentration can optionally range from about 20% (w/w) to about 30% (w/w) of the solution. Thus, it is contemplated that the selected concentration can be about 20% (w/w), about 25% (w/w), or about 30% (w/w) of the solution. In an additional aspect, it is contemplated that the stem cells of the solution can be provided at a selected density ranging from about 1 million cells/mL of solution to about 30 million cells/mL of solution. In this aspect, it is contemplated that the selected density of the stem cells can optionally range from about 5 million cells/mL of solution to about 20 million cells/mL of solution. Thus, it is contemplated that the selected density can optionally be about 5 million cells/mL of solution, about 10 million cells/mL of solution, or about 20 million cells/mL. In one aspect, the DNA of the solution can be pDNA (pLUC/pEGFP-N1/pBMP-2). In this aspect, the pDNA can be provided at a selected concentration ranging from about 5 mg/mL of solution to about 75 mg/mL of solution. Optionally, it is contemplated that the selected concentration of pDNA can range from about 10 mg/mL of solution to about 60 mg/mL of solution. Thus, it is contemplated that the selected concentration of pDNA can be about 10 mg/mL of solution, about 30 mg/mL of solution, or about 60 mg/mL of solution. In another aspect, the DNA of the solution can be pDNA (pLUC/pEGFP-N1/pVEGF). In this aspect, the pDNA can be provided at a selected concentration ranging from about 0 mg/mL of solution to about 30 mg/mL of solution. Optionally, it is contemplated that the selected concentration of pDNA can range from about 0 mg/mL of solution to about 20 mg/mL of solution. Thus, it is contemplated that the selected concentration of pDNA can be about 0 mg/mL of solution, about 10 mg/mL of solution, or about 20 mg/mL of solution. In a further aspect, when the DNA of the bio-ink composition comprises pDNA encapsulated microparticles, it is contemplated that the microparticles can have a selected molecular weight ranging from about PLGA 30-70 to about PLGA 95-5. Optionally, it is contemplated that the selected molecular weight of the microparticles can range from about PLGA 50-50 to about PLGA 85-15. Thus, it is contemplated that the selected molecular weight of the microparticles can optionally be about PLGA 50-50, about PLGA 75-25, or about PLGA 85-15.

In one exemplary aspect, the bio-ink composition can comprise a solution of about 10 million stem cells per milliliter, about 50 mg pDNA per milliliter (pLUC/pEGFP-N1/pBMP-2), about 50 mg pDNA per milliliter (pLUC/pEGFP-N1/pVGEF), about 20% (w/w) Pluronic® F127 and about 3 mg collagen type-I per milliliter.

It is contemplated that the disclosed hydrogel-based bio-ink composition can be configured to facilitate tissue formation when the bio-ink composition is delivered into a tissue defect as further disclosed herein. It is further contemplated that hydrogel-based bio-ink compositions typically do not facilitate tissue formation ex vivo due to limited cell to cell interactions, degradation issues and phenotypic instability. However, it is contemplated that in situ printing of bio-ink compositions comprising BMSCs and genes (pDNAs) as disclosed herein can facilitate tissue formation. It is further contemplated that the printing of non-viral vectors that are safe and efficient in transfecting target cells can overcome the shortcomings of direct protein and growth factor delivery.

Methods of Treating Tissue Defects Using In-Situ Bioprinting

Disclosed herein is a method of treating a tissue defect of a selected tissue of a subject. In one aspect, the method can comprise printing a tissue construct directly onto or within the tissue defect. In exemplary aspects, the tissue construct can be a bio-ink composition as disclosed herein. In these aspects, it is contemplated that the stem cells within the bio-ink composition can differentiate into the selected tissue following printing of the bio-ink composition onto or within the tissue defect. It is further contemplated that the thermosensitive polymer of the bio-ink composition can effect solidification of the bio-ink composition when the bio-ink composition contacts the selected tissue.

In exemplary aspects, the step of printing a tissue construct can comprise sequentially printing two or more biomaterials directly onto or within the tissue defect to form the tissue construct. For example, in one aspect, the step of printing a tissue construct can comprise printing a first bio-ink composition within the tissue defect and then printing a second bio-ink composition as disclosed herein onto the first bio-ink composition. In exemplary aspects, the second bio-ink composition can be different than the first bio-ink composition. For example, it is contemplated that the second bio-ink composition can optionally comprise at least one component that is not present in or present at a different concentration in the first bio-ink composition. Optionally, it is contemplated that the first bio-ink composition can optionally comprise at least one component that is not present in or present at a different concentration in the second bio-ink composition. Although the sequential printing of first and second bio-ink compositions is disclosed herein, it is contemplated that any desired number of bio-ink compositions can be sequentially printed on or within a tissue defect as disclosed herein.

In further exemplary aspects, the step of printing the tissue construct (e.g., the bio-ink composition) can comprise printing the tissue construct in a selected pattern. In these aspects, it is contemplated that the selected pattern can be a spiral pattern or a zig-zag pattern. However, it is contemplated that any desired pattern can be used. It is contemplated that printing of the tissue construct in a spiral pattern (with minimal or negligible gaps) can generate a substantially non-porous tissue construct. In other aspects, it is contemplated that printing of the tissue construct in a zig-zag pattern can generate a substantially porous tissue construct. In these aspects, it is contemplated that the resulting porous tissue construct can be configured to generate capillarization through the pores of the tissue construct.

In operation, it is contemplated that the direct printing of a bio-ink composition having biodegradable microparticles as disclosed herein can provide sequential and sustained release of different pDNAs that encode different growth factors. It is further contemplated that the release of these pDNAs can be mediated by variations in bioprinting protocols.

Figure 2:
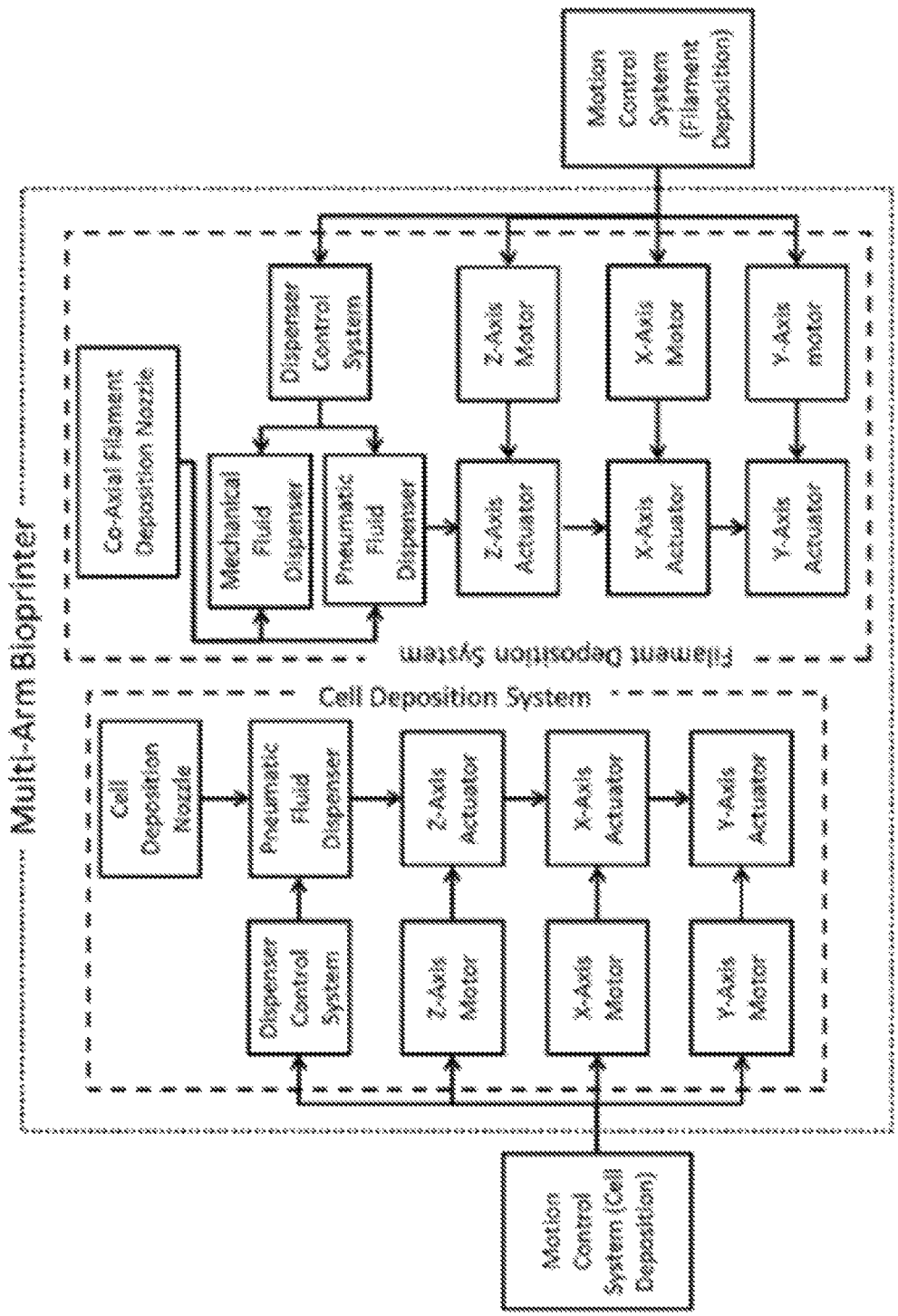
FIG. 2 is a schematic diagram depicting the operation of an exemplary bioprinter as disclosed herein.

In exemplary aspects, and with reference to FIG. 2, the bioprinting system can comprise a bioprinter as disclosed herein (referred to as the 'Multi-arm Bioprinter (MABP)'), a fluid deposition system, a motion control system, and a computer to run the motion control system and the fluid deposition system. The MABP unit can be placed in a laminar flow hood (Air Science, Fort Meyers, FL, USA) for sterilization purposes during the printing process. The motion control system can translate the tool paths for material deposition into signals to drive the motors on the MABP. The stepper motor drivers can actuate the motors on the MABP based on the signals generated from the motion control software. The fluid deposition system can control the deposition rate of the biomaterials within the nozzle assemblies of the bioprinter throughout the deposition process.

Optionally, the MABP hardware can comprise two identical three-axis linear motion systems mounted on the same table, where the x-, y-, and z-axes are the three principal axes in a Cartesian frame. This configuration can enable independent and concurrent dispensing of multiple materials. The system can be arranged with a biomaterial deposition system. Each deposition system can comprise three stepper motors and linear actuators mounted in a gantry configuration, with the dispensing nozzle connected to the fluid dispenser, and the barrel mounted on the z-axis actuator, the z-axis actuator mounted on the x-axis actuator, and the x-axis actuator mounted on the y-axis actuator. This design can enable the two nozzles to be actuated independently and the printed structure to remain stationary during the deposition process. The fluid dispensers can be controlled by the dispenser control system.

The MABP can be fabricated using standard parts to minimize development time. The frame can be constructed using an aluminum T-slotted framing system (80/20 Inc., Columbia City, IN, USA) due to ease of construction and reconfiguration. Linear actuators (Thomson Industries Inc., Radford, VA, USA) capable of actuating at least 200 mm in the x-direction, at least 300 mm in the y-direction, and at least 100 mm in the z-direction can be used to translate the rotational motion of the stepper motor (Probotix, Peoria, IL, USA) into a linear motion. These components can enable the machine to achieve a theoretical maximum linear velocity of 30 mm/s with a resolution of 0.016 mm. A profile bearing (e.g., a 15 mm profile bearing, McMaster-Carr Supply Company, Chicago, IL, USA) can be mounted on each end of the x-axis frame to support the static and dynamic loads in the x-direction to prevent the y-axis linear actuator from reaching its maximum payload capacity. The profile bearings can be mounted on 15 mm wide hardened steel guide rails that are 460 mm in length (McMaster-Carr Supply Company, Chicago, IL, USA). The table top can be fabricated from a precision ground 7075 aluminum plate (12.7 mm thick). Individual components can be aligned using a dial indicator mounted on the spindle of a CNC mill. The entire system can be aligned using a dial indicator on a granite table.

The machine control system can actuate the motors based on the signal generated from the control software. The motion control system can comprise a breakout board, power supply, and motor drivers. The breakout board can provide access to the individual pins of the parallel port, which can be used to connect motor drivers and limit switches. The motor drivers can be configured to actuate the motors at the desired rotational acceleration, velocity, and distance based on the signal sent from the computer through the parallel port. The MABP motion control system, which can be an open loop system, can comprise two identical 3-axis motion control systems. Each motion control system can optionally comprise an RF-isolated CNC Breakout Board (Probotix, Pekin, IL, USA), three stepper motor drivers (Probotix, Pekin, IL, USA), and one power supply (Probotix, Pekin, IL, USA).

The fluid deposition system can comprise two pneumatic dispensers (Nordson Corp., Westlake, OH, USA), a mechanical dispenser (New Era Pump System Inc., Farmingdale, NY), and a standard dispensing tip. Optionally, the fluid deposition system can further comprise a co-axial dispensing tip (co-axial nozzle) as further disclosed herein. The pneumatic dispensers can be used to dispense the biomaterial, which can have a high viscosity. The mechanical dispenser can be used to dispense a solution, which can have a relatively low viscosity. Optionally, a biomaterial can be deposited using a deposition nozzle containing an angled portion (e.g., a 45 degree bend) to minimize the distance between the two nozzles. These systems can be triggered by the dispenser control system, which can actuate the fluid dispensers using commands contained in the toolpath plan. In exemplary aspects, when the fluid deposition system comprises a co-axial nozzle, the co-axial nozzle can be used to print a vascular network. In these aspects, it is contemplated that alginate can be deposited in the core of the co-axial nozzle, while calcium chloride can be deposited from the outer sheath of the co-axial nozzle.

In some exemplary aspects, a co-axial nozzle can optionally comprise a 16 gauge outer nozzle (1650 µm outer diameter (O.D.), 1194 µm inner diameter (I.D.)) and a 22 gauge inner nozzle (711 µm O.D., 406 µm I.D.) to control the dispensing of both a hydrogel and a crosslinker (e.g., a crosslinking solution). It is contemplated that the co-axial nozzle can be configured to ensure that the crosslinking solution encapsulates the hydrogel while being direction-independent. The co-axial nozzle assembly can comprise a feed tube, an outer tube, and an inner tube. The feed tube can be used to feed the crosslinking solution into the cavity formed between the outer and inner tubes, while the hydrogel can be fed through the inner tube to print the vascular network. A hole of the same outer diameter as the feed tube can be created in the barrel of the outer tube for feed tube attachment. The luer lock hub on the barrel of the outer tube can be removed using a lathe, and its tip can be shortened about 16 mm, measured from the tip of the inner nozzle. The outer barrel can be shortened to prevent the co-axial nozzle from clogging as a result of the hydrogel adhering to the outer barrel due to surface tension. The inner tube can be inserted and aligned until it is concentric with the outer barrel and can subsequently be laser-welded. The feed tube can be attached to the outer tube using laser welding as well. The entire assembly can subsequently be reinforced with J-B STIK steel-reinforced epoxy putty.

A computer-aided design (CAD) model of the MABP operation process can be obtained through reverse engineering methods such as CT scans or MRI. The model segmentation process can slice the CAD model into layers with a specified thickness using Rhinoceros 4.0 software by exporting the CAD model. Toolpaths for first and second biomaterials can be subsequently generated for each layer of the multi-layered 3D tissue structure. The toolpath sequencing strategy can ensure that a first biomaterial is deposited between portions of a second biomaterial in an appropriate timeframe to alleviate collision between the two nozzles. The sequenced toolpaths can be translated into motor signals by their respective control software, and the motors on the MABP can be actuated by the motion control system based on the motor signals to print the desired structure during the fabrication phase.

This process can optionally be implemented using two separate machine control software programs: GRBL, a microcontroller-based motion control software program, and Mach 3, a widely used computer-based motion control software program. G-code can be sent to the microcontroller line-by-line from a text file using a script written in Python. The command used to trigger the deposition operation can be sent to Mach 3 using a virtual serial port connection. A script written in Visual Basic can listen through the virtual serial port for this command when the optional stop is triggered in Mach 3 to start the subsequent section.

Exemplary Advantages of the Disclosed Compositions, Systems, and Methods

In exemplary aspects, the compositions, systems, and methods disclosed herein can achieve various advantages over existing compositions, systems, and methods. It is contemplated that the disclosed compositions, systems, and methods can significantly contribute to the scientific basis of bioprinting. It is contemplated that the disclosed compositions, systems, and methods can permit in situ bioprinting of porous tissue constructs for the first time and be applied to critical size bone defects in order to enhance bone tissue regeneration. It is further contemplated that direct printing of tissue constructs into tissue defects can open up great venues for in situ bioprinting, where the great success achieved by the disclosed compositions, systems, and methods can have a significant impact on translating the disclosed bioprinter technologies from bench to bedside. It is further contemplated that the composite bio-ink composition disclosed herein, which can optionally be reinforced with collagen type-I (a protein that is the main component of the organic part of the bone), bone marrow stem cells (BMSCs), a thermo-sensitive polymer, and gene-activated matrices (GAMs) encapsulating plasmid-DNA (pDNA), can permit release of pDNA from GAM and transfect BMSCs to secrete multiple growth factors that are essential in bone formation. It is further contemplated that the processing of the disclosed composite bio-ink composition can enable future research attempts to use the composition for other tissue printing applications. It is further contemplated that the disclosed compositions, systems, and methods can be used to provide bioprinting-mediated gene therapy, which has a very high transformative potential and can pioneer a new research era and build the fundamentals of spatiotemporally controlled gene therapy applications enabled by bioprinting. It is further contemplated that the disclosed bioprinting systems can enable printing on angled surfaces and rapid fabrication of multiple tissue constructs in tandem within defect sites.

In additional exemplary aspects, it is contemplated that the direct bioprinting of tissue analogues into multiple defects as disclosed herein can eliminate the need for pre-shaping or reshaping of a scaffold based on the defect geometry. It is further contemplated that this can mitigate the laboriousness of scaffold preparation and overcome the risks associated with deactivation of pDNA, contamination, and limited activity of stem cells in vitro.

In further exemplary aspects, it is contemplated that in situ bioprinting as disclosed herein can allow printing of bone tissue with controlled morphology and geometry that can allow one to engineer tissue properties by optimizing scaffold parameters for bone healing such as pore size, fiber diameter, biomaterial concentration, gene loading settings, and the like.

In further exemplary aspects, it is contemplated that bioprinting as disclosed herein can enable precise deposition of cells, genes or cytokines inside the defect compared to manual interventions. By direct in situ cell and gene delivery, it is contemplated that bone induction and repair can be elicited precisely at specific anatomic sites. It is further contemplated that the bioprinting as disclosed herein can permit localized control, such as the printing of different genes and cytokines at different layers.

In further exemplary aspects, it is contemplated that multi-arm bioprinting as disclosed herein can enable concurrent testing and exploration of multiple bone tissue constructs with minimized operation time. It is further contemplated that minimizing anesthesia time can be crucial due to ethical, health and economic considerations. Thus, it is further contemplated that the proposed multi-arm bioprinting can significantly reduce the time of printing.

In further exemplary aspects, it is contemplated that the rotating robotic arms of the bioprinter disclosed herein can enable deposition and printing of a bio-ink composition as disclosed herein inside non-horizontal defects (with angled bottom surfaces). It is further contemplated that calvarial defects can be created at random locations on the skull, and it can be inconvenient to change the position and posture of the anesthetized animal during bioprinting.

In further exemplary aspects, it is contemplated that nanoplexes of pDNA and cationic polymers can be prepared and loaded into biodegradable microparticles that provide controlled and sustained release of the nanoplexes with reduced toxicity relative to using the nanoplexes alone. It is further contemplated that these microparticles can be amenable to scale up and pharmaceutical manufacturing and can provide prolonged gene expression over defined periods of time in localized environments. It is further contemplated that the microparticles can comprise polymers that have a long track record of safety in biomedical applications.

In further exemplary aspects, it is contemplated that standard defects made by surgery tools can be easy for manipulation and loading of fabricated bone tissue constructs. However, it is further contemplated that naturally occurring bone defects resulting from trauma, surgical excision or cranioplasty can be random in morphology and geometry and need to be captured precisely. It is contemplated that the integration of a laser-based scanning system into the bioprinting system as disclosed herein can efficiently overcome this issue.

With tunable bio-ink and tissue construct properties, and controlled pDNA delivery using gene-activated matrices, it is contemplated that the disclosed compositions, systems, and methods can initiate major scientific research, which can pave the road to the future of medicine with automated technologies to build engineered tissue and body parts on humans.

It is contemplated that in situ bioprinting using extrusion-based deposition as disclosed herein can have several major challenges associated with biological, biomaterial and engineering aspects such as printing difficulties on non-planar or non-horizontal surfaces, the need for a highly effective extrudable bio-ink enabling instant solidification (without the need of an external solidifier such as UV light or a chemical crosslinker) in a living body, the need for a biologically appealing ink for enhanced tissue formation, and regulatory issues related to animals necessitating safe delivery of the tissue construct in minimum time under anesthesia. As disclosed herein, the disclosed compositions, systems, and methods can overcome these challenges.

Exemplary Aspects

In one exemplary aspect, disclosed herein is a bioprinter for dispensing at least one biomaterial, comprising: a processor configured to determine a desired tool path; a support assembly; at least two printer heads, each printer head operatively coupled to the processor and comprising: an arm assembly having a proximal portion and a distal portion, the proximal portion of the arm assembly being operatively coupled to the support assembly such that the arm assembly is selectively moveable relative to at least a first axis; and a nozzle assembly operatively coupled to the distal end of the arm assembly, wherein the nozzle assembly is configured to receive and dispense the at least one biomaterial as the arm assembly is selectively moved relative to the first axis, and wherein the processor is configured to selectively adjust the positioning of the arm assembly of each printer head relative to at least the first axis in accordance with the desired tool path.

In another exemplary aspect, the nozzle assembly of at least one printer head of the at least two printer head assemblies has a longitudinal axis and comprises: an outer nozzle having a proximal end, a distal end, an outer surface, and an inner surface, the inner surface defining a central bore and an inner diameter of the outer nozzle, the outer surface defining an inlet positioned in communication with the central bore, wherein the inner surface of the distal end of the outer nozzle defines an outlet in communication with the central bore, the outlet having a diameter; an inner nozzle having a proximal end, a distal end, an outer surface, and an inner surface, the outer surface defining an outer diameter of the inner nozzle, the inner surface defining a central bore, the inner surface of the proximal end defining an inlet, the inner surface of the distal end defining an outlet, wherein the inner nozzle is at least partially received within the central bore of the outer nozzle such that the outer nozzle and the inner nozzle have a common longitudinal axis that is in substantial alignment with the longitudinal axis of the nozzle assembly, the outer diameter of the inner nozzle being less than the diameter of the outlet of the outer nozzle to thereby define a receiving space between the outer surface of the first nozzle and the inner surface of the outer nozzle; and wherein the inlet of the outer nozzle is configured to receive at least one biomaterial and deliver the at least one biomaterial to the receiving space, and wherein the outlet of the outer nozzle is configured to dispense the at least one biomaterial from within the receiving space, and wherein the inlet of the inner nozzle is configured to receive at least one biomaterial and deliver the at least one biomaterial to the central bore of the inner nozzle, and wherein the outlet of the inner nozzle is configured to dispense the at least one biomaterial from within the central bore of the inner nozzle.

In a further exemplary aspect, the distal portion of the arm assembly of at least one printer head is selectively rotatable relative to the proximal portion of the arm assembly, and wherein the nozzle assembly is configured to receive and dispense the at least one biomaterial as the arm is selectively moved relative to the first axis and the distal portion of the arm assembly is selectively rotated relative to the proximal portion of the arm assembly.

In an additional exemplary aspect, the nozzle assembly of at least one printer head of the bioprinter comprises means for maintaining the at least one biomaterial within the nozzle assembly at a desired temperature until the at least one biomaterial is dispensed from the nozzle assembly.

In another exemplary aspect, the nozzle assembly of at least one printer head of the bioprinter comprises means for maintaining the at least one biomaterial within the nozzle assembly at a desired temperature until the at least one biomaterial is dispensed from the nozzle assembly.

In another exemplary aspect, the nozzle assembly of the at least one printer head comprises a pipette portion that receives the at least one biomaterial, the pipette portion having an outer surface, wherein the means for maintaining the at least one biomaterial within the nozzle at a desired temperature comprises a heating system.

In another exemplary aspect, the pipette portion of the nozzle assembly of the at least one printer head comprises a tip portion, and wherein the heating system comprises a circumferential heating chamber that circumferentially surrounds the outer surface of the tip portion of the pipette portion.

In another exemplary aspect, the means for maintaining the at least one biomaterial within the nozzle at a desired temperature further comprises a cooling system.

In another exemplary aspect, the cooling system comprises a circumferential chamber configured to surround a portion of the outer surface of the pipette portion, wherein the circumferential chamber has at least one fluid inlet and at least one fluid outlet axially spaced from the at least one fluid inlet, wherein the at least one fluid inlet and the at least one fluid outlet are configured to permit axial flow of at least one coolant material within the circumferential chamber to thereby cool the pipette portion.

In a further exemplary aspect, the arm assembly of each printer head is selectively moveable relative to at least a first axis and a second axis, wherein the second axis is substantially perpendicular to the first axis.

In an exemplary aspect, disclosed herein is a bioprinting system for treating a tissue defect of a subject, comprising: a scanner configured to scan the tissue defect and to generate an output indicative of the location of the tissue defect; and the bioprinter, wherein the processor of the bioprinter is configured to receive the output from the scanner, and wherein the processor of the bioprinter is configured to selectively adjust the positioning of the arm assembly of each printer head to permit printing of the at least one biomaterial directly into the tissue defect.

In an exemplary aspect, disclosed herein is a method of producing a tissue construct using the bioprinter.

In another exemplary aspect, the inner nozzle of the bioprinter dispenses a first biomaterial, and wherein the outer nozzle dispenses a second biomaterial, thereby forming a two-layer cylindrical tissue construct, wherein the two-layer cylindrical tissue construct comprises an outer layer of the second biomaterial and an inner layer of the first biomaterial, the inner layer being circumferentially surrounded by the outer layer.

In another exemplary aspect, the outer nozzle dispenses a biomaterial, and wherein the inner nozzle does not dispense a biomaterial, thereby forming a tubular tissue construct.

In an exemplary aspect, the tissue construct comprises at least one layer, each layer of the tissue construct comprising: a vascular network, the vascular network defining at least one central channel, wherein the vascular network is positioned in a selected pattern to define void space within the layer of the tissue construct; and a plurality of cellular elements positioned within the void space, wherein the vascular network is configured to permit diffusion of cell growth media from the at least one central channel to surrounding cellular elements of the plurality of cellular elements.

In another exemplary aspect, the selected pattern of the vascular network comprises a grid pattern.

In another exemplary aspect, the plurality of cellular elements of the tissue construct comprises a plurality of substantially cylindrical cellular elements.

In another exemplary aspect, the plurality of cellular elements of the tissue construct comprises a plurality of cellular spheroids.

In another exemplary aspect, the selected pattern of the vascular network comprises a serpentine pattern.

In another exemplary aspect, the plurality of cellular elements of the tissue construct comprises a plurality of substantially cylindrical cellular elements.

In another exemplary aspect, the plurality of cellular elements of the tissue construct comprises a plurality of cellular spheroids.

In another exemplary aspect, the at least one layer of the tissue construct comprises a plurality of layers.

In an exemplary aspect, disclosed herein is a method of producing a vascular network using the bioprinter, the vascular network comprising: at least one vascular conduit, each vascular conduit having a wall defining a central channel, wherein the at least one vascular conduit is printed in a selected pattern, wherein the at least one vascular conduit is configured to permit diffusion of cell growth media from the central channel of each vascular conduit through the wall of the vascular conduit.

In an exemplary aspect, disclosed herein is a method of treating a tissue defect of a selected tissue of a subject, comprising: printing a tissue construct directly onto the tissue defect using the bioprinter.

In an exemplary aspect, disclosed herein is a method of treating a tissue defect of a selected tissue of a subject, comprising: printing a tissue construct directly onto the tissue defect using the bioprinting system.

In another exemplary aspect, the tissue construct is a bio-ink composition, the bio-ink composition comprising: collagen; and a thermosensitive polymer, wherein the thermosensitive polymer is configured to effect solidification of the bio-ink composition when the bio-ink composition contacts the selected tissue.

In another exemplary aspect, the bio-ink composition further comprises stem cells, wherein the stem cells are configured to differentiate into the selected tissue.

In another exemplary aspect, the bio-ink composition further comprises deoxyribonucleic acid (DNA).

In another exemplary aspect, the selected tissue comprises bone.

In another exemplary aspect, the thermosensitive polymer comprises a thermosensitive gel.

In another exemplary aspect, the DNA of the bio-ink composition comprises plasmid DNA.

In another exemplary aspect, the DNA of the bio-ink composition comprises pDNA encapsulated micro-spheroids.

In another exemplary aspect, the stem cells comprise bone marrow stem cells.

Exemplary applications of the disclosed bioprinter are disclosed in the following non-limiting examples. Additionally, exemplary, non-limiting tissue constructs, and methods and systems for producing those tissue constructs, are described in the following examples.

Example One

Materials and Methods

Materials

A sodium alginate solution was formed by dissolving 4% (w/v) sodium alginate (Sigma Aldrich, United Kingdom) in deionized water, and a calcium chloride solution was formed by dissolving 4% (w/v) calcium chloride (CaCl2) (Sigma Aldrich, Japan) in deionized water. These parameters were considered for material preparation due to structural integrity and acceptable cell viability in hybrid printed structures. Food dye (August Thomsen Corporation, USA) was added to the alginate mixture for visualization purposes. Food dye was omitted for the cell viability studies disclosed herein. The crosslinking between the alginate solution and the calcium chloride solution formed the hydrogel.

Cell Preparation

Cartilage progenitor cells (CPCs) were isolated using known methods. Cells were cultured at 37° C. in 5% CO2 in DMEM/F12 (1:1) supplemented with 10% fetal bovine serum (FBS), 50 µg/µl L-ascorbate, 100 µg/µl penicillin, 100 µg/ml streptomycin, and 2.5 µg/µl Fungi zone. The culture media was changed every other day. CPCs were passaged onto tissue culture dishes, and passage 3 cells were used for bioprinting. Cells were harvested using 0.25% Trypsin-EDTA (Life Technologies, NY) prior to printing. An alginate solution was prepared by adding UV-sterilized sodium alginate powder into a DMEM-base culture media. In this step, a concentration of 4 million cells/ml was used. Cells were mixed with the sodium alginate solution (4% w/v in deionized water) immediately after harvesting and were kept at room temperature before printing. A vortex mixer was used multiple times to get uniform cell distribution in alginate precursor solution.

Experimental Setup

The experimental setup (see FIG. 1B) comprised a bioprinter as disclosed herein (referred to as the 'Multi-arm Bioprinter (MABP)'), a fluid deposition system, and a computer to run the motion control system and the fluid deposition system. The MABP unit was placed in a laminar flow hood (Air Science, Fort Meyers, FL, USA) for sterilization purposes during the printing process. The motion control system translated the tool paths for material deposition into signals to drive the motors on the MABP. The stepper motor drivers actuated the motors on the MABP based on the signals generated from the motion control software. The fluid deposition system controlled the deposition rate of the alginate and calcium chloride throughout the deposition process. The MABP design, implementation, and operation are described herein.

Hardware Design and Implementation

Figures 3A, 3B:
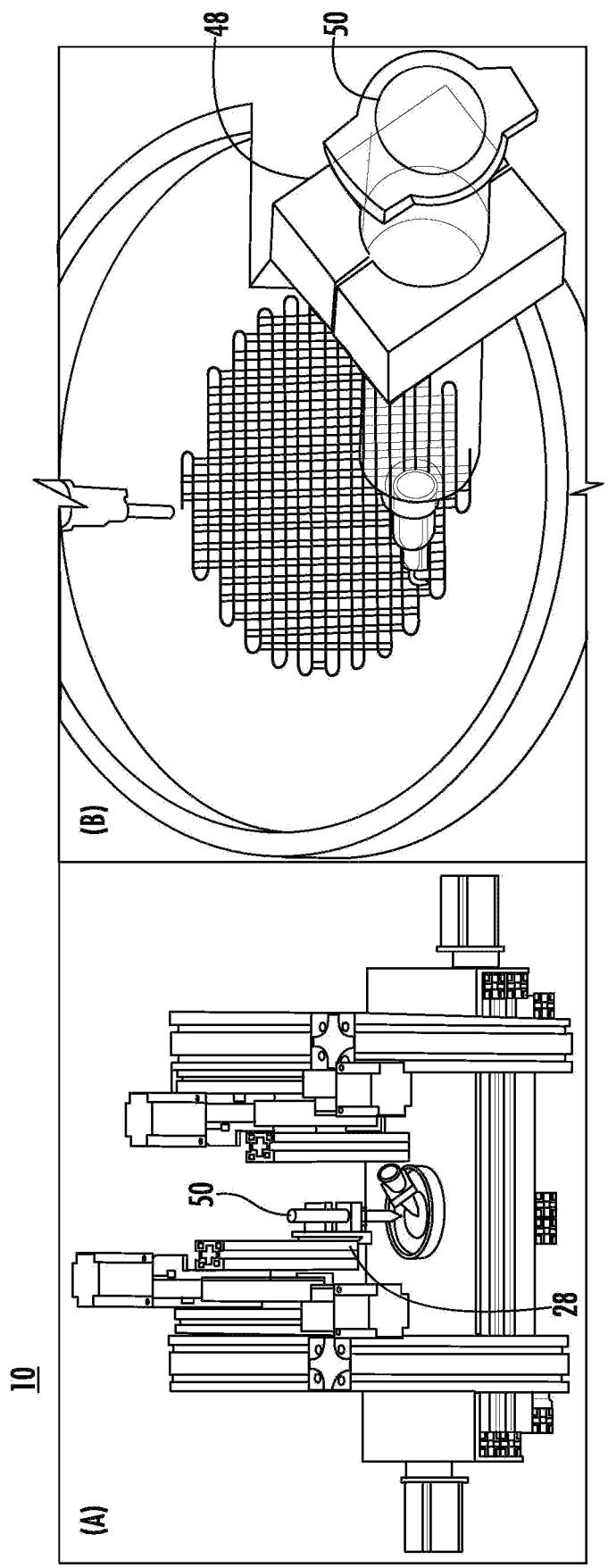
FIG. 3A depicts a printing platform of an exemplary bioprinter as disclosed herein.
FIG. 3B depicts a vascular network and cell spheroid deposition system of an exemplary bioprinter as disclosed herein.
Figure 4:
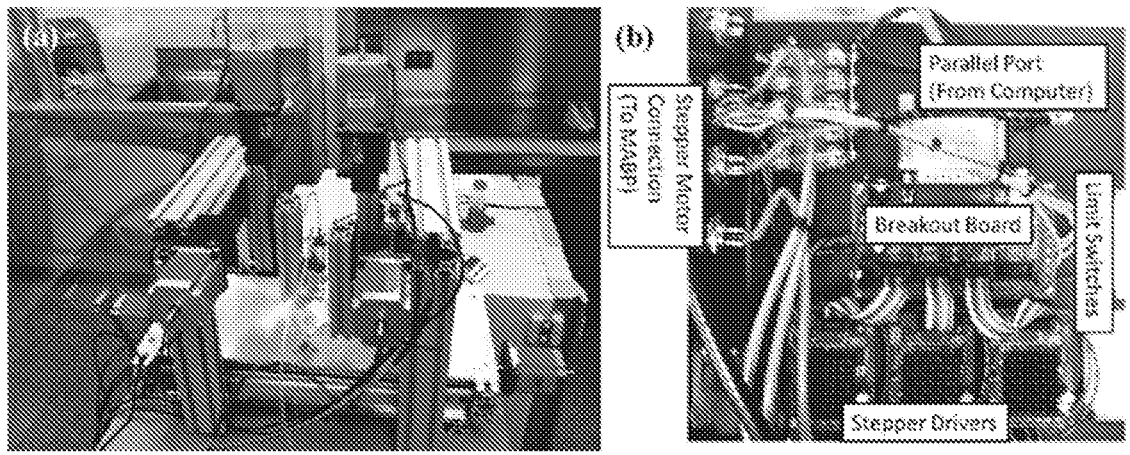
FIG. 4A depicts a bioprinter having two arms that can move independently and concurrently in three axes, as disclosed herein.
FIG. 4B depicts an exemplary motion control system of a bioprinter as disclosed herein.
Figure 5:
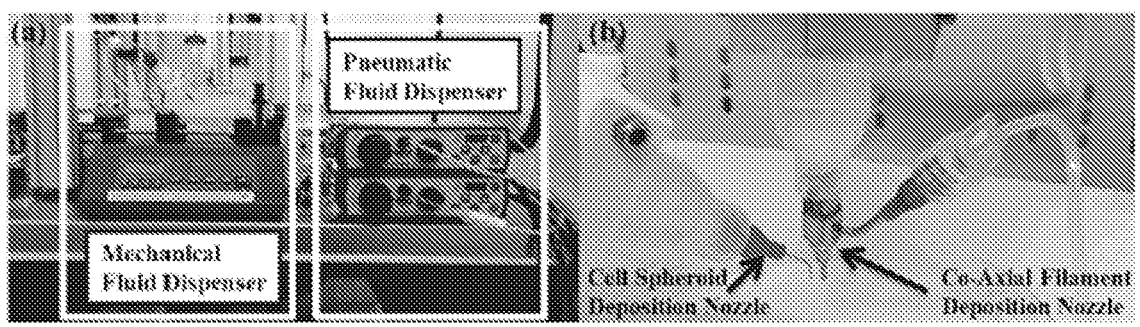
FIG. 5A depicts an exemplary mechanical dispenser for dispensing crosslinking solution and two exemplary pneumatic dispensers for dispensing hydrogels for gel spheroid formation and vascular network printing, as disclosed herein.
FIG. 5B depicts an exemplary angled nozzle for cell spheroid deposition and an exemplary co-axial nozzle for vascular network printing, as disclosed herein.

The MABP hardware comprised two identical three-axis linear motion systems mounted on the same table, as shown in FIG. 2, where the x-, y-, and z-axes are the three principal axes in a Cartesian frame. This configuration enabled independent and concurrent dispensing of multiple materials. The system was arranged with a vascular network and a cell spheroid deposition system. Each deposition system comprised three stepper motors and linear actuators mounted in a gantry configuration, with the dispensing nozzle connected to the fluid dispenser, and the barrel mounted on the z-axis actuator, the z-axis actuator mounted on the x-axis actuator, and the x-axis actuator mounted on the y-axis actuator. This design enabled the two nozzles to be actuated independently and the printed structure to remain stationary during the deposition process. The fluid dispensers were controlled by the dispenser control system. A virtual prototype of this system is shown in FIGS. 3A-3B.

The fabrication of the MABP emphasized the use of standard parts to minimize development time. The frame was constructed using an aluminum T-slotted framing system (80/20 Inc., Columbia City, IN, USA) due to ease of construction and reconfiguration. Linear actuators (Thomson Industries Inc., Radford, VA, USA) capable of actuating 200 mm in the x-direction, 300 mm in the y-direction, and 100 mm in the z-direction were used to translate the rotational motion of the stepper motor (Probotix, Peoria, IL, USA) into a linear motion. These components enabled the machine to achieve a theoretical maximum linear velocity of 30 mm/s with a resolution of 0.016 mm. A 15 mm profile bearing (McMaster-Carr Supply Company, Chicago, IL, USA) was mounted on each end of the x-axis frame to support the static and dynamic loads in the x-direction to prevent the y-axis linear actuator from reaching its maximum payload capacity. The profile bearings were mounted on 15 mm wide hardened steel guide rails that are 460 mm in length (McMaster-Carr Supply Company, Chicago, IL, USA). The table top was fabricated from a precision ground 7075 aluminum plate (12.7 mm thick). Individual components were aligned using a dial indicator mounted on the spindle of a CNC mill. The entire system was aligned using a dial indicator on a granite table.

Machine Control System

The machine control system (see FIGS. 4A-4B) actuated the motors based on the signal generated from the control software. The motion control system comprised a breakout board, power supply, and motor drivers (see FIG. 4B). The breakout board provided access to the individual pins of the parallel port, which were used to connect motor drivers and limit switches. The motor drivers actuated the motors at the desired rotational acceleration, velocity, and distance based on the signal sent from the computer through the parallel port. The MABP motion control system, which was an open loop system, comprised two identical 3-axis motion control systems. Each motion control system contained an RF-isolated CNC Breakout Board (Probotix, Pekin, IL, USA), three stepper motor drivers (Probotix, Pekin, IL, USA), and one power supply (Probotix, Pekin, IL, USA).

Fluid Deposition System

The fluid deposition system (see FIG. 5A and FIG. 5B) comprised two pneumatic dispensers (Nordson Corp., Westlake, OH, USA), a mechanical dispenser (New Era Pump System Inc., Farmingdale, NY), a co-axial dispensing tip, and a standard dispensing tip. The pneumatic dispensers were used to dispense the biomaterial, which had a high viscosity. The mechanical dispenser was used to dispense the crosslinking solution, which had a relatively low viscosity. The vascular network was deposited using a co-axial nozzle, where the alginate was deposited in the core and calcium chloride was deposited from the outer sheath. Cell spheroids were deposited using a deposition nozzle containing a 45 degree bend to minimize the distance between the two nozzles, as depicted in FIG. 5B. These systems were triggered by the dispenser control system, which actuated the fluid dispensers using commands contained in the toolpath plan.

Co-Axial Nozzle Design and Fabrication

A co-axial nozzle comprising a 16 gauge outer nozzle (1650 μm outer diameter (O.D.), 1194 μm inner diameter (I.D.)) and a 22 gauge inner nozzle (711 μm O.D., 406 μm I.D.) controlled the dispensing of both the hydrogel and the crosslinker. Initial development of this machine showed that the hydrogel structure collapsed when insufficient crosslinking agent was added, causing poorly defined geometries to be produced. It is contemplated that uncontrollable layer height increases can cause the dispensing nozzle to remove the filament strands (of the vascular network) deposited from the previous layer when too much crosslinking agent is added. The coaxial nozzle was developed for this application to ensure that the crosslinking solution encapsulates the hydrogel while being direction-independent.

The co-axial nozzle assembly comprised a feed tube, an outer tube, and an inner tube (see FIG. 6A). The feed tube was used to feed the crosslinking solution into the cavity formed between the outer and inner tubes, while the hydrogel was fed through the inner tube to print the vascular network, as shown in FIG. 6A. A hole of the same outer diameter as the feed tube was created in the barrel of the outer tube for feed tube attachment. The luer lock hub on the barrel of the outer tube was removed using a lathe, and its tip was shortened 16 mm, measured from the tip of the inner nozzle. The outer barrel was shortened to prevent the co-axial nozzle from clogging as a result of the hydrogel adhering to the outer barrel due to surface tension. The inner tube was inserted and aligned until it was concentric with the outer barrel and was subsequently laser-welded. The feed tube was attached to the outer tube using laser welding as well. The entire assembly was subsequently reinforced with J-B STIK steel-reinforced epoxy putty, as depicted in FIG. 6C.

MABP Operation

The MABP operation process using a bioprinter as disclosed herein is shown in FIG. 7. A computer-aided design (CAD) model can be obtained through reverse engineering methods such as CT scans or MRI.

The model segmentation process sliced the CAD model into layers with a specified thickness using Rhinoceros 4.0 software by exporting the CAD model. Toolpaths for vascular network (e.g., filament) and spheroid deposition were subsequently generated for each layer of the multi-layered 3D structure. The toolpath sequencing strategy ensured that the spheroids were deposited between portions of the vascular network in the appropriate timeframe to alleviate collision between the two nozzles. This was important because the spheroid deposition nozzle cannot travel ahead of the vascular network deposition nozzle. Doing so can cause nozzle damage and possibly machine damage. The sequenced toolpaths were translated into motor signals by its respective control software, and the motors on the MABP were actuated by the motion control system based on the motor signals to print the desired structure during the fabrication phase.

This process was implemented using two separate machine control software programs: GRBL, a microcontroller-based motion control software program, and Mach 3, a widely used computer-based motion control software program. G-code is sent to the microcontroller line-by-line from a text file using a script written in Python. The command used to trigger the cell spheroid deposition operation was sent to Mach 3 using a virtual serial port connection. A script written in Visual Basic listens through the virtual serial port for this command when the optional stop is triggered in Mach 3 to start the subsequent section.

System Validation

The development of new hardware required a validation study to demonstrate its capabilities and areas of improvement. The system validation for this machine entailed fabricating a multi-layer tissue construct while concurrently depositing spheroids between portions of the vascular network and performing a cell viability study to ensure that the printing process is biologically compatible. Several different tests can be performed first to validate the independent operation of the cell deposition system and the vascular network deposition system to obtain the dispensing parameters for the cell-laden hybrid structure fabrication process. The first test was to validate the operation of the vascular network fabrication system. Subsequent tests were performed to determine the appropriate flow rate of the crosslinking solution through the co-axial nozzle and the dispensing parameters that can be used to fabricate cell spheroids of the appropriate diameter. The obtained parameters are subsequently used for the multi-arm hybrid biofabrication process. A cell viability study is conducted to determine the effects of the multi-arm hybrid biofabrication process on the cells.

Multi-Layer Tissue Construct Fabrication

One object of the multi-layer fabrication process is to ensure that the system is capable of producing hydrogel tissue constructs with well-defined porous geometries. A 20 mm×20 mm tissue construct with 0-90° laydown orientation containing a filament-to-filament distance of 2 mm was fabricated with the vascular network deposition system on the MABP. Arc fitting, in which the directional changes of the nozzle are accomplished using an arc to alleviate sharp corners, was used to minimize over-deposition when the deposition direction is changed. Alginate was dispensed from a dispensing nozzle 12.7 mm in length with an inner diameter of 200 µm using a pressure of 100 kPa onto a piece of filter paper 70 mm in diameter soaked in crosslinking solution. Additional crosslinking solution was sprayed onto the tissue construct during the fabrication process to ensure the tissue construct integrity was maintained. Layer height was increased 0.1 mm every two layers if the system demonstrated sufficient reliability. Nozzle travel velocity, which is the travel velocity of the nozzle with respect to the printing stage, was set at 1000 mm/min.

Co-Axial Nozzle Operation

A rheology study was conducted to determine the effects of the crosslinking solution deposition rate on final filament width using the co-axial nozzle and the effects of hydrogel dispensing pressure on the final filament width. The deposition pressure was held at 45 kPa to determine the effects of the crosslinking solution deposition rate on the final filament width. The crosslinking deposition rate was held at 400 µm/min to determine the effects of the deposition pressure on final filament width. Nozzle travel velocity was set at 1000 mm/min, the maximum travel speed of the MABP to minimize filament width. A two-layer 20 mm×20 mm tissue construct with 0-90° laydown orientation containing a filament-to-filament distance of 2 mm (within each layer's vascular network) was printed onto a piece of filter paper containing the crosslinking solution placed on a petri dish for the rheology study. The crosslinking solution on the filter paper was used to provide adherence of the paper onto the petri dish. The first layer of the tissue construct was 40 mm×20 mm because of filament inconsistency during the beginning of the filament extrusion. The extended section was subsequently trimmed and removed. Nozzle height remained unchanged for the two layers. One width measurement was taken at the center of each filament strand of the vascular network on the second layer of the tissue construct using a digital microscope (BA310, Motic Incorporation Inc., Canada). The second layer was measured instead of the first since it was less likely to be subjected to the crosslinking solution contained on the filter paper.

Measurements were taken at the center of the vascular network to minimize width variation due to directional changes. The filament strands on the vascular network edges were not measured due to significant variations.

Cell Spheroid Fabrication

A separate rheology study was conducted to determine the effects of dispensing time on spheroid diameter. Cell spheroids were fabricated by setting a time interval and dispensing pressure on the pressure dispenser, causing a spheroid to form on the dispensing tip. The nozzle is then lowered onto a microscope slide, and the surface tension between the droplet and the crosslink solution removed the droplet from the nozzle. The spheroids were made with a 27 gauge (420 µm O.D., 200 µm I.D.) dispensing nozzle using a dispensing pressure of 241 kPa, while varying the dispensing time interval.

Cell-Laden Hybrid Structure Fabrication

The goal of the cell-laden hybrid structure validation is to fabricate a multi-layer 20 mm×20 mm tissue construct with 0-90° laydown orientation containing a filament-to-filament distance of 2 mm (within the vascular network of each layer) while having cell spheroids concurrently deposited between the filaments. Cell spheroid deposition was initiated after the second arc was made on the second layer using the obtained crosslinking flow rate for filament fabrication and time interval for spheroid formation. Nozzle travel velocity and dispensing pressure were identical to previous experiments.

Cell Viability Analysis

An 8-layer 20 mm×20 mm hybrid tissue structure was printed in a 0-90° laydown orientation with a filament-to-filament distance of 2 mm (within the vascular network of each layer) using the alginate solution with the co-axial nozzle at a dispensing pressure of 42 kPa and nozzle travel velocity of 1000 mm/mm using the vascular network deposition system on the MABP.

Crosslinking solution flowed at 350 μm/min. Spheroids were formed with a dispensing pressure of 124 kpa and a dispensing time of 200 ms. Cell viability assay was carried out by LIVE/DEAD staining as disclosed herein to both alginate vascular networks and spheroids at day 1, day 4, and day 7. Briefly, Calcein acetoxymethylester (calcein AM) and ethidiumhomodimer-2 (Invitrogen™ Life Technologies, Carlsbad, CA), at a concentration of 1.0 mM each, were used for labeling living cells with bright green fluorescent and non-viable cells with red fluorophore. A 30-minute incubation period was carried out during staining, and samples were imaged using a fluorescent microscope (Leica Microsystems Inc., Buffalo Grove, IL, USA).

Statistical Analysis

Statistical significance of the experimental data for the filament width (of the vascular network) and spheroid diameter was determined by one-way analysis of variance (ANOVA) with a significance level of $p<0.05$ using Microsoft Excel. Nine Filament width measurements were obtained for each tissue construct, and a total of five tissue constructs were fabricated for each dispensing parameter. Forty-five samples were obtained at each dispensing parameter for cell spheroid diameter measurements. Statistical significance of the experimental data for cell functionality was determined by a paired-wise combined with tukey post-hoc test at a significance level $p<0.05$. The percentage of viable cells for each experimental group was calculated by averaging the values of three different samples. All measurements were presented as mean±standard deviation.

Results and Discussion

Multi-Layer Tissue Construct Fabrication

Tissue constructs with 20 layers were fabricated using the vascular network deposition system. The tissue constructs showed that the system was able to produce tissue constructs with highly reproducible architecture with well-defined geometries in well-integrated shape (see FIGS. 8A-C). The two-week culture studies showed that the printed tissue constructs in cell-type oxygenized media were still structurally integrated, demonstrating its potential for long-term cultures as well (see FIG. 8D).

Co-Axial Nozzle Operation

The width of the filaments of the vascular networks was measured at crosslinking fluid dispensing rates of 300 μl/min, 400 μl/min, and 500 μl/min. The filament measurements were 579±29 μm at a dispensing rate of 300 μl/min, 562±13 μm at 400 μl/min, and 575±20 μm at 500 μl/min, as shown in FIG. 9A. The results showed that there is no statistical significance, and therefore filament width does not vary with the flow rate of the crosslinking solution at the range in which the measurements were obtained. This was due to continuous crosslinker flow (regardless of flow rate) enclosing hydrogel flow and keeping its diameter nearly constant. The structure started to collapse when the flow rate was less than 300 μl/min due to weak crosslinking of the extruded filament that did not allow quick diffusion of calcium ions into the filament. Poor layer adhesion was noted when the flow rate was above 500 μl/min, which can cause the structure to dissolve when submerged in cell culturing medium. Due to the high flow rate of the crosslinker above 500 μl/min, crosslinking was nearly completed during the extrusion process that did not allow further crosslinking of the filament after the extrusion process. Hence, filaments of the vascular network did not adhere to other filaments strongly. It is contemplated that other biomaterials with crosslinking-based gelation mechanism such as chitosan can behave similarly due to the above-mentioned phenomena. The higher measurement variation at 300 μl/min can be attributed to inconsistent flow of the crosslinking solution, causing some parts of the hydrogel to crosslink while others did not.

Filament width was also measured at hydrogel dispensing pressures of 35 kPa, 40 kPa, 45 kPa, and 50 kPa. The filament measurements were 406±18 μm at a dispensing pressure of 35 kPa, 479±28 μm at 40 kPa, 562±13 μm at 45 kPa, and 630±32 μm at 50 kPa, as shown in FIG. 9B. The results showed a linear relationship between dispensing pressure and filament width. The high variance at a dispensing pressure of 50 kPa can be attributed to a relatively slow nozzle travel velocity with respect to the given pressure, resulting in an uneven filament width and poorly defined geometries of the vascular network.

Cell Spheroid Fabrication

The cell spheroid fabrication measurements showed that the sphere diameter was 1323±20 μm at a time interval of 250 ms, 1608±35 μm at 275 ms, 1703±20 μm at 300 ms, and 1853±39 μm at 350 ms. The results showed little variability in cell spheroid diameter at a given time interval and also showed that the correlation was non-linear from a dispensing time interval between 250 ms and 350 ms, as shown in FIG. 10A. A sample measurement of the spheroid is provided in FIG. 10B.

Cell-Laden Hybrid Structure

Figure 11:
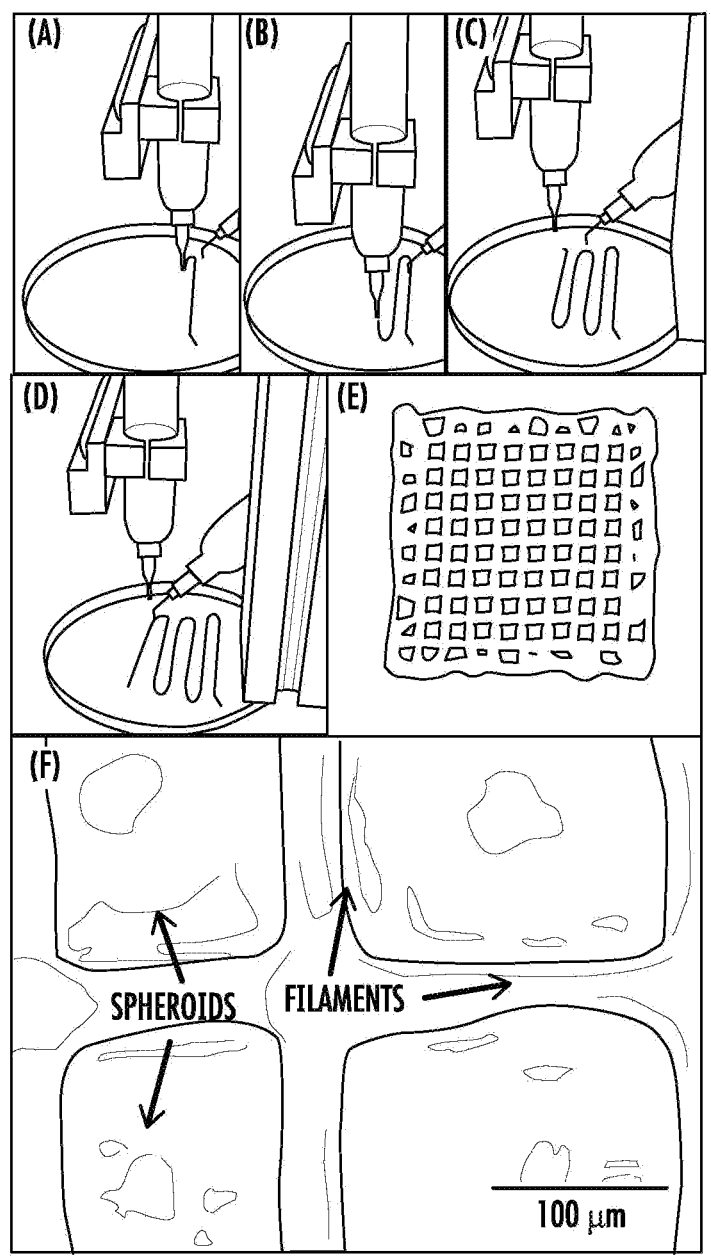

The cell-laden hybrid structure study used parameters obtained from the co-axial nozzle and the spheroid diameter validation. The co-axial nozzle validation shows that the filament width is 572±12 μm regardless of the crosslinking depositing rate. A crosslinking deposition rate of 400 μl/min was used since the data showed that it provided the greatest filament consistency. The cell spheroid should ideally be 1500 μm for the spheroid to fit in the space between the adjacent filament, being that that filament-to-filament distance was 2000 μm and the filament width was 572 μm using the given parameters. 2000 μm distance was preferred while cell spheroids were slightly interfering with the filaments and crosslinking that enabled attachment of the spheroids to the filaments. This provided structural integrity of the hybrid constructs, where spheroids did not spread around in culture after the fabrication. The spheroid deposition data showed that a time interval of 250 ms can yield the desired results. However, a time interval of 275 ms was used to ensure that the spheroid attached to the adjacent filament strands since it can produce a larger spheroid diameter. The spheroid deposition phase is shown in FIG. 11. The deposition process revealed that the spheroid deposition system was operating much slower than the vascular network fabrication system. Approximately 6 of the 64 spheroids were deposited before the filament deposition process was completed, which showed negligible savings in fabrication time. The resulting structure, however, shows well-defined filament and construct geometry as shown in FIG. 11D. FIG. 11E demonstrates precisely place spheroids between filaments in a multi-layer hybrid structure under light microscopy. The hybrid structure shows great promise for tissue engineering with increased cell density and potential to develop heterocellular architecture. This printing process can be further refined to print multiple cell types by implementing a secondary dispensing system onto the cell deposition arm.

Cell Viability

Fluorescent microscopy was used to check cell viability after the printing process with live/dead fluorescent staining from random filaments and spheroids on the tissue constructs. Viable cells were labeled with calcein AM (green), while dead cells were stained with ethidium homodimer (red). Cells did not proliferate much within first 12 hours post-printing. One day after printing, cell viability of both the vascular network (including filaments) and spheroids were relatively low: 43.92±0.04% and 60.15±0.05%, respectively. During in vitro culture, cell viability increased after 3 days and reached up to 76.06±0.04% for filaments and 79.99±0.06% for spheroids. Although the initial printing process can result in noticeable cell damage and death for both spheroids and the vascular network due to shear stress generated at the interface of the metal nozzle tip and the cellular alginate solution, as well as compressive stress generated by high pneumatic dispensing pressure, injured cells were recovering and other cells were proliferating during prolonged culture, and viability was 87.23±0.03 and 92.87±0.02% at day 7 post printing for vascular networks and spheroids, respectively (see FIG. 12A). As can be seen in FIG. 12B-C, most of the cells were stained with calcein AM at the end of 7-day in vitro culture. Although cells can be seeded after the fabrication as well, seeding cells during the fabrication (which can be enriched with more cells seeded after fabrication) increases the cell density in the resulting tissue construct. In addition, seeding cells after fabrication cannot be successful for some hydrogels such as alginate without surface modifications. Cells cannot be able to attach on the surface of the hydrogel.

In this case, encapsulating cells during fabrication was the only way for seeding cells inside the tissue construct.

Example Two

FIG. 13 illustrates the conceptual model of organ printing through integration of a vascular network with a cellular assembly. The concept allows constructing structures with a vascular network that acts like blood vessels, allowing media perfusion through an extracellular matrix that can support cell viability in 3-D. In FIG. 13, vascular network is printed in a 0°-90° lay-down pattern to develop 3-D structures. Oxygenized perfusion media can be pumped into channels of the vascular network for circulation purposes. Round ends are considered for the zigzag deposition pattern to prevent blockage of media flow. After parallel printing of each vascular network layer, cellular spheroids, i.e., tissue spheroids or cell-encapsulated microspheres, can be deposited between channels of the vascular network in the form of droplets using another robotic arm; semipermeable fluidic channels allow transport and diffusion of media to the cellular environment. This strategy enabled printing a semipermeable vascular network in tandem with printing cellular assembly. Concurrent printing can potentially reduce the fabrication time, which is crucial for the development of scale-up technologies, such as the multi-arm bioprinters disclosed herein. It is contemplated that spheroids can significantly enhance cell viability of stem cell-derived organ-specific cells, allowing the development of further organ fabrication techniques in the near future. Printing encapsulated cells in spheroids also greatly reduces shear-stress induced cell damage compared to printing cells directly loaded within biomaterial media. In general, cells are subjected to shear stress during the printing process, and cell injury and DNA damage should be minimized. The disclosed concept can also allow inclusion of multiple cell types in a spatially organized way by integrating another printer unit mounted on the robotic arm to print a secondary type of spheroids precisely.

Figure 14:
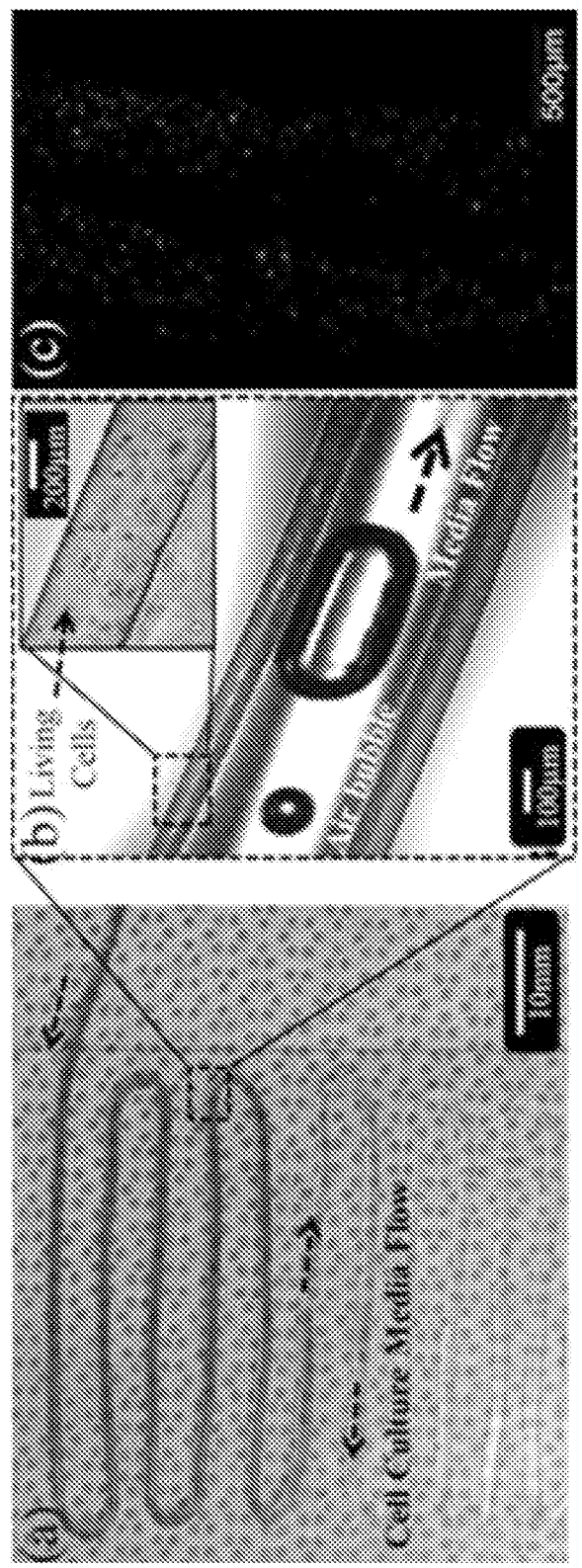

FIG. 14 illustrates oxygenized media perfusion through a printed channel of a vascular network, with the channel having a 44 cm length and 1 mm width with a 500-μm lumen diameter. The cell media was circulated through the channel without any blockage or swirling, which showed a great potential for developing embedded channels and serving as a vascular network for thick tissue fabrication. Direct printing of these channels allowed them to be integrated within a hybrid bioprinting platform and also facilitated patterning them into very complex shapes. It is contemplated that mechanobiological properties of printed channels can be investigated and electrospun nanofiber reinforcement can be performed to match the mechanical properties with that of blood vessels. Elasticity and tensile strength are essential to be biomimetically mediated. Viability of cartilage progenitor cells (CPCs) encapsulated within the printed vascular network showed 97.6±1.2% one day post-printing and maintained high cell viability on day 4, with a percentage of 95.8±1.2 where living cells are shown around the lumen on the cut-away view [see FIG. 14C].

Example Three

This example displayed the viability and functionality of cartilage progenitor cells (CPCs) during post-encapsulation in sodium alginate and printing through a pressure-assisted bioprinting system. The bioprinting process dispenses cell-encapsulated sodium alginate through a coaxial nozzle system. Cells are inevitably subjected to different mechanical stimulus within the alginate solution. These stimuli associated with the bioprinting process have an effect on cell viability following completion of the fabrication process, and also induce phenotypic alteration of cells in post-printing incubation. Four important parameters chosen in this study are nozzle diameter, alginate dispensing pressure, and cell seeding density and alginate concentration. Their effect on the viability and functionality of CPCs after the bioprinting process is reported. CPCs were used for a proof of concept in this study, various other cell types can be applied with the proposed system in future studies.

Materials and Methods

Materials

Prior to making a hydrogel solution, sodium alginate powder (Sigma Aldrich, United Kingdom) and calcium chloride powder (Sigma Aldrich, United Kingdom) was treated with ultraviolet (UV) light for sterilization three times for a 30-minute cycle. UV-sterilized sodium alginate was dissolved in deionized water to make 2%, 4% and 6% (w/v) solutions. Solutions were mixed with a magnetic stirrer until homogeneity was reached. Similarly, the cross-linking solution was prepared by dissolving calcium chloride in ultra-purified water (Invitrogen™ Life Technologies, Carlsbad, CA) at 4% (w/v).

Cell Preparation

Bovine CPCs were isolated from and cultured at 37° C. in 5% $CO_2$ in DMEM/F12 (1:1) supplemented with 10% fetal bovine serum (Invitrogen™ Life Technologies, Carlsbad, CA), 50 μg/μl L-ascorbate, 100 μg/μl penicillin, 100 μg/ml streptomycin, and 2.5 μg/μl Fungizone. The culture media was changed every other day. CPCs were passaged onto tissue culture dishes, and passage 1 cells were used for bioprinting. After harvesting, cells were gently mixed with the sodium alginate solution by repeated pipetting to get uniform distribution. Cell density varied from 2×10⁶/ml to 8×10⁶/ml in the alginate solution. CPCs were used in this study because their progenitor cells are sensitive to biochemical and mechanical changes, which has potential in cartilage tissue engineering applications.

Bioprinting Setup

An additive manufacturing-based robotic pressure-assisted bioprinting platform has been developed to do precise spatial deposition of cell-laden biomaterial as well as growth factors and biochemical compounds for tissue engineering constructs fabrication. The system used in this study consists of a single-arm bioprinter, a pressure regulator (EFD® Nordson), and a syringe pump (New Era Pump System Inc., Farmingdale, NY), which enable printing cell-encapsulated biomaterials through a pressure-assisted computer-controlled system. A coaxial nozzle design as disclosed herein was applied to fabricate tubular channels. Its opening diameter equals the difference between the inner diameter of the outer nozzle and the outer diameter of the inner nozzle. Viscous sodium alginate solution was extruded through the sheath section of the coaxial nozzle with low-pressure compressed air, while the calcium chloride solution was dispensed through the core section of the coaxial nozzle (see FIG. 21A). Crosslinking took place in the interface of the two materials, forming a tubular structure. Shear stress generated by this system is illustrated in FIG. 21B.

Dispensing Rheology of Coaxial Flow

The shear rate of a non-Newtonian flow through the coaxial nozzle can be approximated as:

$$\tau = \left(\frac{-\Delta P}{L}\right)\frac{R}{2}\left(\xi - \frac{\lambda^2}{\xi}\right) \quad (1)$$

In Equation (1), $\Delta P$ is the pressure change along the capillary, $L$ is the capillary length of the coaxial nozzle, $R$ is the inner radius of outer nozzle and $\xi=r/R$, $r$ is the radius of flow at a specific point inside the coaxial nozzle, with $r\in[\sigma R, R]$ (R is the inner radius of outer nozzle and $\sigma R$ equals to the outer radius of the inner nozzle). $\lambda$ is a constant locating the position of the maximum flow velocity and its value depends on the power-law flow behavior index (n) and $\sigma$ ($\sigma=r_{minimum}/R$). The values of independent variables in Equation (1) can be easily obtained except $-\Delta P/L$, which can be calculated as follows:

$$\frac{-\Delta P}{L} = \frac{Q^n}{\frac{n\pi R^3}{(3n+1)}\left(\frac{R}{4K}\right)^{1/n}\{(1-\lambda^2)^{(n+1)/n} - \sigma^{(n-1)/n}(\lambda^2-\sigma^2)^{(n+1)/n}\}} \quad (2)$$

In Equation (2), K is the power-law consistency coefficient and Q is the volumetric flow rate.

Bioprinting Study

Cells were evenly distributed in alginate solution before bioprinting, and were successfully encapsulated in tubular channels during the fabrication process. Cell viability assays were then performed to evaluate cell survival in response to varying bioprinting parameters. Prior to test-processing parameters, different cell density and sodium alginate concentrations were examined to find the optimal value in terms of high cell viability. Later, two printing process parameters were studied: a different-sized coaxial assembly for $I_{23G}O_{16G}$, $I_{26G}O_{16G}$ (I: inner nozzle; O: outer nozzle), and alginate dispensing pressures at 5, 10, and 20 psi. $I_{23G}O_{16G}$ consists of a 23 gauge (330 μm inner diameter, 650 μm outer diameter) inner nozzle and a 16 gauge outer nozzle (1190 μm inner diameter, 1460 μm outer diameter), while $I_{26G}O_{16G}$ has a 26 gauge inner nozzle (230 μm inner diameter, 457 μm outer diameter) and a 16 gauge outer nozzle. A calcium chloride crosslinking solution was dispensed at a constant rate for 2 ml/min in all experiments. Three samples were used for each experimental group (n=3). Different cell densities were first used in a viability study for a single nozzle (16 G) to determine the optimal number to be used in later study. Direct crosslinking of the hanging alginate droplet on the nozzle tips was used as the control for all groups. 5-15 cm of printed tubular cell-laden channels was collected for each sample Immediately after printing, each sample was kept in Hanks Balanced Salt Solution (HBSS) (Invitrogen™ Life Technologies, Carlsbad, CA) supplemented with 4% (w/v) calcium chloride for maintained crosslinking. Samples were washed with HBSS supplemented with 100 U/ml penicillin, 100 μg/ml streptomycin, and 2.5 μg/ml fungizone for sterilization before incubation in cell culture media. Cell viability was evaluated at three incremental time points: 12 h, 24 h, and 72 h, for exactly the same samples in each group throughout the time course.

Post-printing cell functionality study was presented to examine bioprinting-induced cell phenotypic change. Longer samples (>50 cm) printed at optimal cell density were subjected to two weeks culture in DMEM-based media. For the control group, the same number of printed samples was dissolved in cell releasing buffer (55 mM sodium citrate, 30 mM EDTA, 0.15 M NaCl) after complete crosslinking in HBSS, following consequent plating of CPCs for monolayer culture instead of 3-D tubular channel encapsulation. Quantitative RT-PCR was used to check cartilage-associated genetic marker expression.

Cell Viability Assay

Calcein acetoxymethylester (calcein AM) and ethidium-homodimer-2 (Invitrogen™ Life Technologies, Carlsbad, CA), at a concentration of 1.0 mM each, was used. Calcein AM labels living cells with bright green fluorescent. Ethidium homodimer is a red fluorophore that stains nonviable cells but cannot penetrate living cells. Each sample was washed with HBSS before live/dead staining. After 30-minute incubation, samples were imaged using an Olympus FluoView™ FV1000 laser scanning confocal microscope (LSCM) (Olympus NDT Inc., MA). Z-axis projections were assembled from images of each sample from surface to bottom with a depth of 1000 μm at 20-μm intervals. ImageJ software (National Institutes of Health, Bethesda, Maryland) was used for automated counting of red- and green-stained CPCs in z-axis projections, and percentages of viable cells were calculated. The percentage of viable cells for each experimental group was calculated by averaging the values of three different samples.

Cell Functionality Evaluation

Encapsulated CPCs were then released from cellular channels by dissolving them in dissolving buffer (55 mM sodium citrate, 30 mM EDTA, 0.15 M NaCl). Cells were centrifuged and washed twice in a phosphate buffer saline (PBS) (Invitrogen™ Life Technologies, Carlsbad, CA). Then the pellets were homogenized in TRIzol® reagent (Invitrogen™ Life Technologies, Carlsbad, CA), and total RNA was extracted using the RNeasy Mini Kit (QIAGEN, Valencia, CA) according to the manufacturer instruction. Cartilage-specific gene expression (collagen type II, aggrecan, and Sox9) was measured by real-time PCR in monolayer cultured CPCs and alginate encapsulated CPCs. Collagen type II is the basis for articular cartilage, and collagen type II gene is a marker related to chondrocyte phenotype and function. Aggrecan is a protein that in humans is encoded by the ACAN gene, which is an integral part of the extracellular matrix in cartilage tissue. Sox-9 is a transcription factor related to chondrogenic differentiation, which is the main function of CPCs. Primers were purchased from Integrated DNA Technologies (Coralville, IA). Table 1 summarized the information of primers used in real time PCR analysis.

Statistical Analysis

The statistical significance of experimental data was determined by two-way analysis of variance (ANOVA) for the dispensing pressure and nozzle diameter studies. One-way ANOVA was used for the cell density and alginate concentration studies, respectively. The paired-wise test was combined with the Tukey post-hoc test at a significance level of less than 0.05 (p<0.05) using SPSS.

Results

Bioprinted Cell-Laden Tubular Channels

Fabrication was performed using 4% alginate solution with a dispensing rate of 0.2 ml/min, and 4% crosslinker solution was dispensed at 1.5 ml/min for gelation purposes. The average inner and outer diameters of the fabricated tubular channels were 135±13 µm and 309±22 µm, respectively. Printed structures were then examined under a Motic® BA310 digital microscope (Motic in North America, Canada). Pumping of food dye solution assisted by a syringe pump was performed on the printed tubular channel to confirm its media transportation ability. As presented in FIG. 22, tubular channels were successfully manufactured by coaxial nozzle design assisted by a bioprinter with continuous uniform structural integrity. Perfusion of oxygenized cell media without any swirling or leakage through a >10 cm long channel showed their ability to support media transportation at flow rate of 30 ml/min. Sufficient structural integrity were maintained during three hours perfusion demonstrated its mechanical strength (see FIG. 22A). Experiments showed that tubular channels (7 cm in length), which has been soaked in 0.5% calcium chloride solution for 5 hours after fabrication, had 5.65±1.78 kPa maximum tensile stress with 5.91±1.12 kPa Young's modulus. Intentional bubble inclusion clearly illustrated the hollow feature of the printed structure, and cells were individually encapsulated and uniformly distributed in sodium alginate, forming a cellular wall of printed tubular structures (see FIG. 22B). Cell-laden tubular channels were able to maintain their morphology as well as hollow feature after 7 days incubation (see FIG. 22C).

Dispensing Rheology of Coaxial Flow

In order to calculate the shear stress, the value of $-\Delta P/L$ was calculated using Equation (2), where K=14960 and n=0.86 for 4% alginate. The volumetric flow rate was obtained from experimental measurements and plotted in FIG. 23A and $-\Delta P/L$ is presented in FIG. 23B that was used in Equation (1) to calculate the shear stress. The shear stress distribution in coaxial nozzles with 5 psi, 10 psi and 20 psi alginate dispensing pressures is demonstrated in FIG. 23C. As depicted from FIG. 23C, shear stress reaches its maximum value on the outer surface of the inner nozzle. Then, the shear stress diminishes as r increases and vanishes at the inflection point on somewhere around the middle point of the space between nozzles. The inflection point does not necessarily locate in the middle of the space between nozzles; however, its location depends on the value of $\lambda$. After the inflection point, the shear stress changes direction and increases as the r increases. This result is consistent with the observation in FIG. 25, in which most dead cells were observed on tubular channels walls, particularly more dead cells were observed on the inner wall than the outer wall. FIG. 23D shows maximum shear stress value under various dispensing pressures. Maximum shear stress increases as the alginate dispensing pressure increase. This explained why cell viability significantly decreases with increased alginate dispensing pressure.

Effect of Cell Density and Sodium Alginate Concentration on Post-Printing Viability The first experiment was conducted to assess the effect of cell density in alginate solution and alginate concentration on cell viability, in order to determine the optimal values for later studies. The three cell seeding densities used are $2 \times 10^6$/ml, $4 \times 10^6$/ml, and $8 \times 10^6$/ml in 2%, 4%, and 6% (w/v) alginate solution was printed through an 18 G single nozzle, with an inner diameter of 1.19 mm. Each data point was an average of three representative live/dead confocal images from three samples in each group. For each cell density, the dispensing pressure was studied at 5, 10, and 20 psi. Twelve hours post-printing and before cell proliferation, live/dead cell staining was carried out, and images were quantitatively analyzed by Image J. As shown in FIG. 23A, although decreased cell viability was observed with increasing alginate dispensing pressure, there was no significant difference in the viability of different cell densities at the same pressure, with the highest average around 72% at 5 psi. However, cell viability decreased with increasing alginate concentration (see FIG. 23B). The highest cell viability was 89% for 2% alginate, with a significant drop (31%) for 6% alginate. Since 4% alginate offered acceptable cell viability at 68% and reasonable structural integrity of the printed channels, a 4% alginate solution and $2 \times 10^6$ cells/ml can be used.

Figure 25:
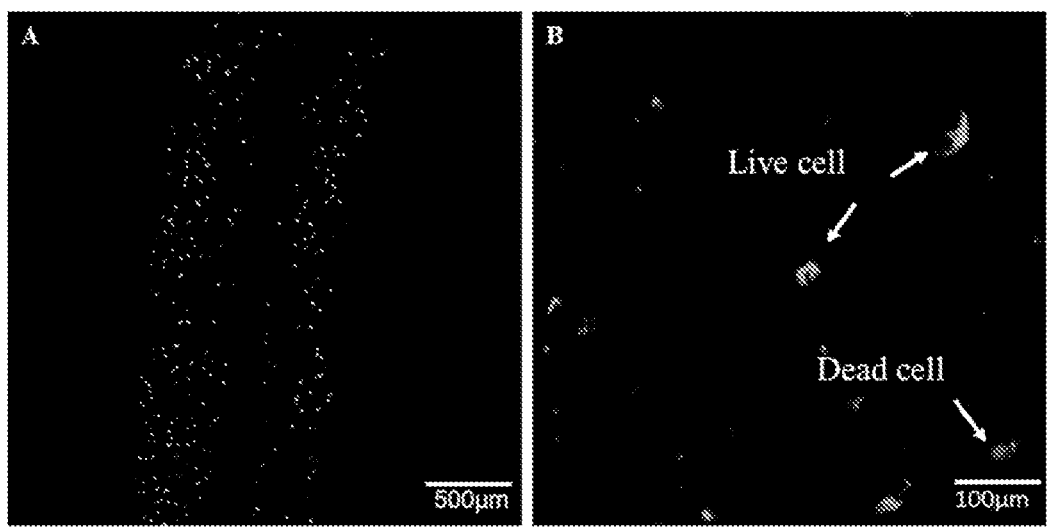

Effect of Coaxial Nozzle Size and Alginate Dispensing Pressure on Cell Viability To examine the effect of the bioprinting process on cell viability, experimental studies were designed to assess the effect of the nozzle size and alginate dispensing pressure on the viability of cells. The viability was calculated by averaging three representative live/dead confocal images for each sample. Analysis was first performed by segregating the samples into two experimental groups according to different coaxial nozzle assemblies: $I_{23G}O_{16G}$ (OD=550 µm) and $I_{26G}O_{16G}$ (OD=730 µm). For each coaxial nozzle, various dispensing pressures were studied at 5, 10, and 20 psi. A z-axis stack of confocal images is shown in FIG. 25, demonstrating live/dead cells, their relative ratios, and their distribution in printed cellular channels (the first 10 images from the top surface were eliminated to show the hollow feature of the printed structures). Quantitative viability assays are presented in FIGS. 24 and 26 to show the effects of alginate dispensing pressure and coaxial nozzle size.

Based on the Figures, it is obvious that cell viability varies with varying alginate dispensing pressures and different coaxial nozzle sizes. Printed cell viability decreases with increasing alginate dispensing pressure, and higher viability was observed in a coaxial nozzle of a larger size ($I_{26G}O_{16G}$). Changing the alginate dispensing pressure resulted in a significant difference in cell viability among experimental groups over the time course, especially at early time points. For the nozzle $I_{23G}O_{16G}$ (550 µm), a significant decrease in cell viability was observed in the bioprinted tubular structures compared with the control group shortly after printing (12 h) and at the 24 h time point as well (see FIG. 26A). The cell viabilities of the experimental groups at 12 h for varying alginate dispensing pressure (5, 10, and 20 psi) were 68%, 51.75%, and 40%, respectively. For a given representative alginate dispensing pressure (10 psi), a small nozzle $I_{23G}O_{16G}$ (550 μm) resulted in a statistically significant drop in cell viability between the experimental group and the normal control group within 12 h post-printing and at the 24 h time point (see FIG. 26B), while there was no significant change in cell viability in channels printed by the larger nozzle, $I_{26G}O_{16G}$ (730 μm AD). The cell viabilities of the control group were 95%, and the experimental groups with nozzles size of 730 μm and 550 μm were, 92% and 68%, respectively.

An empirical mathematical model was derived to predict cell viability V (%) at 12 hr. Two variables, spaces between nozzles ($X_1$-cm) and alginate dispensing pressure ($X_2$-psi), are considered as independent prediction factors. The predicted cell viability and experimental cell viability are plotted in FIG. 27 for both nozzle $I_{23G}O_{16G}$ and $I_{26G}O_{16G}$. According to FIG. 27, the predicted cell viability percentage is relatively close to the experimental results. The average percentage of error of the prediction model is small (6.43%).

$$V=-213.68X_1^2+33.61X_1-0.07X_2-0.2 \tag{3}$$

Post-Printing Cell Recovery During Incubation

Cell viability increased during incubation from 12 h to 72 h post-printing. From confocal imaging, the ratio of red fluorescent dead cells decreases, while green fluorescent live cells increases (see FIG. 28).

Quantitative analysis of cell viability at different time points was also performed. FIG. 29 showed an increasing trend of cell viability in the printed structure with the $I_{26G}O_{16G}$ coaxial nozzle. For all dispensing pressures (i.e., 5, 10, and 20 psi), a significant increase in cell viability (97%, 97%, and 98%, respectively) was observed at the 72 h time point. Cell viability in all groups was approaching or exceeding the control group at the end of 72 h incubation. For the 5 psi and 10 psi dispensing pressures, cell viability did not increase significantly over the 24 h period, but noticeable increases were observed at the 72 h time point from 89% to 97% and from 69% to 97%, respectively. For the 20 psi dispensing pressure, there was a remarkable increase in cell viability at both the 24 h (63%) and 72 h (98%) time point compared with the 12 h (36%) time point.

Post-Printing Cell Functionality

As cartilage progenitor cells are tissue-specific stem cells of cartilage tissue, they have the potential to undergo chondrogenic differentiation. When differentiated, their main function is to produce extra cellular matrix (ECM) of articular cartilage. Gene expression analysis is sufficient to check cell functionality based on their genetic markers for specific ECM proteins. Gene expression analysis revealed relatively higher expression of cartilage-specific marker genes in CPCs encapsulated in hollow fibers versus monolayer cultured CPCs. In real-time PCR analysis, collagen type II (COL-2), Sox-9 showed over a two-fold change, which indicated that CPCs were better differentiated towards chondrogenic lineage, making cartilage-specific protein to serve as extracellular matrix. Aggrecan genes (ACAN) were up-regulated to over twelve-fold in bioprinted structures, which further supports that the tubular alginate channel is an ideal environment for CPCs to differentiate and carry out their cartilage-producing function (see FIG. 30).

Discussion

In this study, the proposed bioprinting system together with the coaxial nozzle assembly successfully generates cellular vessel-like tubular cell-laden channels with media transportation capability. Further exploration into the external stimuli generated by the printing system, biomaterial solution, and cell-biomaterial interaction was performed to assess the effect on cells at different spatial and temporal levels during and after bioprinting. In the presented system, the cells were impacted by biomaterial rheological properties, dispensing pressure, crosslinking solution concentration dispensing speed, coaxial nozzle size, and cell seeding density.

These results indicate that the effects of four parameters studied here—cell density, alginate concentration, alginate dispensing pressure, and coaxial nozzle size—on cell viability were not equal. There was no significant change in cell viability when varying cell seeding density from $2\times10^6$/ml to $8\times10^6$/ml, while a noticeable drop of cell viability, from 89% to 31%, was observed when increasing the alginate concentration from 2% to 6%. This can indicate that alteration in biomaterial rheological properties has more impact than cellular interaction on cell damage during the bioprinting process. Increased alginate concentration resulted in higher viscosity, which generate higher shear stress inside the nozzle, especially at the interface between the nozzle and the biomaterial, causing more cell death.

For two dispensing parameters, alginate dispensing pressure and coaxial nozzle size, viability studies were carried out in a time-dependent manner. Within 12 h after bioprinting, the average cell viability significantly decreases with increased alginate dispensing pressure and smaller coaxial nozzle (the lowest viability was 36% at 20 psi by $I_{23G}O_{16G}$). This initial cell damage is likely induced by mechanical stresses generated by the shear at the nozzle wall. As shown in FIG. 31, cell viability decreased dramatically as the maximum shear stress increased. In the disclosed coaxial nozzle system, there exist two interfaces between the cellular material and the nozzle wall, which further increases the possibility of shear-stress-induced cell damage compared to a single nozzle printing system. As presented in FIGS. 25 and 28A, most of the dead cells were distributed along the edge of the walls of printed structures, where shear stresses were the highest. The percentage of dead cells in FIG. 28C was different at both interfaces (outer and inner nozzle interface). Furthermore, increased cell viability at the 24 h and 72 h time points (see FIG. 26) can indicate that damaged cells are able to recover from their compromised status during post-printing incubation. A remarkable increase in cell numbers (see FIG. 26B) and cell viability 72 h after bioprinting with higher dispensing pressures (10 psi and 20 psi) indicates that cells can actually undergo reversible damage rather than permanent cell death, and that many of them were able to proliferate during in vitro culture. This observation can also indicate a potential advantage of the tubular channel structure, which is able to support culture media transportation and provide superior gas exchange within alginate hydrogel.

Moreover, the high expression level of the cartilage-specific genes Col-2, ACAN, and Sox-9 in the printed tubular structure confirmed that progenitor cell function was not altered by the bioprinting system. Instead, CPCs were more likely to differentiate towards their desired lineage, carrying out their ECM-producing function in a printed 3-D tubular structure rather than culturing them in petri dish.

Although promising results demonstrated the advantages of the system, several limitations have to be recognized in this study. First, the size of fabricated tubular channels was associated with coaxial nozzle assembly capability, which is not able to reach sub-micron scale by current fabrication techniques. More sophisticated nozzle assembly as well as deposition system is needed to further fabricate sub-micron or even nano-scale tubular structure. Moreover, whether proposed system is able to process other material with different gelation mechanism awaits further investigation. Similarly, crosslinking solution can be introduced through the inner section of coaxial nozzle for crosslinking-based polymerization (i.e. chitosan), while a temperature control unit can be integrated with coaxial nozzle system to print thermo-sensitive hydrogels such as collagen, agarose, gelatin, etc., by which cold water can be extruded through the core section to initiate polymerization. Furthermore, studies should be taken to investigate viability and functionality of vascular cells upon encapsulation and incubation to obtain more convincing data for proposed vascular system bioprinting.

Example Four

In this study, a novel bioprinting fabrication process is introduced, where a vascular network can be directly printed in complex shapes without any need of pre/post processes. An exemplary vascular network, in the form of hollow filaments, was directly printed by a pressure-assisted robotic system using hydrogels. Geometric characterization of the vascular network was performed through studying multiple biomaterials and their dispensing rheology. Then, the vascular network was embedded in bulk hydrogel to evaluate its structural integrity and media perfusion capability. Further, the media transportation capability of the printed and embedded vascular network was examined by perfusing oxygenized cell culture media through the patterned channels of the vascular network. A cell viability study was carried out to access the effect of perfusion on encapsulated cells.

Materials and Methods

Materials

Prior to making a hydrogel solution, sodium alginate powder (Sigma Aldrich, United Kingdom), chitosan powder (Sigma Aldrich, Iceland), and calcium chloride powder (Sigma Aldrich, United Kingdom) were treated with ultraviolet (UV) light for sterilization three times for a 30-minute cycle. UV-sterilized sodium alginate was dissolved in deionized water to make 3%, 4%, 5%, and 6% (w/v) solutions. UV-sterilized chitosan was dissolved in 1.0 M acetic acid (Fluka Analytical, Germany) to make 2%, 2.5%, 3%, and 4% (w/v) solutions. Solutions were mixed with a magnetic stirrer (HANNA Instruments, Rhode Island, USA) until homogeneity was reached. Similarly, the crosslinking solution was prepared by dissolving UV-sterilized calcium chloride in ultra-purified water (Invitrogen™ Life Technologies, Carlsbad, CA) at 4% (w/v). 1.0 M sodium hydroxide (Fluka Analytical, Germany) is used to crosslink the chitosan solution.

Cell Preparation

In order to evaluate the efficiency of the printed vascular network for cell viability, cartilage progenitor cells (CPCs) were used in this study. CPCs were cultured at 37° C. in 5% $CO_2$ in DMEM/F12 (1:1) supplemented with 10% fetal bovine serum (Invitrogen™ Life Technologies, Carlsbad, CA, USA), 50 µg/µl L-ascorbate, 100 µg/ul penicillin, 100 µg/ml streptomycin, and 2.5 µg/ul Fungizone. Culture media was changed every other day. Cells were harvested until a sufficient amount can be achieved for bioprinting. After harvesting, cells were centrifuged down and resuspended in 4% sodium alginate, and gently mixed with alginate solution by a vortex mixer to get uniform distribution. The cell seeding density used in this study was $2 \times 10^6$ cells/ml.

Biofabrication of the Vascular Network

The vascular network fabrication system consisted of five parts: a single-arm bioprinter; a homemade co-axial nozzle unit; a syringe pump (New Era Pump System Inc., Farmingdale, NY, East Providence, RI, USA), which was used to dispense crosslinker; a liquid dispenser (EFD® Nordson), which was used to dispense biomaterial; and a computer that was used for robotic control. FIG. 32A shows a representative model of the experiment setup developed in Pro/Engineer software. Two coaxial nozzle assemblies were used in this research: an assembly with 26 gauge (230 µm inner diameter (I.D.) (Integrated Manufacturing Solution, USA), 457 µm outer diameter (O.D.)) inner needle, and an 18 gauge (840 µm I.D., 1270 µm O.D.) outer needle used for the experiment in the below section entitled "Effect of Biomaterial Concentration on Vascular Network Dimensions," and another assembly with a 23 gauge (330 µm I.D., 650 µm O.D.) inner needle and an 18 gauge (840 µm I.D., 1270 µm O.D.) outer needle used for the experiment in the below section entitled "Effects of Dispensing Parameters on Vascular Network Dimensions." Biomaterial and its crosslinker solutions were loaded separately into the coaxial nozzle unit. The coaxial nozzle assembly consisted of three parts: a feed tube, an outer tube, and an inner tube. A representative model of the coaxial nozzle with hydrogel and crosslinker solution flow paths is demonstrated in FIG. 32B. During the printing process, the coaxial unit was mounted on the single-arm robot, which was controlled by a computer. Hydrogel solutions were pumped into the feed tube, which was used to feed hydrogel solution (alginate or chitosan) into the space formed between the outer and inner tubes. Hydrogel solution flowed through this space and dispensed out from the outer tube tip. Crosslinker was dispensed through inner tube. When the two solutions contacted, crosslinking (or gelation) started, and a tubular gel was formed with a hollow channel. The gelation process was an instantaneous chemical reaction as the crosslinker ions binding the hydrogel chains together. The penetration of crosslinker ions in hydrogel solution depends on the concentration of crosslinker ions, diffusion time, and the kinetics of crosslinking. As soon as materials were dispensed from the coaxial nozzle tip, a portion of the vascular network formed. The hydrogel solution dispensed from the outer tube was crosslinked and became the gel shell, where crosslinker flow through the inner part formed the hollow core.

Media Perfusion System

To test media transportation and perfusion capability of the vascular network, a customized system was developed. FIG. 33 demonstrates the experimental perfusion system in a tissue culture incubator (Panasonic Healthcare Company of North America, IL, USA). It consisted of a compact digital fluid pump (Cole-Parmer, IL, USA) to provide media flow, a culture media reservoir with 1 liter capacity, and an X—Y—Z axis motion stage (Edmund Optics, NJ, USA) to facilitate precise positioning and alignment of nozzle tip. Medical-grade tubes (PharMed, OH, USA) were used to connect the three main components of the perfusion system. 22 gauge flexible nozzle tips (Nordson, OH, USA) were used to connect the vascular network with the tubing system, and micro vessel clips were used to prevent leakage at the connection. Cell culture media was aspirated by the digital pump from the media reservoir and transported into a single channel (of the vascular network) and then cycled back to the reservoir.

Cell Viability Analysis

Immediately after bioprinting, samples were kept in Hanks Balanced Salt Solution (HBSS) (Invitrogen™ Life Technologies, Carlsbad, CA, USA) supplemented with 4%

(w/v) calcium chloride to maintain crosslinking. Samples were washed with HBSS supplemented with 100 U/ml penicillin, 100 µg/ml streptomycin, and 2.5 µg/ml fungizone for sterilization before incubation. After washing, a cellular vascular network was cultured with the perfusion system at 37° C. in 5% $CO_2$. Channels of the vascular network, 10-15 cm in length, were cultured in a customized T-75 culture flask with perfusion of DMEM-base cell culture media through the channels. The flow rate was set at 10 ml/hour for 12-hour continuous pumping. Cell viability assays were performed immediately after culturing to evaluate cell survival in response to media perfusion and perfusion-induced mechanical stimulation. A 5 cm long vascular network was printed for each sample, and three samples were used for each experimental group (n=3). For cell viability analysis, samples underwent fluorescent microscopic examination. The vascular networks were stained with calcium acetoxymethylester (calcein AM) and ethidiumhomodimer-2 (Invitrogen) at a concentration of 1.0 mM each. Calcein AM is metabolized in living cells to form a bright green fluorescent product that accumulates in the cytosol. Ethidium homodimer is a red fluorophore that stains the DNA of nonviable cells but cannot penetrate living cells with intact plasma membranes. The staining medium was aspirated, and new medium was added to wash off any residual stains on the vascular network surface before fluorescent illumination. After a 30-minute incubation period, the vascular network was imaged under a Leica fluorescent microscope (Leica Microsystems Inc., Buffalo Grove, IL, USA). Images were collected from three different locations randomly chosen from each sample. ImageJ (National Institutes of Health, Bethesda, MD, USA) was used for automated counting of red- and green-stained CPCs in each image, and the percentages of viable cells were calculated. The percentage of viable cells for each sample was calculated by averaging the values of three different locations.

Embedding a Vascular Network in Bulk Hydrogels

For embedding a vascular network in bulk hydrogels, the vascular network was printed directly into calcium chloride pools in petri dishes and soaked in the solution for over 30 minutes until the vascular network became fully crosslinked. During the crosslinking process, another petri dish was prepared and coated with 3-5 mm 4% alginate solution on the bottom. A coated petri dish was then fixed onto a horizontal shaker and underwent 3-5 minutes of shaking to get a uniform distribution with a flat surface. A completely crosslinked vascular network was then aligned on top of the alginate-coated petri dish to get a zigzag pattern with arc turns. Another layer of alginate solution was then slowly pulled onto the patterned vascular network without introducing any air bubbles or clearance between layers. A horizontal shaker was also used here to ensure an even surface for the second layer. 4% calcium chloride solution was then carefully sprayed onto the petri dish to cover the whole surface of the alginate. The entire structure was merged in a calcium chloride solution until gelation was fully completed, after which a vascular network was embedded into bulk alginate gel. Similar procedures were used to embed an alginate vascular network by 3% chitosan and 1.0 M sodium hydroxide as crosslinking solution. A vascular network embedded in bulk constructs was then used for media transportation and perfusion tests. Media with food dye was pumped through the perfusion system both for single-layer and multi-layer vascular networks to further show their functionality.

Statistical Analysis

In the below sections entitled "Effect of Biomaterial Concentration on Vascular Network Dimensions" and "Effects of Dispensing Parameters on Vascular Network Dimensions," more than 50 pieces of data were obtained by measuring different vascular networks and different sections of printed vascular networks under a digital microscope (Motic®, BA310, Motic Incorporation Inc., Canada). The data shown herein were an average of all 50 pieces of data. The statistical analysis was carried out using Minitab 16. For all data, normality and independent tests were performed to ensure the data used for statistical significance analysis followed the test assumption. The statistical difference analysis among groups was conducted by analysis of variance (ANOVA). Groups with a significance level of $p<0.05$ were considered as significant.

Results and Discussions

Fabrication of a Vascular Network

The fabricated alginate and chitosan vascular networks are shown in FIGS. 34A-34C. The alginate vascular network had relatively better mechanical and structural integrity compared to that of chitosan. The fabricated alginate vascular network was continuous and had uniform diameter (see FIG. 34A). As shown in FIG. 34B, although a uniform chitosan vascular network was obtained, its structural integrity was limited so that it was fragile and ruptured easily. The disclosed fabrication platform was also capable of fabricating constructs with 3D complex architecture. Fabrication was performed with 4% alginate solution with a dispensing rate of 0.2 ml/min, which demonstrated acceptable cell viability and good structural integrity. 4% calcium chloride solution was used as the crosslinker, which was dispensed at 1.5 ml/min. FIG. 34C shows an 8-layer alginate vascular network printed by the robotic system, which demonstrated the effectiveness of the fabrication platform.

Effect of Biomaterial Concentration on Vascular Network Dimensions

In this study, hydrogels including chitosan and alginate were explored to determine their fabrication feasibility. In the first experiment, 2%, 2.5%, 3% and 4% chitosan solutions were prepared to print a vascular network. 1.0 M sodium hydroxide was used to crosslink the chitosan solution. However, only 2.5% and 3% chitosan were feasible to fabricate a structurally well-integrated vascular network with the selected fabrication parameters. The mechanical integrity of 2% chitosan was weak; a channel of the vascular network snapped before a uniform channel formed. The viscosity of 4% chitosan was too high to be dispensed from the coaxial nozzle. It is contemplated that a higher dispensing pressure can allow ejecting the high viscosity solution but can also induce considerable shear stress reducing cell viability. Thus, FIG. 35A shows vascular network dimension data obtained from a vascular network with 2.5% and 3% solution concentration. As chitosan concentration increased, channel and core diameters as well as wall thickness decreased given the same dispensing pressure. FIG. 35B shows the effect of alginate concentration on vascular network dimensions. In this study, 3%, 4%, 5%, and 6% alginate and 4% $CaCl_2$ were used to fabricate vascular networks. In general, alginate with a solution concentration greater than 6% demonstrated limited cell viability and is not recommended for cell encapsulation experiments. The 4% alginate group had the smallest vascular network dimensions including the core and the channel diameter as well as the wall thickness. The results in FIG. 35B revealed that there was no distinct trend between alginate concentration and vascular network (e.g., filament) dimensions. Indeed, the dimensions of printed vascular networks were primarily affected by the diffusion rate of $Ca^{2+}$ ions, which was a function of alginate concentration and the thickness of the alginate ejected from the coaxial nozzle. In other words, alginate concentration affected the diffusion rate of $Ca^{2+}$ ions as well as the thickness of the hollow filament (of the vascular network) ejected from the nozzle per the fixed dispensing pressure. Similarly, the concentration of $CaCl_2$ also had an effect on the channel diameter of a fabricated vascular network. For example, FIG. 36A shows a partially crosslinked alginate vascular network which was fabricated with 4% alginate and 2% $CaCl_2$. This can be explained by gelation process, which depends on crosslinker and alginate concentrations as well as the flow rate of crosslinker through the core section. Due to low $Ca^{2+}$ concentration in 2% $CaCl_2$ solution, only a small portion of the deposited alginate was crosslinked. This can be alleviated by increasing the concentration of $CaCl_2$. The wall thickness of the vascular network can be critical for its functionality in both delivering perfused media through the core and allowing its diffusion for viability of encapsulated cells. The diffusion limit for hydrogels was around 200 μm, which indicated that if the wall thickness of the fabricated vascular network is smaller than 200 μm, there is a high chance of cell viability. However, it is contemplated that smaller wall thickness is not always desirable. Mechanical and structural integrity of a vascular network can decrease as the wall thickness decreases. FIG. 36B illustrates a vascular network with a thin wall, in which a channel of the vascular network was collapsed at several locations due to weak mechanical integrity.

Effects of Dispensing Parameters on Vascular Network Dimensions

Figure 37:
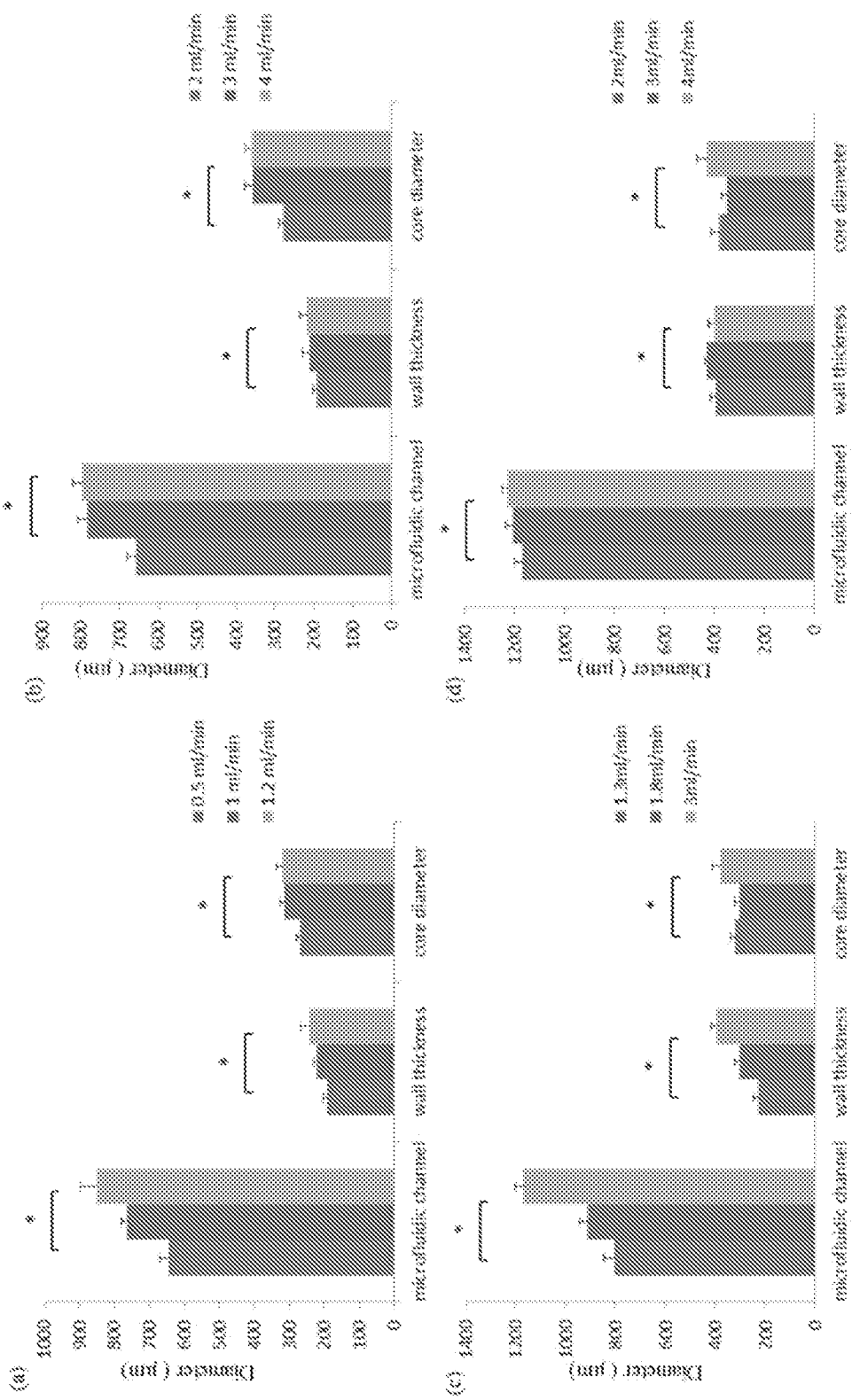

In this experiment, effects of dispensing parameters on vascular network dimensions were studied. 4% alginate and 4% $CaCl_2$ were used to fabricate an alginate vascular network, and 3% chitosan and 1.0 M sodium hydroxide were used to fabricate a chitosan vascular network. Alginate dispensing pressure, $CaCl_2$ dispensing rate, chitosan dispensing pressure and sodium hydroxide dispensing rate were varied to understand the effect of dispensing rates on vascular network dimensions. FIG. 37 illustrates the effect of the above-mentioned parameters on vascular network dimensions. The diameters of channels of the vascular network increased as biomaterial or crosslinker dispensing rates increased. Increasing biomaterial dispensing rate resulted in greater volume of biomaterial dispensed per unit time generating enlarged channels. This also resulted in thicker walls during extrusion (see FIG. 37A-C). Increasing crosslinker flow rate generated more tension on the vascular network wall in a radial direction, expanding the channels in cross-sectional profile that increased both core and channel diameter. No direct relationship was observed between wall thickness and the crosslinker flow rate (see FIG. 37B-D).

Media Perfusion and Cell Viability Upon Perfusion

FIG. 38(a) illustrates oxygenized media perfusion through an alginate vascular network pattern 44 cm in length and 1 mm in width with 500 μm lumen diameter. The cell culture media was circulated through the channels of the vascular network with relatively low Reynolds number without any blockage and swirling that shows a great potential for serving as a vascular network for thick tissue fabrication. Direct printing of these vascular networks allows them to be integrated within a hybrid bioprinting platform and also facilitates patterning them into very complex shapes. FIG. 38B shows the media flow with intentionally generated air bubbles under the digital microscope. The bubble was moving along the media flow. Cells were encapsulated in the hydrogel solution during the printing process and uniformly distributed in a printed vascular network (see FIG. 38C). The fluorescent microscope image showed quantifiable dead cells (red) under live/dead cell staining (see FIG. 38D), but further quantifiable investigation of cell viability under media perfusion culture showed most of the cells were viable (green) along the whole length of printed vascular network. FIG. 38E showed that average cell viability was 62.7±0.05% after 12 hours media perfusion post-printing. The diffusion of cell culture media was only realized through the internal surface of channels of the vascular network; however, it is contemplated that introducing the oxygenized cell media exogenously such as immersing the vascular network inside the media during perfusion can further support cell viability. Neither leakage nor breakage was observed during perfusion of the media; however, some media permeated across the vascular network wall due to the permeability of hydrogel. 1.55 ml media was permeated on an 8 cm length channel of the vascular network at a perfusion rate of 30 ml/min in 3 hours. The fabricated vascular network had acceptable mechanical properties as well. The elongation of the channel of the vascular network due to perfusion was 0.4 cm.

Vascular Networks Embedded in Hydrogels

Alginate vascular networks were prepared and embedded in both bulk chitosan and alginate. Media with different color food dye was used to visualize fluid flow. When embedded in 4% alginate, the vascular networks displayed a well-oriented pattern and structural integrity. It also transported media without blockage or disturbance (see FIG. 39A). Multi-directional media perfusion flow through two layers of alginate vascular networks was also successfully performed (see FIG. 39B), indicating its potential to be integrated into thick tissue fabrication. However, when embedded into chitosan hydrogel, alginate vascular networks showed rupture, especially at the turning point (see FIG. 39C). Also, they failed to transport media smoothly, and leakage was observed at the start point of perfusion (see FIG. 39D). In general, mechanical loading induced by the weight of bulk hydrogels affected structural morphology of vascular networks by collapsing them at respective locations. However, it is contemplated that this can be reduced by improving mechanical properties of the vascular network such as using optimum fabrication parameters and/or reinforcing nanofibers. Experiments showed that vascular network channels (7 cm in length), which had been soaked in 0.5% calcium chloride solution for 5 hours after fabrication, had 5.65±1.78 kPa maximum tensile stress with 5.91±1.12 kPa Young's modulus.

Example Five

The focus of this example was fabrication of a hybrid architecture enclosing vasculature-embedded cell aggregates for fabrication of perfusable miniature pancreatic organs. Scaffold-free cell aggregate printing was conducted in tandem with a novel printable vasculature network. FIG. 40 illustrates a schematic representation of the experimental plan. First, human iPS cells were differentiated into IPCs in an efficient way. Next, a micro-fluidic based approach was used to create scaffold-free IPC aggregate strands made of purely cells and extracellular matrix, with no biopolymer inclusion. Then, the fabricated cell aggregate strands (the bio-ink) were loaded into one cartridge, and the other cartridge was loaded with hydrogel and smooth muscle cells. The aggregate strands and hydrogel/smooth muscle cells were printed in tandem using a methodology in which IPC bio-ink was printed directly in cylindrical cell aggregate strands and high-density smooth muscle cells were printed in conduits serving as a vasculature network for perfusion purposes. Upon printing, cell aggregates can fuse to each other around the vasculature and then be transferred into a perfusion chamber for further fusion and maturation. During the perfusion culture, we can evaluate the performance of pancreatic organs such as insulin secretion in-vitro and then transplant it into a T1D mouse model for in-vivo performance.

Figure 41:
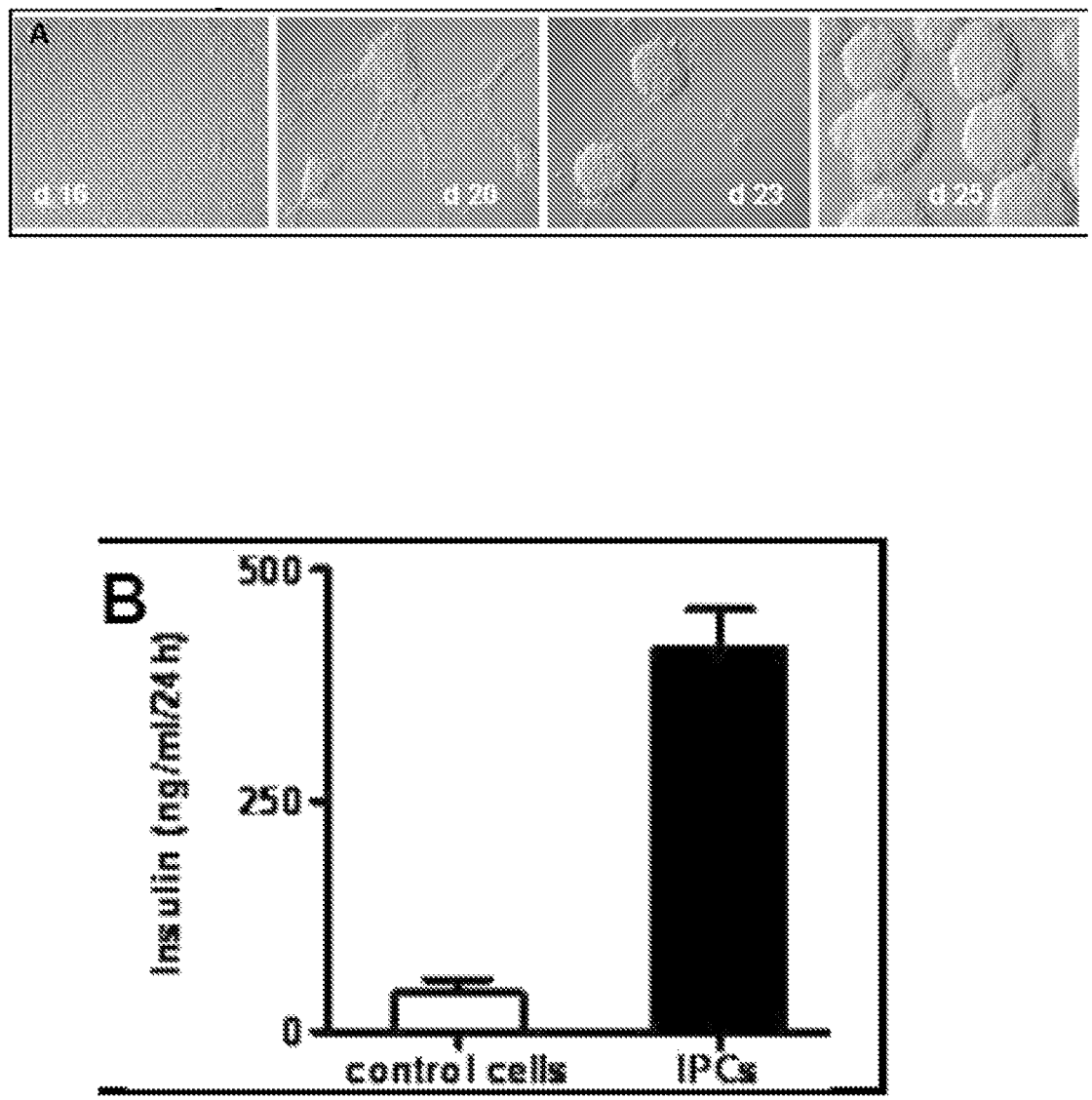

Biofabrication of a Novel Bio-Ink: IPC Aggregate Strands as Building Blocks for Pancreatic Organ Printing Preliminary data differentiating human iPS cells into IPCs is shown in FIG. 41. IPCs were cultivated overnight in 24 well plates, and supernatants were collected. Control cells were parental fibroblasts. Insulin was measured in these supernatants using a Roche insulin immunoassay. On day 16, the cells formed a monolayer, which began to change into cell clusters. These clusters had cell projections almost identical to neurons. By day 20, the clusters were polymorphic. It is contemplated that the projections seen around day 20 can be neuronal cells. Further cultivation showed that the cells formed bigger spheres by day 23. By day 25, they formed cell clusters, which were used for transplantation into diabetic mice. The formation of these spheres was similar to those observed after multipotent cells were isolated from the pancreas and differentiated. The spheres produced insulin. The spherical clusters also made it easier to compare their efficacy to secrete insulin compared to a defined number of pancreatic islets. To determine whether the newly generated IPCs secrete insulin, IPCs were cultivated in low glucose overnight, and supernatants were collected. They were assayed for human insulin using the Roche Cobas insulin kit. Parental fibroblasts were used as controls. The newly generated IPCs secreted insulin into the supernatant. FIG. 41B shows insulin secretion by these cells in low glucose. It is contemplated that these studies can be immediately relevant to the management of T1D in humans.

An additional methodology evaluated the fabrication of scaffold-free cell aggregate strands as building blocks for tissue assembly. Scaffold-free cell aggregates were fabricated in a long cylindrical form and loaded into the bioprinter, which was used for direct printing. To collect preliminary data on the validity of the proposed protocol, the feasibility of the method was tested using various cells such as beta TC3 cells (an insulinoma-like cell that secretes insulin), cartilage progenitor cells, and fibroblast cells. Briefly, over 200 million TC3 cells were pelleted down at 3000 rpm for 5 minutes. The resulting pellet was transferred into a capillary micropipette of 300 µm diameter and incubated at 37° C. with 5% CO2 overnight. Using a custom syringe unit, the cell suspension was injected into alginate tubular conduits. The conduits were fabricated using the methodology schematically described in FIG. 42, where semipermeable tubular conduits were used as semi-permeable capsules for cell aggregation by confining the ends with vessel clips. FIG. 43A shows the physical results of the experiment generating acceptable cohesiveness to handle being transferred into the bioprinter unit. Approximately 100% cell viability was achieved, where live-dead staining (green) showed barely visible dead cells (stained in red) in cylindrical aggregates in 3D (see FIG. 43B). Immunohistochemistry analysis was performed on the fabricated aggregates to test expression of several markers including C-peptide (which is a pre-curser for insulin), insulin and glucagon. FIGS. 43C-D show C-peptide and insulin expression, which were highly positive compared to the control group (DAPI only). FIG. 43E demonstrates glucagon expression, which remained negative. Because the cell aggregate strands demonstrated strong expression of insulin, it is contemplated that similar functionality from IPCs can be expected.

It is contemplated that the same procedures can be followed with IPCs for purposes of fabricating IPC aggregate strands. Viability tests and reverse transcription polymerase chain reaction (RT-PCR) can then be performed to determine gene expression, and an ELISA test for the insulin secretion of these strands can be performed before printing (quantitated in ng/mg protein). An ELISA test can be performed using glucose stimulation at different incubation levels. A wide array of semi-permeable capsule dimensions can be used to determine the effect of media diffusion on the viability of cell aggregates as well as their cohesiveness and compression properties, which can be tested using a micrometer based device. Indeed, it is contemplated that the compression strength and cohesiveness characteristics of these aggregates can be critical for handling and bioprintability. It is contemplated that these properties can be improved through nano-scale collagen reinforcement. Collagen-I nanofibers can be manufactured using an electrospinning setup. Electrospun fibers can be manufactured using various polymers and biomaterials. Upon fabrication, collagen-I nano fibers can be reinforced to improve mechanical properties and strength that will improve the cohesiveness as well as the interaction of cells. An immunohistochemistry study can be performed to characterize insulin, glucagon, and C-peptide expression. In addition, the cell-to-cell interaction can be characterized by studying E-cadherin expression, which demonstrates if cells are forming well-integrated aggregates. The physiological responsiveness of cell aggregates can be determined using a seahorse assay. The mechanical properties can be studied, and an optimum range for our application can be investigated by controlling cell density, growth factor expression and media diffusion in capsules, and culture times.

Hybrid Bioprinting of Perfusable 3D Pancreatic Miniature Organ Models

An approach that enables printing a vascular network directly was developed. The system allowed printing vascular conduits directly based on a pattern through a computer-controlled system. Upon revitalization, human umbilical vein smooth muscle cells (HUVSMC) were cultured at 37° C. in 5% CO2 in medium 231 supplemented with smooth muscle cell growth supplement, 10 µg/µl penicillin, 10 µg/ml streptomycin, and 2.5 µg/µl fungizone. Culture media was replenished every other day until HUVSMCs reached 70-80% confluent, after which cells were harvested by 0.25% trypsin-EDTA, washed by cell culture media, and pelleted in a 15 ml conical tube. HUVSMCs were gently mixed with 3% sodium alginate solution by a vortex mixer to obtain uniform cell distribution. HUVSMCs were seeded at a density of $10 \times 10^6$ cells/ml. Then, HUVSMCs were directly printed in a tubular shape by maintaining a constant controllable flow of crosslinker through the core, enabling instantaneous gelation while leaving unblocked tubular constructs. The results showed tubular vasculature can be printed in 3D in any complex shape defined by a predetermined design (see FIGS. 44A-D for a 103 cm long vasculature, branched vasculature and an eight-layer network). Vasculature with an external diameter ranging from 500 µm to 2 mm, and a lumen diameter ranging from 150 µm to 1 mm, can be directly printed.

Perfusing through an approximately 103 cm zigzag pattern was successful (see FIG. 44A). Fluorescence imaging with live/dead cell staining in FIG. 44E showed the printed HUVSMCs-laden vasculature, where 85.5±1.1% viability was achieved with seven days of perfusion through the lumen only. Cell viability increased further while HUVSMCs proliferated. Greater viability was achieved by perfusion through the lumen in addition to media support exogenously. Perfusing media kept the cells viable because of the super-diffusive properties of alginate as shown in FIG. 44F. A six-week culture of vasculature resulted in relatively strong and cohesive structures with well-defined structural integrity and reasonable elastin deposition shown by Verhoeff-Van Gieson staining (See FIG. 41G).

The ability of a six-week-cultured 1 cm long smooth muscle vasculature to enable media perfusion was examined. It was longer than the cell aggregate strands (5 mm long) to be able to hook up to the perfusion chamber. FIG. 45A shows the process steps followed by stacking fibroblast cell aggregate strands around a smooth-muscle vasculature. After 1 day in static culture, cell aggregate strands started fusing to each other until satisfactory structural integrity was achieved. Later, the tissue was connected to the perfusion culture, and perfect maturation was obtained in seven days. FIGS. 45B-E demonstrate the process step by step. The tissue construct was fabricated inside a mold first to keep it mechanically integrated until sufficient maturation was obtained. Later, cell aggregate strands were further fused and matured as shown in FIGS. 45D-E. FIG. 45F shows fusion of aggregate strands under fluorescence microscope, where complete fusion was achieved in Day 7. It is contemplated that this can provide great potential for scale-up tissue/organ printing and demonstrates that the proposed cell aggregate strands can serve as building blocks for scale-up tissue/organ fabrication, which is supported by the continuous perfusion.

A bioprinter as disclosed herein was used to produce the tissue constructs. One arm was equipped with a coaxial nozzle assembly for printing the vascular network, and the other arm was equipped with a custom unit to print cylindrical IPC aggregates. The nozzle configuration enabled close motion of printer units. The printer was located in a vertical flow hood for the sterilization of the process. The effects of process parameters (i.e., dispensing speed, nozzle specifications, cell density, viscosity, and dimensional properties of cell aggregate strands) on the viability of printed cell aggregates were investigated. Gene expression and ELISA tests can be performed post-printing, and the results can be compared with those of strands before printing. In addition, fusion between printed strands can be characterized through fluorescence imaging, and the time it takes for sufficient fusion and maturation can be researched through immunohistochemistry by studying insulin, C-peptide, E-cadherin and glucagon expression.

In order to fabricate the miniature pancreatic organ along with its vasculature, vasculatures can be printed layer by layer to provide both mechanical support and media transport for cell aggregates. FIG. 46 demonstrates this concept for a scale-up organ printing process, where two units of the bioprinter can run in tandem, printing two distinct materials: continuous vasculature and IPC aggregate strands. It is contemplated that insulin-producing cell aggregate strands can have a considerable number of cells to facilitate high cell viability, and they can be used as building blocks to construct the organ due to their quick fusion and maturation capabilities. It is further contemplated that the cell aggregate strands can fuse to each other and enclose the vasculature network. The vasculature network can be connected to the perfusion chamber for continuous perfusion of the cell-type media for maturation of the organ as well as in-vivo evaluation of the fabricated organs, which is discussed below.

Validation of the Formation and the Effectiveness of Printed Pancreatic Organs In-Vitro and In-Vivo:

Upon fabrication of the organ constructs, the constructs can be placed in a custom-made perfusion chamber to ensure the stability of constructs before and during perfusion. Vascular network inlets and outlets can be connected to perfusion tubes to facilitate circulation of the media. Next, the media can be perfused through the system using multiple multi-channel peristaltic pumps. The media in the reservoir can be replenished every other day after culturing in the incubator. When the media is perfused and circulated through a continuous vascular network, the media can diffuse out across the semi-permeable vascular constructs to cell aggregates for their viability, fusion, maturation, and functionality. It is contemplated that an embedded vasculature network can support oxygenation of cell aggregates in larger scale Immunohistochemistry and histology analyses can be performed to understand the fusion, density, and maturation of IPC aggregates. Insulin production after glucose stimulation can be measured at the different incubation stages, and RT-PCR can be performed to determine gene expression. Staining for different cell markers can also be performed.

The ability of IPCs to secrete insulin in a glucose-responsive manner can also be examined First, the miniature organs can be treated with various glucose concentrations of 0, 2.5, 5, 10, 20, and 25 mM, and supernatants can be collected after 5 minutes and 30 minutes, respectively. Insulin levels can be measured by ELISA and quantitated in ng/mg protein. Further, tissues can be subjected to low glucose, high glucose, low glucose+Tolbutamide (a sulfonylurea inhibitor of ATP-dependent potassium channel), and high glucose+Nifedipine (a blocker of L-type calcium channel) treatment, and then insulin can be measured by ELISA. It is contemplated that increased insulin secretion can occur in the presence of low glucose and agonists and inhibition of insulin secretion can occur with high glucose+Nifedipine.

It is further contemplated that the efficacy of printed organs in diabetic mice generated by streptozotocin treatment can also be examined Since the mouse is such a small animal, the printed organs will be quite small, around 1 cm×1 cm×0.4 cm. Thus, it is contemplated that the transplant can occur under the subdermis of the ear, which is a highly vascularized site. It is contemplated that the subdermis of ear can be an ideal site for neonatal cardiac transplants. The serum glucose levels can be measured over 10 months, and the in-vivo glucose tolerance of the organs can be monitored. It is contemplated that the mice can normalize their glucose levels. However, in the early stages post-transplant, it is contemplated that it can be necessary to insert insulin pellets into the mice until the transplanted organs start to produce sufficient amounts of insulin to sustain normoglycemia. It is contemplated that these studies can be immediately relevant to the management of T1D in humans. The mice can be sacrificed, and their pancreatic organs can be stained by H&E to rule out any β-cell recovery and also to study the printed organs by histology and immune fluorescence.

In the following examples, in situ bioprinting of bone tissue using a bio-ink as disclosed herein was performed. Bioprinting of bone tissue directly onto a defect site was studied. Bioprinting-mediated gene therapy was also studied, and it is contemplated that such therapy can be highly transformative and can pioneer the translation of robotics bioprinting technology into operating rooms. These examples focused on the following aspects: 1) processing and characterization of a bio-ink as disclosed herein, and studying its bioprintability; 2) understanding bioprinting-mediated sequential gene delivery; 3) studying in situ multi-arm bioprinting as disclosed herein; and 4) characterization and testing of in situ bioprinted bone tissue.

Example Six

The focus of this example was to study a bio-ink composition as disclosed herein that can enable printing of porous tissue analogues. It is contemplated that a bio-ink composition as disclosed herein can provide several advantages in comparison to existing compositions.

For example, it is contemplated that a thermo-sensitive gel can be integrated into the bio-ink composition, thereby enabling rapid solidification of the tissue analogue when it contacts the living body. This capability can allow for production of porous tissue analogues that have tunable mechanical, biological, anatomical, and gene release kinetics. Additionally, it is contemplated that the bioprinting of BMSCs in collagen type-I and a thermo-sensitive gel will not impair cell viability; rather, it preserves biological content including cells and the pDNA (loaded in microparticles in nanoplexes form) and facilitates cell proliferation and functionality. It is further contemplated that bioprinting as disclosed herein can enable safe and efficient delivery of non-viral vectors to transfect target BMSCs, thereby triggering the BMSCs to differentiate into osteoblasts and to deposit the osteoid matrix that mineralizes to form mature bone tissue.

Processing and Characterization of a Novel Composite Bio-Ink

Disclosed below are exemplary methods of processing and characterizing a composite bio-ink. Collagen type-I can be extracted from Inbred 14 week-old male Fisher (CDF®) white rats (F344/DuCrl, ~250 g). Rats can be sacrificed in a humane manner, and tails can be dissected to harvest collagen as follows. The tails can be soaked in 70% ethanol solution to remove debris. Tendons can be dissected out from the surrounding fascia, collected in phosphate buffered saline (PBS) (1λ), and then extensively washed with cold PBS. The tendons can be sterilized in 70% ethanol solution at 4° C. for 1 h and transferred to a sterile bottle with a stir bar and subsequently suspended in 0.1% acetic acid solution and stirred at 4° C. for 48 h. To separate the solubilized collagen, the resulting solution can be centrifuged at 16,000 rcf, at 4° C. for 90 min. Collagen solution can then be neutralized gently with 1N NaOH solution. The concentration of the final collagen solution can be determined using a Bio-Rad protein assay (Bio-Rad). Using this protocol, an abundant amount of collagen type-I can be obtained. For the thermo-sensitive gel, Pluronic F127 (Sigma-Aldrich) can be produced into 4° C. deionized water at various concentrations between 20-30% (w/w), which fall within a bioprintable range.

The procedure below can be used for preparation of pDNA loaded PLGA microparticles. First, the chemically competent DH5α™ bacterial strain (*Escherichia coli* species) can be transformed with pDNA to amplify the plasmid. The pDNA in the transformed cultures can then be expanded in *E. coli* in Lennox L Broth overnight at 37° C. in an incubator shaker at 300 rpm. pDNA can be extracted using GenElute™ HP endotoxin-free plasmid maxiprep kit and can be analyzed for purity using a NanoDrop 2000 UV-Vis Spectrophotometer (Thermoscientific) by measuring the ratio of absorbance (A260 nm/A280 nm). Microparticles can be prepared by adding 500 ml polyethylenimine (PEI) solution drop wise to 500 ml pDNA (pLUC/pEGFP-N1/pBMP-2) and pDNA (pLUC/pEGFP-N1/pVGEF) solutions containing 50 mg pDNA and mixed by vortexing for 20 s. The mixture can be incubated at room temperature for 30 min to allow complex formation between the positively charged PEI (amine groups) and the negatively charged pDNA (phosphate groups). Microparticles can be made using different N (nitrogen) to P (phosphate) ratios (molar ratio of amine groups of PEI to phosphate groups in pDNA backbone) by varying the PEI amounts and maintaining the amount of pDNA constant (N/P ratios of 5 and 10).

To obtain the bio-ink, a solution of Pluronic F127 and collagen type-I can be prepared and mixed with BMSCs and pDNA encapsulated micro-particles. In the final solution, there can be 10 million cells/ml, 50 mg pDNA/mL (pLUC/pEGFP-N1/pBMP-2), 50 mg pDNA/mL (pLUC/pEGFP-N1/pVGEF), 20% (w/w) Pluronic F127 and 3 mg/mL collagen type-I. Pluronic F127 and collagen concentrations can be varied in the bio-ink, and the rheology of bio-ink solution can be characterized. A Bohlin Rheometer can be used to characterize viscosity, shear modulus, storage modulus (elastic response) and loss modulus (viscous behavior). In addition, mechanical testing including compression modulus and stress relaxation can be performed using a dynamic mechanical analysis instrument (DMA Q800 V7.0 Build 113, TA Instruments, New Castle, DE).

The prepared solution can then be transferred to the bioprinter with a nozzle unit as disclosed herein (see FIGS. 48A-48B). The nozzle-unit can maintain the bio-ink solution at 15° C. in a liquid state using a water-flow assisted cooling system. When the bio-ink is extruded through the nozzle tip, the heating chamber at the nozzle tip can enable instantaneous gelation of the thermo-sensitive gel. This can provide printing of the bio-ink in solid-state as the bio-ink comes out of the nozzle tip at 37° C. The bioprinter can be located in a vertical laminar flow hood (LF Series, Air Science) under sterilized conditions for ex vivo studies.

It is contemplated that the rheology of the bio-ink composition and the gelation characteristics and extrusion behavior through the nozzle tip can be analyzed. It is further contemplated that the effects of chilling and heating temperatures, viscosity of the new bio-ink composition under various temperatures between 15-37° C., dispensing pressure, shear rate, nozzle capillary length and nozzle tip diameter can be evaluated to determine the bioprintability of the bio-ink composition. Temperature along the capillary can be measured with an infrared camera (FLIR), which can be calibrated using a thermocouple. The printed strand diameters can be characterized by varying the process parameters disclosed herein. Upon optimizing parameters by obtaining desired gelation and continuous printing of the bio-ink in solid-state, porous and non-porous scaffolds can be 3D printed onto a Petri dish placed on a 37° C. degree heated-table (mimicking body temperature). Using the systems and methods disclosed herein, the tissue analogue can then be printed into a bone defect with a diameter of about 5 mm and depth of about 2 mm in vitro in both a spiral shape and a traditional zigzag pattern, and the samples can be cultured in vitro. The printed samples can be kept overnight in the incubator at 37° C., thereby permitting the collagen type-I to gel completely. A LIVE/DEAD assay (Invitrogen) over a 1 week incubation period can be used to evaluate cell viability. In addition, it is contemplated that proliferation activities of cells can be studied using a MTT proliferation kit (Invitrogen) over a selected period. It is further contemplated that these proliferation activities can be characterized using a micro-plate reader. After satisfactory performance of the in vitro printed tissue analogues, it is contemplated that in situ printing of the bio-ink directly on live rat models can be performed as disclosed herein.

Results

The bioprintability of an exemplary bio-ink composition, both inside a bone defect and in a petri-dish as a freestanding scaffold, were analyzed. FIGS. 49A-D show the bioprinter with a nozzle unit printing 8-layers of the bio-ink loaded with BMSCs into a bone defect. BMSCs were isolated from rats and then expanded for use in other experiments. Printed BMSCs demonstrated high cell viability of 92±1.7% after bioprinting. Some preliminary freestanding scaffolds of 20-layers were printed using the same bio-ink.

An exemplary composite biomaterial, without the thermosensitive gel, worked well when it was implanted into the bone defect through manual loading. Thus, it is contemplated that the bio-ink composition disclosed herein can generate functional bone tissue formation when printed in situ. It is further contemplated that cell damage can be reduced by optimizing bioprinting parameters. In addition, it is contemplated that the cells within the bio-ink composition can be loaded in high density and can recover themselves in vivo. Methods of printing into bone defects with angled-orientation in vitro were demonstrated.

Bioprinting-Mediated Gene Delivery

In the approach disclosed herein, a thermoreversible gel that contains extracellular matrix components such as collagen and a block copolymer (PF127) can be bioprinted. This gel can be mixed with BMSCs and biodegradable micro-particles that are loaded with pDNA encoding BMP-2 (that triggers bone tissue formation) and pDNA encoding VEGF (that triggers vascularization) in a specific sequence to allow for optimum bone tissue formation. It is contemplated that this approach can provide controlled, localized and sustained release of biomolecules such as pDNA with high efficiency and low toxicity. It is further contemplated that the release profile of pDNA can be controlled and mediated by bioprinting parameters including printed filament diameter, porosity, bio-ink composition and microparticle properties. It is further contemplated that the microparticles of the bio-ink composition can be designed to provide sequential release of nanoplexes of pDNA encoding BMP-2 followed by nanoplexes of pDNA encoding VEGF to enable the current sequence of delivery for maximum bone regeneration. It is still further contemplated that the bio-ink composition can comprise biodegradable microparticles to provide sequential and sustained release of different pDNAs encoding different growth factors enabled by in situ bioprinting.

Characterization of Microparticles and Mediation of their Release Profile Via Bioprinting Two different microparticles loaded with PEI-pDNA nanoplexes can be prepared using a double emulsion solvent evaporation method as described herein. One microparticle type can encode BMP-2 and the other one can encode VEGF. Then, the microparticles can be characterized by measuring the size, zetapotential, and surface morphology of the microparticles and loading and release profiles of pDNA from the microparticles. The effect of bioprinting parameters on the release profile of pDNA can be explored. Release studies of bioprinted tissue constructs can be performed using different parameters including filament diameter, porosity, bio-ink composition, microparticle properties, and loading percentages. This can help to mediate the release profile of pDNA using bioprinting.

Understanding Sequential Delivery and Transfection Efficiency of Microparticles

The ability of the pDNA loaded microparticles to transfect BMSCs with pDNA BMP2 and pDNA VEGF, respectively, can be characterized using ELISA kits. BMSC proliferation and differentiation in the bio-ink can be characterized using histological analysis and confocal microscopy imaging. The optimal time frame and sequence of delivery of the plasmids for minimal toxicity and maximal proliferation and differentiation of the BMSCs can be determined. It is contemplated that the levels of mRNA can generally be correlated to protein expression and be more sensitive than protein measurements for short-term observations. Alkaline phosphatase (ALP), core binding factor alpha (Cbfa)-1, and osteocalcin (OCN) can be measured by RT-PCR and used to indicate osteogenic differentiation of BMSCs.

Preliminary Results

The data disclosed herein show that biodegradable microparticles that are loaded with pDNA-PEI nanoplexes and provide controlled release of the nanoplexes can be produced. The data demonstrate that the biodegradable particles loaded with PEI-pDNA complexes give an initial burst release of the complexes that accounts for up to 30-40% of the total load before providing more sustained release of the remaining complexes over a longer period of time. The exact release degree of the burst and subsequent prolong release was dependent on the excipients used to load the pDNA, the loading methodology and the formulation parameters used during particle preparation. For example, use of larger molecular weight PLGAs resulted in a proportional increase in the duration of the sustained release of the pDNA (see FIG. 50A).

The data disclosed herein demonstrated the functionality of pDNA in transfecting BMSCs. The data demonstrated the transfection of BMSCs after 4 h or 24 h treatment of PEI microparticles (FIGS. 50B-50C). Confocal images showed the characteristic green fluorescence in the transfected cells at both 4 h and 24 h due to expression of the gene and formation of the EGFP-N1 protein. In these fixed cells, phalloidin permeated the plasma membrane to stain the cytoplasmic F-actin in red. The cell nuclei were stained blue by DAPI. The cells in the control groups (untreated cells, cells treated with uncomplexed pEGFP-N1 and PEI-treated cells) did not show any green fluorescence. Quantitative and qualitative data confirmed the capability of the PEI-pDNA complexes to efficiently transfect BMSCs.

It is contemplated that the antacid-based salt $MgCO_3$ can be incorporated into the bio-ink composition to prevent a build-up of acidic oligomers, thereby improving the biological activity of the pDNA. This salt can be tested at a range of concentrations from 1-5%.

In-Situ Multi-Arm Bioprinting

Disclosed herein is an in situ bioprinting approach, where a new composite bio-ink composition is printed within multiple defect sites directly using the bioprinter disclosed herein (the MABP). This approach can enable fabrication of bone tissue analogues with controlled porosity, biological loading, and mechanical and anatomical properties for enhanced tissues formation in a short-period of time. The in situ, extrusion-based bioprinting approach can enable fabrication of porous tissue analogues with tunable biological, mechanical and anatomical properties. This approach can also support tissue growth through the porous construct, which can be particularly important for endothelial cells to migrate and create capillarization inside newly generated bone tissue. The delivery of high cell-density tissue analogues as disclosed herein can avoid the need for a labor intensive scaffold preparation process. The outlined approach can facilitate direct bioprinting of the bone tissue analogues as opposed to the traditional costly and labor intensive method of printing constructs, freeze-drying them, and loading cells followed by implantation.

It is contemplated that the rapid delivery of tissue analogues as disclosed herein can be accomplished without deteriorating the DNA. One significant challenge of conventional prefabricated scaffolds is the need to know the dimensions of the defect prior to any surgical procedure because the scaffold has to be pre-formed and fabricated prior to implantation. It is contemplated that in situ bioprinting as disclosed herein can eliminate the prior need for in vitro scaffold fabrication and can enable delivery of a pDNA loaded scaffold at the site of surgery without the need to know the specific dimensions of the defect.

The MABP disclosed herein can enable deposition of multiple bone tissue analogues in tandem under limited anesthesia time, thereby expediting the tissue printing process. In addition, the MABP disclosed herein can provide low for testing of different constructs with different biological and anatomical structures on the same animal model. Multiple animal samples can be placed under the bioprinter to further increase the efficiency.

Studying In Situ Bioprinting and Performing Pre and Post Surgeries

Inbred 14 week-old male Fisher) (CDF® white rats (F344/DuCrl, ~250 g) can be obtained from Charles River Laboratories International, Inc. (Wilmington, MA) and housed and cared for in animal facilities. The animals can be anaesthetized by intra-peritoneal injection of ketamine (80 µg/kg)-xylazine (8 µg/kg) mixture. Next, a sagittal incision, approximately 1.5-2 cm, can be made on the scalp of each rat, and the calvaria can be exposed by blunt dissection. Two 5 mm diameter×2 mm depth critical-sized defects can be generated using a round carbide bur on the parietal bone, on both sides of the sagittal suture. The dura mater (the membrane surrounding the brain) can remain intact during the surgery. Dura mater plays an important role in bone healing, and it is the source of osteogenic cells and the osteoinductive factors during calvarial wound healing.

Next, the rat can be fixed on the bioprinter table using sutures to guarantee no movement of the head under anesthesia although the bioprinter table does not move at all. The bioprinter pipettes can be positioned at the center of the defects, which are considered as the reference points for the motion of the bioprinter arms. Using multiple bioprinter arms, porous and non-porous tissue analogues can be printed at the same time. For porous or non-porous patterns, the bio-ink can be printed in zigzag and spiral patterns, respectively. It is contemplated that porous tissue analogues can be used for bone ingrowth and vascularization, while nonporous tissue analogues can be used as control samples. While defects on the rat calvaria are not horizontally oriented and their position with respect to each other changes from rat to rat, two rotational joints controlled by servo motor units can be added on the printer arms as disclosed herein to create rotation capabilities similar to wrists on human arms. With the help of the two rotational joints, the bioprinter unit on the robot arm can be collinear to the normal of the defect and enable ideal printing of the bone tissue.

The effect of porosity can also be tested. Tissue analogues with different pore sizes ranging from about 250 to about 350 µm (reasonable pore sizes for bone tissue growth) and various loading rates of the bio-ink composition can be tested. After bioprinting, the incision can be closed in layers using sterile silk sutures. Buprenorphine (0.15 mg, intramuscular), as an analgesic, can be administered to each rat thereafter, and the animals can be carefully monitored during post-operative recovery.

Results

The Multi-Arm BioPrinter as disclosed herein was used. The bioprinter can be controlled by a computer system and can run with pneumatic or mechanical controllers (based on requirements) to dispense the bio-ink. The bioprinter can be a sensor-based system, and advanced toolpath algorithms can be configured to prevent contact between the arms of the bioprinter. The bioprinter was positioned in a surgery room, and a bio-ink composition as disclosed herein was printed on two defects of the rat calvaria that were spaced by approximately 2 cm.

This calvarial defect model involved orthotopic bone sites that make the results more physiologically relevant than those from bone induction in muscle pockets and subcutaneous sites. The 5 mm defect size is a standard defect size used in the literature for regeneration of bone in calvarial critical sized bone defects. A toolpath plan was formulated to deposit the bio-ink composition inside the defects on in vitro bone models before performing the in situ printing. The nozzle units on both arms were equipped with a glass-pipette in different configurations, and the center of each defect was introduced to the bioprinter as the reference point for initializing motions of robot arms. The bioprinter was operable on a rat model, enabling in tandem printing of multiple tissue analogues. The demonstrated rat model disclosed herein was euthanized, but an animal protocol that will allow in situ bioprinting on live rat models has been developed.

Bioprintability of multiple tissue constructs in tandem was tested using the MABP, showing success with bioprinting constructs into the defects. In exemplary procedures, naturally forming defects can have intricately shaped (e.g., concave) cavities, and the surgeon can reshape these defects into convex or other forms to allow for proper bioprinting. Alternatively, when the bioprinter is operatively coupled to a scanner system as disclosed herein, the scanner system can determine the geometry of these defects and import data to process planning software that generates a toolpath to be used during the in situ bioprinting.

Characterization and Testing of In Situ Printed Tissues

Performing Micro-Computed Tomography (µCT)

Upon completion of the surgery, the animals can be transferred to an animal facility, and the facility can take care of all the animals, feed them and ensure that the animals are monitored after surgical procedures. After 4 weeks, all the animals can be euthanized and the bony segments containing the regions of interest can be cut from the calvarial bone and fixed in 10% neutral buffered formalin. Newly-generated bone can be evaluated for its volume and connectivity using 3D microfocus x-ray microcomputed tomography imaging (µCT40, Scanco Medical AG). First, the specimens can be scanned in 70% ethanol at 55 kVp and 145 mA with a voxel size of 10 mm and an integration time of 300 ms. Using the manufacturer's software, a constant 3.5 mm diameter circular region of interest can be centered at the defect center and span a total of 50 constructed slices, such that a total cylindrical volume of interest of ~3.8 mm$^3$ oriented perpendicular to the outer table of the calvarium can be analyzed. Bone volume per total volume and connectivity density in the bone defect can be obtained.

Studying Tissue Histology

A histochemistry study for the bone samples can be performed. First, the samples can be decalcified according to the procedure (Surgipath, Decalcifier II) until the end point test returns negative for the presence of calcium. Then, the samples can be fixed in paraffin and sectioned in the sagittal plane with 5 mm thicknesses in the central portion of the defect. Then, Harris hematoxylin and eosin (H & E) staining can be performed according to standard protocols, images can be taken using Olympus Stereoscope SZX12 and an Olympus BX61 microscope. The presence of collagen, new bone formation, and cells can be observed in order to evaluate bone regeneration after 4 weeks in situ bioprinting as described herein. Blood vessels present in the regenerated bone can be analyzed for their total number using histological analysis. Blood vessels can be identified, after immunostaining for von Willebrand factor, at ×200 magnification. Histology images can be checked periodically during the first month in order to observe tissue growth and bio-ink degradation.

Results

In order to demonstrate the proof-of-concept, the study described below showed that manual loading and implantation of the bio-ink material (as a bulk scaffold) resulted in new bone formation. Three groups were tested, including (1) an empty defect without any treatment, (2) cell and pDNA-free bulk collagen scaffold and (3) complex bulk collagen scaffolds loaded with BMSCs and pDNA encoding PDGF. The empty defect images showed that the gap between the healthy native bone edges was unfilled, while the empty scaffold group showed only loose, soft tissue formation with a thin rim of new bone forming at the edges of the defect (see FIGS. 52A1-52A2). For the complex scaffold group, complete bridging of the defect by the mature, mineralized bone tissue was observed, as indicated by the arrows (see FIG. 52A3). μCT scans supported the histology images as well, where generated bone volume/total bone volume for the complex scaffold group in FIG. 52B3 was 44-fold and 14-fold greater than the empty defect (FIG. 52B1) and empty scaffold (FIG. 52B2), respectively. The connectivity density of the regenerated bone was 36-fold and 52-fold greater for the complex-loaded scaffold group than for the empty scaffold group and empty defect control group, respectively. In one aspect, the scaffold was released from the degrading matrix, which then transfected the surrounding cells. It is contemplated that the cells can migrate into the porous matrix containing the complexes followed by their transfection by the complexes. PDGF signaling was also involved in cell migration, tissue remodeling and cellular differentiation of pre-osteoblasts into osteoblasts that initiate bone formation by secreting the osteoid matrix that mineralized to form mature bone tissue. The chemotactic action of PDGF further augmented these processes. Ultimately, new bone material was laid down by the osteogenic cells by communication through cytokine PDGF signaling.

If the printed tissue constructs do not facilitate new bone generation and vascularization, it is contemplated that endothelial cells and/or loading hypoxia inducing factors can also be printed onto the defect. If the bone growth turns out to be unsatisfactory, it is contemplated that the bio-ink capabilities can be improved by increasing BMSC concentration, regulating their differentiation into osteoblasts better with the controlled release of cytokines or by including hyaluronic acid, which is a part of native bone extra-cellular matrix. If the mechanical properties of the bio-ink are unsatisfactory in vivo, then it is contemplated that the mechanical properties can be enhanced by reinforcing nano-spun hard polymers that are osteoconductive, and cell growth can be further promoted by incorporating agents such as hydroxyapatite into the bio-ink composition. An electrospinning facility can be used to make electrospun of nanofibers of osteoconductive biopolymers, chop them into short fibers, load them into the bio-ink composition and bioprint them as reinforcing material in the tissue analogue.

Example Seven

The following example discloses a method for bioprinting 3D large-scale tissues with a perfusable vascular system in vitro to preserve cell viability and tissue maturation. A hybrid bioprinting system to fabricate scale-up tissues and organ models and its application for in vitro tissue engineering and its potential for therapeutic purposes are disclosed herein.

Tissue engineering has shifted the paradigm of traditional medicine from therapeutically treating disease to replacing diseased tissues and organ parts by regenerative medicine approaches. This remarkable leap in medical science has drawn great attention for decades and has brought tremendous opportunities to not only disease treatment, but also drug testing, disease modeling, and other physiological and pathological research.

Traditional tissue engineering has had great success in artificial tissue or organ fabrication by advancement of stem cell technology, materials science, and biomimetic system design. Ever since Robert Langer grew an ear on a mouse back by seeding cells onto a biopolymer scaffold, this technology has enabled bioengineered tissue like cartilage, bone, skin, etc. to be grown in laboratories around the world. These successes were largely limited to tissues with avascular nature, which have lower oxygen consuming rates. However, a long-term obstacle for tissue engineering has been generation of vascularized tissue with blood perfusion capability, which is critical for organogenesis, especially in vivo. Traditional scaffolding methods often fail to provide an efficient media (oxygen, growth factor, water, etc.) transportation system for generation of thick tissues or organs. Several researchers have attempted to control scaffold architecture to mediate media transport capabilities, but the majority have failed in organ or tissue formation due to the lack of an integrated vascular system. One possible solution to improve perfusion through thick scaffolds is embedded microfluidic networks; however, most of the microfluidic fabrication methods are multi-step processes that do not allow direct fabrication of a vessel-like structure for tissue integration.

Organ printing can be defined as layer-by-layer additive robotic fabrication of three-dimensional (3D) functional living tissues or organs. It has been envisioned to push tissue engineering into a new era with the capability to do robotic large-scale living organ fabrication. It was inspired by the natural embryonic developmental process and used cell aggregates in a micro-spherical shape as building blocks with a rapid-prototyping platform. These "mini-tissues" have certain measurable and controllable properties and can be assembled into macro-tissues through the tissue fusion process or directed tissue self-assembly. With this method, scientists used multicellular spheroids made from smooth muscle cells and fibroblasts to successfully generate vascular constructs. It was predicted that this robotic-assisted biomimetic process would be dramatically beneficial for tissue engineering in the near future. In order to integrate a vasculature network within the tissue printing process, the vasculature network can be practically printed without requiring any support material; it also can be printed in complex geometries on a larger scale to feed the oxygenation need of larger tissues.

Cell aggregates possess accelerated fusion and folding capabilities upon contacting each other that is driven by a natural biological process. High cell density within aggregates can be easily obtained by the fusion process, in which traditional scaffolding and cell-laden hydrogel usually depend on cell proliferation afterward. Moreover, cell viability is enhanced due to the large cell-seeding density and reduced mechanical stress experienced compared with direct cell manipulation. Micro-scale organoids, in which heterocellular aggregates possess organ-like functions, have been generated in vitro for pancreatic, liver, and cartilage tissues. Although these techniques seem to be impressive for tissue engineering, especially as bioink for organ printing, their labor-intensive fabrication in limited scale makes their applicability for large-scale tissue/organ fabrication difficult. Moreover, printing them sequentially by ensuring contact between each adjacent spheroid is another hurdle, given the extremely critical handling and sterilization conditions. Without ensuring seamless contact in micro-scale resolution, spheroids can hardly fuse with each other, easily leaving gaps and openings in the tissue. Besides, hydrogels can be required as a transferring medium to deposit spheroids; this cannot achieve complete scaffold-free fabrication and can face side effects of biomaterial degradation. In addition, technologies should be developed to prevent spheroid fusion before printing; otherwise, nozzle clogging is inevitable. New technologies need to be developed to enable scalable, standardized spheroid fabrication to allow large-scale automated tissue fabrication as well as minimize cell damage both transcriptionally and functionally. In terms of tissue maturation, the cellular fusion process needs to be well characterized to understand cell interactions under various mechanical and biological cues. Cellular reaction upon fusion also needs to be addressed to elaborate on how extracellular matrix (ECM) is secreted by cells, and how to control ECM production as well as remodeling to ensure the mechanical integrity and strength of the regenerated tissues or organs. The most challenging issue currently faced in organ printing technology is the generation of a "built-in" vascular system within 3D thick tissues or organs with perfusion capability. An integrated bioreactor is also in demand upon establishing a perfusable vascular network for continuously supplying oxygen and nutrients sufficient for cell growth and tissue maturation.

This example discloses a large-scale vascularized tissue printing process via a hybrid fabrication approach, which allows a vascular system and tissue to be printed in tandem. Disclosed herein is a biomimetic design approach to develop perfusable tissues using a biologically driven fusion, folding, and maturation process. Large-scale hybrid tissues can be fabricated by the integration of a vasculature network in multi-scale with tissue-specific cell aggregate strands, which are considered tissue strands, followed by rapid fusion, remodeling and maturation of the perfusable tissues. Geometric modeling for hybrid tissue construct fabrication is performed, and future directions for tissue printing are also disclosed.

Hybrid Fabrication of 3D Perfusable Tissues

In order to fabricate viable, functional tissues and organ counterparts in 3D, the integration of a vascular network is the foremost component that needs to be taken care of Without vascularization, engineered 3D thick tissues or organs cannot get enough nutrients, gas exchange, and waste removal, all of which are needed for maturation during perfusion. This results in low cell viability and malfunction of artificial tissues. Systems must be developed to transport nutrients, growth factors, and oxygen to cells while extracting metabolic waste products such as lactic acid, carbon dioxide, and hydrogen ions so the cells can grow and fuse together, forming the tissues. Cells in a large 3D tissue construct cannot maintain their metabolic functions without vascularization, which is traditionally provided by blood vessels. A vascular network is indeed a very complex hierarchy, where large-scale arteries and veins are connected by a complex micro-scale capillary system and where media exchange takes places between the blood and the tissue. Every single cell is supplied by capillaries for its normal metabolism, in order to stay viable and be able to proliferate for maintaining tissue integrity and function. Bioprinting technology, on the other hand, currently does not allow multi-scale tissue fabrication, where bifurcated vessels are required to be manufactured with capillaries to mimic natural vascular anatomy. Although several researchers have investigated developing vascular trees using computer models, only a few attempts have been made toward fabricating bifurcated or branched channels. Successful maturation towards functional mechanically integrated bifurcated blood vessel network is still a challenge. Thus, disclosed herein is a method of fabricating a vascular network within the hybrid tissue, which can be performed in two steps: (1) bioprinting of a macro-scale vasculature network in tandem with vascularized tissue strands, and (2) biologically driven tissue fusion and assembly with envisioned capillary sprouting from macro-vasculature to the tissue. The former presents more of a bioprinting approach than the latter, which is mainly biologically mediated.

a. Design for Hybrid Bioprinting Approach

Disclosed herein is a method of fabricating perfusable tissues in 3D using a hybrid bioprinting approach. In an aspect, the method combines vasculature printing and tissue-specific cell aggregate strand printing in a single platform. FIG. 46 illustrates the concept for a scale-up tissue printing, where two units of the bioprinter can run in tandem, printing two distinct materials. Strands are made of purely cells and their ECM, and they can be used as building blocks to construct the scale-up organ due to their quick fusion, folding and maturation capabilities. A printable vascular network in a continuous single luminal form in macro-scale can be more practical to be integrated with additive manufacturing-based bioprinting. In this way, semipermeable vasculature can be printed continuously with a predetermined 0°/90° lay-down pattern similar to the traditional additive manufacturing techniques. In order to eliminate blockage of vasculatures, arc fitting is used at U-turns between two vasculatures during zigzag printing. Upon fabrication, oxygenized media can be perfused through the macro-vascular network and diffused out to the tissue strands to keep them viable. In order to print the scale-up hybrid model, the Multi-Arm Bioprinter (MABP) can be used. The MABP (see FIG. 1B) can facilitate synchronization and coordination between multiple arms through a sensor-based system that enables crosstalk between multiple arms so that two arms can communicate in an intelligent way, ensuring collision-free motion. One arm can be equipped with a coaxial nozzle assembly for printing the vascular network, and the other arm can be equipped with a custom unit to print tissue-specific cell aggregate strands. The nozzle configuration can enable close motion of printer units. The introduced MABP can reduce the fabrication time, which is crucial for scale-up technologies, and can enable continuous deposition, which can yield more consistent results since material deposition during starts and stops is not as uniform as it is during the rest of the process. Continuous deposition can also alleviate nozzle clogging since it generally occurs when the material is in static conditions. Most importantly, nozzle motions can have more flexibility in z-axis, which is critical while printing vasculature with variational dimensions that necessitate instantaneous changes between the nozzle tip and the printing stage to eliminate blockage of the lumen, which is quite difficult to achieve with a traditional single-arm bioprinter.

Direct Bioprinting of Macro-Vasculature Network

Figure 53:
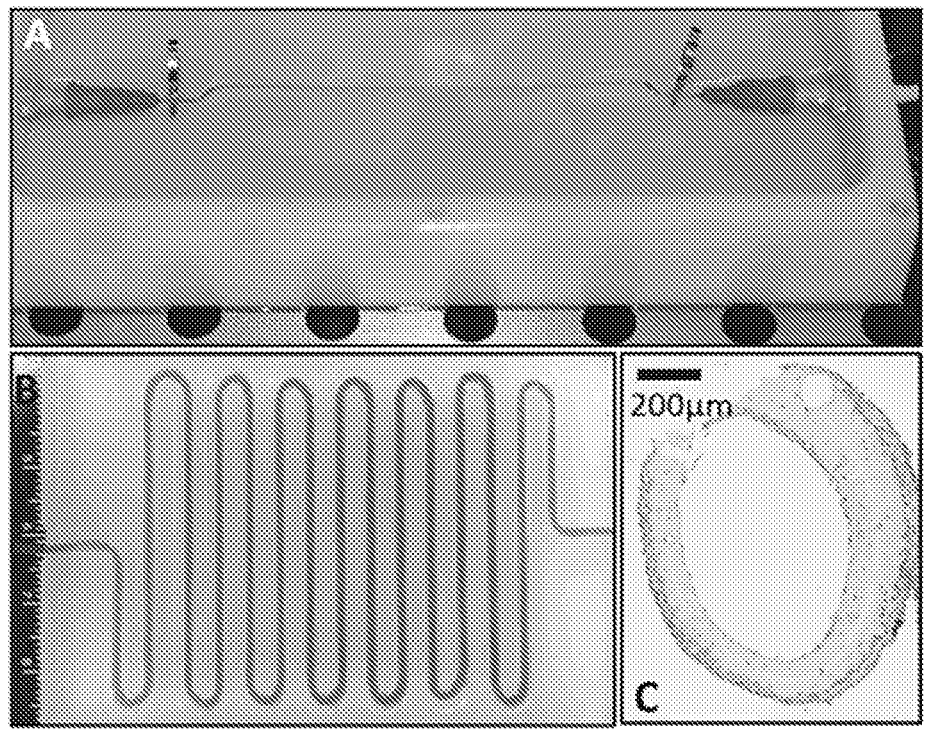

The vasculature network in hybrid bioprinting can be directly printed using a pressure-assisted coaxial nozzle unit demonstrated in FIG. 6C. Biomaterials such as sodium alginate, collagen and chitosan or their composites encapsulating different cell types existing in natural blood vessels such as smooth muscle, fibroblasts and endothelial cells can be printed without any support materials that make them practical for further applications. With continuous flow chemical crosslinker through the core section of the coaxial nozzle, vasculatures can be printed directly. Fabrication of vasculature with controllable dimensions in the micro- and sub-millimeter-scale is quite feasible as disclosed herein. FIG. 53 shows examples of fabricated vasculatures using 4% (w/v) sodium alginate crosslinked with 4% calcium chloride ($CaCl_2$) solution. The sodium alginate dispensing pressure was set at 21 kPa, and the $CaCl_2$ dispensing rate was set at 16 ml/min. The printing speed of the robot arm was set at 14 mm/s $2^{nd}$ passage of human umbilical vein smooth muscle cells (HUVSMCs) were encapsulated with a density of $10 \times 10^6$ cells/ml, where further culture was provided under pulsatile flow mimicking a hemodynamically equivalent environment. Geometrically well-defined vasculatures can be manufactured at any geometry, length and orientation, without occlusion or rupture that might result in leakage or burst (see FIG. 54B). In addition, they are highly permeable, which enables diffusion of media in the radial direction upon perfusion with a pumping system, which is similar to natural blood vessels. An 8.2±0.3 µL/min filtration rate was achieved within three hours of perfusion. Although they have acceptable mechanical properties to sustain both tensile and compressive forces with reasonable matrix deposition in a short period of time (see FIG. 53C), further enhancement can be helpful to improve their strength through exogenous collagen and elastin fibers generated by methods such as electrospinning Vasculatures, in general, are able to support printed tissue strands, which usually do not have sufficient mechanical strength and integrity alone to build 3D tissue. Vasculatures can be printed into a highly organized 3D framework for tissue strands to attach on, providing an initial microenvironment in which they can develop and ultimately fuse to each other. In addition, previous studies have demonstrated the capability of the bioprinting system to fabricate vasculature with controllable dimensions in the micro- and sub-millimeter-scale by altering process parameters, which gives substantial flexibility to the process. In other words, different-sized vasculatures can be printed to fit specific functional needs.

Bioprinting and Biofabrication of Vascularized Tissue Strands

In general, tissue strands can be generated by mono-culturing or co-culturing cells including endothelial cells for capillary formation using microfluidics-based or molding-based fabrication approaches. Aggregation of cells can take one to two weeks, depending on the applied fabrication technique as well as the type and size of cells used. Harvested cells can be mixed and aggregated at a predetermined optimal ratio for in vitro angiogenesis. Tissue strands can be fabricated in any length; however, the diameter can be limited to the applied aggregation technique as well as diffusion limit of oxygen (see FIG. 54A). The greater the diameter is, the lower the cell viably in the inner sections of the tissue strands, although neovascularization can also be achieved. The tissue strands can then be loaded into the bioprinter unit using custom tools and directly printed with the vasculature network layer by layer predetermined by the toolpath plan generated by a computer-aided design (CAD) model.

Aggregated tissue strands present high viability and rapid fusion capabilities. $2 \times 10^8$ fibroblast cells were used and the average cell viability on day 1 post fabrication was 75±0.5%, which gradually increased to 77±0.5%, and finally reached to 87±3% on day 7. When placed or printed next to each other, tissue strands underwent quick and seamless fusion, forming a complete tissue patch in a week (see FIGS. 54B-C). FIG. 54D shows F-actin expression demonstrating that fibroblasts in tissue strands are metabolically active as well. Other studies have also shown great ability of angiogenesis within tissue spheroids made of endothelial cells and hepatocytes or pancreatic cells. A similar phenomenon can be envisioned for tissue strands as well if appropriate culture conditions are followed. This scaffold-free approach provides a practical approach in printing larger constructs. It enables printing tissue aggregates continuously, which prevents gaps and breakage in the printed construct.

i. Geometric Modeling of Hybrid Constructs

The proposed design is mathematically represented in order to fulfill fabrication and post-fabrication requirements, which can be used to determine design variables for bioprinting. As can be seen in FIG. 55, arc fitting can be used at U-turns between two consecutive vasculatures during zigzag printing, which eliminates occlusion of vasculatures. The first and the last vasculatures in each layer can be printed longer than the tissue strands and other vasculatures in order to connect the construct to the perfusion system easily. During hybrid bioprinting, it is not practical if the tissue strand diameter is relatively smaller than that of vasculatures, while tissue strands fuse to each other during in vitro culture and contracts in some extent. Using smaller diameter tissue strands thus brings several issues such as longer fabrication time, less structural integrity and formation of gaps in the tissue when folding takes place. Tissue strands cannot be greater than the vasculature in diameter as well; otherwise, clearance can be generated between the tissue and vasculature, which can result in media accumulation in the clearance during perfusion. Thus, the diameter of the tissue strand can be the same as that of the vasculature, which can be adjusted before or during bioprinting process. For a square layer as shown in FIG. 55, the diameter of the vasculature and tissue strands are equal and denoted by D (µm). In addition to relative size of diameters, the number of tissue strands between two contiguous vasculatures is also important due to media diffusion requirement. Concentrations of solutes such as nutrients and oxygen around vasculatures can change gradually. In order to provide an efficient media transportation system, the variation of solute concentration gradients around vasculatures can be minimized, which can be achieved by designing distance between consecutive vasculatures. The distance between two contiguous vasculatures at which the nutrients diffuse to, based on cellular consumption of nutrients, is called the Krogh length $$\lambda_K \sim \sqrt{\frac{D_s c_O}{R_C}} \; (\mu m),$$

where $D_s$ (μm²/s), $R_C$ (mol/ls) and $c_o$ are diffusion constant of the concerning solute in the tissue strands, consumption rate of the solute by cells, and concentration of the solute in the vasculature, respectively. The number of tissue strands between two contiguous vasculatures (n) can be thus calculated as:

$$n \le \frac{\lambda_K}{D} = \frac{1}{D}\sqrt{\frac{D_s c_O}{R_C}} \tag{1}$$

where, n has to be an integer. In order to maximize the consumption of the concerning solute, n can be the largest integer equal to or smaller than the right side of Equation (1). In addition, the curvature of U-turn can be easily calculated based on the number of tissue strands and their diameter. The fabrication of tissue strand is highly expensive and time consuming. It can take a month or more to expand significantly high number of cells to be used in tissue strand fabrication. On the other hand, preparation of materials for vasculature printing is negligibly cheap. In order to make the tissue printing process practical and make the best use of the material, it is essential to calculate the volume of cell aggregates before printing them. If the number of straight vasculatures is $n_c$, the width W (μm) of the square construct can be calculated as $W=n_cD+2D+(n_c-1)nD$, which can be reorganized as:

$$W = 3D + (n_c-1)(n+1)D \tag{2}$$

The total volume of cell aggregates $V_{total}$ (μm³) needed for tissue strand printing for each layer can be then calculated as follows:

$$V_{total} = \begin{cases} \frac{3\pi D^3}{2} + \frac{\pi D^3(n_c-1)}{8}\left[4+9n+n(n+1)(2n_c-3)+\sqrt{n^2-1}+2x_n\sum_{i=1}^{\frac{n-1}{2}}\sqrt{n^2-4i(i+1)-1}\right], \\ \text{for } n = 2n+1 \\ \frac{3\pi D^3}{2} + \frac{\pi D^3(n_c-1)}{8}\left[4+9n+n(n+1)(2n_c-3)+2\sum_{i=1}^{\frac{n}{2}}\sqrt{n^2-4(i^2-1)-1}\right], \\ \text{for } n = 2m \end{cases} \tag{3}$$

subject to:

$m \in \square^-$, $x_n = \begin{cases} 0 & n = 1 \\ 1 & n \ne 1 \end{cases}$

With mathematical formulations presented herein, the operator can eliminate the risk of tissue death due to lack of oxygen or vital nutrients, and make the tissue printing process practical and maximize the utilization of cell aggregates, which is one of the challenges in this process.

Envisioned Biologically-Driven Capillary Sprouting: Bridging Capillaries and Main Vasculatures Like all other tissue engineering techniques, generation of a functional tissue or organ with an internal vascular network is an ultimate goal. To successfully create vascularization in multi-scale within the introduced hybrid tissue concept, a fabricated hybrid construct can be placed in a custom-made perfusion chamber, which can then be connected to a circulating tubing system to facilitate continuous supply of the cell culture media in vitro (see FIG. 56). The perfusion chamber can serve as a bioreactor to not only ensure sufficient support for hybrid tissue, but also to provide an environment similar to in vivo condition. The connecting tubing can be precisely inserted into the inlet and outlet of vasculatures using a micro-positioning system. Upon positioning the whole perfusion system into an incubator, oxygenized cell culture media can be delivered through the system using multi-channel peristaltic pumps. The media in the reservoir can be replenished at a regular base after culturing. Growth factors like fibroblast growth factor (FGF) and epidermal growth factor (EGF), which are essential for angiogenesis, can be supplemented within the circulating culture media. The printed tissue strands can fuse to each other in 3D, creating a larger tissue enclosing the vasculature during in vitro incubation in a customized bioreactor with continuous media perfusion. Upon the formation of a 3D tissue construct, the above-mentioned angiogenesis growth factors can be applied for further in vitro culturing to drive the natural process of vascularization between the main vasculature and pre-vascularized tissue strands, creating sprouting. Ultimately, a thick 3D tissue construct can be fabricated with a biomimetic vasculature system and be readily available for transplantation, disease modeling or drug screening. This is a major breakthrough toward fabrication of larger scale organs.

Studies have been done to construct perfusable blood vessel connecting capillaries cardiac tissue by a 3D cell sheet fabrication technology, in which endothelial cells within cardiac cells sheet sprouted and connected to the main blood vessel upon perfusion of growth factor-rich culture media. Other studies have also shown that a pre-vascularized hepatic bud, when transplanted in vivo, can successfully anastomose to the main blood vessel and survive for a long period of time, carrying out its function. All of these highlights offer foreseeable potential for the hybrid bioprinting technique to have a similar nature-driven process upon perfusion. When the media is perfused through a continuous vascular network within the hybrid tissue, the biological signals, as well as the media gradient along the perfusion direction within the media, can guide endothelial cell reorganization, migration, carry out of angiogenesis within the tissue strands, and enable sprouting towards the media supply direction (FIG. 57).

Newly generated capillaries within tissue strands can create bridging with main vasculatures, so that media supplied through these newly formed capillaries can guarantee the survival of tissue strands for longer period of time.

Prolonged media circulation within the newly generated vessel system can also accelerate the tissue maturation process by supplying sufficient growth factors, which drive tissue-specific cells to secrete ECM and further facilitate tissue strands fusion from all directions in 3D, producing a functional vascularized perfusable tissue. Later, the matured tissue can be used for drug testing by directly delivering different drugs via the perfusing system to evaluate tissue response. Moreover, bioprinted tissue can be implanted in vivo by anastomosing the main vasculature to the host to replace damaged or diseased tissues or organs.

Proof-of-Concept Study

In this section, a proof of concept of the tissue self-assembly around a 1.5 cm long smooth muscle vasculature is disclosed. The vasculature was fabricated using the parameters disclosed herein, enabling media perfusion without any occlusion. It was longer than the cell aggregate strands (5 mm long) so it hooked up to the perfusion chamber. The tissue construct was maintained in static culture first upon fabrication to keep it mechanically and structurally integrated until sufficient maturation was obtained. After 1 day in culture, fibroblast cell aggregate strands started fusing to each other. Later, perfect maturation was obtained in seven days. In general, the duration can depend on the cell type and the culture conditions (i.e., static, perfusion, etc.) used. It was observed that the tissue attached to the vasculature completely (see FIGS. 58A-B). The cross-sectional view in FIG. 58C demonstrates that tissue strands enclosed the vasculature and adhered to the smooth muscle matrix tightly. Therefore, tissue strands can be used for the demonstrated large-scale hybrid tissue bioprinting concept.

This example demonstrates an approach in fabrication of living tissues and organs on a larger scale using 3D printing technology, where scale-up tissue printing can be performed in two major steps: (i) printing a continuous vasculature network in tandem with the rest of the multicellular vascularized tissue strands and (ii) biological maturation where tissue fusion and maturation occurs along with envisioned biologically driven capillary sprouting from the main vasculature steam. The proof-of-concept of tissue self-assembly around a smaller-scale macro-vasculature was demonstrated. Although the MABP can be used in developing larger-scale tissues with the proposed design strategy along with an associated toolpath plan for both arms, further research in both bioprinting technology and developmental biology needs to be conducted to biomimetically develop tissues for transplant and in vitro testing for various tissue types.

Example Eight

The ability to create three dimensional (3D) thick tissues is still a major tissue engineering challenge. It requires the development of a suitable vascular supply for an efficient media exchange. An integrated vasculature network is particularly needed when building thick functional tissues and/or organs with high metabolic activities, such as the heart, liver and pancreas. In this example, human umbilical vein smooth muscle cells (HUVSMCs) were encapsulated in sodium alginate and printed in the form of vasculature conduits using a coaxial deposition system. Detailed investigations were performed to understand the dehydration, swelling and degradation characteristics of printed conduits. In addition, because perfusional, permeable and mechanical properties are unique characteristics of natural blood vessels, for printed conduits these properties were also explored herein. The results show that cells encapsulated in conduits had good proliferation activities and that their viability increased during prolonged in vitro culture. Deposition of smooth muscle matrix and collagen was observed around the peripheral and luminal surface in long-term cultured cellular vascular conduit through histology studies.

There has been a great success in engineering artificial organs such as skin, cartilage and bladders while they have simple morphology and architecture, low cell oxygen consumption rates, and no requirements for blood vessels. However, difficulties have been experienced with engineering thick, complex tissues or organs, such as heart, liver or kidney, primarily due to the lack of an efficient media exchange system.

Fabrication of vascular tissues, with their complex cross-sectional structure, unique mechanical properties and hierarchical organization, presents a great challenge to tissue engineering. In the past three decades, several methodologies have been developed for the fabrication of vasculature conduits, including decellularized tissues, cell sheet conduits, biodegradable synthetic polymer-based constructs and natural biomaterial-based blood vessel constructs. Decellularized tissues offer several advantages, including their composition purely consisting of decellularized matrix (DCM) as well as their appealing mechanical properties. However, significant shrinkage is observed during decellularization due to rigorous decellularization process effecting the chemical composition, biological activity, and biomechanical properties of the remaining ECM. The cell sheet approach has appealing mechanical properties but poor structural organization. The synthetic polymer-based approach is the most studied approach. Although great success has been made in the fabrication of large-diameter vascular constructs, the synthetic-based method encounters issues in engineering small-diameter constructs with a diameter smaller than 5 mm. Small-diameter vascular constructs fabricated using synthetic materials have poor intermediate and long-term patency rates. Natural biomaterials have great biocompatibility and biodegradability, and provide an ideal substrate for cell attachment and proliferation. However, as an inherent weakness, the mechanical properties of natural biomaterials are limited. Vasculature conduits fabricated by available methods cannot generate an efficient media exchange system with perfusable networks to be incorporated into thick tissue fabrication because of their cumbersome fabrication procedures and nonprintable characteristics.

Bioprinting is a promising method for tissue fabrication providing high precision, high automation and high flexibility. 3D bioprinting is a layer-by-layer bioadditive approach, which involves cells during the fabrication process and allows the precise simultaneous 3D positioning of multiple cell types. Although bioprinting brings more flexibility to the fabrication of artificial vascular systems, incorporation of a small-diameter vascular system in thick tissue fabrication is still a challenge.

In this example, human umbilical vein smooth muscle cells (HUVSMCs) were encapsulated and printed by a coaxial nozzle system. Perfusable vasculature conduits with controlled dimensions were printed. The bioprinting system disclosed herein can fabricate vasculature conduits of any length within a short fabrication time and can be easily incorporated into thick tissue fabrication and organ printing process. Dehydration, swelling and degradation characteristics of vasculature conduits were investigated in detail because they offered important information about the degradation process of alginate conduits, which is critical for mechanical integrity as well as tissue regeneration. The perfusion and permeability capabilities, and unique mechanical properties are important characteristics of natural blood vessel. Thus, perfusion and permeability capabilities and mechanical properties of conduits made of different alginate concentrations were also explored. Cell viability was tested over a seven-day incubation period, and histology examinations were carried out to evaluate smooth muscle formation over a six-week culture period.

Materials and Methods

Materials

Prior to making a hydrogel solution, sodium alginate powder (Sigma Aldrich, U.K.) and calcium chloride ($CaCl_2$) powder (Sigma Aldrich, U.K.) were treated with ultraviolet (UV) light for sterilization three times for a 30-minute cycle each time. UV-sterilized sodium alginate was dissolved in sterile deionized water to make 3%, 4% and 5% (w/v) solutions. Solutions were mixed with a magnetic stirrer (HANNA Instruments, U.S.) at room temperature until homogeneity was reached. Similarly, the crosslinking solution was prepared by dissolving UV-sterilized $CaCl_2$ particles in ultra-purified sterile water (Invitrogen™ Life Technologies, U.S.) at 4%, 5% and 6% (w/v). With the exception of those in the section entitled "Perfusion and permeability testing," all alginate conduits used were crosslinked with a 4% $CaCl_2$ solution.

Cell Preparation

Primary human umbilical vein smooth muscle cells (HUVSMCs) (Invitrogen™ Life Technologies, U.S.) were grown in 75 $cm^2$ cell culture flasks in Medium 231 (Invitrogen™ Life Technologies, U.S.), supplemented with smooth muscle cell growth supplement (SMGS) (Invitrogen™ Life Technologies, U.S.), 10 U/µl penicillin, 10 µg/ml streptomycin, and 2.5 µg/µl fungizone (Invitrogen™ Life Technologies, U.S.). Cells were incubated at 37° C. in 98% humidity and 5% $CO_2$. Cell culture medium was changed every 2 days. When the cultures reached 70% confluence, the cells were detached from the flasks using a 0.25% trypsin-EDTA solution (Invitrogen™ Life Technologies, U.S.), washed twice, re-plated for expansion or resuspended in 4% sodium alginate solution and gently mixed by a vortex mixer to get uniform distribution. Cells in passages 2-5 and at a density of $10 \times 10^6$ cells/ml were used in the experiments.

Fabrication of Vasculature Conduits

The fabrication system consisted of five parts: a single-arm robotic printer (EFD® Nordson, U.S.); a homemade coaxial nozzle unit; a syringe pump (New Era Pump System Inc., U.S.); a liquid dispenser (EFD® Nordson, U.S.); and a computer for robotic control (see FIG. 60A). A 14-25 gauge coaxial nozzle, fabricated with a 14 gauge outer needle (inner diameter=540 µm and outer diameter=1830 µm) and a 25 gauge inner needle (inner diameter=250 µm and outer diameter=520 µm), was used throughout all experiments. HUVSMCs loaded alginate and $CaCl_2$ solutions were dispensed through the sheath and core sections of the coaxial nozzle, respectively (see FIG. 60B). When they contacted, crosslinking started immediately, forming conduits. The alginate dispensing pressure was set at 21 kPa, and the $CaCl_2$ dispensing rate was set at 16 ml/min. For fabrication of branched conduits, a window was opened at the wall of the stem conduit (larger) with a microsurgery scissor (Fisher Scientific, U.S.), which facilitated the insertion of the branch conduit (smaller). Upon insertion and alignment, a thin layer of alginate solution was sealed around the branching site.

Scanning Electron Microscopy (SEM) Imaging

After fabrication, conduits were soaked in a 4% CaCl2 solution for 12 hours to increase mechanical properties. First, conduits were randomly cut into short sections perpendicular to their longitudinal axis. Then, the cell media was completely rinsed off with phosphate buffered saline (PBS) (Sigma Aldrich, U.S.) followed by fixing cells in conduits at room temperature for two hours. Next, samples were rinsed three times using the same buffer used for the fixative (10 min per rinse) and post-fixed for one hour in 1% osmium tetroxide in the same buffer. Then, samples were dehydrated in graded ethanol solutions (from 25% to 100%). After dehydration, the samples were platinum coated to improve image quality. Images were taken using a scanning electron microscope (Hitachi S-4800).

Dehydration, Swelling and Degradation Tests

Upon fabrication conduits were soaked in 4% $CaCl_2$ solution for 30 minutes to ensure sufficient crosslinking. Thereafter, conduits were dehydrated at room temperature for four days. The dehydrated conduits were then soaked in a PBS (Sigma Aldrich, U.S.) solution for swelling and degradation studies. In these experiments, acellular conduits were used. The shrinkage rate by weight (SRW) and swelling ratio (SR) were calculated using the following equations:

$$SRW\left(1 - \frac{W_d}{W_o}\right) \times 100\% \tag{1}$$

$$SR = \frac{W_i - W_d}{W_d} \times 100\% \tag{2}$$

where $W_o$ is the original conduit weight right after fabrication, $W_i$ is the swollen conduit weight at the predetermined time point and $W_d$ is the dehydrated conduit weight.

Dimensional Characterization of Vasculature Conduits During Dehydration, Swelling and Degradation Conduit dimensions were measured using a light microscope (Motic®, BA310, U.S.) equipped with a digital camera. Conduit dimension measurements were conducted throughout the swelling and degradation tests. The four-hour point was selected as a measurement point because the swelling ratio of 5% conduits reached its maximum value at four hours. 5% alginate conduits were used in this experiment while their swelling ratio curve started decreasing earliest. The diameter shrinkage rate (DSR) was calculated as:

$$DSR = \left(1 - \frac{D_d}{D_o}\right) \times 100\% \tag{3}$$

where $D_o$ is the original conduit diameter after fabrication, and $D_d$ is the conduit diameter after dehydration.

Mechanical Testing

After fabrication, conduits were crosslinked and soaked in $CaCl_2$ solution for 24 hours. Soaking them in $CaCl_2$ solution minimized the effect of residence time on samples. A Biotense Perfusion Bioreactor (ADMET, Inc., U.S.) was used to evaluate tensile strength characteristics. Each sample was a maximum of 30 mm long and mounted on rectangular mini sandpaper in order to prevent slippage during the test. Upon applying the mechanical load, conduits were ruptured in the middle or near edges. Displacement and load information data were recorded by a data acquisition system (MTestQuattro System, U.S.). The estimated burst pressure (BP) was calculated from ultimate tensile strength (UTS) measurements by rearranging the Laplace law for a pressurized thin-walled hollow cylinder, where BP is the estimated burst pressure (mmHg); T represents the wall thickness (μm) of conduits; and LD represents the unpressurized lumen diameter (μm) (see Equation 4 below).

$$BP = 2\frac{UTS \times T}{LD} \quad (4)$$

2.8 Perfusion and Permeability Testing

To test media perfusion and permeability capabilities of conduits, a customized perfusion system was developed. The media perfusion system consists of three parts: a cell culture media reservoir, a digital pump (Cole-Parmer, U.S.) and a custom-made perfusion chamber with a clear cover to prevent evaporation. Flexible needles inserted into conduits were selected depending on the lumen diameter of conduits. Surgery clips were used to fix the two ends of the conduits during perfusion to prevent leakage at the interface section. 3%, 4% and 5% alginate, and 4%, 5% and 6% $CaCl_2$ solutions were used in perfusion experiments in order to explore the permeability of acellular conduits. Permeability was characterized using diffusion rate. Diffusion rate (μl/hour) was calculated by obtaining the volume of media diffused out from conduits to the perfusion chamber in an hour. For easy manipulation, conduits were soaked in $CaCl_2$ solution for 24 hours. Directly after printing, conduits were soft and mechanically weak; this made the insertion of needles very challenging. This finding is also consistent with the literature, which pointed out that the elastic modulus of alginate increases as the gelation time increases, within 24 hours. In all perfusion experiments, the original length of conduits was fixed at 8 cm.

Cell Viability

Following printing, cellular conduits were incubated at 37° C. in a 5% $CO_2$ humid atmosphere for 1, 5 and 7 days. HUVSMCs viability in conduits was determined by using Viability/Cytotoxicity fluorescence test, calcein AM and ethidium homodimer-1. Conduits were perfused with 1.0 mM calcium acetoxymethylester (calcein AM) and 1.0 mM ethidium homodimer-2 (Invitrogen™ Life Technologies, U.S.) and incubated for 30 min at 37° C. Calcein-AM labels healthy cells green and ethidium homodimer labels dead cells red. Following the 30 min exposure, cells were examined using a Leica fluorescence microscope (Leica Microsystems Inc., U.S.). Images were collected from three different locations randomly chosen from each sample. ImageJ (National Institutes of Health, U.S.) was used for automated counting of red- and green-stained HUVSMCs in each image, and percentages of viable cells were calculated.

Cell Proliferation Study

Following printing, constructs were placed in a 6-well tissue culture plate, and incubated at 37° C. in a 5% $CO_2$ humid atmosphere for 1, 5 and 7 days. The proliferation of HUVSMCs was quantified by means of MTT [(3-(4,5-dimethylthiazol-2-yl)-2,5-diphenyltetrazolium-bromide)] assay (Invitrogen™ Life Technologies, U.S.), which directly measures the cellular metabolic activity through the biodegradation of tetrazolium salt by viable and active cells. Following each time point, conduits were cultured in the presence of a 1% (v/v) MTT solution (5 μg/mL) for 4 h at 37° C. and 5% $CO_2$. Following this culture period, 200 μL (in triplicate) of the supernatant was transferred from each well to a 96-well flat-bottom plate and the absorbance of the formazan dye was determined at 550 μm using a PowerWave X Microplate Reader (Bio-Tek, U.S.).

Tissue Histology

In addition to the assessment of short-term cell viability, conduits were cultured for a prolonged time period, followed by a histology examination. After six weeks of in vitro culturing in smooth muscle cell differentiation media, fixed conduits were frozen and sectioned at 5 μm for histological examination. Verhoeff-Van Giesen staining was used to visualize collagen deposition, where collagen stains a red color. All the procedures were carried out per the manufacturers' instructions. Sample slides were examined under an Olympus BX-61 brightfield fluorescence microscope (Olympus America, U.S.) at different magnifications.

Statistical Analyses

The results shown in dimensional characterization experiments were an average of all 50 pieces of data. The statistical analysis was carried out using Minitab 17. The statistically significant difference was determined using the two-tailed student's t-test. Groups with a significance level of $p<0.05$ were considered as significant. Standard error bars in all FIGS. represent standard deviations. For experiments in the sections entitled "Dehydration, swelling and degradation tests", "Mechanical testing", "Perfustion and permeability testing", and "Cell vioability and proliferation", sample size (n) is three.

Results and Discussions

Fabrication of Vasculature Conduits

With fixed fabrication parameters, the average conduit and lumen diameter of 5% alginate conduits were 1449±27 μm and 990±16 μm, respectively. A microscope image of a conduit is shown in FIG. 60A. Uniform, smooth and well-defined walls can be observed in the FIG. A long printed vasculature conduit with a length of approximately 80 cm was zigzag patterned and perfused with cell culture media (FIG. 60B). No occlusion or leakage was observed during the perfusion process. FIG. 60C is a two-week-cultured conduit. Long-term cultured conduits maintained their structural integrity with a well-identified lumen center and conduit wall. FIG. 60D shows the emulation of a branched vasculature by combining two conduits. Cell culture media pumped from the main stem can be successfully perfused out from both branch stems.

Dehydration, Swelling and Degradation Tests

Alginate conduits with different concentrations were dehydrated at room temperature for four days. After dehydration, the majority of conduits remained in tubular shape. FIG. 61A shows a macroscopic photo of dehydrated 5% conduit. The conduit diameter shrank to 788 μm, which was 54.4% of the original conduit diameter (FIGS. 61B and 61C). For all alginate concentration groups including the 3%, most of conduits maintained their tubular shape.

FIG. 62D is the SRW of conduits made of different alginate concentrations. During dehydration process, 3% alginate conduits lost more weight than others. The SRW decreased as alginate concentration increased. The SRW of 3%, 4% and 5% alginate conduit groups were 95.8%, 94.2% and 90.4%, respectively. Statistical significance was observed between groups.

Swelling experiments were performed following the dehydration tests. FIG. 62A shows the swelling ratio curve over time for the 3%, 4% and 5% alginate conduit groups. For conduits made of different alginate concentrations, the swelling ratio curves depict obviously different trends. The initial slope of the swelling ratio curve of the 3% conduits was large, which indicates a high swelling rate. Since swelling and degradation experiments were performed at the same time, swelling ratio was also affected by dissociation of calcium alginate in PBS solution. FIG. 62B summarizes the time to reach the maximum swelling ratio ($T_{ms}$). $T_{ms}$ decreased as alginate concentration increased. FIG. 62C shows the maximum swelling ratio. The maximum swelling ratio also decreased as alginate concentration increased, and the 3% group had the largest swelling capacity among all groups. FIG. 62D compared the liquid reabsorption capacities ($W_{max}/W_o$) of the three groups, where $W_{max}$ is the conduits' maximum swelling weight achievable. For conduits made of different alginate concentrations, $W_{max}/W_o$ remained similar, around 33%. This number indicated that dehydrated conduits from all groups "reabsorbed" liquid up to 33% of the original weight, despite their significantly different maximum swelling ratios. The $W_{max}/W_o$ value for the 3%, 4% and 5% alginate vasculatures were 32.2±0.0062%, 33.3±0.0054% and 33.4±0.0037%, respectively. Compared to other groups, the 3% group had a smaller $W_{max}/W_o$ value; however it was not statistically significant.

Dimensional Characterization of Vasculature Conduits During Dehydration, Swelling and Degradation As shown in FIG. 63A, alginate concentration had significant influence on conduit dimensions. Conduits made of 4% alginate had the smallest conduit and lumen diameters, and the largest wall thickness. Small conduit and lumen diameter does not indicate a small wall thickness; rather, wall thickness can be affected by several factors such as crosslinking degree, nozzle configuration, dispensing flow rate of alginate and $CaCl_2$ solutions, swelling, alginate shrinkage, conduit elasticity, etc. The conduit diameters after dehydration are shown in FIG. 63B. Dehydrated 3% alginate conduits had the smallest diameter, and the diameter of the dehydrated conduits increased as the alginate concentration increased. FIG. 63C shows the DSR of conduits made of different alginate concentrations; this was obtained using Equation (3). The DSR represents the shrinkage in uniaxial direction only. If it is assumed that the ionically crosslinked alginate structure is homogeneous, the shrinkage process can possess isotropic homogeneity, which means that shrinkage rates along all directions are the same. Three-dimensional shrinkage rates for the 3%, 4% and 5% conduits were 96.8%, 93.62% and 83.9%, respectively. The 3% group had the largest dehydration shrinkage rate and lost more weight and volume than the other groups. Both the DSR and SRW decreased as the alginate concentration increased. The values of DSR and SRW were similar and consistent. The shrinkage rate obtained in dehydration experiments can be an indicator for porosity of conduits (porosity is a measurement of void). A higher construct porosity is strongly desirable, as long as the construct can provide enough mechanical support for cells to grow on and make their own matrix. Ideal pore size for vascular grafts ranges from 10 µm to 45 µm, which is much higher than the porosity range in bioprinted conduits. FIG. 63D shows dimensional changes on 5% alginate conduits throughout the dehydration, swelling and degradation experiments. After four hours of soaking in PBS, although the conduits reached their maximum swelling ratio, the diameters of the swollen conduits were much smaller than the originally fabricated ones. Their diameters were only 64.4% of the originally fabricated ones.

Lumen diameter, conduit diameter and wall thickness all changed over time during the swelling and degradation processes, which was evidence of the occurrence of the swelling and degradation processes at the same time. The decrease in conduit diameter can be explained by presence of the degradation phenomenon. The decrease in lumen diameter, on the other hand, was mainly due to the swelling process. On the outer wall of conduits, the degradation process dominated the dimensional change. On the luminal wall of conduits, limited media can penetrate through pores and reach the lumenal surface. The degradation rate was much slower than the swelling rate, and the swelling process dominated the dimensional change; thus, the lumen diameter of the conduits decreased over time. The conduits' dimensional changes were significant during the first several days and became insignificant later on. This illustrates that both the swelling process and the degradation process slowed down over time. The slowdown of the swelling process occurred because the alginate conduits reached their maximum swelling capacity, whereas the degradation process slowed down for a much more complicated reason. The degradation of alginate hydrogel was due to the loss of $Ca^{2+}$ ions. During the swelling and degradation experiments, PBS was not replenished. Over time, the $Ca^{2+}$ ions in alginate and the PBS reached an equilibrium state, and thus the degradation process slowed down accordingly. Alginate has been used as biomaterial for vascular tissue graft applications and in general it has reasonable degradation rate in in vivo performance.

Mechanical Testing

The mechanical tests were performed to explore the mechanical properties of conduits. Table 1 (below) demonstrates the tensile strength, elastic modulus, ultimate strain and calculated burst pressure of conduits with different alginate concentrations. It illustrates that the tensile strength of the 3% alginate conduits (110±5.8 kPa) was lower than that of the 4% group (382±19 kPa). A higher concentration of alginate resulted in a higher Young's modulus, from 105±7.5 kPa for 3% conduits to 341±23 kPa for 4% alginate conduits. The ultimate strain for the 3% alginate conduits was higher than the 4% groups, and the evaluated burst pressure increased as alginate concentration increased. The ultimate strain and evaluated burst pressure for 3% conduits were 0.82±0.18 and 43.24 mmHg, and for 4% conduits were 0.69±0.13 and 303.73 mmHg, respectively. A higher concentration of alginate resulted in significantly higher tensile strength, Young's modulus and burst pressure along with lower ultimate strain.

TABLE 1

Mechanical properties of vasculature conduits

| | 3% Alginate conduits | 4% Alginate conduits |
|---|---|---|
| Tensile Strength (kPa) | 110 ± 5.8 | 382 ± 19 |
| Young's Modulus (kPa) | 105 ± 7.5 | 341 ± 23 |
| Ultimate Strain | 0.82 ± 0.18 | 0.69 ± 0.13 |
| Burst Pressure (mmHg) | 43.24 | 303.73 |

The difference between the 3% and 4% groups' estimated burst pressure is much more than that of tensile strength and Young's modulus. This is because burst pressure was estimated from the mechanical testing measurements and under the same fabrication parameters, the 3% group had greater lumen diameter as well as thinner conduit wall. Although 4% alginate conduits have much higher burst pressure compared with the 3% group, when it is compared with natural blood vessel, in which burst pressure is around 3561 mmHg, it is evident that further improvement is needed in future experiments. For example, connective tissue proteins such as collagen and elastin can be produced in nano-fiber form using nano-manufacturing techniques, i.e., electrospinning or electrohydrodynamic jetting, and reinforced into vasculature conduits to improve mechanical properties.

Perfusion and Permeability Testing

To determine the influence of cell culture media perfusion rate on the fabricated conduits and their diffusion capability, the flow rate of cell culture media was set at 1 ml/min, 2 ml/min and 3 ml/min, respectively. FIG. 65A demonstrates the influence of media perfusion rate on conduits' dimensions. As shown in FIG. 65A, media perfusion rate had a significant influence on lumen diameter as well as conduit diameter. Both lumen diameter and conduit diameter increased as perfusion rate increased. As shown in FIG. 65B, perfusion time also had an influence on conduit dimensions. A 3 ml/min perfusion rate was chosen in this experiment because a larger perfusion rate is supposed to have more significant results. Cell culture media was perfused at 3 ml/min for one hour and three hours. Conduit diameter and lumen diameter were measured after perfusion. Results show that perfusion flow with a longer perfusion time had a greater influence on conduit dimension changes. Conduits that underwent a longer perfusion experiment had larger lumen and greater conduit diameter. When the conduit dimension changed, the diffusion rate changed accordingly. FIG. 65C plots conduit diffusion rate under different perfusion rates. With a higher perfusion rate, the diffusion rate became greater. FIG. 65D demonstrates that perfusion time also influenced diffusion rate of media in conduit. The diffusion rate increased as perfusion time increased, where diffusion rate shown in FIG. 65D is the average diffusion rate per hour. The permeated cell culture media through conduit walls was collected and measured per hour. The data in the 3 ml/min-2 h group included only the cell culture media diffused through the conduit in the second hour. FIG. 65E shows the diffusion rates in 3%, 4% and 5% alginate conduits, at a perfusion rate of 3 ml/min. The 3% alginate conduits crosslinked with 4% $CaCl_2$ were fragile due to their weak mechanical properties (as already demonstrated in Table 1) and thin wall thickness (see FIG. 65A). They were not suitable for the perfusion experiment, so their data were not included in FIG. 65E. Among all conduits crosslinked with the 6% $CaCl_2$ groups, the 3% alginate conduits demonstrated the highest diffusion rate, which was 405±11 μl/hour. For those conduits crosslinked by the same concentration of $CaCl_2$, the diffusion rate decreased as alginate concentration increased, due to alginate hydrogel porosity decreased as alginate concentration increased. In addition, the diffusion rate increased as the crosslinker concentration decreased.

The perfusion and permeability characterization experiments were carried out to understand the diffusion capability of media through conduits. As shown herein, both lumen diameter and conduit diameter increased as perfusion rate increased. This phenomenon can be explained by axial stress. A higher perfusion rate corresponds to a larger axial stress inside the conduit. Because the alginate conduit is an elastic material, a higher axial stress can enlarge the conduit diameter further. The results also show that both perfusion rate and perfusion time had a significant influence on the diffusion rate. The main reason for the change in diffusion rate was the change in conduit dimensions. Conduits perfused with higher rates tended to have larger lumen diameter and thinner wall thickness, which increased the diffusion rate.

Cell Viability and Proliferation

As demonstrated in FIG. 66A, initial cell viability was 73±2% before printing. Cell viability was substantially affected during bioprinting and reduced to 33±7%. During in vitro culture, cell viability rose to 68±6% on day 3 and kept increasing until day 7; it increased to 84±1%, which also exceeded the initial cell viability (73±2%) before printing. Individual cells encapsulated in alginate matrix within the wall of the conduit were highlighted in a SEM image as presented in FIG. 66B. Cells were rounded while encapsulation in high concentration alginate network did not allow them to spread in short term culture. FIG. 66C shows a fluorescence microscopy image of a three-day-cultured conduit, in which the majority of cells were viable.

Although the bioprinting system had an influence on cell viability, primarily due to the shear-stress-induced cell damage during the extrusion process, HUVSMCs encapsulated in conduits had good proliferation activities. During in vitro culture after bioprinting, cell viability kept increasing from the first day through day 7 and even exceeded the original cell viability. This indicates that after fabrication, those injured cells not only were able to recover, but also were able to proliferate during incubation and support new tissue formation. Higher cell viability can be achieved by decreasing shear stress during the bioprinting process by using a larger coaxial nozzle or a lower extrusion pressure.

An MTT assay was performed to evaluate the metabolic activity of the HUVSMCs encapsulated in conduits. As shown in FIG. 66D, cell viability was affected by the bioprinting process, where cell proliferation on free-cell suspension on Petri dish (PD) was greater than that of encapsulated ones; however, cells could grow and recover. The proliferative rate of the cells increased with culture period, which is in agreement with the cell viability results.

Tissue Histology

A histology study was performed to evaluate long-term cultured conduits for cell morphology and tissue-specific ECM formation. Printed conduits maintained their structural integrity with a well-defined lumen and conduit wall and ECM deposition in the inner and outer boundaries after six weeks in vitro culture (see FIG. 67A). Verhoeff-Van Gieson staining shows smooth muscle matrix deposition around cells and throughout the conduit wall (light pink color). Thick cell sheets were formed on the peripheral and luminal surfaces with multiple layers of cells (see FIGS. 67B-67C), smooth muscle deposition stained with a purple-pink color. Cell sheets were closely attached on the conduit walls. While encapsulated cells were uniformly distributed in the conduit after bioprinting and do not attach on the surface of alginate, it is possible that cells migrated from their original lacunae towards the gradient of culture media to both the lumen side and the peripheral side, where there were greater oxygen and nutrient supplies. Upon migrating towards oxygen and growth factor gradients, cells started to grow and synthesized smooth muscle forming ECM close to the peripheral and luminal surfaces. This indicates that continuous perfusion of culture media through the lumen can facilitate further cell migration and proliferation toward the lumen side in long-term-cultured conduits, potentially increasing smooth muscle formation. Some of the encapsulated cells resided in their original lacunae and were largely intact, with a rounded stained nucleus and lighter stained cytoplasm (see FIG. 67C for longitudinal sectioning). For future attempts, uniformity of ECM distribution across the conduit can be obtained by increasing cell density and applying continuous perfusion in culture.

HUVSMC-encapsulated conduits were bioprinted in a practical way, which can be integrated into thick tissue fabrication or organ printing processes. The presented system offered several advantages, including that it had no post-fabrication procedure, and enabling direct bioprinting of complex media exchange networks. A functional branched network was also demonstrated. The dehydration, swelling and degradation characteristics of conduits were investigated, along with their perfusability, mechanical strength and permeability capabilities because these properties are crucial for long-term function in perfusing and delivering media for thick tissues. Cell viability was affected by the bioprinting process; however, it was able to increase during incubation and later exceed original cell viability. In prolonged culture, cells within cellular conduits maintained their integrity and were able to carry out their functions. Reasonable extra-cellular matrix deposition was observed on both the peripheral and luminal surfaces. Conduits fabricated by a higher alginate concentration had lower cell viability, slower degradation process, less porosity and lower permeability capacity, as well as higher mechanical properties and bioprintability. In general, 4% works well for the application due to its bioprintability and mechanical and biological properties.

Example Nine

Organ printing uses tissue spheroids as building blocks together with additive manufacturing technique to engineer tissue or organ replacement parts. Although a wide array of cell aggregation techniques has been investigated, and gained noticeable success, the application of tissue spheroids for scale-up tissue fabrication is still worth investigation. In this example, a micro-fabrication technique used to create tissue strands at the scale of 500-700 µm as a "bioink" for future robotic tissue printing is disclosed. Printable alginate micro-conduits can be used as semi-permeable capsules for tissue strand fabrication. Mouse insulinoma beta TC3 cell tissue strands were formed upon 4 days post fabrication with reasonable mechanical strength, high cell viability close to 90%, and tissue specific markers expression. Fusion was readily observed between strands when placing them together as early as 24 h. Also, tissue strands were deposited with human umbilical vein smooth muscle cells (HUVSMCs) vascular conduits together to fabricated miniature pancreatic tissue analog. Disclosed herein is a method of using tissue strands as "bioink" for scale-up bioprinting of tissues or organs.

Introduction

Tissue engineering has been focusing on the fabrication of vascularized 3D tissue for decades. Most recently, 3D bioprinting, especially organ printing, has shown great potential to realize automated robotic fabrication of 3D vascularized tissues and organs that are readily available for in vitro studies and/or in vivo transplantation. Tissue spheroids, which are spherical shaped cell aggregates have been studied and have shown their potential as the building blocks for organ printing. Without involvement of any hydrogel, tissue spheroids can easily mimic the embryonic development process by self-assembly into larger tissues.

Because of their ideal morphological and biological properties, tissue spheroids are great candidates for additive biofabrication of tissues. Visconti and his colleagues used fibroblast and smooth muscle cell derived tissue spheroids to build branched vascular structure, showing their exceptional ability of self-assembly and fast maturation. In addition, this technique has been used for β-cells where spheroids ranging from 200-400 µm in diameter produced more insulin than did a monolayer cell culture. Faulkner Jones et. al have developed a system to fabricate embryonic stem cell spheroids, which showed high viability as well as maintained pluripotency. Recent studies have developed several approaches for scalable robotic biofabrication of tissue spheroids. A modified hanging-drop system was developed by two companies, which allows high reproducibility, and easiness for robotic integration. Digital microfluidic system has also been used for generating tissue spheroids in large-scale. Most recently, hydrogel micropatterning has also been developed and modified by several groups for 3D formation of micro-scale tissue spheroids. Although, tissue spheroid-based aggregate techniques are promising for advancing tissue engineering, their labor-intensive fabrication in limited scale makes their applicability for large-scale tissue/organ fabrication difficult. Besides the fabrication process, printing tissue spheroids sequentially by ensuring contact between each adjacent spheroid is another hurdle, given the extremely critical handling and sterilization conditions. Without ensuring contact, spheroids cannot fuse to each other, easily leaving gaps and openings in the tissue. In addition, hydrogels are required as a transferring medium to deposit spheroids. Furthermore, technologies should be developed to prevent spheroid fusion before printing to eliminate nozzle clogging.

Disclosed herein is a method of bioink generation, which enables scale-up fabrication of vascularized tissues. Tissue strands were fabricated within a semi-permeable capsule system directly fabricated by coaxial nozzle bioprinting. Cell viability test revealed minimal cell damage upon fabrication. Tissue strand fusion started as soon as 24 hours post-printing, and nearly completed on day 7 Immunofluorescence staining showed overall tissue specific markers insulin and C-peptide expression on matured tissue strands. Hybrid fabrication of cellular conduits with tissue strands were successfully conducted showing their potential for vascularized tissue fabrication. This example provides a method for cell aggregation in tissue strand form, which can serve as feeding material for bioprinting, and can realize 3D organ printing.

Materials and Methods

Cells and Materials Preparation

Sodium alginate solution was used as biomaterial for vascular conduits fabrication as well as tubular capsule fabrication. Sterilized sodium alginate powder was dissolved in deionized water to get 4% (w/v) solutions. Similarly, the cross-linking solution was prepared by dissolving calcium chloride in ultra-purified water (Life Technologies, Carlsbad, CA) at 4% (w/v).

Human umbilical vein smooth muscle cells (HUVSMC) were purchased from Life technology. Upon revitalization, cells were cultured at 37° C. in 5% $CO_2$ in Medium 231 supplemented with smooth muscle cell growth supplement, 10 µg/µl penicillin, 10 µg/ml streptomycin, and 2.5 µg/µl Fungizone. For vascular conduit fabrication, HUVSMCs were harvested and introduced into alginate solution and then homogenized by Votex mixer (Fisher Scientific, Waltham, MA, USA). HUVSMC-containing alginate solution was used as "bioink" for direct vascular conduit bioprinting with coaxial nozzle system. Mouse insulinoma beta TC3 cells were cultured in DMEM, supplemented with 10% fetal bovine serum, 10 µg/ml streptomycin, 1% non-essential amino acid, 1 mM sodium pyruvate and 2 mM glutamine, in 37° C. in 5% $CO_2$. All culture media and supplements were purchased from Life Technologies (Carlsbad, CA, USA).

Fabrication of Tubular and Cell-Laden Conduits

Disclosed is a bioprinting approach that enables printing vascular network directly through a coaxial nozzle system. Briefly, 4% sodium alginate tubular capsules were printed by a co-axial nozzle system (22 G inner nozzle and 14 G outer nozzle), serving as a semi-permeable capsule for tissue strand fabrication, allowing media diffusion. Similarly, 4% (w/v) sodium alginate solution with HUVSMCs at a density of $10\times10^6$ was used for vascular conduits fabrication. Using the coaxial nozzle, HUVSMCs encapsulated within alginate were printed in tubular shape by maintaining constant controllable flow of crosslinker (4% (w/v) calcium chloride) through the core section of the coaxial nozzle enabling instantaneous gelation and leaving an unblocked vascular conduit. These vascular conduits were further cultured in vitro, and used as macro-vasculature for hybrid tissue fabrication, which is discussed herein.

Tissue Strands Fabrication and Characterization

Mouse insulinoma bTC3 cells were harvested and centrifuged at 3,500 rpm. The resulting pellet was incubated at 37° C. with 5% $CO_2$ for overnight in DMEM-based media with 2% fetal bovine serum, supplemented with 10 μg/μl penicillin, 10 μg/ml streptomycin, and 2.5 μg/μl Fungizone (Life Technologies, Carlsbad, CA, USA), in order to have sufficient coherency and mechanical integrity during further processing. Cell pellet was then injected into tubular conduits by a custom syringe unit (Hamilton Company, Reno, NV, USA). The encapsulated structure was incubated for at least 4 days and then dissolved by 1% sodium citrate solution for 10 minutes, leaving pure tissue strands behind. The dimension of tissue strands was measured by Image J (National Institutes of Health, Bethesda, MD, USA) analysis on microscopic images over two weeks. FIG. 68 demonstrates the procedure for tissue strands fabrication.

Cell viability was tested at different time points (Day 1, 4, 7, and 10) for tissue strands. Briefly, each sample was washed with PBS and underwent 30 minutes fluorescence staining with LIVE/DEAD staining kit (Life Technologies, Carlsbad, CA), and directly imaged using a Leica fluorescent microscope (Leica Microsystems Inc., Buffalo Grove, IL, USA). Images were collected from six different locations randomly chosen from each sample. ImageJ software (National Institutes of Health, Bethesda, MD, USA) was used for automated intensity calculation of red- and green-stained tissue strands, and percentages of viable signal were calculated by dividing green fluorescent intensity with sum of red fluorescent intensity and green fluorescent intensity.

To evaluate tissue specific protein expression, immunofluorescence staining was used for bTC3 cell specific markers: C-peptide, a precursor for insulin, and insulin. Samples were imaged with confocal microscope (Zeiss LSM 710, Berlin, Oberkochen, Germany). Antibodies for C-peptide, and insulin were purchased from Santa Cruz Biotechnology, Inc. (Dallas, USA.), and Abcam (Cambridge, USA) and applied per the instruction of the manufacturers.

Hybrid Tissue Fabrication

Figure 69:
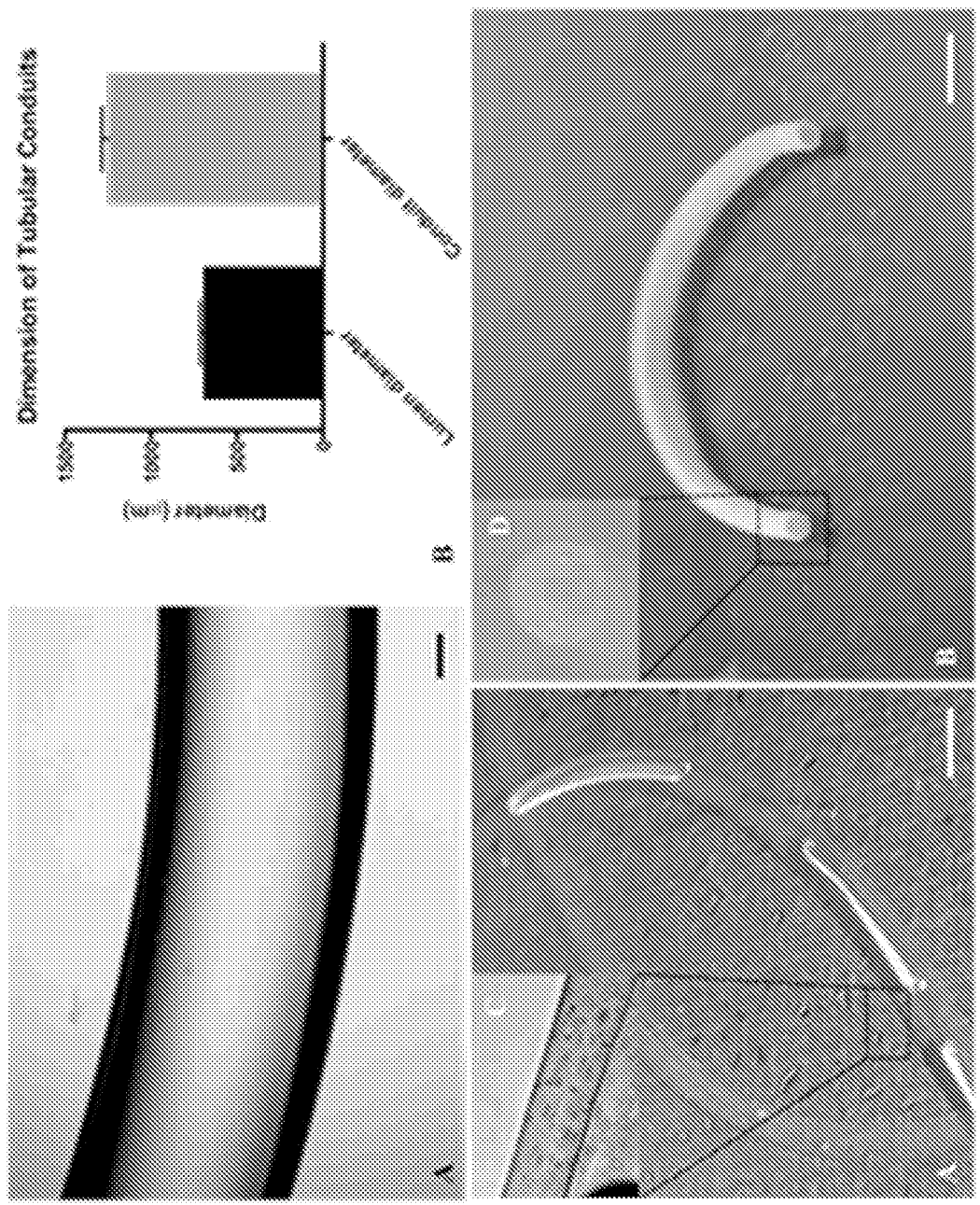

Matured tissue strands were tailored as 5 mm long building unit, and deposited layer by layer, with a vascular structure embedded in the center to mimic the vascularized tissue. Firstly, 6 tissue strands each with a length of 5 mm were closely assembled as the first two base layers, following by a third layer of tissue strands with a vascular conduits in the center with the length of 20 mm. Finally, another two layers of tissue strands were laid on top to enclose the vasculature completely. Upon fabrication, the hybrid structure was kept in a customized polycarpolactone (PCL) mold to ensure initial integrity, and incubated at 37° C. with 5% $CO_2$. FIG. 69 shows a schematic FIG. for the process.

Results

Fabrication and Characterization of Semi-Permeable Conduits

Tubular conduits were successfully printed with continuous uniform structure, as presented in FIG. 70A. The average lumen diameter and vasculature diameter of fabricated conduits were 709±15.9 μm and 1248.5±37.2 μm, respectively (FIG. 70B). Cells were individually encapsulated and uniformly distributed in vascular conduits (FIG. 70C). Upon 4 weeks incubation in HUVSMC cell-specific media, vascular conduits were enriched with extra cellular matrix while maintaining hollow lumen (FIG. 70D). Matured vasculature conduits were kept in culture until they were used in hybrid fabrication with tissue strands.

Tissue Strands Fabrication and Maturation

Figure 70:
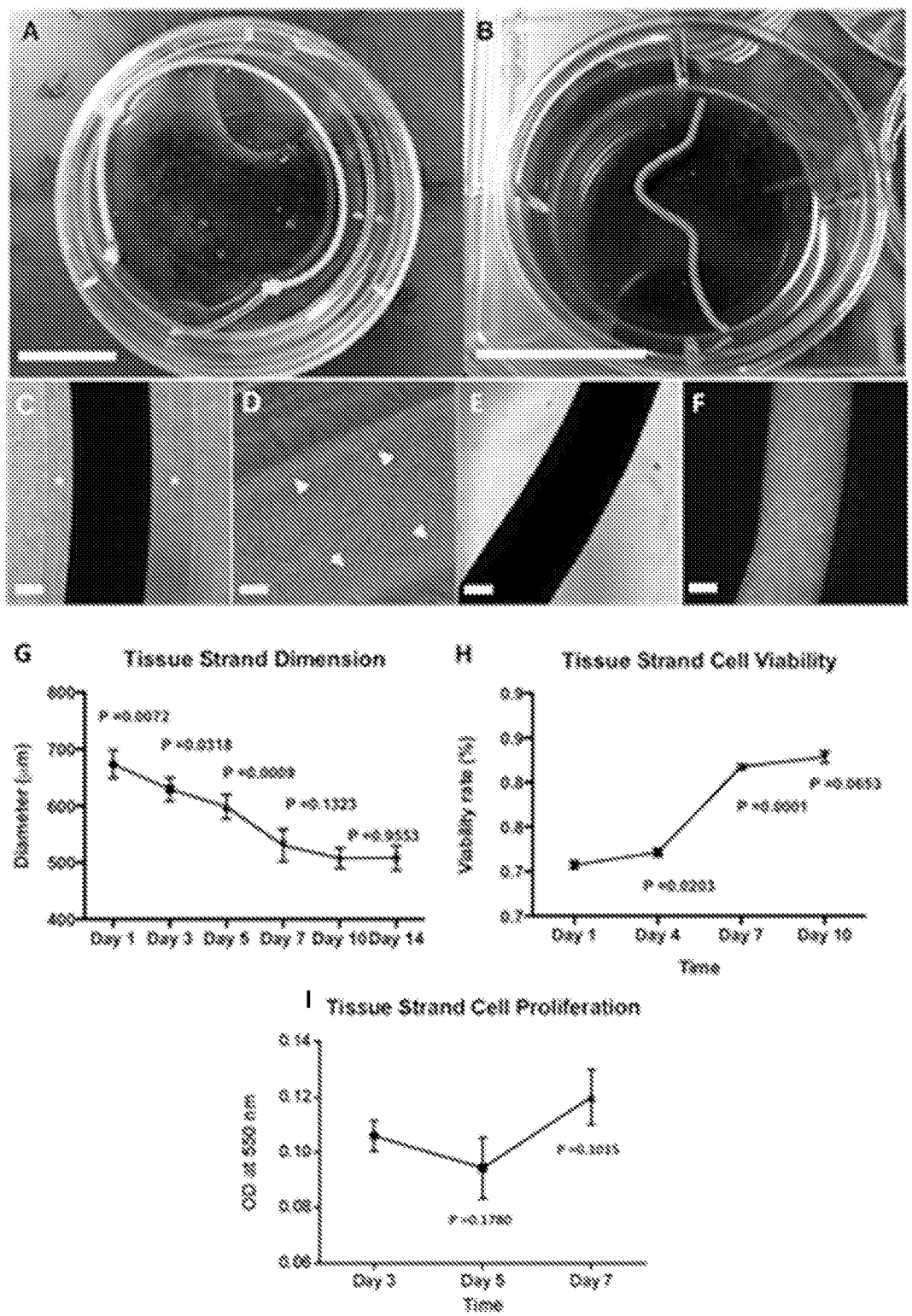

Cell pellet made from $2.0\times10^8$ was successfully transferred into about 150 mm long micro-tubular system (FIG. 70A, C, D). Tissue strands were formed with reasonable integrity and mechanical strength upon de-crosslinking of conduits after 4 days of in vitro incubation (FIG. 70B, E). The average diameter of tissue strands was about 639±47 μm (FIG. 70 G). Cell viability was maintained upon fabrication as well as during culture (FIG. 70F). The average viability on day 1 post fabrication was 75±0.5%, and gradually increased to 77±0.5%, and finally reached to 87±3% on day 7 (FIG. 70H).

To test the fusion potential of fabricated tissue strands, two individual strands were placed onto 150 mm petri dish with contact. Fusion started as early as 24 h post fabrication during incubation (FIG. 71A, D, G), and further fused with more cell migration and ingrowth into each other between two strands on day 4 (FIG. 71B, E, H). At day 7, two strands were almost completely fused into one large strand due to interfacial tension, with contracted morphology, and no visible gap between each other (FIG. 72C, F, I).

To evaluate the expression of tissue specific proteins, two markers were used for immunofluorescence labeling with specific antibodies. As shown in FIG. 72, substantial amount of cells were positively stained with C-peptide (A, C), as well as insulin (B, D) in tissue sections after fabrication and in vitro culture. This indicates that cells within tissue strands still maintained their insulin expression. Notably, positive staining was not only observed around cell nucleus, but also present in the intercellular space (FIGS. 72C-72D)

Fabrication of Hybrid Tissue Constructs

Macro-vasculature tissues were successfully fabricated. Although evident gaps were observed between tissue strands immediately after fabrication, the gradual fusion between strands held them as an entire unit during in vitro incubation (FIG. 73A). The hybrid structure was able to present itself as an integrated structure in culture media, with notable fusion, and diminished gaps between strands on day 3 (FIG. 73B). The hybrid tissue continued to fuse, remodel and mature in prolonged culture, and presented itself as a seamless vascularized tissue (FIG. 73C). Also, cell migration and ingrowth into the vascular wall were also observed at the interfaces of tissue strands and vasculature (FIG. 73D, E). A histological image also displays fused tissue strands around the vasculature (FIG. 73F).

Discussion and Conclusion

A scalable tissue strand fabrication technique was developed, which can be used as a "bioink" to facilitate scale-up organ printing process. The traditional tissue spheroid fabrication technique was modified, by applying tissue strands made of pure cells for tissue or organ fabrication with assistance of robotic printer. The micro-tubular conduits served as a great reservoir for fabricating tissue strands, which demonstrated nearly 90% cell viability, fast fusion, and maintained functionality with tissue specific markers expression. The capability of tissue strands as "bioink" for robotic bioprinting was successfully demonstrated in the hybrid tissue fabrication, where bTC3 tissue strands were deposited together with HUVSMC laden vascular conduits, mimicking a vascularized pancreatic tissue. Multiple cell types, like endothelial cells and fibroblasts can be included in vascular conduits and to further resemble the natural counterpart. Also, endothelial cells can be co-cultured with bTC3 cells to make self-vascularized tissue strands, and used for scale-up tissue printing. In that way, the vascularized tissue strands can connect with the main cellular conduits in 3D, forming a fully vascularized tissue analog.

Example Ten 3D bioprinting has taken tissue engineering to a new era with the interdisciplinary effort spanning biology, medicine, and engineering. As the foundation of organ printing, cell aggregates, or tissue spheroids have recently been attracting enormous attention, where spheroid-shaped cell aggregates are used as building blocks for tissue fabrication. Although a wide array of cell aggregate techniques has been investigated, there has been no reported research in fabrication of printable cell aggregate strands for scale-up tissue fabrication. In this example, a micro-fabrication technique used to create cell aggregate strands as a feeding material for robotic tissue printing is disclosed. Printable alginate micro-conduits were used as semi-permeable capsules facilitating cell aggregation and maturation, followed by dissolving the capsules leaving cell aggregate strands. Bovine articular cartilage chondrocytes strands were formed upon 4 days post fabrication with reasonable mechanical strength, structural integrity, as well as high cell viability. Tissue fusion was readily observed between strands as soon as 24 hours after placing them together, and further during prolonged culture. Histology analysis showed significant cartilage specific matrix deposition in tissue strands. Immunohistochemistry examination showed cartilage specific type II collagen and aggrecan protein expression. Real-time PCR also showed significantly higher cartilage specific gene expression in comparison with cultured chondrocytes. Disclosed herein is a method for cell aggregate fabrication, which can expedite tissue maturation, thus, facilitate the organ printing process.

Introduction

In order to print living cells in a 3D tissue construct, biomaterials can be used as a transferring medium from the printer to the printed structure; however, biomaterial inclusion should be minimized due to degradation-related complications, fewer cell-to-cell interactions in the biomaterial curser, and the long-term side effects of cells waiting in precursor solution (uncross-linked biomaterial) in the bioprinter barrel. Tissue spheroids can be a solution to these problems by using spherical shaped aggregates that are manufactured from pure cells. Without involvement of any biomaterial, tissue spheroids can easily mimic the embryonic development process by easily fusion into larger tissue and organ parts. Because of their ideal morphological and biological properties, tissue spheroids have recently been studied, and proposed as building blocks in computer-aided additive biofabrication for various tissues. Visconti and colleagues have used fibroblast and smooth muscle cell-derived tissue spheroids to build branched vascular structure, showing their potential for tissue fusion and quick maturation. In addition, they have been used for 13 cells where spheroids ranging from 200 to 400 µm in diameter produced more insulin than did a monolayer cell culture. Alan Faulkner et. al have developed a system to fabricate embryonic stem cell spheroid aggregates, which showed high viability as well as maintained pluripotency. Although tissue spheroid-based aggregate techniques are promising for advancing tissue engineering, their labor-intensive fabrication in limited scale makes their applicability for large-scale tissue/organ fabrication difficult. Besides the fabrication process, printing tissue spheroids sequentially by ensuring contact between each adjacent spheroid is another hurdle, given the extremely critical handling and sterilization conditions. Without ensuring contact, spheroids cannot fuse to each other, easily leaving gaps and openings in the tissue. In addition, hydrogels are required as a transferring medium to deposit spheroids. Furthermore, technologies can be developed to prevent spheroid fusion before printing; otherwise, nozzle clogging is inevitable.

Disclosed herein is a method for fabrication and printing of cell aggregates in continuous strands. Cell aggregates in cylindrical form were fabricated within a semi-permeable microtubular system directly printed by the coaxial nozzle bioprinter. Later, cell aggregate strands were released by dissolving the microtubules, and cultured in vitro for further maturation. Cell viability test revealed minimal cell damage upon fabrication. Cells were also able to maintain their metabolic activity overtime as shown by the cell proliferation test. Tissue strands were able to undergo self-assembly by fusing each other upon guided positioning. Strands' fusion started as soon as 24 hours post-printing, and nearly completed by day 7, demonstrating their potential for scale-up tissue fabrication Immunohistochemistry examination showed significant expression of articular cartilage tissue specific markers both at the transcription level and protein level. Cartilage extracellular matrix was heavily deposited throughout matured tissue strands after 2 week culture, which partially demonstrated the function of fabricated structure. Disclosed herein is a method for cell aggregate fabrication, which can expedite tissue maturation, thus, facilitate organ printing process.

Materials and Methods

Preparation of Tubular Microcapsules

Sodium alginate hydrogel solution was used in this example as biomaterial for tubular conduits fabrication. Prior to making a hydrogel solution, sodium alginate powder (Sigma Aldrich, United Kingdom) and calcium chloride powder (Sigma Aldrich, United Kingdom) was treated with ultraviolet (UV) light for sterilization three times for a 30-minute cycle. Sterilized sodium alginate powder was dissolved in deionized water to get 4% (w/v) solutions. Alginate solution was subjected to magnetic stirring until reach homogeneity. Viscous alginate solution was slightly centrifuged and then kept in uncapped glass jar in cell culture hood for minimizing bubble entrapment in the solution. Similarly, the cross-linking solution was prepared by dissolving calcium chloride in ultra-purified water (Invitrogen™ Life Technologies, Carlsbad, CA) at 4% (w/v). Alginate crosslinks when it has contact with calcium chloride solution on the contacting surface, and gradually polymerize throughout the entire structure. By taking advantage of this property, bioprinting enables printing of tubular conduits directly through a coaxial nozzle system. 4% alginate tubular structure was printed as semi-permeable conduits, serving as a molding capsule for tissue strand fabrication, and allowing media diffusion for gas and nutrient exchange, as well as waste removal from cellular metabolism.

Cell Preparation

The fresh stifle joints from young adult cattle (15-24 months old) were obtained from a local abattoir (Bud's Custom Meats, Riverside, Iowa City, Iowa). Articular cartilage was harvested from the femur condyle and rinsed in Hank's Balanced Salt Solution (Life Technologies, California, USA) supplemented with 100 U/µl penicillin, 100 µg/ml streptomycin, and 2.5 µg/µl fungizone (Invitrogen™ Life Technologies, Carlsbad, CA). Full thickness cartilage samples were minced into fine pieces, and then digested overnight with 0.25 mg/ml collagenase type I and pronase E (1:1) (Sigma-Aldrich, St. Louis, MO) dissolved in culture medium in a shaking incubator overnight (0.25 mg/ml each). After isolation, primary chondrocytes were re-plated and cultured in Dulbecco's modified Eagle's medium (DMEM) and Ham's F12 (1:1 mixture) supplemented with 10% fetal bovine serum (Life Technologies, Grand Island, NY), 50 µg/µl L-ascorbate, 100 U/µl penicillin, 100 µg/ml streptomycin, and 2.5 µg/µl fungizone at 37° C. with 5% $CO_2$. Cells were expanded until desired number was reached, and harvested for further use.

Fabrication of Tissue Strands

Upon harvesting, cells were further washed by PBS, and resuspended in 10 ml culture media and centrifuged at 3,500 RPM. The resulting pellet was incubated at 37° C. with 5% $CO_2$ for overnight in DMEM-based media with 2% fetal bovine serum, supplemented with 10 µg/µl penicillin, 10 µg/ml streptomycin, and 2.5 µg/µl Fungizone (Invitrogen™ Life Technologies, Carlsbad, CA), in order to have sufficient adhesive ability and mechanical integrity during further processing. The next day, cell pellet was aspirated by a customized syringe unit (Hamilton Company, Reno, NV), and was gently injected into tubular conduits. Tubular conduits were used as semi-permeable capsules for cell aggregation by tying ends with vascular clamps (Thomas Scientific, Swedesboro, NJ). Semi-permeable alginate capsules do not allow cells to move out and keep them nutrient-ionized during the aggregation process. The encapsulated structure was incubated for at least 7 days to ensure structural stability and mechanical strength. Then, the conduit was dissolved by breaking crosslinks in alginate network after exposing them to 1% sodium citrate solution for 10 minutes. This left pure cell aggregates in cylindrical form with acceptable cohesiveness to handle for transferring. Microscopic images were taken daily to monitor changes of tissue strands. The dimension of cell strands was measured upon releasing from vascular conduits using ImageJ (National Institutes of Health, Bethesda, Maryland) analysis on microscopic images. A schematic of the overall process is provided in FIG. 74.

Self-assembly is a characteristic property of cellular constructs like tissue spheroids, which granted them the capability to form larger tissue upon cellular fusion. To test the potential of tissue strands for self-assembling into larger tissue, fusion experiments were carried out between matured tissue strands. Briefly, two individual strands were placed onto 150 mm petri dish close to each other with contact and confined by PCL mold. A minimum amount of culture media were supplemented into culture to ensure cell survival. Calcein AM was used for viable cell staining for visualizing cell growth and migration. Fluorescence microscopic images (Leica Microsystems Inc., Buffalo Grove, IL) were taken at different time points to monitor the fusion process with minimal disturbance.

Cell Viability and Proliferation Study

Cell viability assay was carried out by LIVE/DEAD staining per the manufacturer's instructions. Cell Calcein acetoxymethylester (calcein AM) and ethidiumhomodimer-2 (Invitrogen™ Life Technologies, Carlsbad, CA), at a concentration of 1.0 mM each, was used. Calcein AM labels living cells with bright green fluorescent. Ethidium homodimer is a red fluorophore that stains non-viable cells but cannot penetrate living cells. Each sample was washed with HBSS before live/dead staining. After 30-minute incubation, samples were imaged using an Olympus FluoView™ FV1000 laser scanning confocal microscope (LSCM) (Olympus NDT Inc., MA). Z-axis projections were assembled from images of each sample from surface to bottom with a depth of 1000 µm at 20-µm intervals. ImageJ software (National Institutes of Health, Bethesda, Maryland) was used for automated quantification of the intensity of red- and green-stained tissue strands. The percentage of viable cells for each experimental group was calculated by averaging the values of three different locations from three different samples.

The proliferation of encapsulated chondrocytes was analyzed by alamar Blue assay kit. Briefly, tissue strands were cut into 5 mm squares and were washed with Hank's Balanced Salt Solution (Life Technologies, California, USA) and incubated with alamarBlue solution for 1 h. The fluorescence of reduced alamarBlue in the solution was determined using a spectrophotometer at wavelengths of 530-nm excitation and 600-nm emission. Tissue strands were then lysed and subjected to BCA protein assay to standardize alamarBlue fluorescence data.

Total RNA Extraction, Reverse Transcription and RT-PCR Analysis

Cartilage tissue strands were homogenized in TRIzol® reagent (Invitrogen™ Life Technologies, Carlsbad, CA), and total RNA was extracted using the RNeasy Mini Kit (QIAGEN, Valencia, CA) according to the manufacturer's instructions. cDNA was reverse transcribed using TaqMan Micro RNA reverse transcription kits (Life Technologies, Carlsbad, CA) according to instructions from the vendor. SYBR Green Real-Time PCR kits (Life Technologies, Carlsbad, CA) were used to analyze transcription levels of cartilage matrix related genes including: collagen type II, Aggrecan, and chondrogenic transcription factor Sox9. Primers were purchased from Integrated DNA Technologies (Coralville, IA). All gene expression was normalized to β-actin.

Histology and Immunohistochemistry Analysis

Cultured samples were frozen sectioned and fixed in 4% para-formaldehyde prior to histological evaluation. Sections underwent haematoxylin and Safranin O-fast green staining according to standard protocols. For immunohistochemical analysis, 10 µm sections were incubated for 30 min with blocking reagent made from to prevent nonspecific binding, and then incubated with primary antibodies overnight at room temperature. Rabbit anti-human polyclonal antibodies against collagen type II, and Aggrecan were used in this example. Both staining were developed using DAB (Vector Laboratories, Burlingame, CA) followed by Hematoxylin counterstaining (Sigma, St. Louis, MO). Microscopy was performed with an Olympus BX60 microscope (Olympus, Center Valley, PA).

DMMB Assay for sGAG Content Evaluation sGAG content was determined by dimethylmethylene blue (DMMB) dye-binding assay. Briefly, serially diluted samples were prepared and the DMMB solution was added. The absorbance was measured at 530 nm using the VMax Kinetic ELISA microplate reader (Molecular Devices, Inc., Sunnyvale, CA). sGAG content was normalized to DNA content in each specimen, and presented as sGAG per cell. DNA quantification was also carried out. Briefly, two weeks cultured tissue strands as well as native articular cartilage were digested in the papain buffer, and then subjected to DNA quantitation assay. Quant-iT™ PicoGreen dsDNA Assay Kit (Molecular Probes, Inc., Eugene, OR) was used according to manufacturer's instructions. Fluorescence intensity was determined by SpectraMax multidetection microplate reader (Molecular Devices, Inc., Sunnyvale, CA), using the wavelength of 480 nm (excitation) and 520 nm (emission). sGAG content from each sample was normalized to dsDNA content.

Statistical Analysis

All data are presented as the mean±SD and were analyzed by GraphPad Prism 6 (GraphPad Software, Inc., CA, USA) using Student's t-test. P values less than 0.05 were considered significant. Results were presented by mean±SEM. The percentage of viable cells for each experimental group was calculated by averaging the values of three different locations from three different samples.

Results

Fabrication of Semi-Permeable Tubular Conduits

By using coaxial nozzle assembly made of 22 G inner nozzle and 14 G outer nozzle, tubular conduits were successfully extruded with continuous uniform structural integrity, as presented in FIG. 69A. The average lumen diameter and tubular conduits diameter of the fabricated conduits were 709±15.9 μm and 1248.5±37.2 μm, respectively (n=6) (See FIG. 69B). By controlling fabrication parameters, different sizes of conduits can be fabricated. It is possible to fabricated any length of conduits with sufficient continuity and flexibility. This unique strength can allow the production of various sizes of tissue strands upon different requests for further tissue fabrication.

Fabrication of Cartilage Tissue Strands

Cell pellet was successfully transferred into about 150 mm long micro-tubular capsule (FIGS. 70A, 70C and 70D), with minimal loss of cellular material. Macroscopically, tissue strands were formed with good integrity and mechanical strength both in the tubular capsules and upon de-crosslinking of conduits after 4 days of in vitro incubation (FIGS. 70B and 70E).

As shown in FIG. 70A, cellular material was cast into the conduits with close contact to the inner wall of the conduits. Overtime, as tissue strands formed, their sizes started to diminish in the radial direction due to contraction, during which visible gaps were observed between the border of tissue strands and the inner wall of the conduits. FIG. 70G showed the average diameter of tissue strands gradually reduced from the 639±47 μm (Day 1) to 507±18 μm (Day 10), and did not have significant further changes, ending with 508±21 μm (Day 14). Based on an intensity calculation on both live and dead fluorescence channels of fabricated strands, the viability was maintained upon fabrication as well as during incubation. The average viability on Day 1 post fabrication was 75±0.5%, and gradually increased to 77±0.5%, and finally reached the viability of 87±3% at day 7. In cell viability experiments, the maintained high cell viability demonstrates the biocompatibility of the proposed fabrication method, which not only enables fabrication of tissue strands, but also guaranteed minimal cell damage. After conduit fabrication, cell proliferation was only mildly affected, with no significant difference (P>0.05) compared to day 5, while a longer culture time showed a slight increase of growth and proliferation (day 7), which remain stable with the time of culture. It should be noted that the chondrocytes growth in conduit was not due to cellular toxicity of alginate conduit.

Successful fusion of cellular constructs, such as tissue spheroids and tissue strands, is key for proposed scale-up tissue or organ fabrication. Fusion of tissue strands started as early as 24 hr (FIGS. 71A, 71D, and 71G) post fabrication during incubation, and further fused with more cell migration and ingrowth into each other between two strands on day 4 (FIGS. 71B, 71E, and 71H), also the two strand were slightly contacted towards each other, with the edge lightly rounded up. At day 7, two strands were almost completely fused into one larger strand, with more contracted morphology, and not a visible gap between each other (FIGS. 71C, 71F and 71I). This observation supported the capability of tissue strands as building block for large-scale tissue fabrication.

To further validate the potential of tissue strands, the functionality of cultured cartilage tissue strands was observed. Cartilage specific genes and protein markers were assessed. Gene expression analysis revealed relatively higher expression of cartilage-specific marker genes in tissue strands compared with cultured chondrocytes. In real-time PCR, Sox-9 showed a nearly 4-fold change (p=0.0069), which indicated that chondrocytes were better differentiated towards chondrogenic lineage within tissue strands (FIG. 75A). COL2A gene showed a nearly 6-fold increase (p=0.0089) compared with cultured chondrocytes, indicating that cells were actively making cartilage-specific protein to serve as extracellular matrix within tissue strands (FIG. 75B). Aggrecan genes (ACAN) were up-regulated to nearly 3-fold (p=0.014) in tissue strands, which further indicates that the tissue strand is an ideal environment for chondrocytes to differentiate and carry out their chondrogenic function (FIG. 75C).

Histological evaluation of cartilage tissue strands was carried out at the end of 2 weeks in vitro culture. After two weeks of chondrogenic induction, a substantial amount of proteoglycan deposition was observed in tissue strands with strong positive staining for safranin-O (FIG. 76A) close to native cartilage tissue (FIG. 76B). Safranin-O staining was homogeneously distributed throughout the entire tissue strand, and cells within tissue strands also displayed characteristic cobblestone-like morphology (FIG. 76C). Tissue strands have higher cellularity, while native cartilage has relatively lower cell density and higher ratio of extra cellular matrix. Although cells within tissue strands were not fully developed with their lacunae compared with native cartilage (FIG. 76D), further maturation would grant them more differentiated characteristics.

In DMMB assay, sGAG content from tissue strands were 200.9±21.69 μg/ng DNA, while native cartilage had sGAG content of 178.1±11.45 μg/ng DNA (FIG. 76E). Tissue strands showed slightly higher proteoglycan production in comparison with native articular cartilage, while no significant differences present between these two.

To further assess the properties of cartilage tissue strands, immunostaining was used to characterize classic cartilage matrix specific markers (Type II collagen, Aggrecan) expression Immunohistochemistry showed a significant amount of type II collagen (Dark brown) positive staining, (FIG. 77B) as well as aggrecan (Dark purple) positive staining (FIG. 77C), throughout the slides of tissue strands. Stronger staining for both markers was observed at the edges, which represent the outer region of tissue strands. In control images (FIGS. 77A and 77D), only background color was observed. No specific staining was visible at different magnitude. All these data demonstrated that tissue strands could promote chondrocytes differentiation, forming cartilage tissue in vitro. Regenerated cartilage closely resembled the characteristics of native cartilage tissue.

Thus, in this example, a scalable tissue strand fabrication technique was developed, and the technique can use a "bioink" to facilitate a scale-up organ printing process. A conventional tissue spheroid fabrication technique was modified by applying tissue strands made of pure cells for tissue or organ fabrication with the assistance of a robotic printer. The micro-tubular conduits disclosed herein served as a great reservoir for fabricating tissue strands, which demonstrated nearly 90% cell viability, fast fusion, and maintained functionality with tissue specific markers expression.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

REFERENCES

1. Szpalski, C., Barr, J., Wetterau, M., Saadeh, P. B., and Warren, S. M., 2010, "Cranial bone defects: current and future strategies," Neurosurgical Focus, 29(6), p. E8.
2. Khan, S. N., Cammisa, F. P., Sandhu, H. S., Diwan, A. D., Girardi, F. P., and Lane, J. M., 2005, "The Biology of Bone Grafting," Journal of the American Academy of Orthopaedic Surgeons, 13(1), pp. 77-86.
3. Hou, C. H., Yang, R. S., and Hou, S. M., 2005, "Hospital-based allogenic bone bank—10-year experience," Journal of Hospital Infection, 59(1), pp. 41-45.
4. Bender, S. A., Rogalski, J. B., Mills, M. P., Arnold, R. M., Cochran, D. L., and Mellonig, J. T., 2005, "Evaluation of Demineralized Bone Matrix Paste and Putty in Periodontal Intraosseous Defects," Journal of Periodontology, 76(5), pp. 768-777.
5. Zhang, X., Chang, W., Lee, P., Wang, Y., Yang, M., Li, J., Kumbar, S. G., and Yu, X., 2014, "Polymer-Ceramic Spiral Structured Scaffolds for Bone Tissue Engineering: Effect of Hydroxyapatite Composition on Human Fetal Osteoblasts," PLoS ONE, 9(1), p. e85871.
6. Mouriño, V., and Boccaccini, A. R., 2010, "Bone tissue engineering therapeutics: controlled drug delivery in three-dimensional scaffolds," Journal of The Royal Society Interface, 7(43), pp. 209-227.
7. Nandi, S. K., Ghosh, S. K., Kundu, B., De, D. K., and Basu, D., 2008, "Evaluation of new porous β-tri-calcium phosphate ceramic as bone substitute in goat model," Small Ruminant Research, 75(2-3), pp. 144-153.
8. Betz, V., Betz, O., Harris, M., Vharas, M., and Evans, C. H., 2008, "Bone tissue engineering and repair by gene therapy," Frontiers in Bioscience 13, pp. 933-841.
9. Fong, K. D., Warren, S. M., Loboa, E. G., Henderson, J. H., Fang, T. D., Cowan, C. M., Carter, D. R., and Longaker, M. T., 2003, "Mechanical Strain Affects Dura Mater Biological Processes: Implications for Immature Calvarial Healing," Plastic and Reconstructive Surgery, 112(5), pp. 1312-1327.
10. Aalami, O. O., Nacamuli, R. P., Lenton, K. A., Cowan, C. M., Fang, T. D., Fong, K. D., Shi, Y.-Y., Song, H. M., Sahar, D. E., and Longaker, M. T., 2004, "Applications of a Mouse Model of Calvarial Healing: Differences in Regenerative Abilities of Juveniles and Adults," Plastic and Reconstructive Surgery, 114(3), pp. 713-720.
11. Gary, R., and Arin, G., 2012, "Autogenous Bone Graft: Basic Science and Clinical Implications," Journal of Craniofacial Surgery, 23(1), pp. 323-327.
12. Elsalanty, M. E., and Genecov, D. G., 2009, "Bone Grafts in Craniofacial Surgery," Cranial Maxillofac Trauma Reconstruction, 2(03), pp. 125-134.
13. Roohani-Esfahani, S. I., Dunstan, C. R., Li, J. J., Lu, Z., Davies, B., Pearce, S., Field, J., Williams, R., and Zreiqat, H., 2013, "Unique microstructural design of ceramic scaffolds for bone regeneration under load," Acta Biomaterialia, 9(6), pp. 7014-7024.
14. Yang, F., Wang, J., Hou, J., Guo, H., and Liu, C., 2013, "Bone regeneration using cell-mediated responsive degradable PEG-based scaffolds incorporating with rhBMP-2," Biomaterials, 34(5), pp. 1514-1528.
15. Yuan, H., Fernandes, H., Habibovic, P., de Boer, J., Barradas, A. M. C., de Ruiter, A., Walsh, W. R., van Blitterswijk, C. A., and de Bruijn, J. D., 2010, "Osteoinductive ceramics as a synthetic alternative to autologous bone grafting," Proceedings of the National Academy of Sciences, 107(31), pp. 13614-13619.
16. Kneser, U., Schaefer, D. J., Polykandriotis, E., and Horch, R. E., 2006, "Tissue engineering of bone: the reconstructive surgeon's point of view," Journal of Cellular and Molecular Medicine, 10(1), pp. 7-19.
17. Zhou, S., Li, Y.-B., Wang, Y.-Y., Zuo, Y., Gao, S.-B., and Zhang, L., 2014, "Injection-molded porous hydroxyapatite/polyamide-66 scaffold for bone repair and investigations on the experimental conditions," Polymer Engineering & Science, 54(5), pp. 1003-1012.
18. Naznin, S., and Min, W., 2012, "PHBV/PLLA-based composite scaffolds fabricated using an emulsion freezing/freeze-drying technique for bone tissue engineering: surface modification and in vitro biological evaluation," Biofabrication, 4(1), p. 015003.
19. Thadavirul, N., Pavasant, P., and Supaphol, P., 2013, "Development of Polycapraloctone Porous Scaffolds By Combining Solvent Casting, Particulate Leaching, and Polymer Leaching Techniques for Bone Tissue Engineering," Journal of Biomedical Materials Research Part A, DOI: 10.1002/jbma.35010 (In Press).
20. Zhou, C., Shi, Q., Guo, W., Terrell, L., Qureshi, A. T., Hayes, D. J., and Wu, Q., 2013, "Electrospun Bio-Nanocomposite Scaffolds for Bone Tissue Engineering by Cellulose Nanocrystals Reinforcing Maleic Anhydride Grafted PLA," ACS Applied Materials & Interfaces, 5(9), pp. 3847-3854.
21. Di Martino, A., Liverani, L., Rainer, A., Salvatore, G., Trombetta, M., and Denaro, V., 2011, "Electrospun scaffolds for bone tissue engineering," Musculoskelet Surg, 95(2), pp. 69-80.
22. Yoshikawa, H., Tamai, N., Murase, T., and Myoui, A., 2009, "Interconnected porous hydroxyapatite ceramics for bone tissue engineering," Journal of The Royal Society Interface, 6(Suppl 3), pp. S341-S348.
23. Tarafder, S., Davies, N. M., Bandyopadhyay, A., and Bose, S., 2013, "3D printed tricalcium phosphate bone tissue engineering scaffolds: effect of SrO and MgO doping on in vivo osteogenesis in a rat distal femoral defect model," Biomaterials Science, 1(12), pp. 1250-1259.
24. Bose, S., Vahabzadeh, S., and Bandyopadhyay, A., 2013, "Bone tissue engineering using 3D printing," Materials Today, 16(12), pp. 496-504.
25. Sabir, M., Xu, X., and Li, L., 2009, "A review on biodegradable polymeric materials for bone tissue engineering applications," J Mater Sci, 44(21), pp. 5713-5724.
26. Khosla, S., Westendorf, J. J., and Modder, U. I., 2010, "Concise Review: Insights from Normal Bone Remodeling and Stem Cell-Based Therapies for Bone Repair," Stem Cells, 28(12), pp. 2124-2128.
27. Milner, P. I., Clegg, P. D., and Stewart, M. C., 2011, "Stem Cell-based Therapies for Bone Repair," Veterinary Clinics of North America: Equine Practice, 27(2), pp. 299-314.
28. Jun, S.-H., Lee, E.-J., Jang, T.-S., Kim, H.-E., Jang, J.-H., and Koh, Y.-H., 2013, "Bone morphogenic protein-2 (BMP-2) loaded hybrid coating on porous hydroxyapatite scaffolds for bone tissue engineering," J Mater Sci: Mater Med, 24(3), pp. 773-782.
29. Hou, L.-T., Liu, C.-M., Liu, B.-Y., Chang, P.-C., Chen, M.-H., Ho, M.-H., Jehng, S.-M., and Liu, H.-C., 2007, "Tissue Engineering Bone Formation in Novel Recombinant Human Bone Morphogenic Protein 2-Atelocollagen Composite Scaffolds," Journal of Periodontology, 78(2), pp. 335-343.
30. Elangovan, S., D'Mello, S. R., Hong, L., Ross, R. D., Allamargot, C., Dawson, D. V., Stanford, C. M., Johnson, G. K., Sumner, D. R., and Salem, A. K., 2014, "The enhancement of bone regeneration by gene activated matrix encoding for platelet derived growth factor," Biomaterials, 35(2), pp. 737-747.
31. Cowan, C., Shi, Y.-Y., Aalami, O., Chou, Y.-F., Mari, C., Thomas, R., Quarto, N., Contag, C., Wu, B., and Longaker, M., 2004, "Adipose-derived adult stromal cells heal critical-size mouse calvarial defects," Nature Biotechnology, 22, pp. 560-567.
32. Doan, L., Kelley, C., Luong, H., English, J., Gomez, H., Johnson, E., Cody, D., and Duke, P. J., 2010, "Engineered cartilage heals skull defects," American Journal of Orthodontics and Dentofacial Orthopedics, 137(2), pp. 162.e1-9.
33. Barnes, G. L., Kostenuik, P. J., Gerstenfeld, L. C., and Einhorn, T. A., 1999, "Growth Factor Regulation of Fracture Repair," Journal of Bone and Mineral Research, 14(11), pp. 1805-1815.
34. Ishidou, Y., Kitajima, I., Obama, H., Maruyama, I., Murata, F., Imamura, T., Yamada, N., Ten Duke, P., Miyazono, K., and Sakou, T., 1995, "Enhanced expression of type I receptors for bone morphogenetic proteins during bone formation," Journal of Bone and Mineral Research, 10(11), pp. 1651-1659.
35. Akihito, M., Munehito, Y., Mamoru, K., Motohiro, O., Yoshio, E., Hiroshi, H., and Scott, B., 2007, "The Effects of Bone Morphogenetic Protein and Basic Fibroblast Growth Factor on Cultured Mesenchymal Stem Cells for Spine Fusion," Spine, 32, pp. 1067-1071.
36. Saijo, M., Kitazawa, R., Nakajima, M., Kurosaka, M., Maeda, S., and Kitazawa, S., 2003, "Heparanase mRNA expression during fracture repair in mice," Histochem Cell Biol, 120(6), pp. 493-503.
37. Evans, C. H., 2010, "Gene therapy for bone healing," Expert Reviews in Molecular Medicine, 12, p. e18.
38. Odde, D. J., and Renn, M. J., 1999, "Laser-guided direct writing for applications in biotechnology," Trends in biotechnology, 17(10), pp. 385-389.
39. Ovsianikov, A., Gruene, M., Pflaum, M., Koch, L., Maiorana, F., Wilhelmi, M., Haverich, A., and Chickkov, B., 2010, "Laser Printing of Cells into 3D Scaffolds," Biofabrication, 2(1), p. 014104.
40. Nahmias, Y., Schwartz, R. E., Verfaillie, C. M., and Odde, D. J., 2005, "Laser-guided direct writing for three-dimensional tissue engineering," Biotechnol Bioeng, 92(2), pp. 129-136.
41. Boland, T., Xu, T., Damon, B., and Cui, X., 2006, "Application of inkjet printing to tissue engineering," Biotechnology journal, 1(9), pp. 910-917.
42. Mironov, V., 2003, "Printing technology to produce living tissue," Expert opinion on biological therapy, 3(5), pp. 701-704.
43. Nair, K., Yan, K., and Sun, W., 2007, "A Multi-Level Numerical Model for Qunatifying Cell Deformation in Encapsulated Alginate Structures" Journal of Mechanics of Materials and Structures, 6(2), pp. 1121-1139.
44. Skardal, A., Mack, D., Kapetanovic, E., Atala, A., Jackson, J. D., Yoo, J., and Soker, S., 2012, "Bioprinted Amniotic Fluid-Derived Stem Cells Accelerate Healing of Large Skin Wounds," Stem Cells Translational Medicine, 1(11), pp. 792-802.
45. Cui, X., Breitenkamp, K., Finn, M. G., Lotz, M., and D'Lima, D., 2012, "Direct Human Cartilage Repair Using Three-Dimensional Bioprinting Technology," Tissue Engineering Part A, 18(11-12), pp. 1304-1312.
46. Keriquel, V., Guillemot, F., Arnault, I., Guillotin, B., Miraux, S., Amédée, J., Fricain, J.-C., and Catros, S., 2010, "In vivo bioprinting for computer- and robotic-assisted medical intervention: preliminary study in mice," Biofabrication, 2(1), p. 014101.
47. Ozbolat, I. T., Chen, H., and Yu, Y., 2014, "Development of 'Multi-arm Bioprinter' for hybrid biofabrication of tissue engineering constructs," Robotics and Computer-Integrated Manufacturing, 30(3), pp. 295-304.
48. Lee, V. K., Kim, D. Y., Ngo, H., Lee, Y., Seo, L., Yoo, S.-S., Vincent, P. A., and Dai, G., "Creating perfused functional vascular channels using 3D bio-printing technology," Biomaterials(0).
49. Bertassoni, L. E., Cardoso, J. C., Manoharan, V., Cristino, A. L., Bhise, N. S., Araujo, W. A., Zorlutuna, P., Vrana, N. E., Ghaemmaghami, A. M., Dokmeci, M. R., and Khademhosseini, A., 2014, "Direct-write bioprinting of cell-laden methacrylated gelatin hydrogels," Biofabrication, 6(2), p. 024105.
50. Malda, J., Visser, J., Melchels, F. P., Jiingst, T., Hennink, W. E., Dhert, W. J. A., Groll, J., and Hutmacher, D. W., 2013, "25th Anniversary Article: Engineering Hydrogels for Biofabrication," Advanced Materials, 25(36), pp. 5011-5028.
51. Mironov, V., Visconti, R. P., Kasyanov V., Forgacs G., Drake C. J., Markwald, R. R., 2009, "Organ printing: Tissue spheroids as building blocks," Biomaterials, 30(12), pp. 2164-2174.
52. Mehesz, A. N., Brown, J., Hajdu, Z., Beaver, W., Silva, J. V. L. d., Visconti, R. P., Markwald, R. R., and Mironov, V., 2011, "Scalable robotic biofabrication of tissue spheroids," Biofabrication, 3(2), p. 025002.
53. Norotte, C., Marga, F. S., Niklason, L. E., and Forgacs, G., 2009, "Scaffold-free vascular tissue engineering using bioprinting," Biomaterials, 30(30), pp. 5910-5917.
54. Pati, F., Jang, J., Ha, D.-H., Kim, S. W., Rhie, J.-W., Shim, J.-H., Kim, D.-H., and Cho, D.-W., 2014, "Printing three-dimensional tissue analogues with decellularized extracellular matrix bioink," Nature Communications, 5, p. 3935.
55. Ozbolat, I. T., and Yin, Y., 2013, "Bioprinting Toward Organ Fabrication: Challenges and Future Trends," IEEE Biomedical Engineering, 60(3), pp. 691-699.
56. Yu, Y., Zhang, Y., and Ozbolat, I. T., 2014, "A Hybrid Bioprinting Approach for Scale-up Tissue Fabrication," ASME Journal of Manufacturing Science and Engineering DOI: 10.1115/1.4028511 (In Press).

57. Xu, T., Zhao, W., Zhu, J.-M., Albanna, M. Z., Yoo, J. J., and Atala, A., 2013, "Complex heterogeneous tissue constructs containing multiple cell types prepared by inkjet printing technology," Biomaterials, 34(1), pp. 130-139.

58. [Guillemot, F., Guillotin, B., Fontaine, A., Ali, M., Catros, S., Kériquel, V., Fricain, J.-C., Rémy, M., Bareille, R., and Amedee-Vilamitjana, J., 2011, "Laser-assisted bioprinting to deal with tissue complexity in regenerative medicine," MRS Bulletin, 36(12), pp. 1015-1019.

59. Guillemot, F., Souquet, A., Catros, S., and Guillotin, B., 2010, "Laser-assisted cell printing: principle, physical parameters versus cell fate and perspectives in tissue engineering," Nanomedicine, 5(3), pp. 507-515.

60. Lee, V., Lanzi, A., Ngo, H., Yoo, S.-S., Vincent, P., and Dai, G., 2014, "Generation of Multi-scale Vascular Network System Within 3D Hydrogel Using 3D Bio-printing Technology," Cell. Mol. Bioeng., pp. 1-13.

61. Melchels, F. P. W., Domingos, M. A. N., Klein, T. J., Malda, J., Bartolo, P. J., and Hutmacher, D. W., 2012, "Additive manufacturing of tissues and organs," Progress in Polymer Science, 37(8), pp. 1079-1104.

62. Wongrakpanich, A., Adamcakova-Dodd, A., Xie, W., Joshi, V. B., Mapuskar, K. A., Geary, S. M., Spitz, D. R., Thorne, P. S., and Salem, A. K., 2014, "The Absence of CpG in Plasmid DNA-Chitosan Polyplexes Enhances Transfection Efficiencies and Reduces Inflammatory Responses in Murine Lungs," Molecular Pharmaceutics, 11(3), pp. 1022-1031.

63. Khoda, A., Ozbolat, I. T., and Koc, B., 2011, "A functionally gradient variational porosity architecture for hollowed scaffolds fabrication," Biofabrication, 3(3), p. 034106.

64. Khoda, A. K. M., Ozbolat, I. T., and Koc, B., 2011, "Engineered Tissue Scaffolds with Variational Porous Architecture," ASME Transcations, Journal of Biomechanical Engineering, 133(1), p. 011001.

65. Snykers, S., Vanhaecke, T., and Rogiers, V., 2006, "Isolation of Rat Bone Marrow Stem Cells," Cytochrome P450 Protocols, I. Phillips, and E. Shephard, eds., Humana Press, pp. 265-272.

66. Yu, Y., Zhang, Y., Martin, J. A., and Ozbolat, I. T., 2013, "Evaluation of Cell Viability and Functionality in Vessel-like Bioprintable Cell-Laden Tubular Channels," Journal of Biomechanical Engineering, 135(9), pp. 091011-091011.

67. Salem, A. K., 2014, "Recent progress on the development of gene-activated scaffolds encoding PDGF for enhanced bone regeneration," Regenerative Medicine, 9(3), pp. 253-254.

68. Hong, L., Krishnamachari, Y., Seabold, D., Joshi, V., Schneider, G., and Salem, A. K., 2011, "Intracellular Release of 17-β Estradiol from Cationic Polyamidoamine Dendrimer Surface-Modified Poly (Lactic-co-Glycolic Acid) Microparticles Improves Osteogenic Differentiation of Human Mesenchymal Stromal Cells," Tissue Engineering Part C, 17(3), pp. 319-325.

69. D'Mello, S., Salem, A. K., Hong, L., and Elangovan, S., 2014, "Characterization and evaluation of the efficacy of cationic complex mediated plasmid DNA delivery in human embryonic palatal mesenchyme cells," Journal of tissue engineering and regenerative medicine DOI: 10.1002/term.1873 (In Press).

70. Intra, J., and Salem, A. K., 2011, "Rational design, fabrication, characterization and in vitro testing of biodegradable microparticles that generate targeted and sustained transgene expression in HepG2 liver cells," Journal of drug targeting, 19(6), pp. 393-408.

71. Intra, J., and Salem, A. K., 2010, "Fabrication, characterization and in vitro evaluation of poly(D,L-lactide-co-glycolide) microparticles loaded with polyamidoamine-plasmid DNA dendriplexes for applications in nonviral gene delivery," Journal of Pharmaceutical Sciences, 99(1), pp. 368-384.

72. Zhang, X. Q., Intra, J., and Salem, A. K., 2008, "Comparative study of poly (lactic-co-glycolic acid)-poly ethyleneimine-plasmid DNA microparticles prepared using double emulsion methods," Journal of Microencapsulation, 25(1), pp. 1-12.

73. Intra, J., and Salem, A. K., 2008, "Characterization of the transgene expression generated by branched and linear polyethylenimine-plasmid DNA nanoparticles in vitro and after intraperitoneal injection in vivo," Journal of Controlled Release, 130(2), pp. 129-138.

74. Abbas, A. O., Donovan, M. D., and Salem, A. K., 2008, "Formulating poly(lactide-co-glycolide) particles for plasmid DNA delivery," Journal of Pharmaceutical Sciences, 97(7), pp. 2448-2461.

75. Zhang, X. Q., Intra, J., and Salem, A. K., 2007, "Conjugation of polyamidoamine dendrimers on biodegradable microparticles for nonviral gene delivery," Bioconjugate Chemistry, 18(6), pp. 2068-2076.

76. Wei, N., Yu, Y., Joshi, V., Schmidt, T., Qian, F., Salem, A. K., Stanford, C., and Hong, L., 2013, "Glucocorticoid receptor antagonist and siRNA prevent senescence of human bone marrow mesenchymal stromal cells in vitro," Cell and Tissue Research, 354(2), pp. 461-470.

77. Hong, L., Wei, N., Joshi, V., Yu, Y., Kim, N., Krishnamachari, Y., Zhang, Q., and Salem, A. K., 2012, "Effects of glucocorticoid receptor small interfering RNA delivered using poly lactic-co-glycolic acid microparticles on proliferation and differentiation capabilities of human mesenchymal stromal cells," Tissue engineering. Part A, 18(7-8), pp. 775-784.

78. Zhu, G. Z., Mallery, S. R., and Schwendeman, S. P., 2000, "Stabilization of proteins encapsulated in injectable poly (lactide-co-glycolide)," Nature Biotechnology, 18(1), pp. 52-57.

79. Hockaday, L. A., Kang, K. H., Colangelo, N. W., Cheung, P. Y. C., Duan, B., Malone, E., Wu, J., Girardi, L. N., Bonassar, L. J., Lipson, H., Chu, C. C., and Butcher, J. T., 2012, "Rapid 3D printing of anatomically accurate and mechanically heterogeneous aortic valve hydrogel scaffolds," Biofabrication, 4(3), p. 035005.

80. Zhang, Y., Yu, Y., and Ozbolat, I. T., 2013, "Direct Bioprinting of Vessel-Like Tubular Microfluidic Channels," Journal of Nanotechnology in Engineering and Medicine, 4(2), pp. 021001-021001.

81. Khatiwala, C., Law, R., Shepherd, B., Dorfman, S., and Csete, M., 2012, "3D Cell Bioprinting for Regenerative Medicine Research and Therapies," Gene Therapy and Regulation, 07(01), p. 1230004.

82. Gosain, A. K., Santoro, T. D., Song, L. S., Capel, C. C., Sudhakar, P. V., and Matloub, H. S., 2003, "Osteogenesis in calvarial defects: contribution of the dura, the pericranium, and the surrounding bone in adult versus infant animals.," Plastic and Reconstructive Surgery, 112(2), pp. 515-527.

83. Nguyen, T.-H., Bao, T. Q., Park, I., and Lee, B.-T., 2013, "A novel fibrous scaffold composed of electrospun porous poly(ε-caprolactone) fibers for bone tissue engineering," Journal of Biomaterials Applications, 28(4), pp. 514-528.

84. Khalil, S., and Sun, W., 2007, "Biopolymer deposition for freeform fabrication of hydrogel tissue constructs," Material Science and Engineering: C, 27(3), pp. 469-478.

85. Ozbolat, I. T., Howard, C., and Yu, Y., 2013, "Bioprinter and Methods of using Same," United States Patent and Trademark Office, USA (Provisional patent submitted).
86. Wang, J., and Glimcher, M., 1999, "Characterization of matrix-induced osteogenesis in rat calvarial bone defects: II. Origins of bone forming cells.," Calcified Tissue International, 65(6), pp. 486-493.
87. Wang, J., Yang, R., Gerstenfeld, L. C., and Glimcher, M. J., 2000, "Characterization of demineralized bone matrix-induced osteogenesis in rat calvarial bone defects: III. Gene and protein expression," Calcified Tissue International, 67(4), pp. 314-320.
88. Joseph, U. U., Arthur, V. S., Ian, W., Vasek, P., Harvey, A. G., Underhill, T. M., and
David, W. H., 2009, "In vivo micro-CT analysis of bone remodeling in a rat calvarial defect model," Physics in Medicine and Biology, 54(7), p. 2147.
89. Khoda, B., Ozbolat, I. T., and Koc, B., 2013, "Modeling of Variational Gradient Porous Architecture with Multi-directional Filament Deposition in 3D Scaffolds" Computer Aided Design and Applications, 10(3), pp. 445-459.
90. Khoda, A. K. M. B., Ozbolat, I. T., and Koc, B., 2013, "Spatially Multi-functional Porous Tissue Scaffold," Procedia Engineering, 59(0), pp. 174-182.
91. Ozbolat, I. T., Khoda, A., Marchany, M., Gardella, J. A., and Koc, B., 2012, "Hybrid tissue scaffolds for controlled release applications," Virtual and Physical Prototyping, 7(1), pp. 37-47.
92. Ozbolat, I. T., Khoda, A., and Koc, B., 2012, "Bioadditive manufacturing of hybrid tissue scaffolds for controlled release kinetics," Proc. International Mechanical Engineering Congress & Exposition.
93. Ozbolat, I. T., and Koc, B., 2012, "3D hybrid wound devices for spatiotemporally controlled release kinetics," Computer Methods and Programs in Biomedicine, 108 (3), pp. 922-931.
94. Ozbolat, I. T., and Khoda, A., 2014, "Design of a New Parametric Path Plan for Additive Manufacturing of Hollow Porous Structures with Functionally Graded Materials," ASME Journal of Computing and Information Science in Engineering, D01:10.1115/1.4028418 (In Press).
95. Bouletreau, P. J., Warren, S. M., Spector, J. A., Peled, Z. M., Gerrets, R. P., Greenwald, J. A., and Longaker, M. T., 2002, "Hypoxia and VEGF Up-Regulate BMP-2 mRNA and Protein Expression in Microvascular Endothelial Cells: Implications for Fracture Healing," Plastic and Reconstructive Surgery, 109(7), pp. 2384-2397.
96. Teng, S.-H., Lee, E.-J., Wang, P., and Kim, H.-E., 2008, "Collagen/hydroxyapatite composite nanofibers by electrospinning," Materials Letters, 62(17-18), pp. 3055-3058.
97. Zhang, Y., Venugopal, J. R., El-Turki, A., Ramakrishna, S., Su, B., and Lim, C. T., 2008, "Electrospun biomimetic nanocomposite nanofibers of hydroxyapatite/chitosan for bone tissue engineering," Biomaterials, 29(32), pp. 4314-4322.
98. Root Analysis Business Research & Consulting, 2014, "3D Bioprinting Market, 2014-2030," British Columbia.
99. Ozbolat, I. T., 2012, "Artificial Organ Fabrication: Towards 3D Organ Printing," Science and Technic, 539, pp. 58-61.
100. Dababneh, A., and Ozbolat, I. T., 2014, "Bioprinting Technology: A Current State-of-the Art Review," ASME Journal of Manufacturing Science and Engineering DOT: 10.1115/1.4028512 (In Press).
101. Yu, Y., and Ozbolat, I. T., 2014, "Tissue Strands as "Bioink" for Scale-up Organ Printing," 36th Annual International IEEE EMBS Conference, J. Duerk, and J. Ji, eds. Chicago, Illinois
102. Zhang, Y., Yu, Y., Akkouch, A., Dababneh, A., Dolati, F., and Ozbolat, I. T., 2014, "In Vitro Characterization of Directly Bioprinted Perfusable Vasculature Conduits," RSC Biomaterials Science DOI: 10.1039/C4BM00234B (In Press).
103. Mason, C., 2005, "Tissue Engineering Skin: A Paradigm Shift in Wound Care," Med. Device Technol., 16(10), pp. 32-33.
104. Langer, R., 2000, "Tissue Engineering," Mol. Ther., 1(1), pp. 12-15.
105. Shor, L., Güçeri, S., Gandhi, M., Wen, X., and Sun, W., 2008, "Solid Freeform Fabrication of Polycaprolactone/Hydroxyapatite Tissue Scaffolds," ASME J. Manuf. Sci. and Eng., 130(2), pp. 021018-021018.
106. Griffith, L. G., and Naughton, G., 2002, "Tissue Engineering—Current Challenges and Expanding Opportunities," Science, 295(5557), pp. 1009-1014.
107. Andersson, H., and Van Den Berg, A., 2004, "Microfabrication and Microfluidics for Tissue Engineering: State of the Art and Future Opportunities," Lab Chip, 4(2), pp. 98-103.
108. Mironov, V., Kasyanov, V., and Markwald, R. R., 2011, "Organ Printing: from Bioprinter to Organ Biofabrication Line," Curr. Opin. Biotechnol., 22(5), pp. 667-673.
109. Visconti, R. P., Kasyanov, V., Gentile, C., Zhang, J., Markwald, R. R., and Mironov, V., 2010, "Towards Organ Printing: Engineering an Intra-organ Branched Vascular Tree," Expert. Opin. Biol. Ther., 10(3), pp. 409-420.
110. Marga, F., Jakab, K., Khatiwala, C., Shepherd, B., Dorfman, S., Hubbard, B., Colbert, S., and Forgacs, G., 2012, "Toward Engineering Functional Organ Modules by Additive Manufacturing," Biofabrication, 4(2), p. 022001.
111. Takebe, T., Sekine, K., Enomura, M., Koike, H., Kimura, M., Ogaeri, T., Zhang, R.-R., Ueno, Y., Zheng, Y.-W., and Koike, N., 2013, "Vascularized and Functional Human Liver from an iPSC-derived Organ Bud Transplant," Nature, 499(7459), pp. 481-484.
112. Greggio, C., De Franceschi, F., Figueiredo-Larsen, M., Gobaa, S., Ranga, A., Semb, H., Lutolf, M., and Grapin-Botton, A., 2013, "Artificial Three-dimensional Niches Deconstruct Pancreas Development in vitro," Development, 140(21), pp. 4452-4462.
113. Schubert, T., Anders, S., Neumann, E., Schölmerich, J., Hofstädter, F., Grifka, J., Müller-Ladner, U., Libera, J., and Schedel, J., 2009, "Long-term Effects of Chondrospheres on Cartilage Lesions in an Autologous Chondrocyte Implantation Model as Investigated in the SCID Mouse Model," Int. J. Mol. Med., 23(4), pp. 455-460.
114. Novosel, E. C., Kleinhans, C., and Kluger, P. J., 2011, "Vascularization is the Key Challenge in Tissue Engineering," Adv. Drug Deliv. Rev., 63(4), pp. 300-311.
115. Mondy, W. L., Cameron, D., Timmermans, J.-P., Clerk, N. D., Sasov, A., Casteleyn, C., and Piegl, L., 2009, "Computer-aided Design of Microvasculature Systems for Use in Vascular Scaffold Production," Biofabrication, 1(3), p. 035002.
116. Zhang, Y., Yu, Y., Chen, H., and Ozbolat, I. T., 2013, "Characterization of Printable Cellular Micro-fluidic Channels for Tissue Engineering," Biofabrication, 5(2), p. 025004.
117. Fujimori, H., Asahina, K., Shimizu-Saito, K., Ikeda, R., Tanaka, Y., Teramoto, K., Morita, I., and Teraoka, H., 2008, "Vascular Endothelial Growth Factor Promotes Proliferation and Function of Hepatocyte-like Cells in Embryoid Bodies Formed from Mouse Embryonic Stem Cells," J. Hepatol., 48(6), pp. 962-973.
118. Brissova, M., Fowler, M., Wiebe, P., Shostak, A., Shiota, M., Radhika, A., Lin, P. C., Gannon, M., and Powers, A. C., 2004, "Intraislet Endothelial Cells Contribute to Revascularization of Transplanted Pancreatic Islets," Diabetes, 53(5), pp. 1318-1325.
119. Sekine, H., Shimizu, T., Sakaguchi, K., Dobashi, I., Wada, M., Yamato, M., Kobayashi, E., Umezu, M., and Okano, T., 2013, "In vitro Fabrication of Functional Three-dimensional Tissues with Perfusable Blood Vessels," Nat. Commun, 4, p. 1399.
120. Liu, H., Collins, S. F., and Suggs, L. J., 2006, "Three-dimensional Culture for Expansion and Differentiation of Mouse Embryonic Stem Cells," Biomaterials, 27(36), pp. 6004-6014.
121. Vander Heiden, M. G., Plas, D. R., Rathmell, J. C., Fox, C. J., Harris, M. H., and Thompson, C. B., 2001, "Growth factors can Influence Cell Growth and Survival through Effects on Glucose Metabolism," Mol. Cell Biol., 21(17), pp. 5899-5912.
122. Song, J. J., Guyette, J. P., Gilpin, S. E., Gonzalez, G., Vacanti, J. P., and Ott, H. C., 2013, "Regeneration and Experimental Orthotopic Transplantation of a Bioengineered Kidney," Nat. Med., 19(5), pp. 646-651.
123. Sakaguchi, K., Shimizu, T., Horaguchi, S., Sekine, H., Yamato, M., Umezu, M., and Okano, T., 2013, "In Vitro Engineering of Vascularized Tissue Surrogates," Sci. Rep., 3(1316), pp. 1-7.
124. M. Chen, M. Przyborowski and F. Berthiaume, *Critical Reviews in Biomedical Engineering*, 2009, 37, 399-421.
125. S. MacNeil, Materials Today, 2008, 11, 26-35.
126. R. Tuli, W. J. Li and R. S. Tuancorresponding, *Arthritis Research & Therapy*, 2003, 5, 235-238.
127. H. Tian, S. Bharadwaj, Y. Liu, H. Ma, P. X. Ma, A. Atala and Y. Zhang, Biomaterials, 2010, 31, 870-877.
128. A. Atala, *British Medical Bulletin: Oxford Journals*, 2011, 97, 81-104.
129. N. W. Choi, M. Cabodi, B. Held, J. P. Gleghorn, L. J. Bonassar and A. D. Stroock, Nature Medicine, 2007, 6, 908-915.
130. W. S. Sheridan, G. P. Duffy and B. P. Murphy, *Journal of the Mechanical Behavior of Biomedical Materials*, 2012, 8, 58-70.
131. J. P. Stegemann and R. M. Nerem, *Annals of Biomedical Engineering*, 2003, 31, 391-402.
132. S. L. Dahl, J. Koh, V. Prabhakar and L. E. Niklason, Cell Transplantation, 2003, 12, 659-666.
133. A. Bader, T. Schilling, 0. E. Teebken, G. Brandes, T. Herden, G. Steinhoff and A. Haverich, *European Journal of Cardio-Thoracic Surgery*, 1998, 14, 279-284.
134. P. B. Canham, E. A. Talman, H. M. Finlay and J. G. Dixon, Connective Tissue Research, 1991, 26, 121-134.
135. N. L'Heureux, S. Pâquet, R. Labbé, L. Germain and F. A. Auger, *The FASEB Journal*, 1998, 12, 47-56.
136. J. M. Caves, V. A. Kumar, A. W. Martinez, J. Kim, C. M. Ripberger, C. A. Haller and E. L. Chaikof, Biomaterials, 2010, 31, 7175-7182.
137. A. Salerno, S. Zeppetelli, E. Di Maio, S. Iannace and P. A. Netti, *Biotechnology and Bioengineering*, 2011, 108, 963-976.
138. C. Xu, W. Chai, Y. Huang and R. R. Markwald, Biotechnology and Bioengineering, 2012, 109, 3152-3160.
139. D. W. Courtman, C. A. Pereira, V. Kashef, D. McComb, J. M. Lee and G. J. Wilson, *Journal of Biomedical Materials Research*, 1994, 28, 655-666.
140. H. M. Sung, C. S. Hsu, H. C. Chen, H. L. Hsu, Y. Chang, J. H. Lu and P. C. Yang, *Artificial Organs*, 1997, 21, 50-58.
141. N. L'Heureux, S. Pâquet, R. Labbé, L. Germain and F. A. Auger., *The FASEB Journal*, 1998, 12, 47-56.
142. B. C. Isenberg, D. E. Backman, M. E. Kinahan, R. Jesudason, B. Suki, P. J. Stone, E. C. Davis and J. Y. Wong, *Journal of Biomechanics*, 2012, 45, 756-761.
143. S. P. Hoerstrup, G. Ziind, R. Sodian, A. M. Schnell, J. Grünenfelder and M. I. Turina, *European Journal Cardio-Thoracic Surgery*, 2001, 20, 164-169.
144. B. Tschoeke, T. C. Flanagan, S. Koch, M. S. Harwoko, T. Deichmann, V. Ellå, J. S. Sachweh, M. Kellomåki, T. Gries, T. Schmitz-Rode and S. Jockenhoevel, *Tissue Engineering*, 2009, 15, 1909-1918.
145. J. O. Hollinger, *An Introductiona to Biomaterial CRC Press, Taylor & Francis Group*, 2011.
146. D. Seliktar, D. Dikovsky and E. Napadensky, *Israel Journal of Chemistry*, 2013, 53, 795-804.
147. S. Khalil, Phd. Thesis, Drexel University, 2006.
148. R. Gauvin, M. Guillemette, T. Galbraith, J. M. Bourget, D. Larouche, H. Marcoux, D. Aubé, C. Hayward, F. A. Auger and L. Germain, *Tissue Engineering*, 2011, 17, 2049-2059.
149. F. Zhang, J. Chang, J. Lu, K. Lin, and C. Ning, *Acta Biomaterialia*, 2007, 3, 896-904.
150. S. Sarkar, C. Hillery, A. Seifalian, G. Hamilton, *Journal of Vascular Surgery*, 2006, 44, 846852.
151. D. L. Wise D. J. Trantolo, K. Lewandrowski, J. Gresser M. V. Cattaneo Biomaterials Engineering and Devices: Human Applications: Volume 1: Fundamentals and Vascular and Carrier Applications Springer-Verlag, 2010.
152. G. Konig, T. N. McAllister, N. Dusserre, S. A. Garrido, C. Iyican, A. Marini, A. Fiorillo, H. Avila, W. Wystrychowski, K. Zagalski, M. Maruszewski, A. L. Jones, L. Cierpka, L. M. de la Fuente and N. L'Heureux, Biomaterials, 2009, 30, 1542-1550.
153. V. Mironov, R. P. Visconti, V. Kasyanov, G. Forgacs, C. J. Drake, and R. R. Markwald, "Organ printing: tissue spheroids as building blocks," Biomaterials, vol. 30, pp. 2164-74, April 2009.
154. K. Kusamori, M. Nishikawa, N. Mizuno, T. Nishikawa, A. Masuzawa, K. Shimizu, et al., "Transplantation of insulin-secreting multicellular spheroids for the treatment of type 1 diabetes in mice," *J Control Release*, vol. 173, pp. 119-24, Jan. 10, 2014.
155. A. Faulkner-Jones, S. Greenhough, J. A. King, J. Gardner, A. Courtney, and W. Shu, "Development of a valve-based cell printer for the formation of human embryonic stem cell spheroid aggregates," *Biofabrication*, vol. 5, p. 015013, March 2013.
156. Y. T. Matsunaga, Y. Morimoto, and S. Takeuchi, "Molding cell beads for rapid construction of macroscopic 3D tissue architecture," *Adv Mater*, vol. 23, pp. H90-4, Mar. 25, 2011.
157. A. B. Bernard, C. C. Lin, and K. S. Anseth, "A microwell cell culture platform for the aggregation of pancreatic beta-cells," *Tissue Eng Part C Methods*, vol. 18, pp. 583-92, August 2012.
158. Y. Yu, H. Zheng, J. A. Buckwalter, and J. A. Martin, "Single cell sorting identifies progenitor cell population from full thickness bovine articular cartilage," *Osteoarthritis Cartilage*, vol. 22, pp. 1318-26, September 2014.

What is claimed is:

1. A bioprinter for dispensing at least one biomaterial, comprising:
a processor configured to determine a desired tool path;
a support assembly;
at least one printer head, each printer head operatively coupled to the processor and comprising:
an arm assembly having a proximal portion and a distal portion, the proximal portion of the arm assembly being operatively coupled to the support assembly such that the arm assembly is selectively moveable relative to at least a first axis; and
a nozzle assembly operatively coupled to the distal portion of the arm assembly,
wherein the nozzle assembly is configured to receive and dispense the at least one biomaterial as the arm assembly is selectively moved relative to the first axis, and
wherein the processor is configured to selectively adjust the positioning of the arm assembly of each printer head relative to at least the first axis in accordance with the desired tool path,
wherein the nozzle assembly of a first printer head of the at least one printer head has a longitudinal axis and comprises:
an outer nozzle having a proximal end, a distal end, an outer surface, and an inner surface, the inner surface of the outer nozzle defining a central bore and an inner diameter of the outer nozzle, the outer surface of the outer nozzle defining an inlet positioned in communication with the central bore of the outer nozzle, wherein the inner surface of the distal end of the outer nozzle defines an outlet of the outer nozzle in communication with the central bore of the outer nozzle, the outlet of the outer nozzle having a diameter;
an inner nozzle having a proximal end, a distal end, an outer surface, and an inner surface, the outer surface of the inner nozzle defining an outer diameter of the inner nozzle, the inner surface of the inner nozzle defining a central bore, the inner surface of the proximal end of the inner nozzle defining an inlet of the inner nozzle, the inner surface of the distal end of the inner nozzle defining an outlet of the inner nozzle, wherein the inner nozzle is at least partially received within the central bore of the outer nozzle such that the outer nozzle and the inner nozzle have a common longitudinal axis that is in substantial alignment with the longitudinal axis of the nozzle assembly, the outer diameter of the inner nozzle being less than the diameter of the outlet of the outer nozzle to thereby define a receiving space between the outer surface of the inner nozzle and the inner surface of the outer nozzle; and
wherein the inlet of the outer nozzle is configured to receive at least one biomaterial and deliver the at least one biomaterial to the receiving space, and wherein the outlet of the outer nozzle is configured to dispense the at least one biomaterial from within the receiving space as a tubular structure, and
wherein the inlet of the inner nozzle is configured to receive at least one biomaterial and deliver the at least one biomaterial to the central bore of the inner nozzle, and wherein the outlet of the inner nozzle is configured to dispense the at least one biomaterial from within the central bore of the inner nozzle as a cylindrical structure,
wherein the inner nozzle extends from the proximal end of the outer nozzle through the outlet of the outer nozzle such that the outlet of inner nozzle extends through the outlet of the outer nozzle.

2. The bioprinter of claim 1, wherein the distal portion of the arm assembly of each printer head is selectively rotatable relative to the proximal portion of the arm assembly, and wherein the nozzle assembly is configured to receive and dispense the at least one biomaterial as the arm assembly is selectively moved relative to the first axis and the distal portion of the arm assembly is selectively rotated relative to the proximal portion of the arm assembly.

3. The bioprinter of claim 2, wherein the nozzle assembly of at least one printer head of the bioprinter comprises means for maintaining the at least one biomaterial within the nozzle assembly at a desired temperature until the at least one biomaterial is dispensed from the nozzle assembly.

4. The bioprinter of claim 3, wherein the means for maintaining the at least one biomaterial within the nozzle at a desired temperature comprises a heating system.

5. The bioprinter of claim 4, wherein the heating system comprises a circumferential heating chamber that circumferentially surrounds at least a portion of the outer surface of the outer nozzle.

6. The bioprinter of claim 4, wherein the means for maintaining the at least one biomaterial within the nozzle at a desired temperature further comprises a cooling system.

7. The bioprinter of claim 6, wherein the cooling system comprises a circumferential chamber configured to surround at least a portion of the outer surface of the outer nozzle, wherein the circumferential chamber has at least one fluid inlet and at least one fluid outlet axially spaced from the at least one fluid inlet, wherein the at least one fluid inlet and the at least one fluid outlet are configured to permit axial flow of at least one coolant material within the circumferential chamber to thereby cool the at least a portion of the outer surface of the outer nozzle.

8. The bioprinter of claim 1, wherein the nozzle assembly of at least one printer head of the bioprinter comprises means for maintaining the at least one biomaterial within the nozzle assembly at a desired temperature until the at least one biomaterial is dispensed from the nozzle assembly.

9. The bioprinter of claim 1, wherein the arm assembly of each printer head is selectively moveable relative to at least the first axis and a second axis, wherein the second axis is substantially perpendicular to the first axis.

10. A bioprinting system for treating a tissue defect of a subject, comprising:
a scanner configured to scan the tissue defect and to generate an output indicative of the location of the tissue defect; and
a bioprinter comprising:
a processor configured to determine a desired tool path;
a support assembly;
at least one printer head, each printer head operatively coupled to the processor and comprising:
an arm assembly having a proximal portion and a distal portion, the proximal portion of the arm assembly being operatively coupled to the support assembly such that the arm assembly is selectively moveable relative to at least a first axis; and
a nozzle assembly operatively coupled to the distal portion of the arm assembly,
wherein the nozzle assembly is configured to receive and dispense at least one biomaterial as the arm assembly is selectively moved relative to the first axis, and wherein the processor is configured to selectively adjust the positioning of the arm assembly of each printer head relative to at least the first axis in accordance with the desired tool path, wherein the processor of the bioprinter is configured to receive the output from the scanner, and wherein the processor of the bioprinter is configured to selectively adjust the positioning of the arm assembly of each printer head to permit printing of the at least one biomaterial directly into the tissue defect, wherein the nozzle assembly of a first printer head of the at least one printer head has a longitudinal axis and comprises:

an outer nozzle having a proximal end, a distal end, an outer surface, and an inner surface, the inner surface of the outer nozzle defining a central bore and an inner diameter of the outer nozzle, the outer surface of the outer nozzle defining an inlet positioned in communication with the central bore of the outer nozzle, wherein the inner surface of the distal end of the outer nozzle defines an outlet of the outer nozzle in communication with the central bore of the outer nozzle, the outlet of the outer nozzle having a diameter;

an inner nozzle having a proximal end, a distal end, an outer surface, and an inner surface, the outer surface of the inner nozzle defining an outer diameter of the inner nozzle, the inner surface of the inner nozzle defining a central bore, the inner surface of the proximal end of the inner nozzle defining an inlet of the inner nozzle, the inner surface of the distal end of the inner nozzle defining an outlet of the inner nozzle, wherein the inner nozzle is at least partially received within the central bore of the outer nozzle such that the outer nozzle and the inner nozzle have a common longitudinal axis that is in substantial alignment with the longitudinal axis of the nozzle assembly, the outer diameter of the inner nozzle being less than the diameter of the outlet of the outer nozzle to thereby define a receiving space between the outer surface of the inner nozzle and the inner surface of the outer nozzle; and wherein the inlet of the outer nozzle is configured to receive at least one biomaterial and deliver the at least one biomaterial to the receiving space, and wherein the outlet of the outer nozzle is configured to dispense the at least one biomaterial from within the receiving space as a tubular structure, and wherein the inlet of the inner nozzle is configured to receive at least one biomaterial and deliver the at least one biomaterial to the central bore of the inner nozzle, and wherein the outlet of the inner nozzle is configured to dispense the at least one biomaterial from within the central bore of the inner nozzle as a cylindrical structure, wherein the inner nozzle extends from the proximal end of the outer nozzle through the outlet of the outer nozzle such that the outlet of inner nozzle extends through the outlet of the outer nozzle.

11. A bioprinter for dispensing at least one biomaterial, comprising:

a processor configured to determine a desired tool path;
a support assembly;
a plurality of printer heads comprising a first printer head and a second printer head, each printer head of the plurality of printer heads being operatively coupled to the processor and comprising:

an arm assembly having a proximal portion and a distal portion, the proximal portion of the arm assembly being operatively coupled to the support assembly such that the arm assembly is selectively moveable relative to at least a first axis; and a nozzle assembly operatively coupled to the distal portion of the arm assembly, wherein the nozzle assembly is configured to receive and dispense the at least one biomaterial as the arm assembly is selectively moved relative to the first axis, and wherein the processor is configured to selectively adjust the positioning of the arm assembly of each printer head of the plurality of printer heads relative to at least the first axis in accordance with the desired tool path, wherein the nozzle assembly of the first printer head of the plurality of printer heads has a longitudinal axis and comprises:

an outer nozzle having a proximal end, a distal end, an outer surface, and an inner surface, the inner surface of the outer nozzle defining a central bore and an inner diameter of the outer nozzle, the outer surface of the outer nozzle defining an inlet positioned in communication with the central bore of the outer nozzle, wherein the inner surface of the distal end of the outer nozzle defines an outlet of the outer nozzle in communication with the central bore of the outer nozzle, the outlet of the outer nozzle having a diameter;

an inner nozzle having a proximal end, a distal end, an outer surface, and an inner surface, the outer surface of the inner nozzle defining an outer diameter of the inner nozzle, the inner surface of the inner nozzle defining a central bore, the inner surface of the proximal end of the inner nozzle defining an inlet of the inner nozzle, the inner surface of the distal end of the inner nozzle defining an outlet of the inner nozzle, wherein the inner nozzle is at least partially received within the central bore of the outer nozzle such that the outer nozzle and the inner nozzle have a common longitudinal axis that is in substantial alignment with the longitudinal axis of the nozzle assembly, the outer diameter of the inner nozzle being less than the diameter of the outlet of the outer nozzle to thereby define a receiving space between the outer surface of the inner nozzle and the inner surface of the outer nozzle; and wherein the inlet of the outer nozzle is configured to receive at least one biomaterial and deliver the at least one biomaterial to the receiving space, and wherein the outlet of the outer nozzle is configured to dispense the at least one biomaterial from within the receiving space as a tubular structure, and wherein the inlet of the inner nozzle is configured to receive at least one biomaterial and deliver the at least one biomaterial to the central bore of the inner nozzle, and wherein the outlet of the inner nozzle is configured to dispense the at least one biomaterial from within the central bore of the inner nozzle as a cylindrical structure, wherein the inner nozzle extends from the proximal end of the outer nozzle through the outlet of the outer nozzle such that the outlet of inner nozzle extends through the outlet of the outer nozzle, wherein the processor is configured to coordinate movement of the first printer head relative to the second printer head.

12. The bioprinter of claim 11, wherein the second printer head is configured to print tissue-specific cell aggregate strands.

* * * * *